(12) United States Patent
Rousche et al.

(10) Patent No.: US 12,121,405 B2
(45) Date of Patent: Oct. 22, 2024

(54) NEEDLE SAFETY SYSTEMS

(71) Applicant: Hemotek Medical Incorporated, Healdsburg, CA (US)

(72) Inventors: Patrick Rousche, Healdsburg, CA (US); Charles Ventura, Cary, IL (US); Adam Hensel, Gahanna, OH (US); Todd Macy, Powell, OH (US); Edward Browka, Oneida, NY (US)

(73) Assignee: Hemotek Medical Incorporated, Healdsburg, CA (US)

( * ) Notice: Subject to any disclaimer, the term of this patent is extended or adjusted under 35 U.S.C. 154(b) by 343 days.

(21) Appl. No.: 17/671,367

(22) Filed: Feb. 14, 2022

(65) Prior Publication Data

US 2022/0354610 A1 Nov. 10, 2022

Related U.S. Application Data

(63) Continuation of application No. PCT/US2020/046536, filed on Aug. 14, 2020.

(60) Provisional application No. 62/886,762, filed on Aug. 14, 2019, provisional application No. 63/028,907, filed on May 22, 2020.

(51) Int. Cl.
| | | |
|---|---|---|
| *A61M 5/158* | (2006.01) | |
| *A61B 90/00* | (2016.01) | |
| *A61M 5/168* | (2006.01) | |

(52) U.S. Cl.
CPC ............. *A61B 90/03* (2016.02); *A61M 5/158* (2013.01); *A61M 5/16813* (2013.01); *A61B 2090/036* (2016.02)

(58) Field of Classification Search
CPC .. A61M 2005/1586; A61M 2005/1588; A61M 2205/13; A61M 39/284; A61M 2205/276; A61M 5/16813
See application file for complete search history.

(56) References Cited

U.S. PATENT DOCUMENTS

| | | |
|---|---|---|
| 2,539,510 A | 1/1951 | Friden |
| 4,407,434 A | 10/1983 | Kempf |
| 4,551,128 A | 11/1985 | Hakim et al. |
| 4,960,259 A | 10/1990 | Sunnanvader et al. |
| 5,108,374 A | 4/1992 | Lemieux |
| 5,300,043 A | 4/1994 | Devlin et al. |
| 5,522,806 A | 6/1996 | Schonbachler et al. |

(Continued)

FOREIGN PATENT DOCUMENTS

| | | |
|---|---|---|
| CN | 101730555 A | 6/2010 |
| FR | 1426230 | 1/1966 |

(Continued)

*Primary Examiner* — Deanna K Hall
(74) *Attorney, Agent, or Firm* — Levine Bagade Han LLP

(57) ABSTRACT

Tissue access devices and methods of using and making the same are disclosed. The devices can have a needle, a housing having wings, a tube having a flow channel, a tube first extension, and a tube second extension, and a torsion spring having a first coil and a second coil. The first coil can have a first coil first arm and a first coil second arm. The first coil first arm can be shorter than the first coil second arm. The second coil can have a second coil first arm and a second coil second arm. The second coil first arm can be shorter than the second coil second arm. The devices can have a sensor. More energy can stored in the torsion spring when the sensor is in a sensor closed configuration than when the sensor is in a sensor open configuration.

20 Claims, 48 Drawing Sheets

(56) References Cited

U.S. PATENT DOCUMENTS

| | | |
|---|---|---|
| 6,126,637 A | 10/2000 | Kriesel et al. |
| 7,044,936 B2 | 5/2006 | Harding et al. |
| 8,313,497 B2 | 11/2012 | Walberg et al. |
| 8,926,571 B1 | 1/2015 | Keith |
| 10,213,548 B2 | 2/2019 | Rousche et al. |
| 10,994,075 B2 | 5/2021 | Rousche et al. |
| 11,446,110 B2 | 9/2022 | Rousche et al. |
| 2001/0003158 A1 | 6/2001 | Kensey et al. |
| 2008/0281276 A1 | 11/2008 | Shekalim |
| 2008/0312666 A1 | 12/2008 | Ellingwood et al. |
| 2009/0069844 A1 | 3/2009 | Green et al. |
| 2013/0218073 A1 | 8/2013 | Ekdahl et al. |
| 2016/0175563 A1 | 6/2016 | Woehr et al. |
| 2017/0021098 A1 | 1/2017 | Rousche et al. |
| 2017/0112531 A1 | 4/2017 | Schoonmaker et al. |
| 2018/0360364 A1 | 12/2018 | Whelan |
| 2018/0368771 A1 | 12/2018 | Gray et al. |
| 2019/0143033 A1 | 5/2019 | Rousche et al. |
| 2020/0008898 A1 | 1/2020 | Rousche et al. |
| 2021/0046241 A1 | 2/2021 | Rousche et al. |
| 2021/0228802 A1 | 7/2021 | Rousche et al. |
| 2023/0056293 A1 | 2/2023 | Rousche et al. |
| 2024/0074829 A1 | 3/2024 | Rousche et al. |
| 2024/0075205 A1 | 3/2024 | Rousche et al. |

FOREIGN PATENT DOCUMENTS

| | | |
|---|---|---|
| JP | 2006-000646 | 1/2006 |
| JP | 2010-526578 | 8/2010 |
| WO | WO 1993/024173 | 12/1993 |
| WO | WO 1995/015779 | 6/1995 |
| WO | WO 2008/139464 | 6/2008 |
| WO | WO 2015/156850 | 10/2015 |
| WO | WO 2018/119309 | 6/2018 |
| WO | WO 2019/213598 | 11/2019 |
| WO | WO 2021/030761 | 2/2021 |

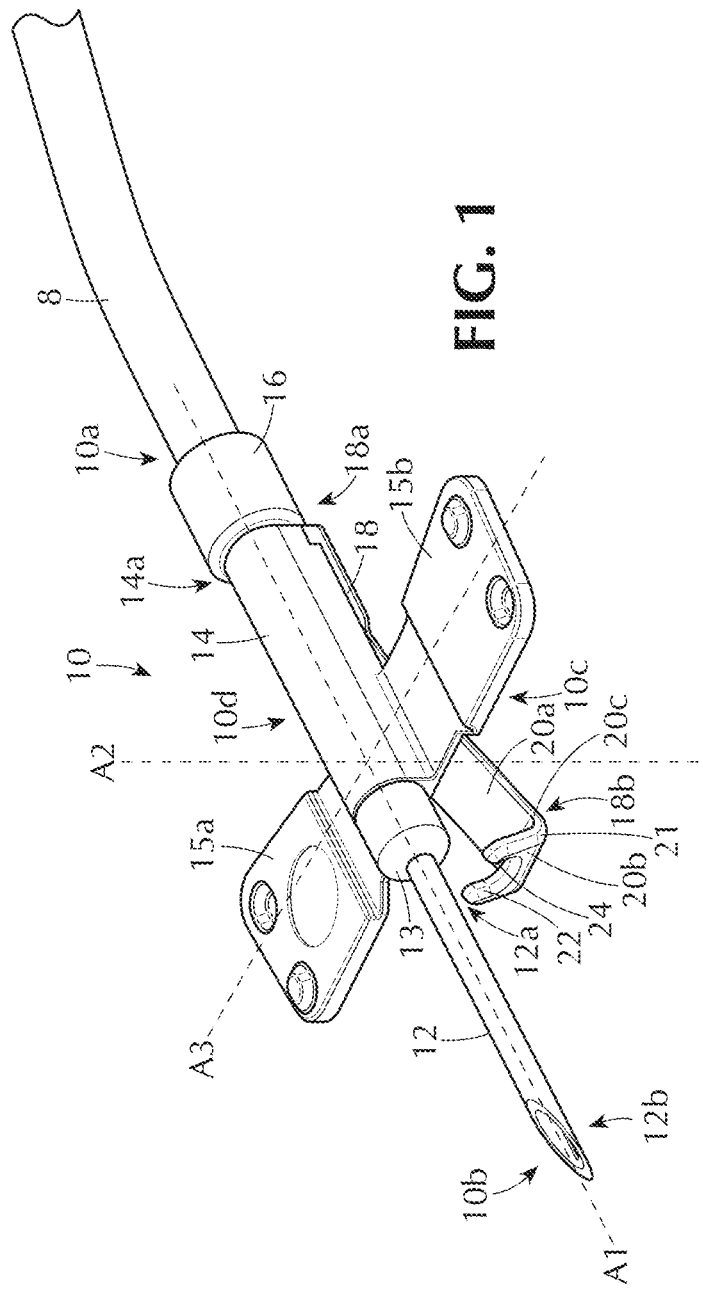

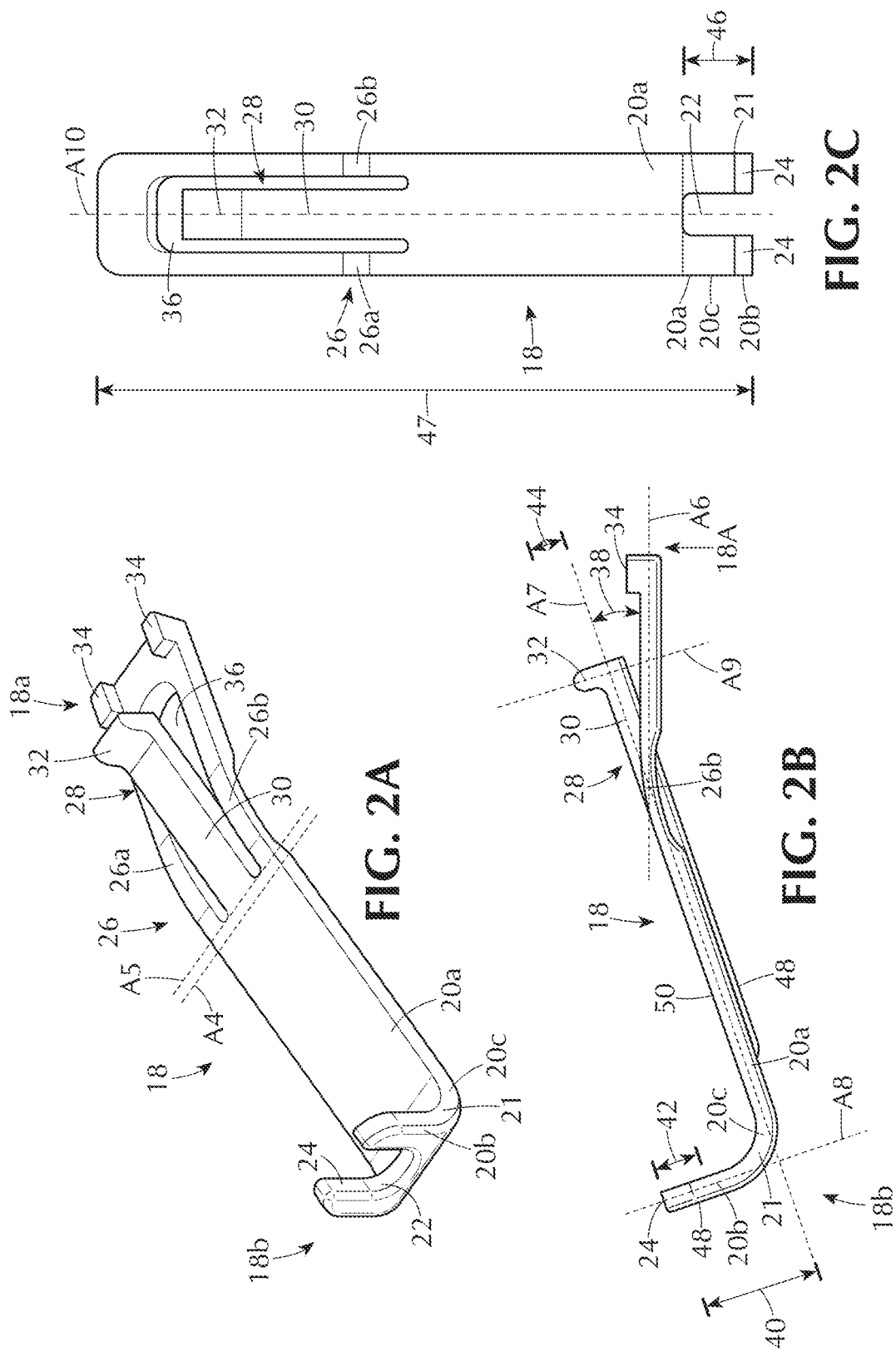

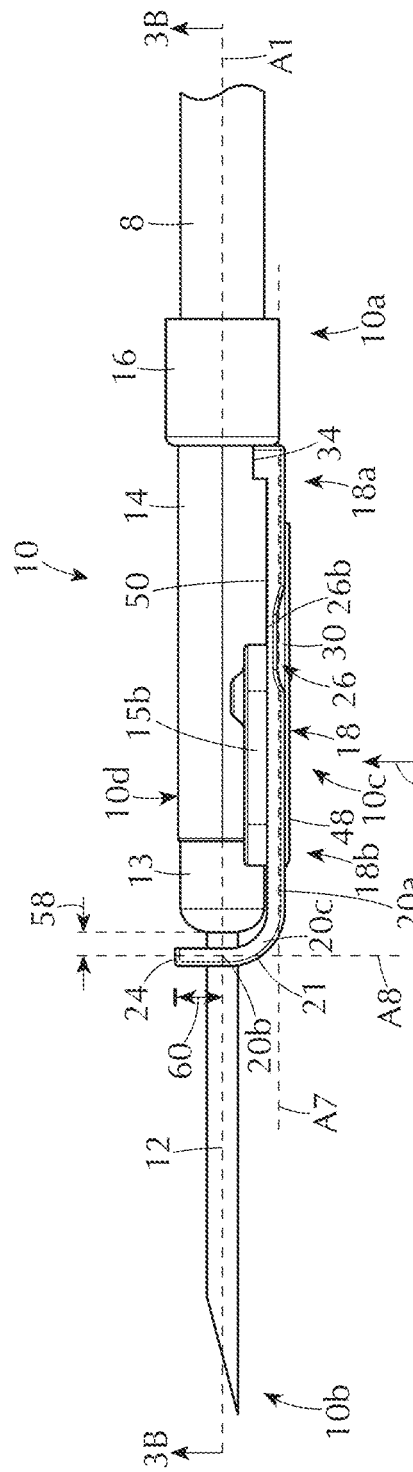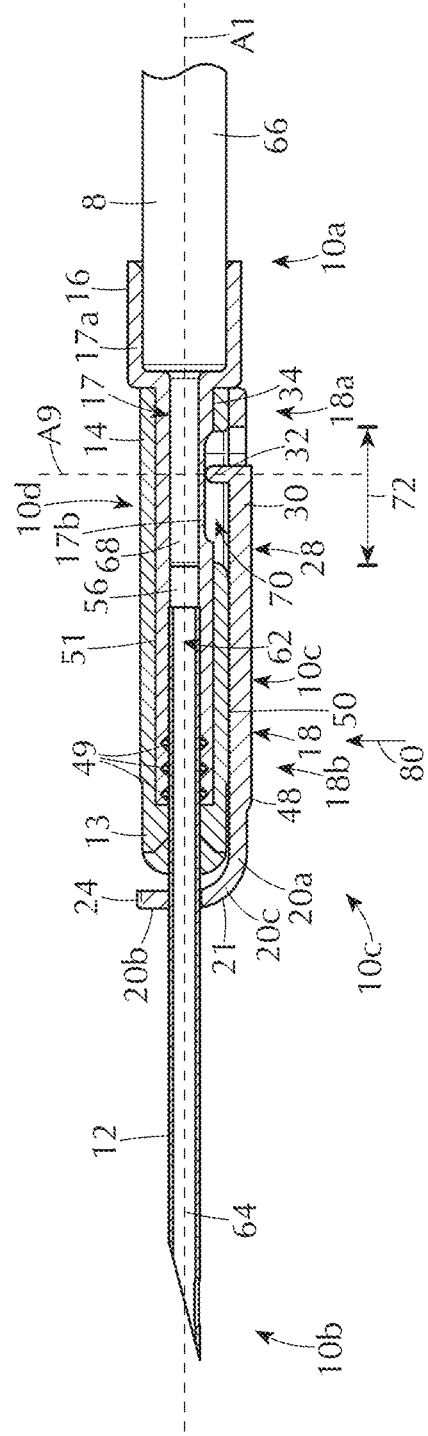

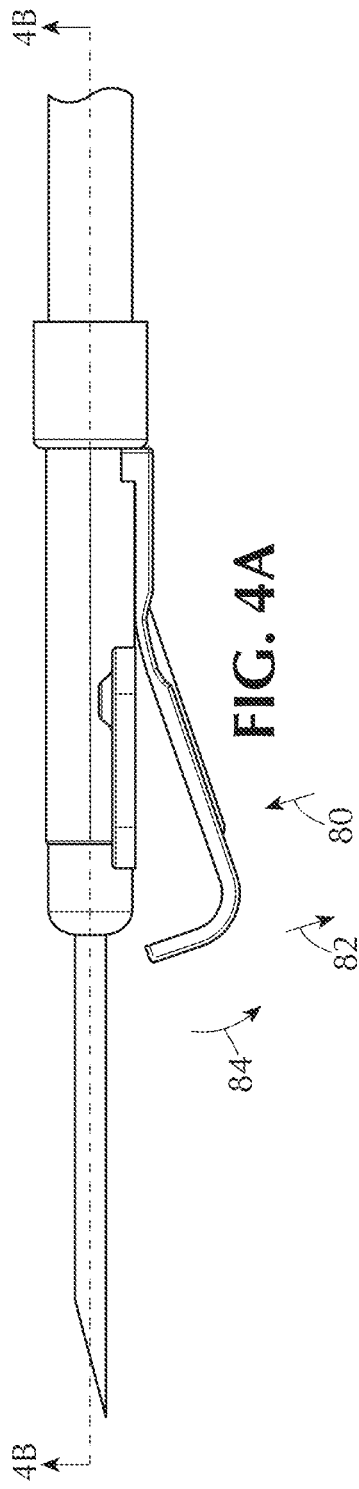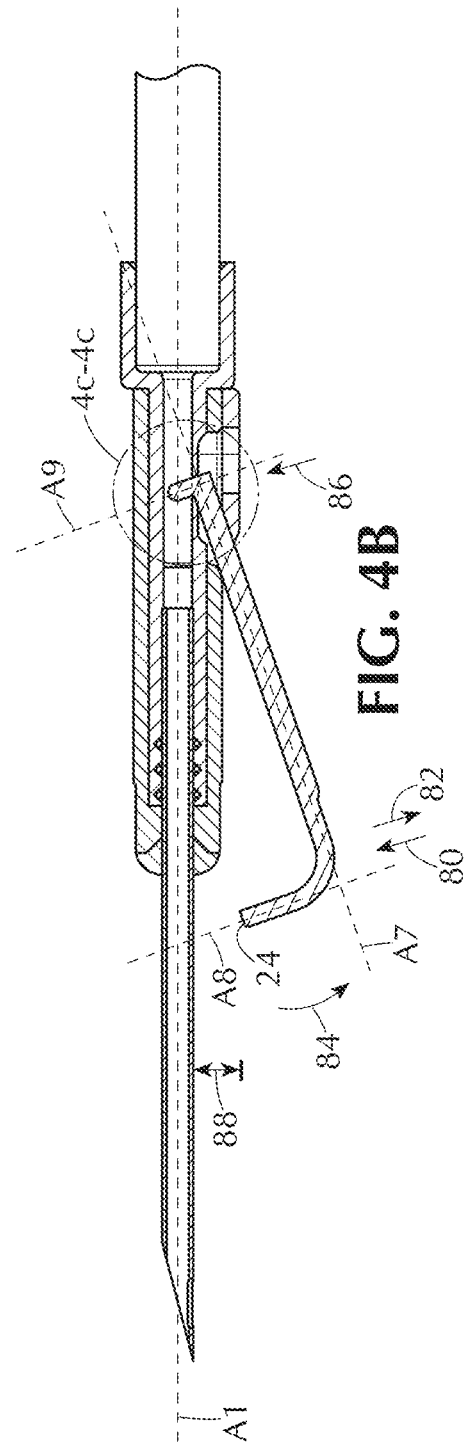

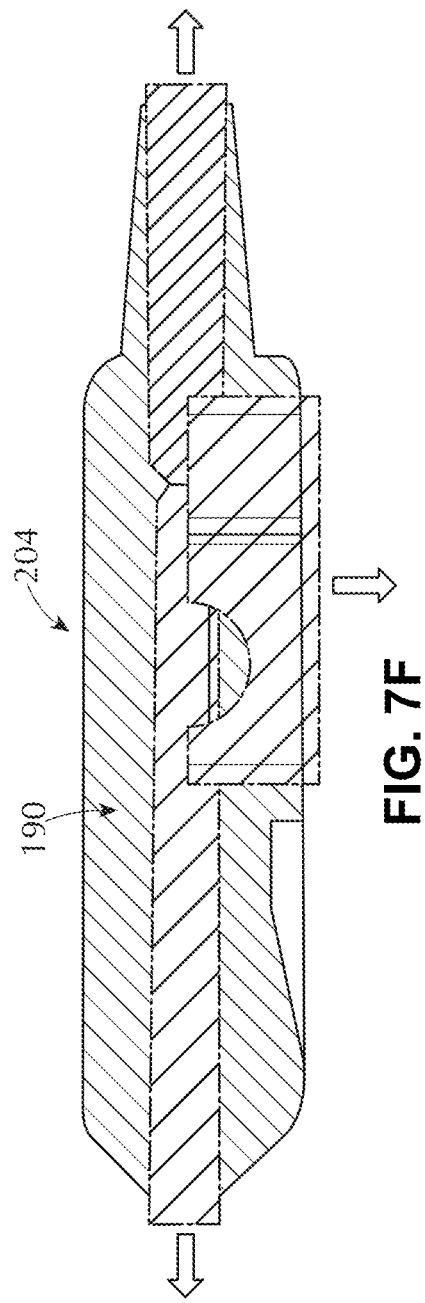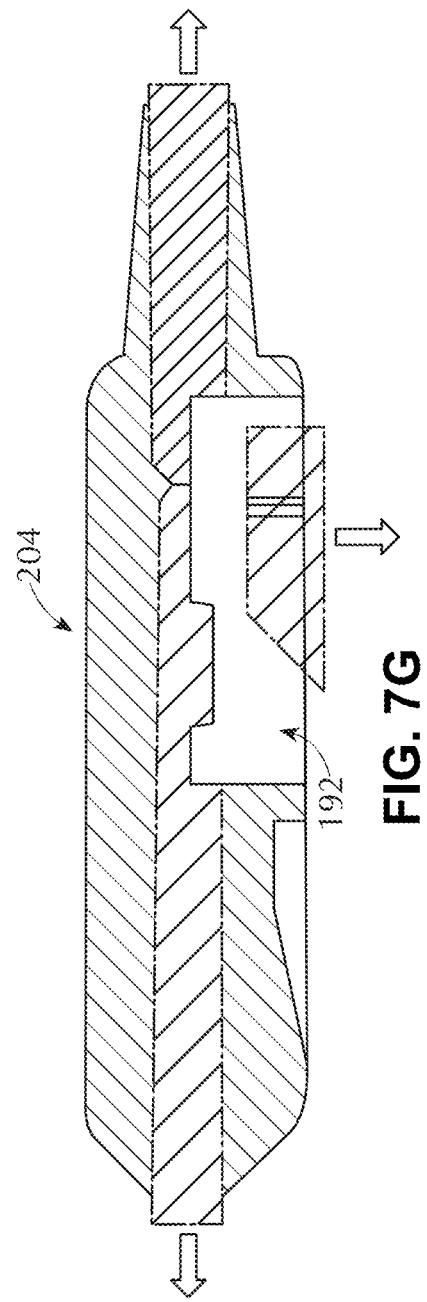

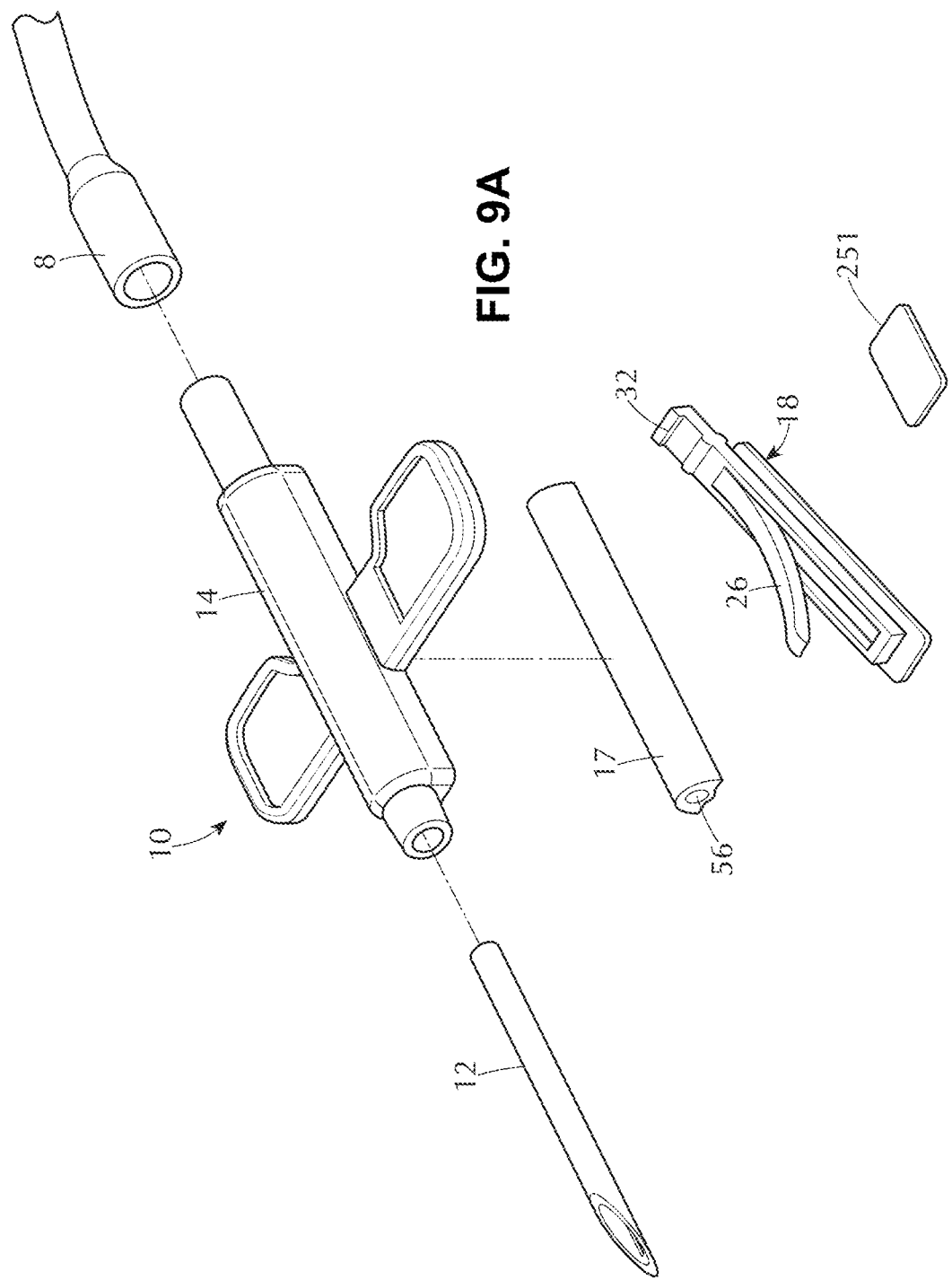

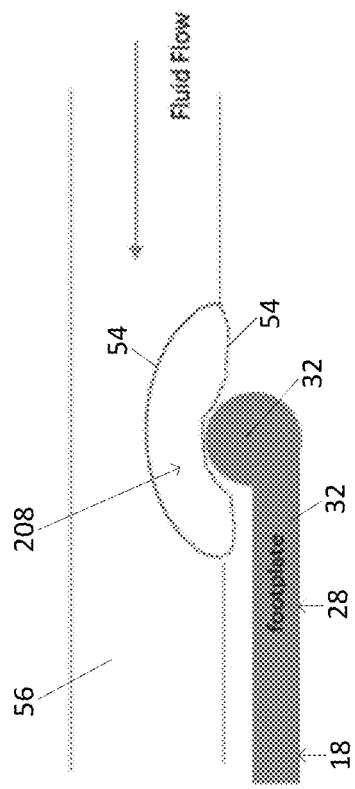
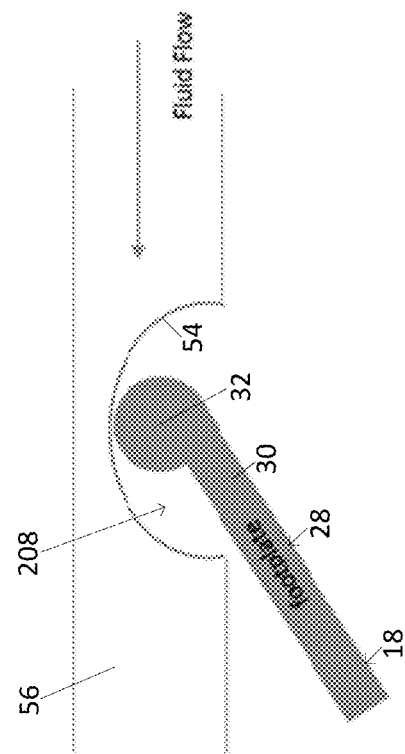
FIG. 13A
FIG. 13B
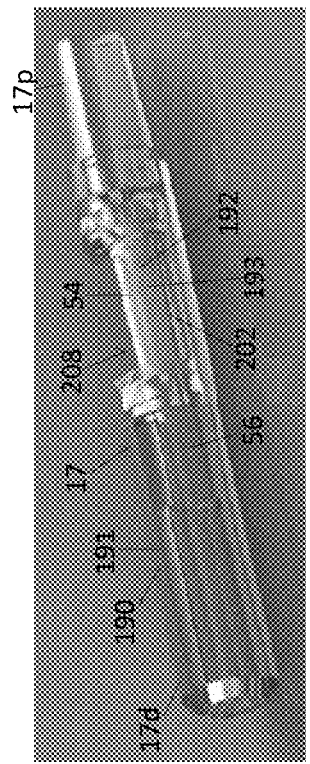
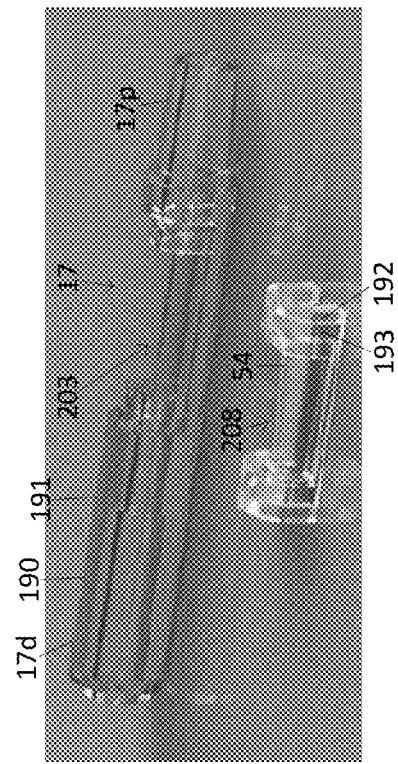
FIG. 12A
FIG. 12B

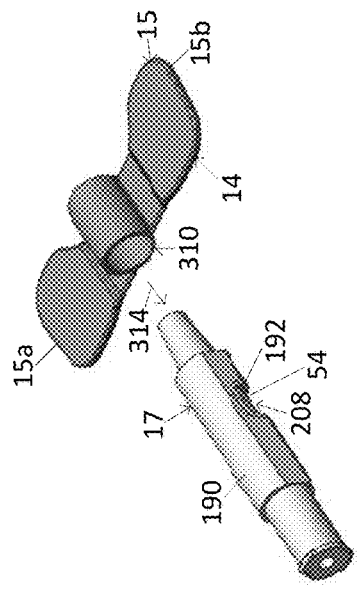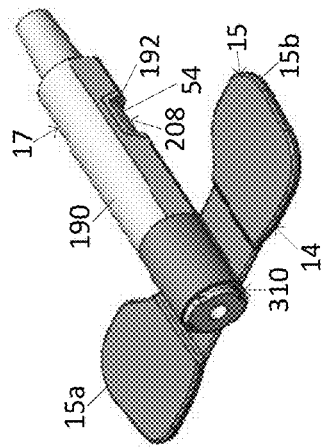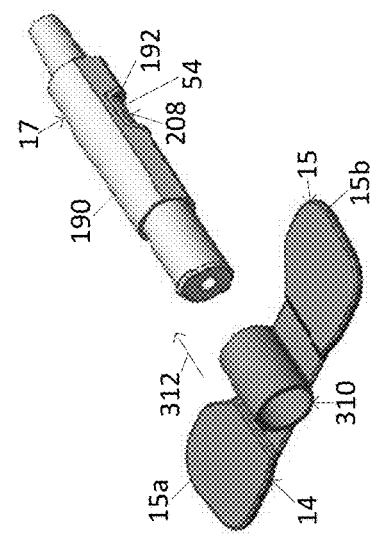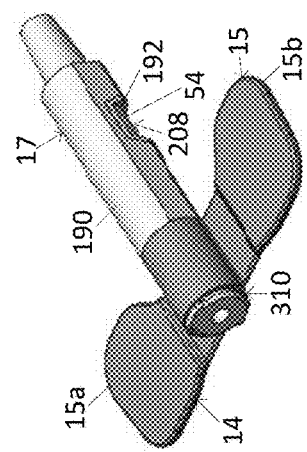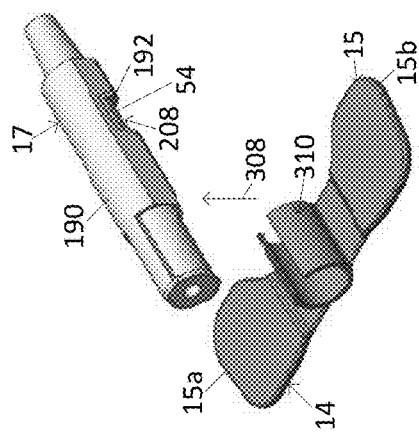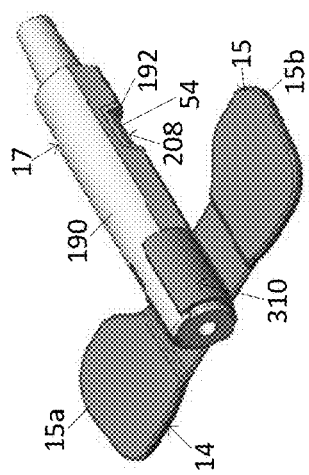
FIG. 14A₁  FIG. 14A₂  FIG. 14B₁  FIG. 14B₂  FIG. 14C₁  FIG. 14C₂

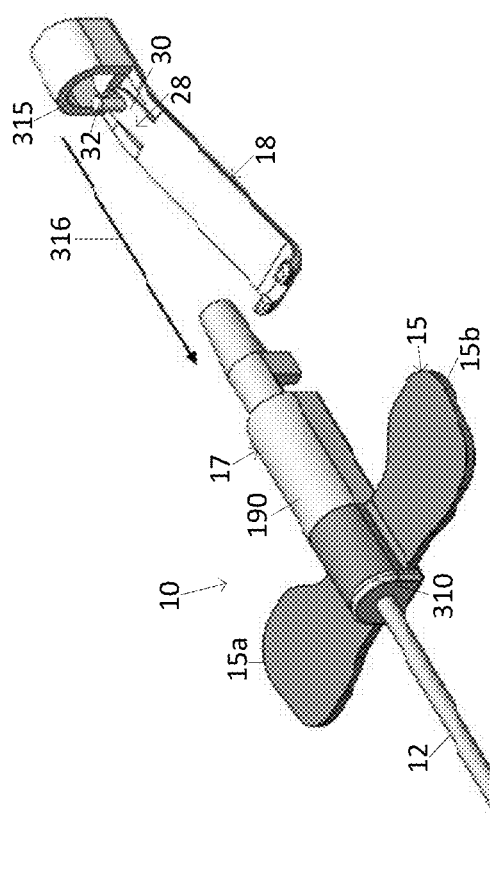
FIG. 15A₁
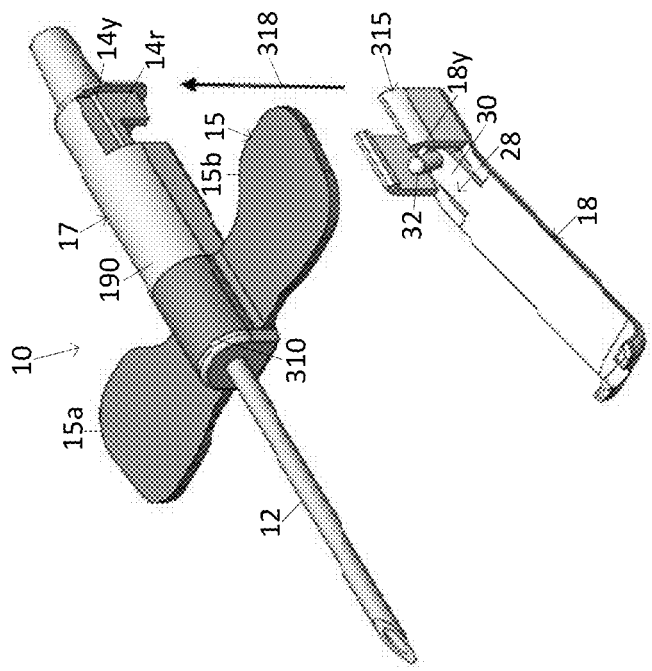
FIG. 15B₁
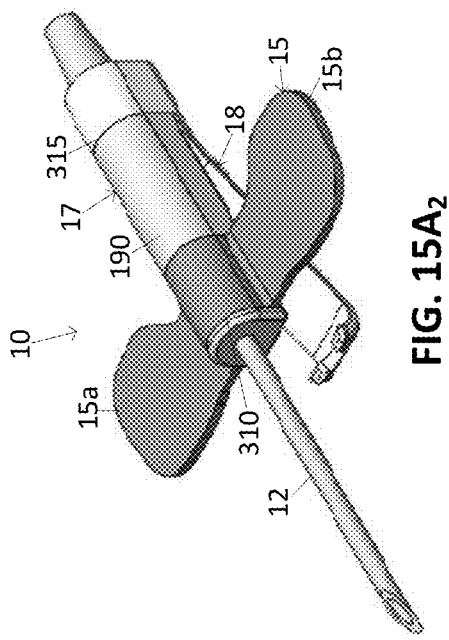
FIG. 15A₂
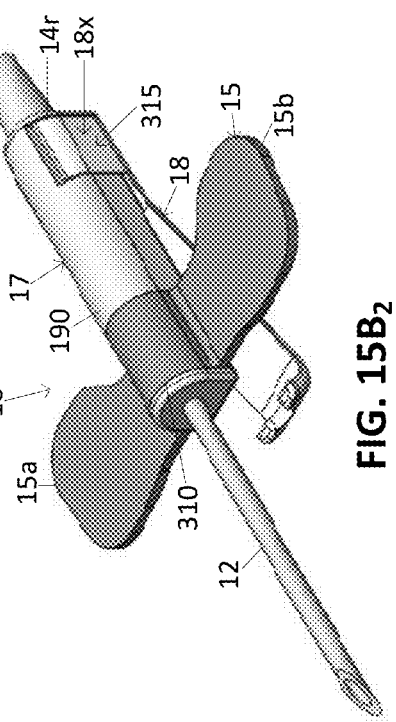
FIG. 15B₂

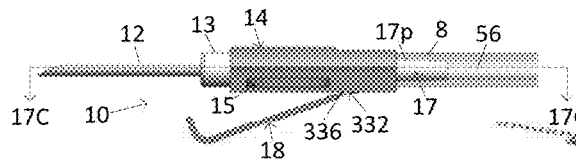
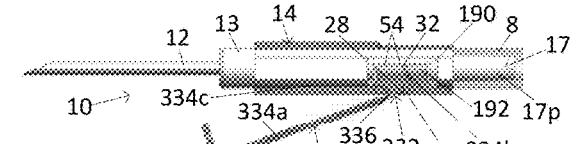
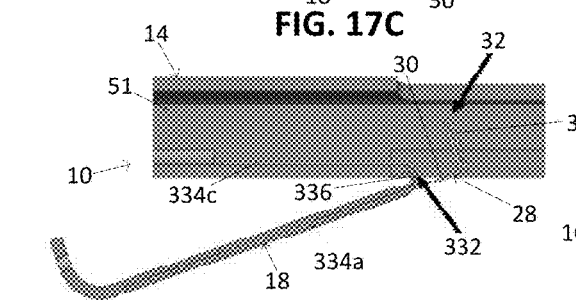
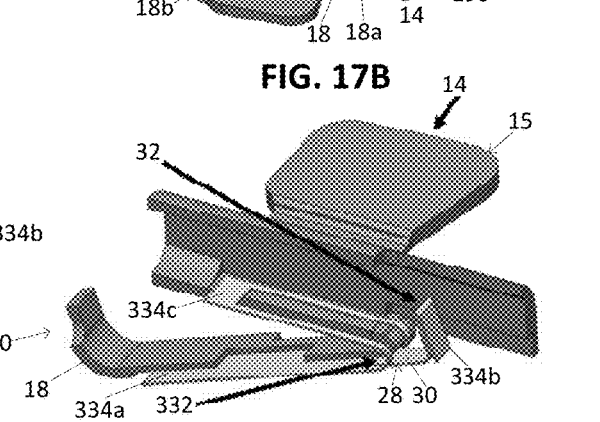
FIG. 17A
FIG. 17B
FIG. 17C
FIG. 17D
FIG. 17E
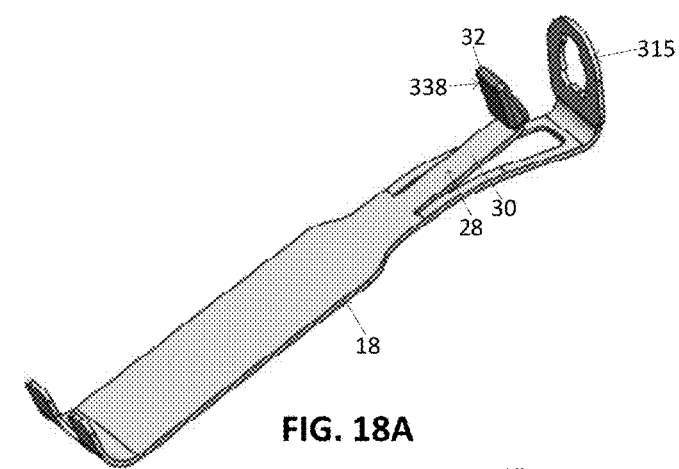
FIG. 18A
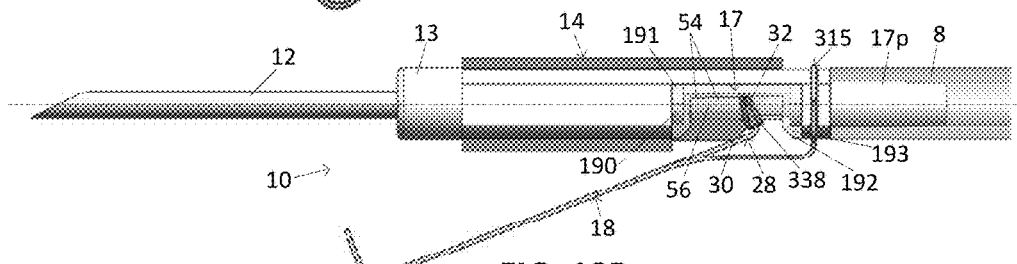
FIG. 18B

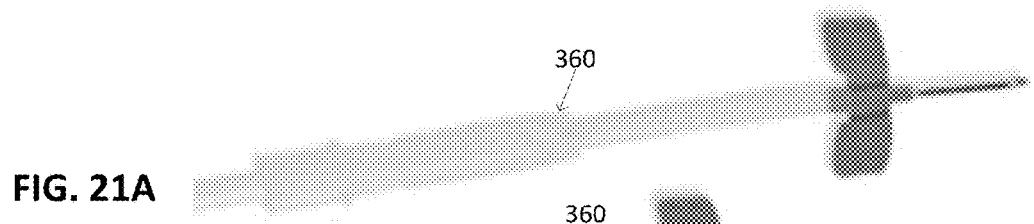
FIG. 21A
FIG. 21B
FIG. 21C
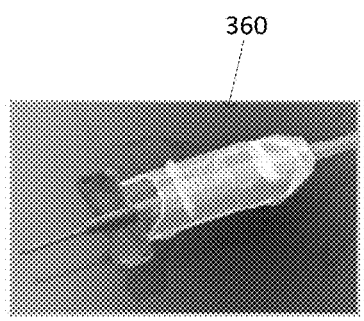 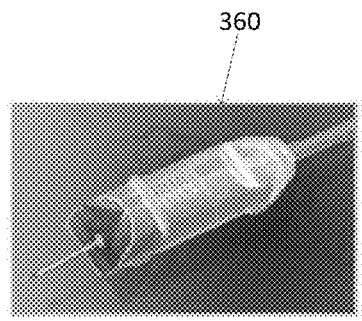 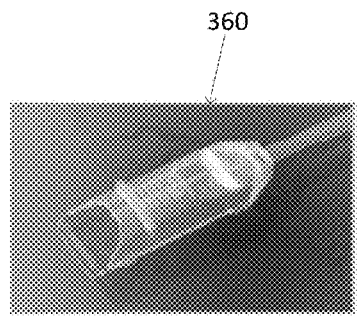
FIG. 22A                FIG. 22B                FIG. 22C
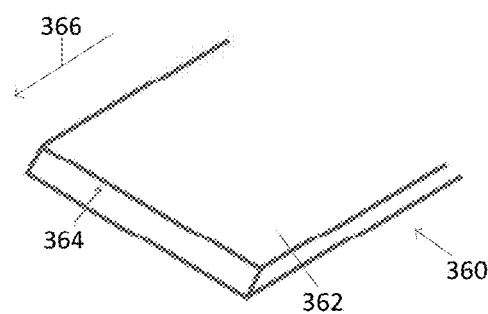
FIG. 23

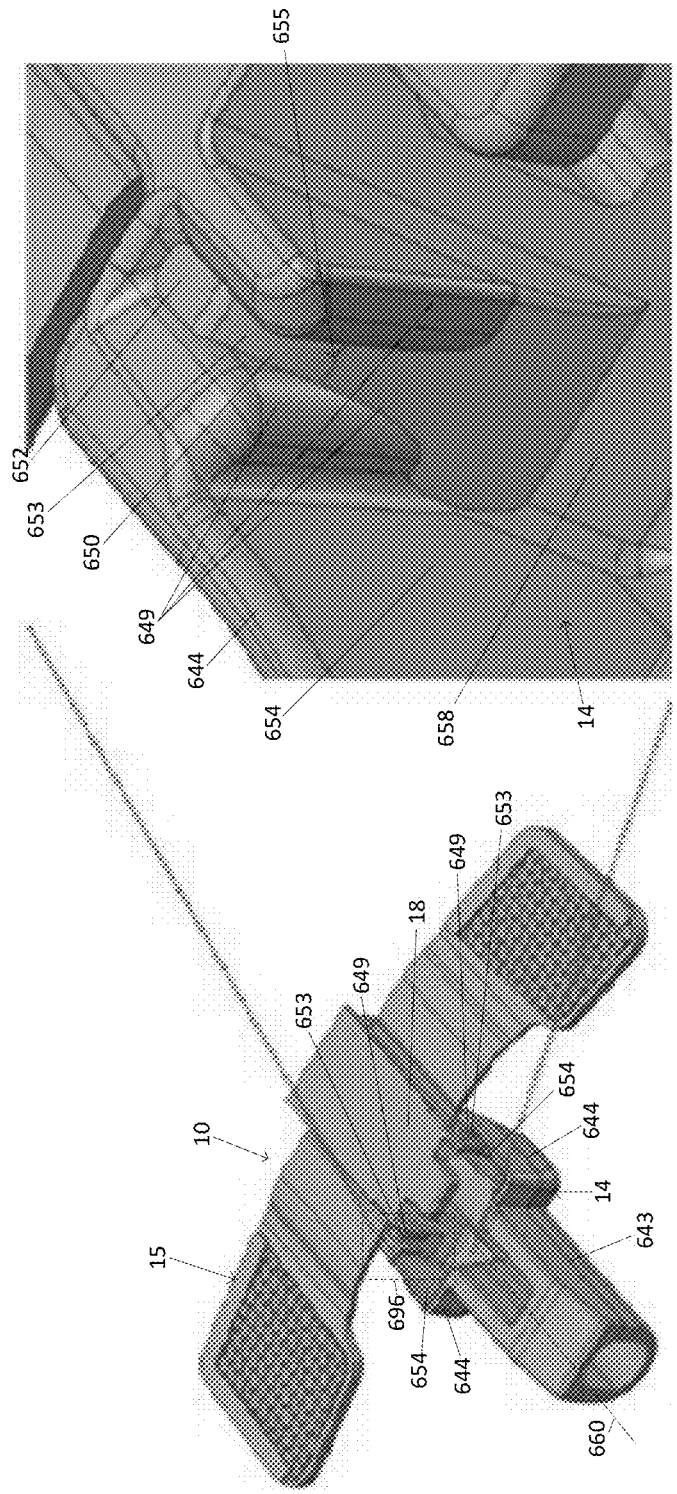

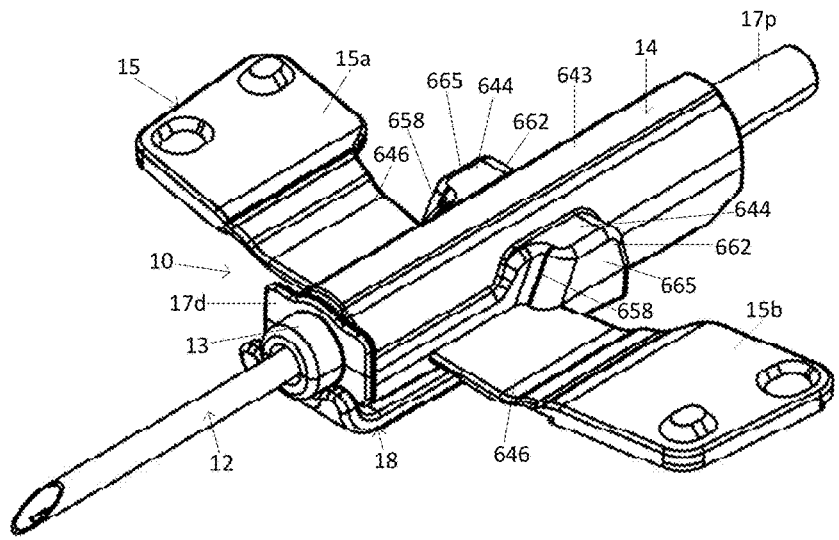
Figure 32A
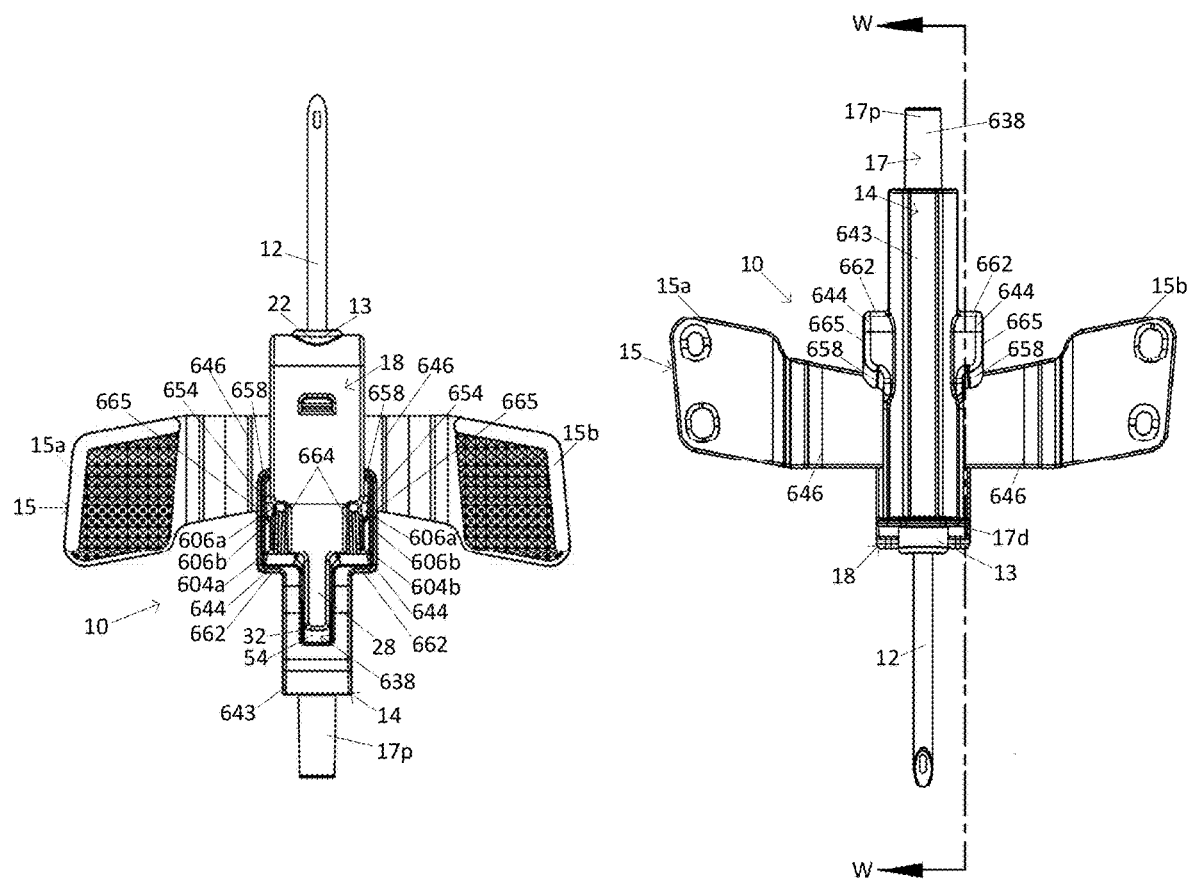
Figure 32B
Figure 32C

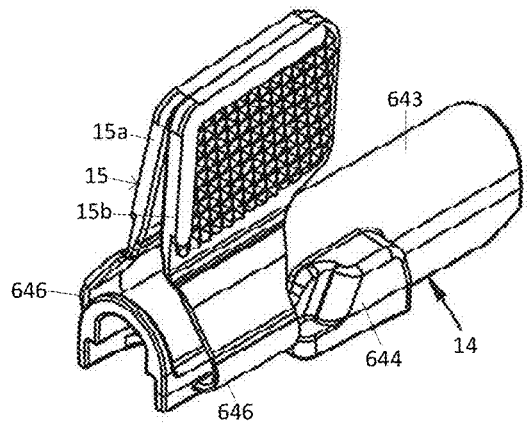
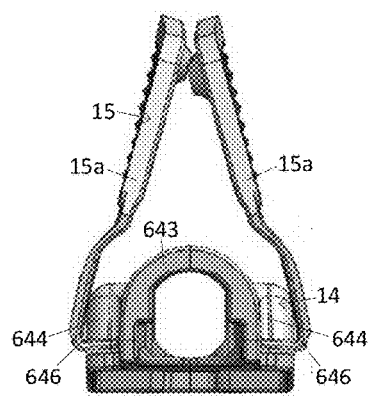
Figure 38A
Figure 38B
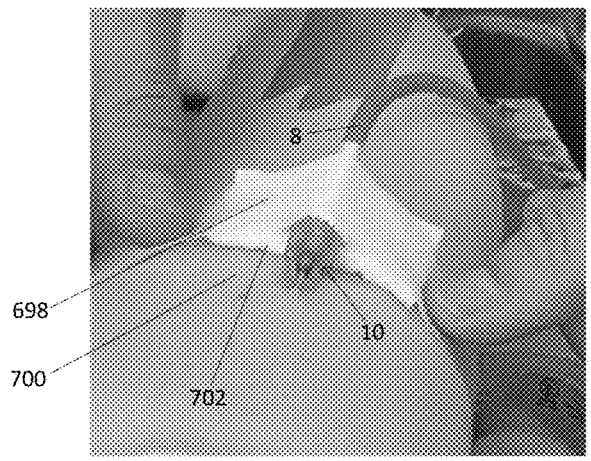
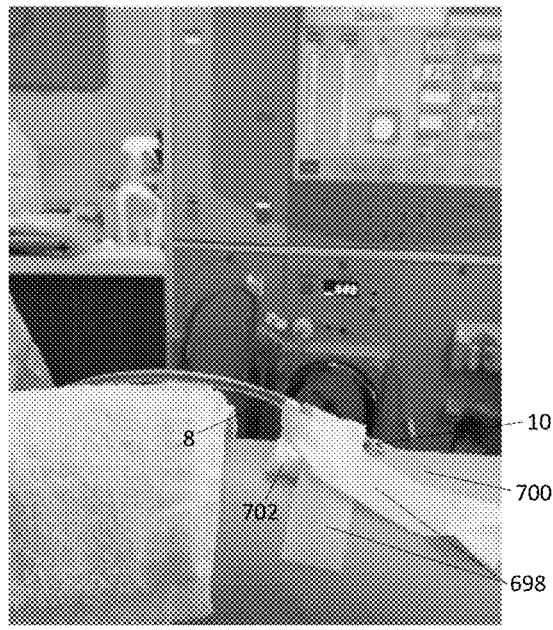
Figure 39A
Figure 39B

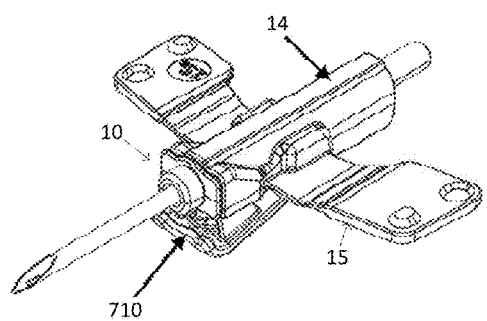
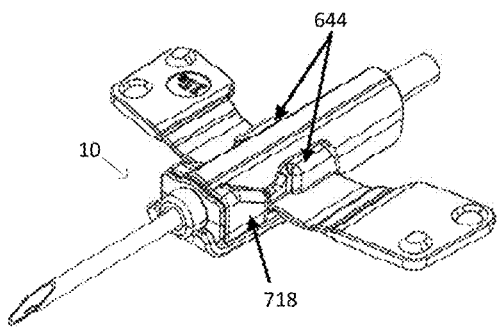
Figure 42A
Figure 42B
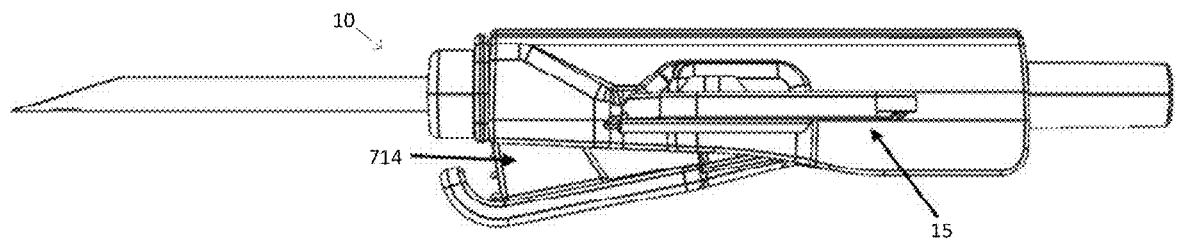
Figure 42C
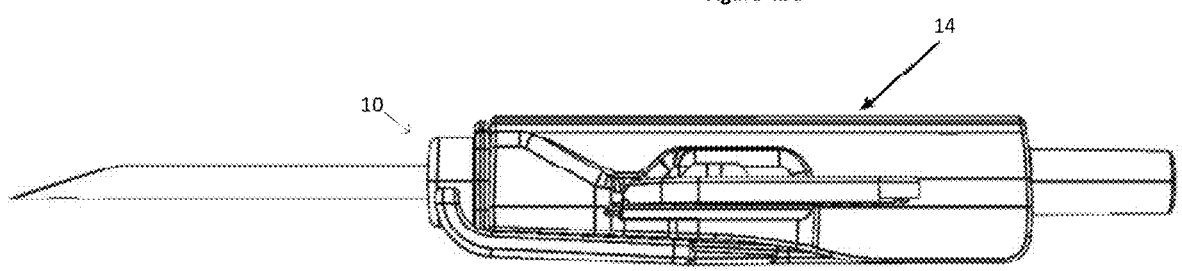
Figure 42D

NEEDLE SAFETY SYSTEMS

CROSS-REFERENCE TO RELATED APPLICATIONS

This application is a continuation of International Application No. PCT/US2020/046536 filed Aug. 14, 2020, which claims the benefit of priority to U.S. Provisional Application No. 62/886,762 filed Aug. 14, 2019 titled Needle Safety Systems XIV and U.S. Provisional Application No. 63/028,907 filed May 22, 2020 titled Needle Safety Systems XIIIa, each of which is incorporated herein by reference in its entirety for all purposes.

BACKGROUND

1. Technical Field

This disclosure relates generally to vascular connections, and more particularly to detection and interruption of dislodged vascular connections. For example, tissue access devices and methods of using and making the same are disclosed, and more particularly, tissue access devices that can detect and interrupt flow and methods of using and making the same are disclosed.

2. Background of the Art

There are a number of techniques that provide a means by which to detect an errant flow of fluid due to dislodgement of a needle from a vascular connection leading fluid from the outside of the body to the inside of the body. Common to many of these is the use of a continuity sensor that looks for an interruption of energy-based signal or some mechanical connection from the tubing to the body. Such systems often use mechanical connectors, a small electrical current, a capacitance, a magnet or even ultrasound as a means of monitoring the fidelity of the connection between the body and the fluid passing element. Others use techniques designed to look for wetness on the theory that a dislodged needle will leak fluid and fluid detection can be used as a surrogate marker for needle dislodgement. By incorporating an external actuation system linked to the fluid pump, these monitoring/detection systems are able to automatically signal the machine pumping fluid to stop pumping in the event of sensed disruption to the vascular connection as a result of needle dislodgement.

A simple alternate to identifying if there is a state whereby errant flow from a dislodged needle is present and induce subsequent automatic machine shut down can be construed as follows: Use a mechanically based system that detects presence of the needle body on the body surface to determine if the needle is or is not inserted into the patient during the fluid delivery process. (Presence of the needle body on the body surface here is used to presume that said needle is likely still inserted within the body itself). A spring-loaded footplate affixed to the bottom of a needle is one of several means by which to perform this sensing operation.

There are multiple spring designs and manufacturing/assembly approaches that can be considered to enable the development of a full needle system and improve needle safety systems. One of these is a coil spring design in which the spring is positioned underneath the needle body between the needle body and the footplate. Another is a torsion spring design in which the spring coils are positioned around the footplate hinge points on the side of the needle body. Another is a standard butterfly design in which an interior feature can be manipulated as needed to control the amount of pre-tension applied to a torsion spring. By manipulating the feature and changing the resulting pre-tension, critical adjustments can be provided that enable optimal spring force for opening and closing, thereby improving overall needle system performance.

Accordingly, a need exists to improve needle safety systems.

BRIEF SUMMARY

This disclosure relates generally to tissue access devices and vascular connections.

Tissue access devices are disclosed. For example, a tissue access device is disclosed that can have a needle and a housing having wings. The device can have a tube having a flow channel, a tube first extension, a tube second extension. The device can have a torsion spring having a first coil and a second coil. The first coil can have a first coil first arm and a first coil second arm. The first coil first arm can be shorter than the first coil second arm. The second coil can have a second coil first arm and a second coil second arm. The second coil first arm can be shorter than the second coil second arm. The device can have a sensor having a first connector, a second connector, and an occluder. The occluder can be connected to the first connector and the second connector. The first connector can have a first connector extension. The second connector can have a second connector extension. The sensor can have a sensor open configuration and a sensor closed configuration. When the device is in a fully assembled configuration, the tube first extension can be in the first connector extension and in the first coil. When the device is in the fully assembled configuration, the tube second extension can be in the second connector extension and in the second coil. When the device is in the fully assembled configuration and the sensor is in the sensor open configuration, the torsion spring can have a first loaded configuration. When the device is in the fully assembled configuration and the sensor is in the sensor closed configuration, the torsion spring can have a second loaded configuration. More energy can be stored in the torsion spring when the torsion spring is in the second loaded configuration than when the torsion spring is in the first loaded configuration.

Tissue access devices are disclosed. For example, a tissue access device is disclosed that can have a needle and a housing having wings. The device can have a tube having a flow channel, a tube first extension, and a tube second extension. The device can have a torsion spring having a first coil, a second coil, a first arm, a second arm, and a third arm. The third arm can be longer than the first arm. The third arm can be longer than the second arm. The device can have a sensor having a first hinge, a second hinge, and an occluder. When the device is in a fully assembled configuration, the tube first extension can be in the first hinge. When the device is in the fully assembled configuration, the tube second extension can be in the second hinge. When the device is in the fully assembled configuration and the sensor is in a sensor open configuration, the torsion spring can have a first loaded configuration. When the device is in the fully assembled configuration and the sensor is in a sensor closed configuration, the torsion spring can have a second loaded configuration. More energy can be stored in the torsion spring when the torsion spring is in the second loaded configuration than when the torsion spring is in the first loaded configuration.

Tissue access devices are disclosed. For example, a tissue access device is disclosed that can have a needle and a housing having wings. The device can have a tube having a flow channel, a tube first extension, and a tube second extension. The device can have a spring on a first lateral side of the housing and on a second lateral side of the housing. The device can have a sensor having a first hinge, a second hinge, and an occluder. Shen the device is in a fully assembled configuration, the tube first extension and the spring can be connected to the first hinge. When the device is in a fully assembled configuration, the tube second extension and the spring can be connected to the second hinge. When the device is in the fully assembled configuration and the sensor is in a sensor open configuration, the torsion spring can have a first loaded configuration. When the device is in the fully assembled configuration and the sensor is in a sensor closed configuration, the torsion spring can have a second loaded configuration. Less energy can be stored in the spring when the spring is in the first loaded configuration than when the spring is in the second loaded configuration.

Tissue access devices are disclosed. For example, a tissue access device is disclosed that can have a needle, a housing, a tube having a flow channel, a torsion spring, and a sensor.

Tissue access devices are disclosed. For example, a tissue access device is disclosed that can have a needle, a housing, a tube having a flow channel, a torsion spring, and a pre-loaded sensor.

Tissue access devices are disclosed. For example, a tissue access device is disclosed that can have a needle, a housing, a tube having a flow channel, a pre-loaded torsion spring, and a sensor.

BRIEF DESCRIPTION OF THE DRAWINGS

The drawings shown and described are exemplary embodiments and non-limiting. Like reference numerals indicate identical or functionally equivalent features throughout.

FIG. 1 illustrates a perspective view of a variation of a tissue access device in an occluded configuration having a sensor.

FIG. 2A illustrates a perspective view of the sensor of FIG. 1.

FIG. 2B illustrates a side view of the sensor of FIG. 2A.

FIG. 2C illustrates a top view of the sensor of FIG. 2A.

FIG. 3A illustrates a side view of the tissue access device of FIG. 1 in a less occluded configuration.

FIG. 3B illustrates a variation of a longitudinal cross-sectional view of the tissue access device of FIG. 3A taken along line 3B-3B.

FIG. 4A illustrates a side view of the tissue access device of FIG. 1.

FIG. 4B illustrates a side view of the tissue access device of FIG. 4A taken along line 4B-4B.

FIGS. 7A-7I illustrate a variation of a tissue access device manufacturing process and variations of the components thereof.

FIGS. 9A-9F illustrate a variation of a tissue access device and components thereof.

FIG. 12A illustrates a variation of an insert.

FIG. 12B illustrates an exploded view of the insert of FIG. 12A.

FIG. 13A illustrates a schematic view of a variation of a tissue access device having a pocket.

FIG. 13B illustrates the variation of FIG. 13A with an occluder in the pocket.

FIG. $14A_1$ illustrates a variation of a method of assembling a tissue access device.

FIG. $14A_2$ illustrates a variation of an assembly of a tissue access device according to the method of FIG. $14A_1$.

FIG. $14B_1$ illustrates a variation of a method of assembling a tissue access device.

FIG. $14B_2$ illustrates a variation of an assembly of a tissue access device according to the method of FIG. $14B_1$.

FIG. $14C_1$ illustrates a variation of a method of assembling a tissue access device.

FIG. $14C_2$ illustrates a variation of an assembly of a tissue access device according to the method of FIG. $14C_1$.

FIG. $15A_1$ illustrates a variation of a method of assembling a tissue access device.

FIG. $15A_2$ illustrates a variation of an assembly of a tissue access device according to the method of FIG. $15A_1$.

FIG. $15B_1$ illustrates a variation of a method of assembling a tissue access device.

FIG. $15B_2$ illustrates a variation of an assembly of a tissue access device according to the method of FIG. $15B_1$.

Figure 16A:
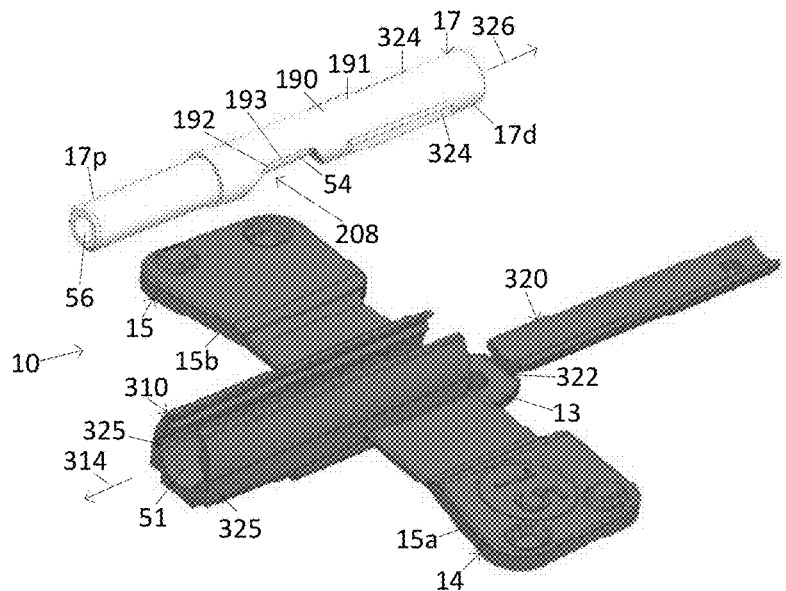

FIG. 16A illustrates a variation of a method of assembling a tissue access device.

Figure 16B:
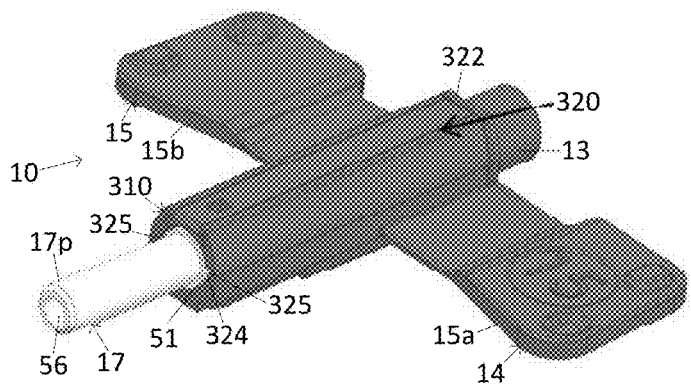

FIG. 16B illustrates a variation of an assembly of a tissue access device according to the method of FIG. 16A.

Figure 16C:
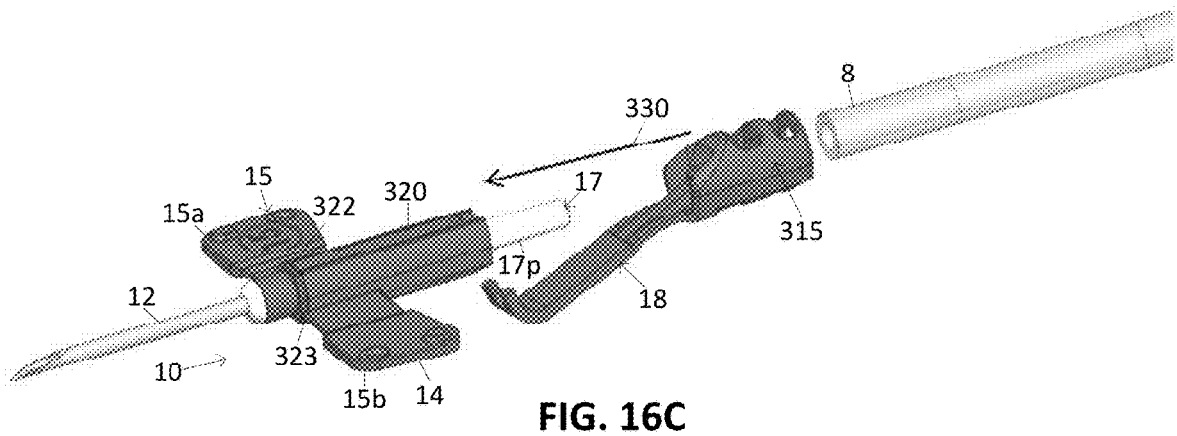

FIG. 16C illustrates a variation of a method of assembling a tissue access device using the assembly of FIG. 16B.

FIG. 17A illustrates a side view of a variation of a tissue access device.

FIG. 17B illustrates a perspective view of the device of FIG. 17A.

FIG. 17C illustrates a cross-sectional view of the tissue access device of FIG. 17A taken along line 17C-17C.

FIG. 17D illustrates a magnified view of a portion of the device of FIG. 17C without the insert.

FIG. 17E illustrates a perspective view of the device of FIG. 17D.

FIG. 18A illustrates a variation of a sensor.

FIG. 18B illustrates a cross-sectional view of a variation of a tissue access device having the sensor of FIG. 18A.

Figure 19:
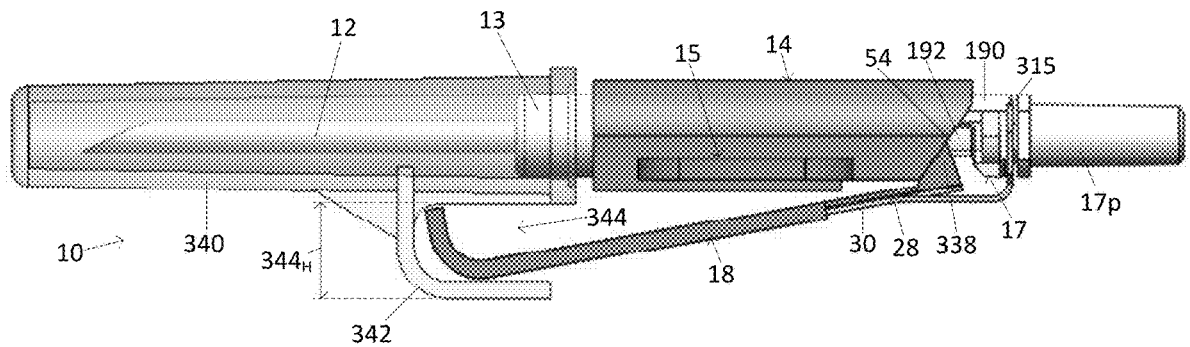

FIG. 19 illustrates a side view of a variation of a tissue access device.

Figure 20A:
Figure 20B:
Figure 20C:
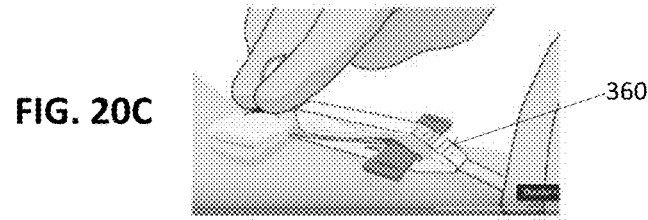

FIGS. 20A-20C illustrate a variation of a method of guarding a needle of a tissue access device.

FIGS. 21A-21C illustrate a variation of a method of guarding a needle of a tissue access device.

FIGS. 22A-22C illustrate a variation of a method of guarding a needle of a tissue access device.

FIG. 23 illustrates a variation of a portion of a needle guard.

Figure 24A:
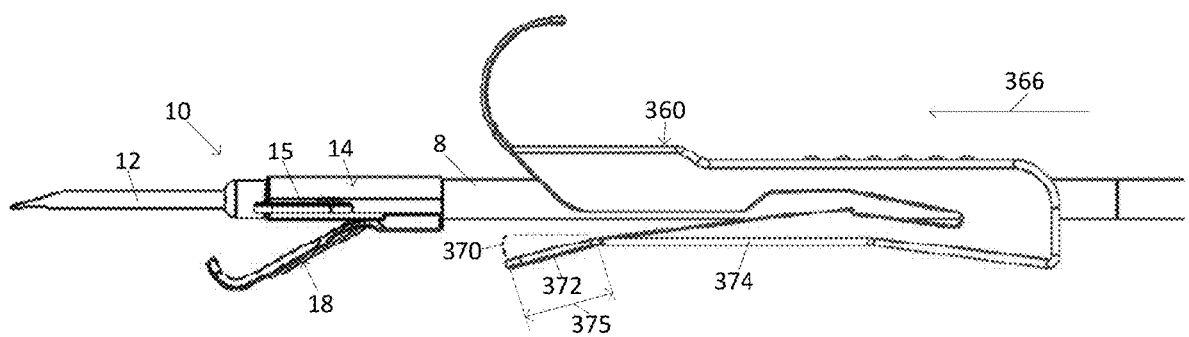

FIG. 24A illustrates a side view of a variation of a tissue access device with a variation of a needle guard.

Figure 24B:
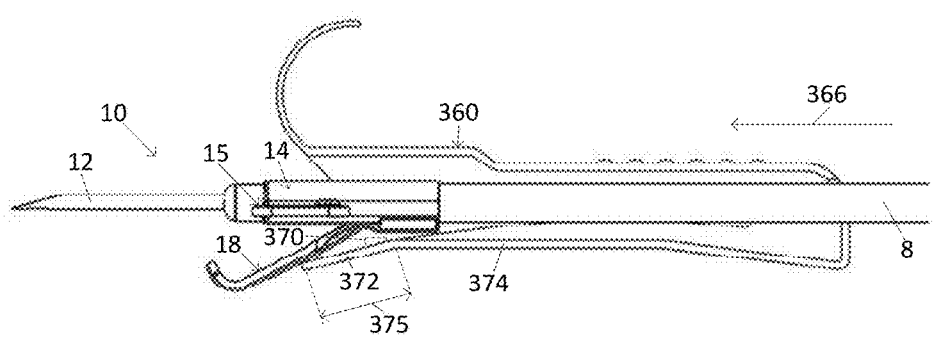

FIG. 24B illustrates the needle guard engaged with a variation of a sensor of the device of FIG. 24A.

Figure 25:
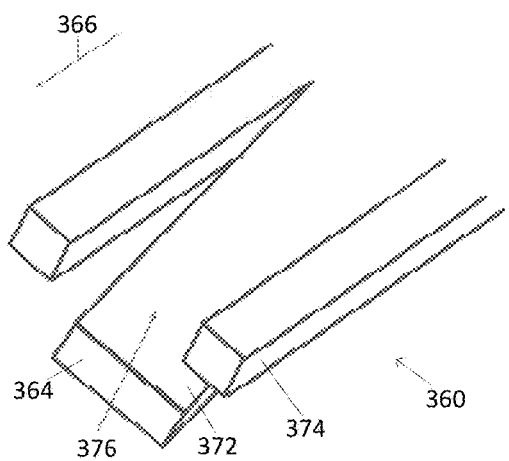

FIG. 25 illustrates a variation of a portion of a needle guard.

Figure 26A:
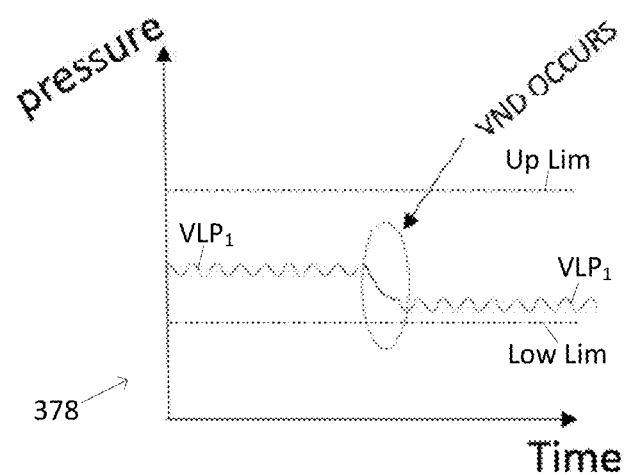

FIG. 26A illustrates a variation of a time vs. pressure graph.

Figure 26B:
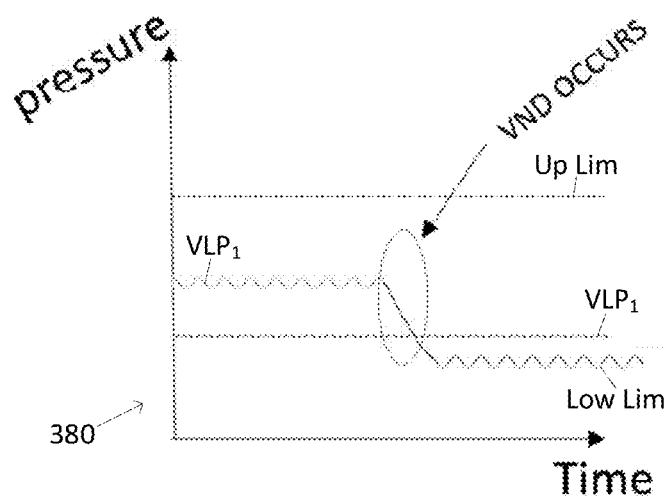

FIG. 26B illustrates a variation of a time vs. pressure graph.

Figure 27A:
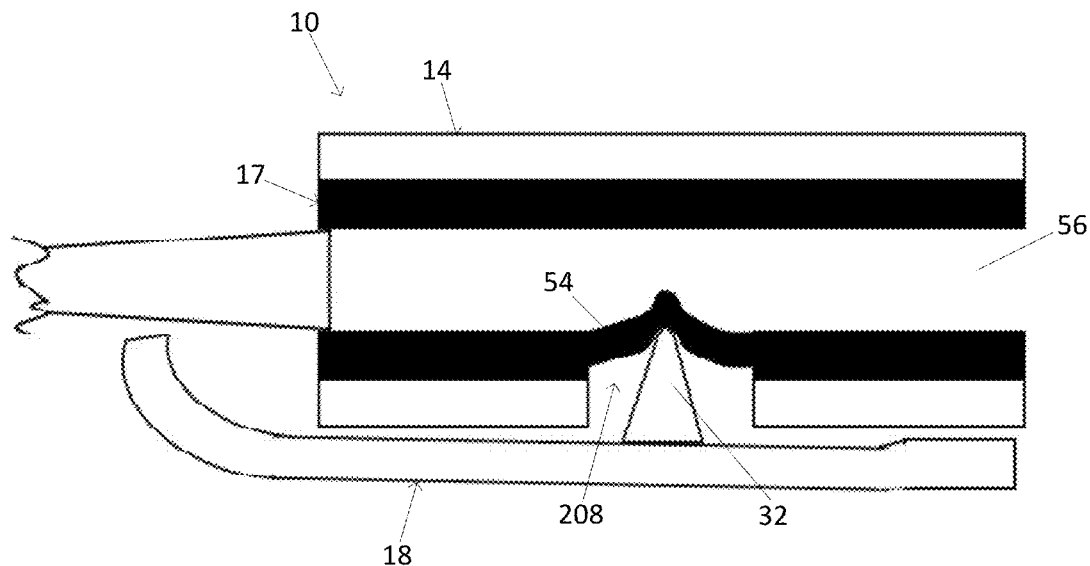

FIG. 27A illustrates schematic view of a variation of a tissue access device.

Figure 27B:
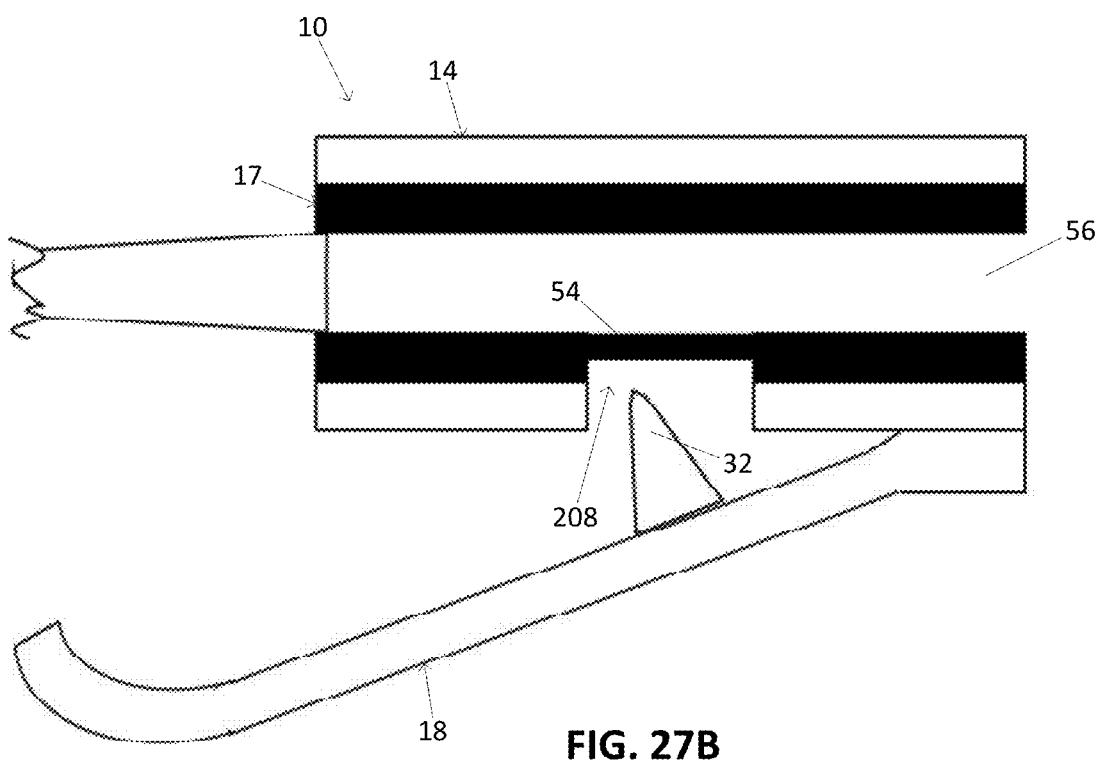

FIG. 27B illustrates schematic view of a variation of a tissue access device.

Figure 28A:
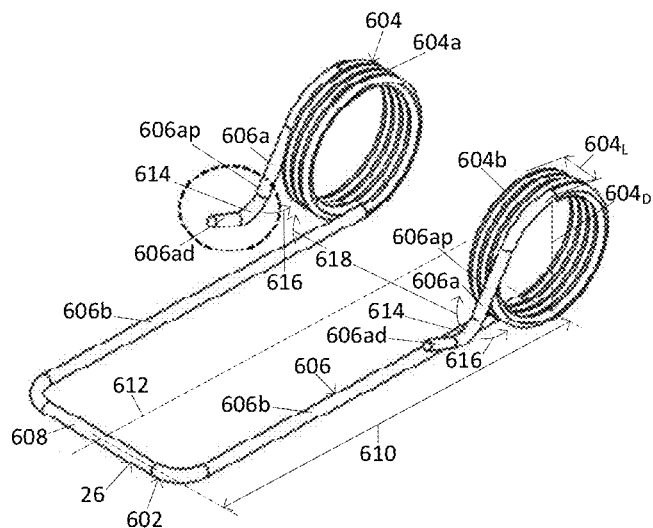

FIG. 28A illustrates a perspective view of a variation of a spring.

Figure 28B:
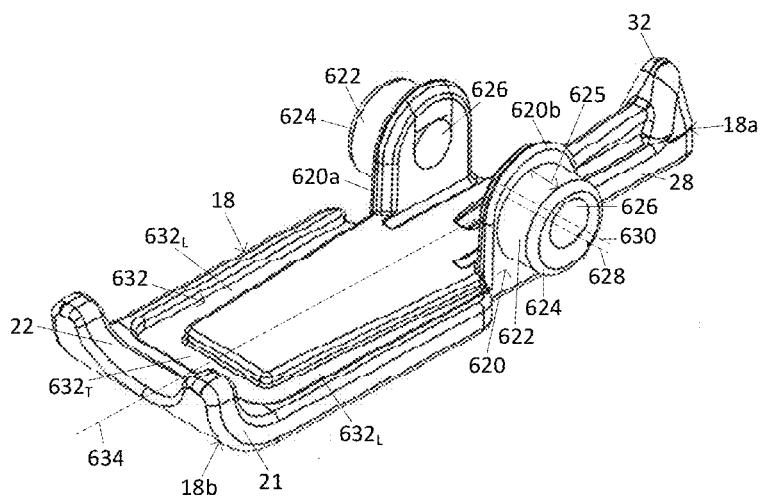

FIG. 28B illustrates a perspective view of a variation of a sensor.

Figure 28C:
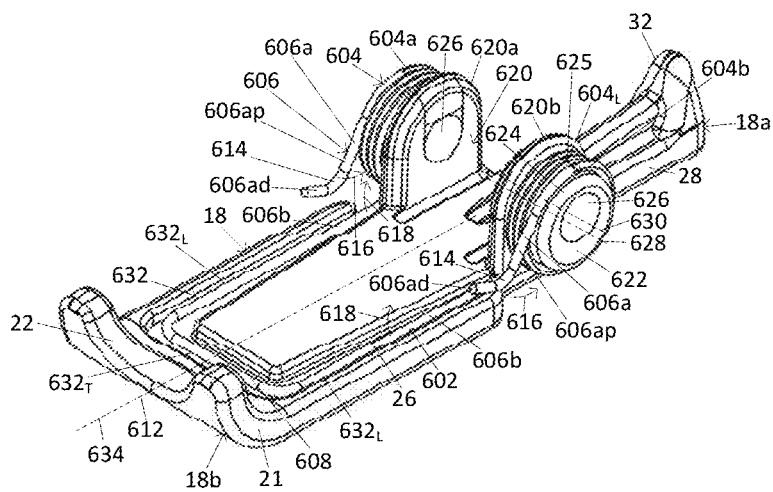

FIG. 28C illustrates a perspective view of a variation of the spring of FIG. 28A attached to the sensor of FIG. 28B.

Figure 29A:
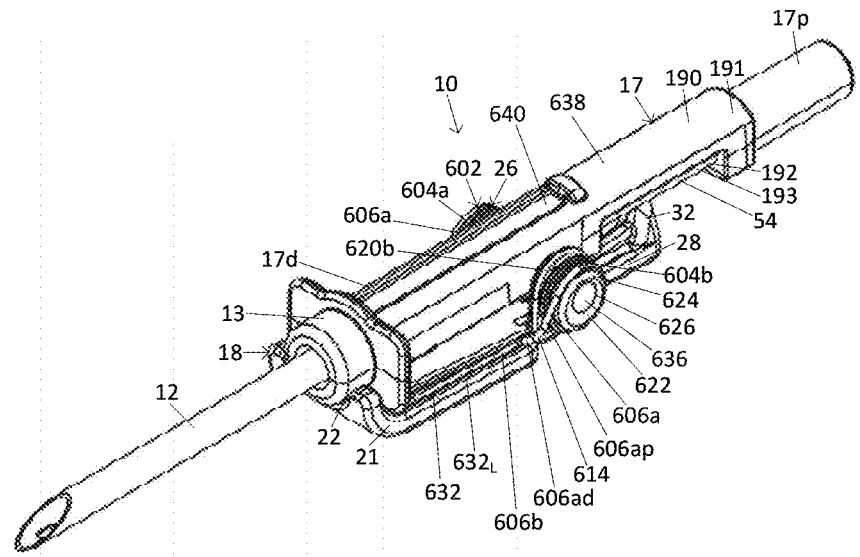

FIG. 29A illustrates a perspective view of a variation of the spring-sensor component of FIG. 28C attached to a variation of a tube.

Figure 29B:
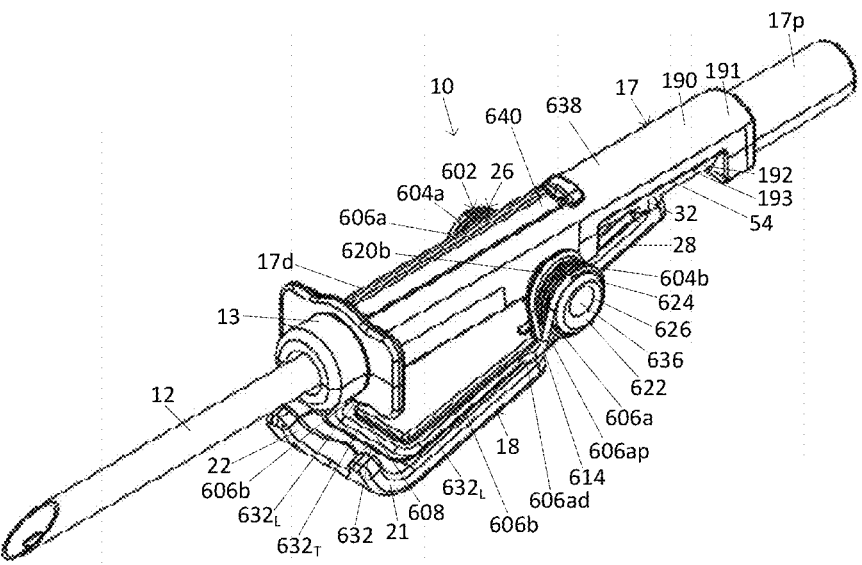

FIG. 29B illustrates a perspective view of a variation of the spring-sensor component of FIG. 28C attached to a variation of a tube.

Figure 29C:
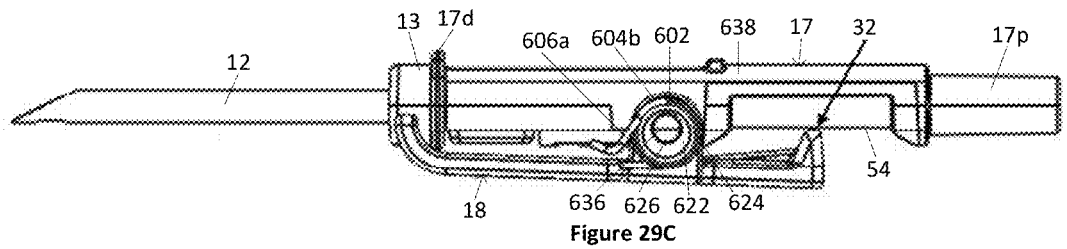

FIG. 29C illustrates a side view of FIG. 29A.

Figure 29D:
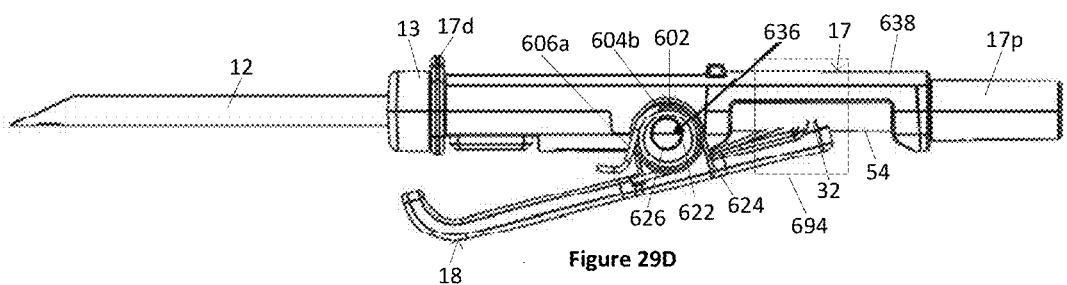

FIG. 29D illustrates a side view of FIG. 29B.

Figure 29E:
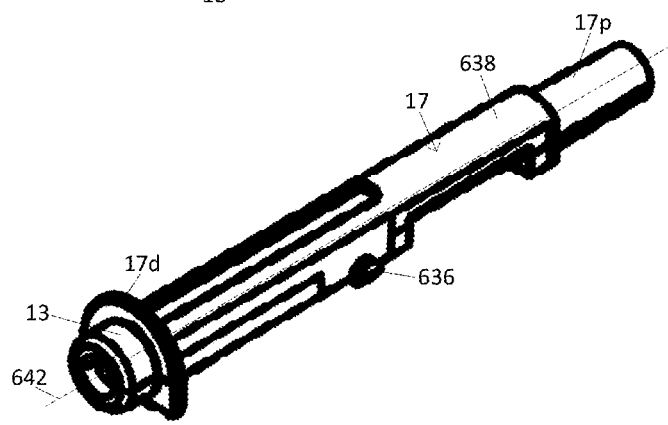

FIG. 29E illustrates a perspective view of a first side of the tube of FIGS. 29A-29D.

Figure 29F:
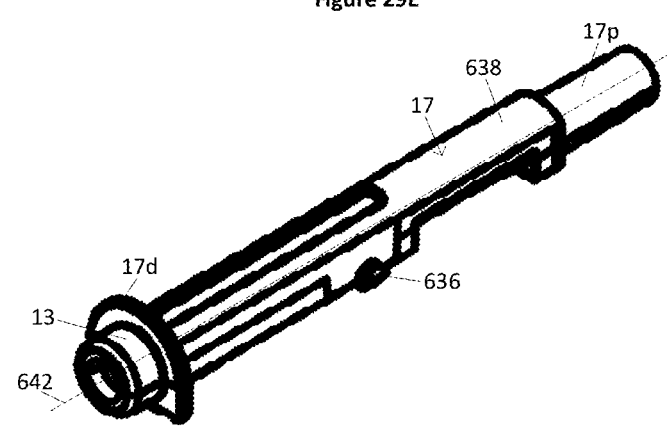

FIG. 29F illustrates a perspective view of a second side of the tube of FIGS. 29A-29D.

Figure 30A:
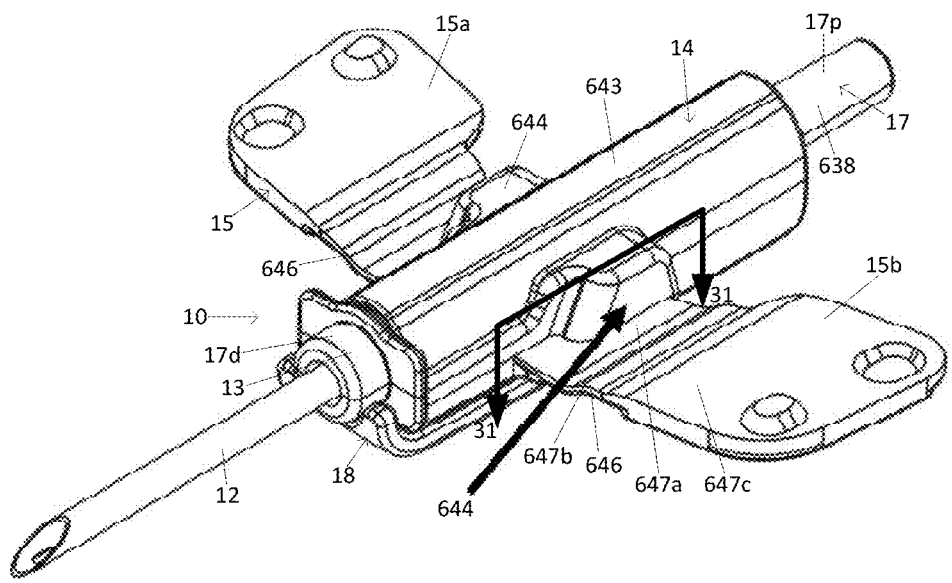

FIG. 30A illustrates a perspective view of a variation of a tissue access device with the sensor in a closed configuration.

Figure 30B:
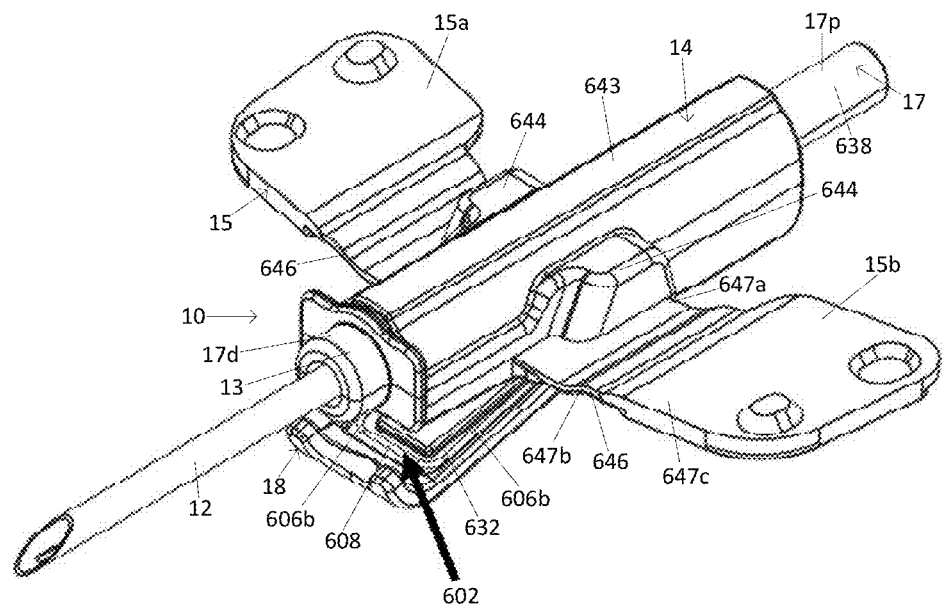

FIG. 30B illustrates the device of FIG. 30A with the sensor in an open configuration.

Figure 30C:
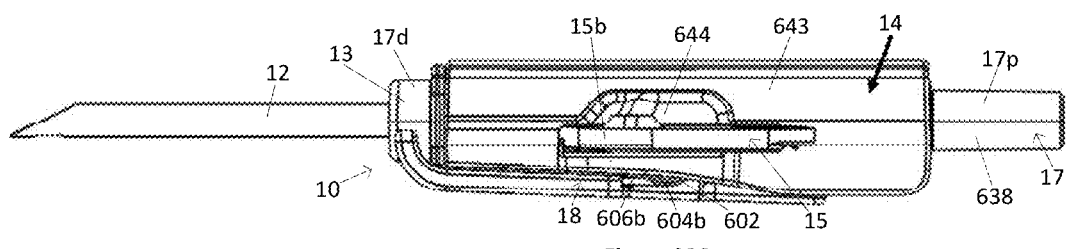

FIG. 30C illustrates a side view of FIG. 30A.

Figure 30D:
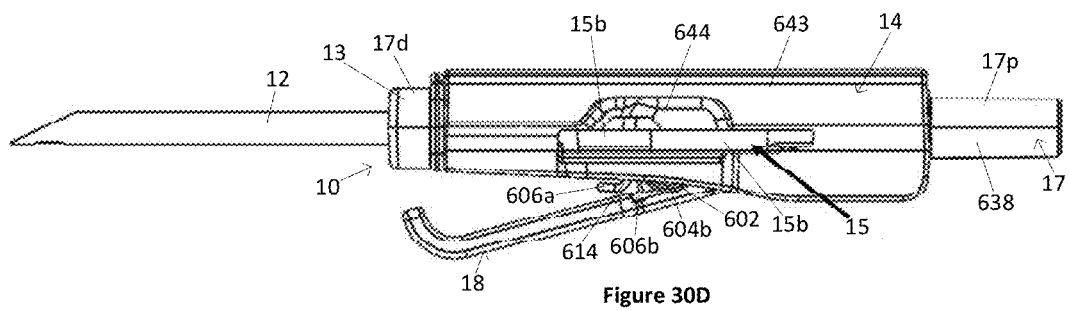

FIG. 30D illustrates a side view of FIG. 30B.

Figure 31A:
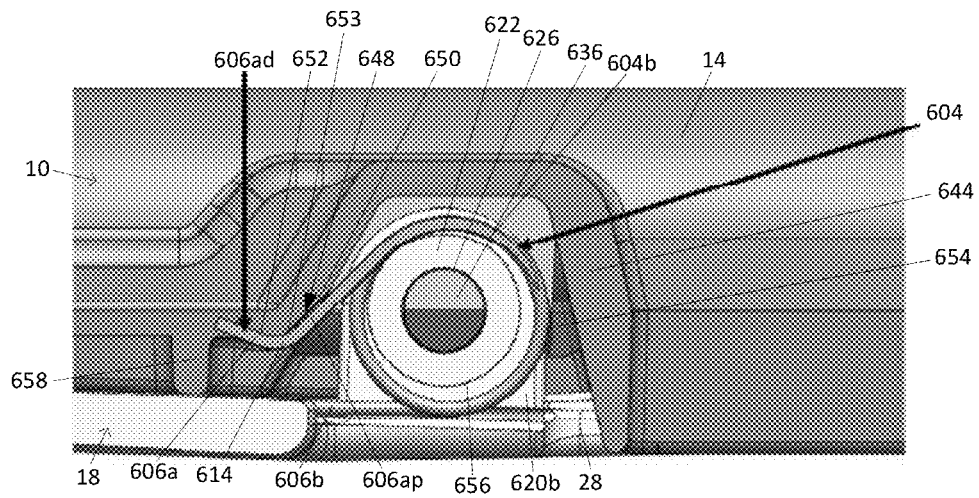

FIG. 31A illustrates a cross-sectional view of a variation of the device of FIG. 30A taken along line 31-31.

Figure 31B:
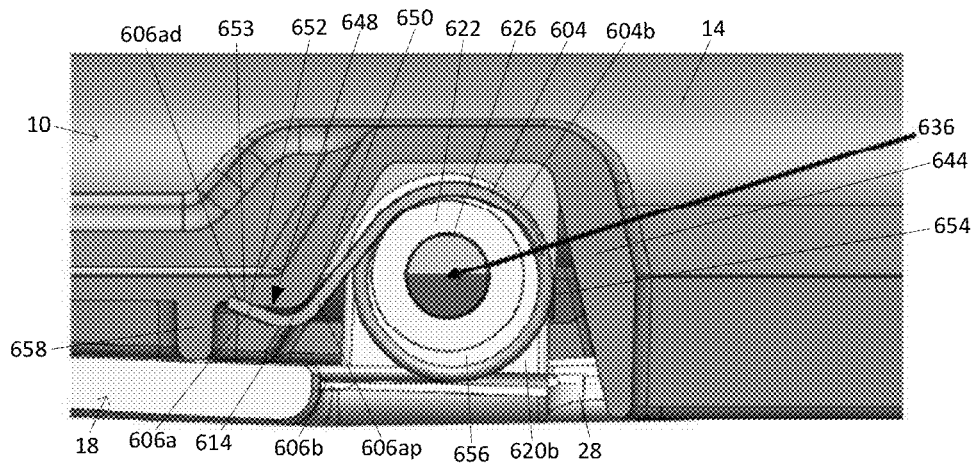

FIG. 31B illustrates a cross-sectional view of a variation of the device of FIG. 30A taken along line 31-31.

Figure 31C:
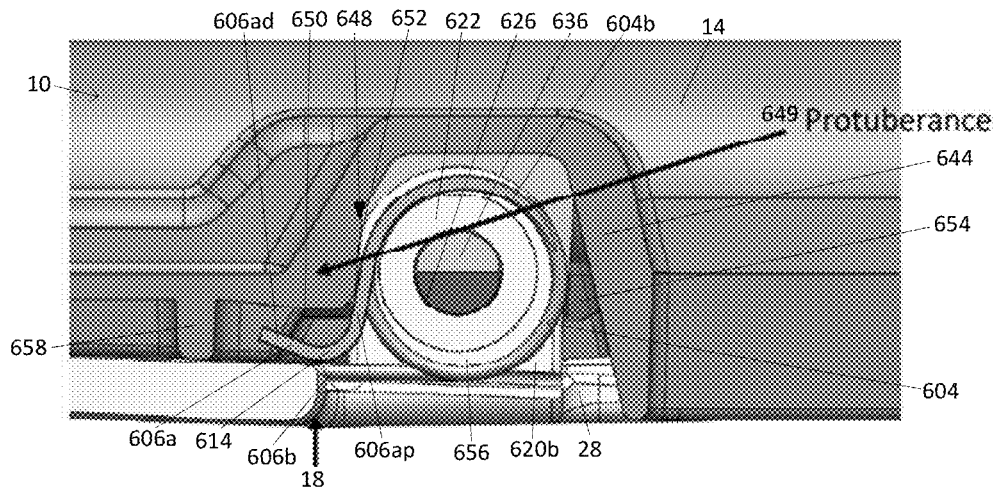

FIG. 31C illustrates a cross-sectional view of a variation of the device of FIG. 30A taken along line 31-31.

FIG. 31D illustrates a bottom perspective view of a variation of a housing.

FIG. 31E illustrates a magnified view of the housing of FIG. 31D at section 696.

FIG. 32A illustrates a perspective view of a variation of a tissue access device.

FIG. 32B illustrates a bottom view of the device of FIG. 32A.

FIG. 32C illustrates a top view of the device of FIG. 32A.

Figure 32D:
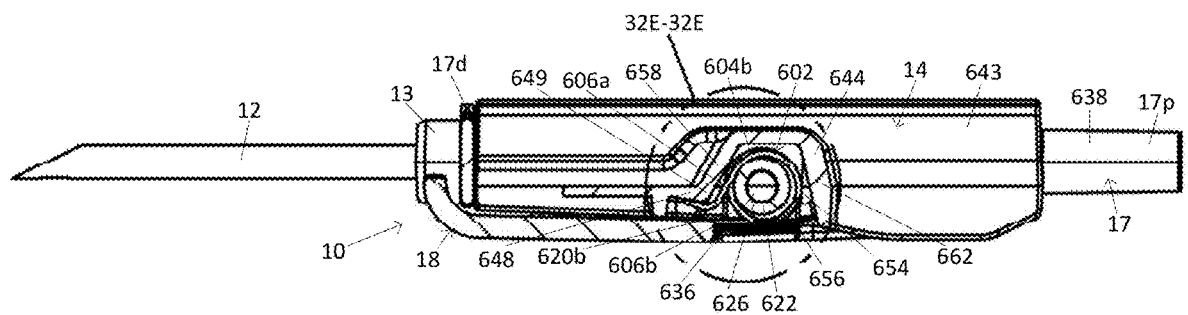

FIG. 32D illustrates a side and cross-sectional view of the device of FIG. 32C taken along line W-W.

Figure 32E:
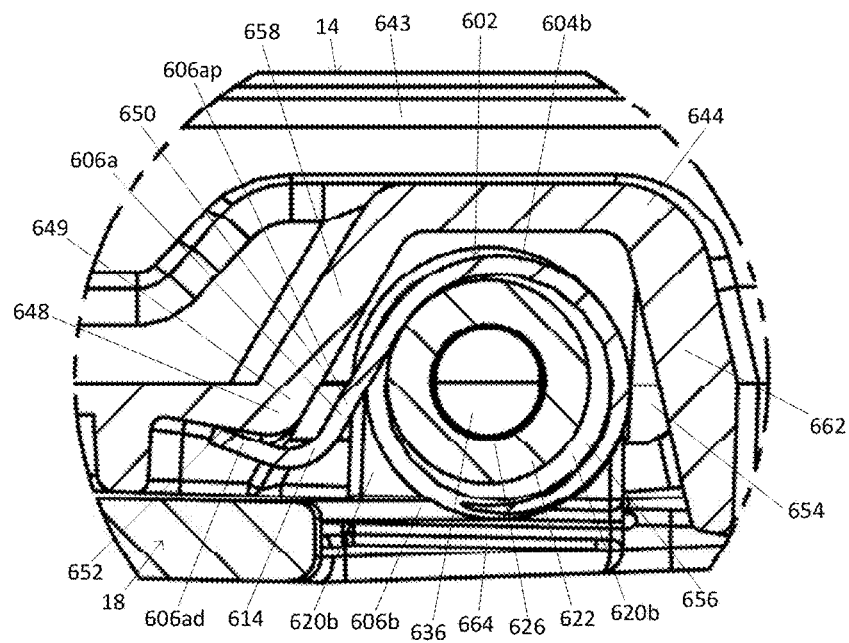

FIG. 32E illustrates a magnified view of FIG. 32D at section 32E-32E.

Figure 32F:
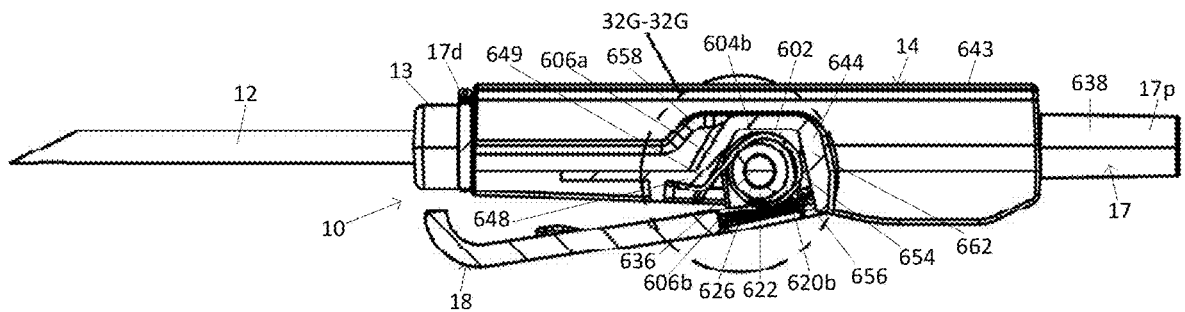

FIG. 32F illustrates a side and cross-sectional view of the device of FIG. 32C taken along line W-W when the sensor is in an open configuration.

Figure 32G:
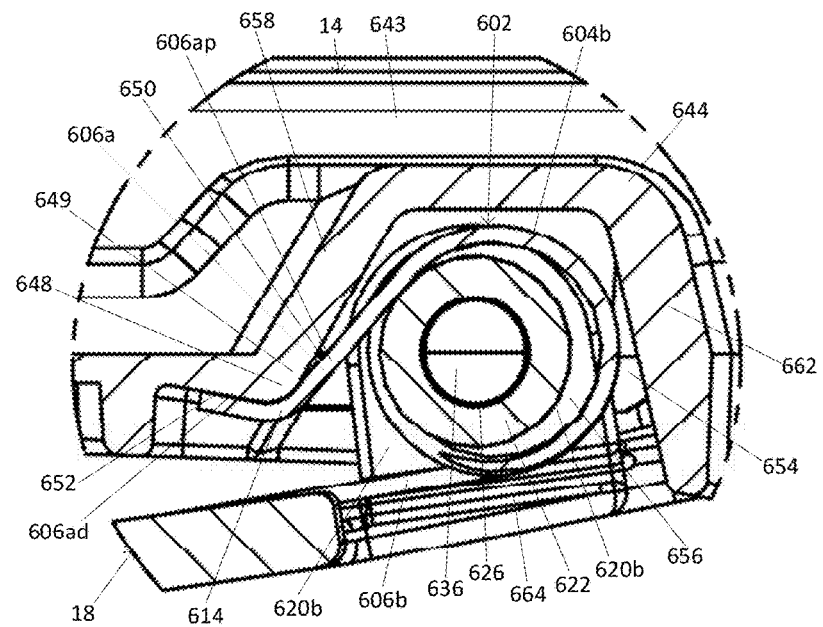

FIG. 32G illustrates a magnified view of FIG. 32F at section 32G-32G.

Figure 33A:
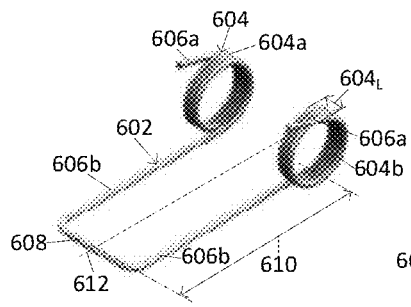

FIG. 33A illustrates a perspective view of a variation of a spring.

Figure 33C:
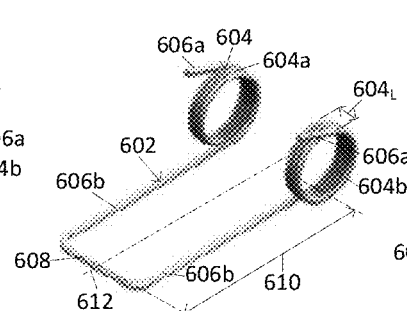
Figure 33E:
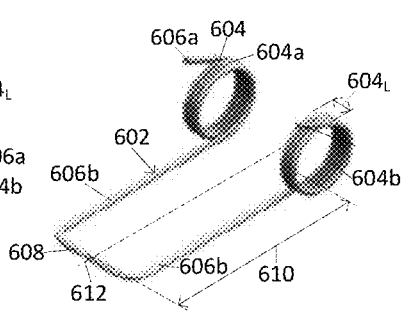
Figure 33B:
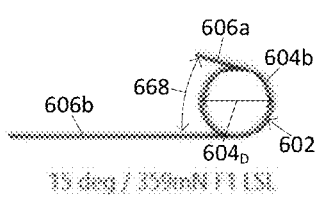

FIG. 33B illustrates a side view of the spring of FIG. 33A.

FIG. 33C illustrates a perspective view of a variation of a spring.

Figure 33D:
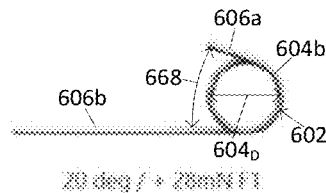

FIG. 33D illustrates a side view of the spring of FIG. 33C.

FIG. 33E illustrates a perspective view of a variation of a spring.

Figure 33F:
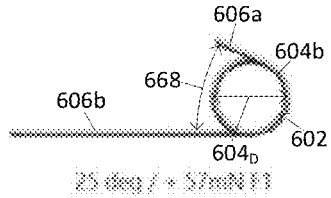

FIG. 33F illustrates a side view of the spring of FIG. 33E.

Figure 33G:
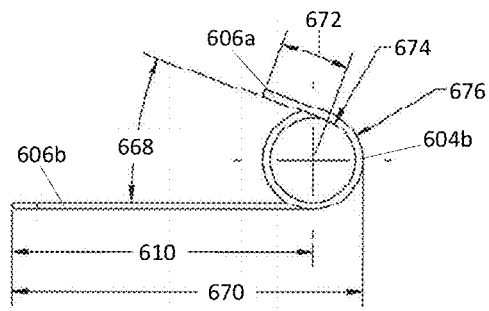

FIG. 33G illustrates a side view of the spring of FIG. 33C.

Figure 33H:
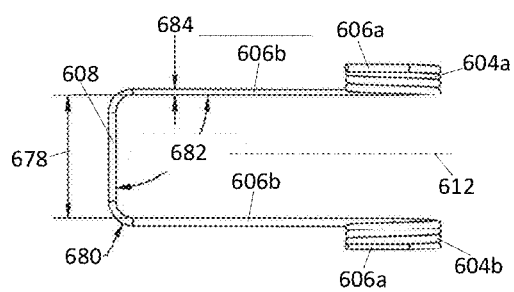

FIG. 33H illustrates a top view of the spring of FIG. 33C.

Figure 33I:
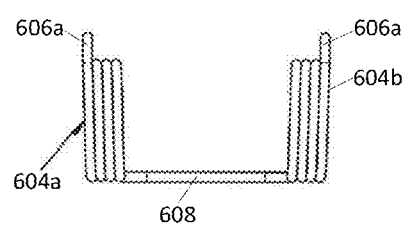

FIG. 33I illustrates an end view of the spring of FIG. 33C.

Figure 34A:
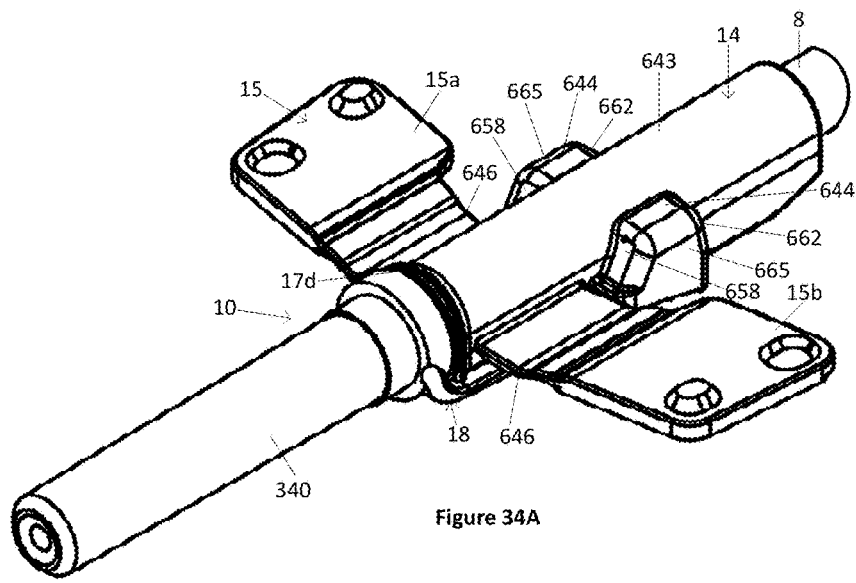

FIG. 34A illustrates a perspective view of a variation of a tissue access device.

Figure 34B:
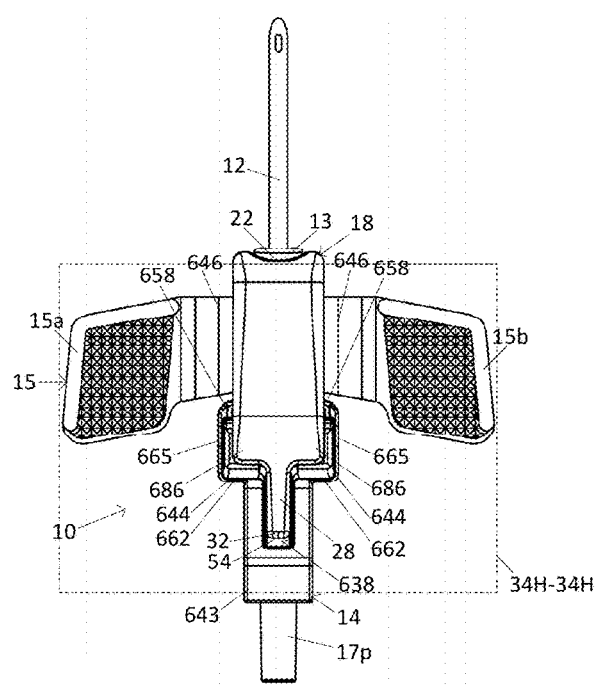

FIG. 34B illustrates a bottom view of the device of FIG. 34A.

Figure 34C:
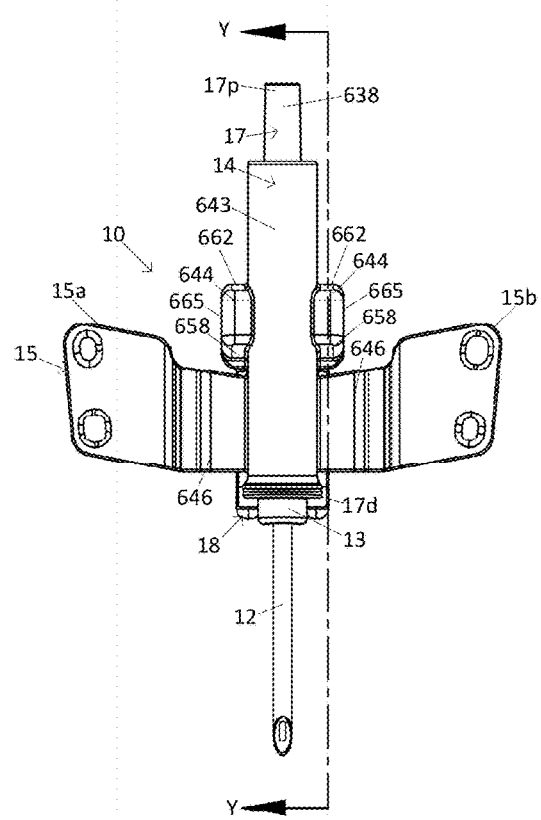

FIG. 34C illustrates a top view of the device of FIG. 34A.

Figure 34D:
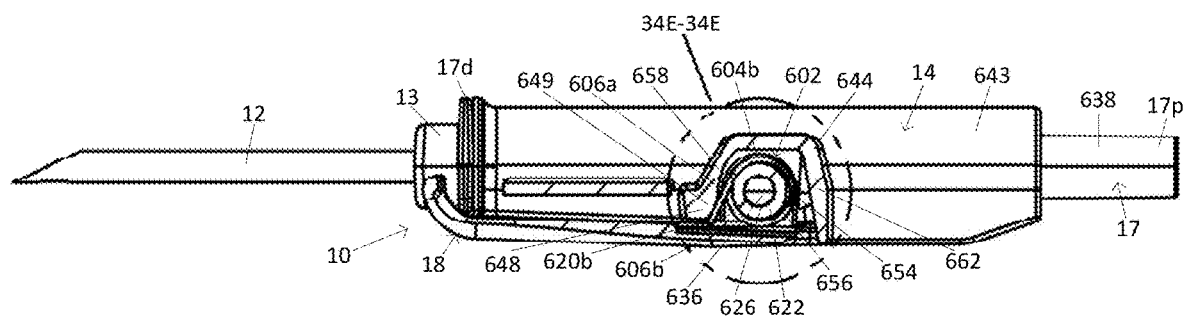

FIG. 34D illustrates a side and cross-sectional view of the device of FIG. 34C taken along line Y-Y.

Figure 34E:
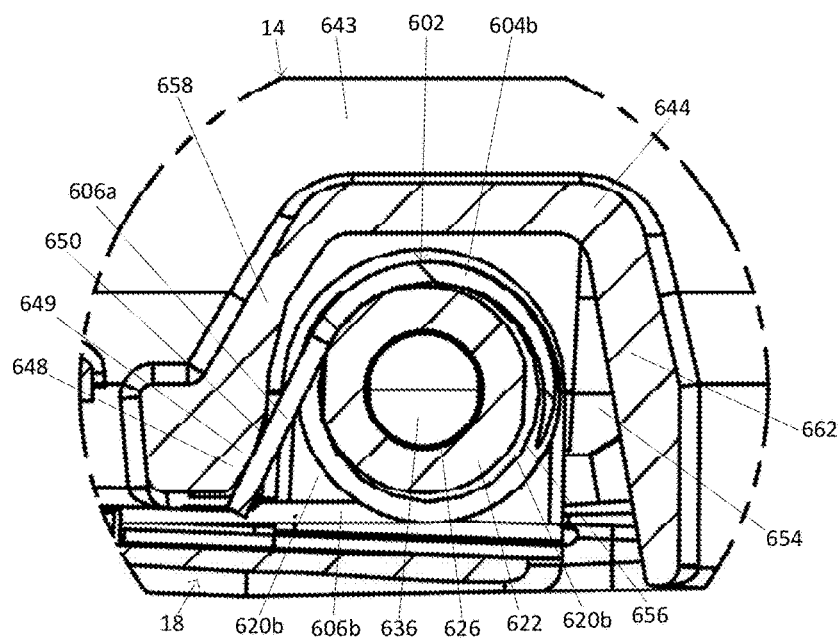

FIG. 34E illustrates a magnified view of FIG. 34D at section 34E-34E.

Figure 34F:
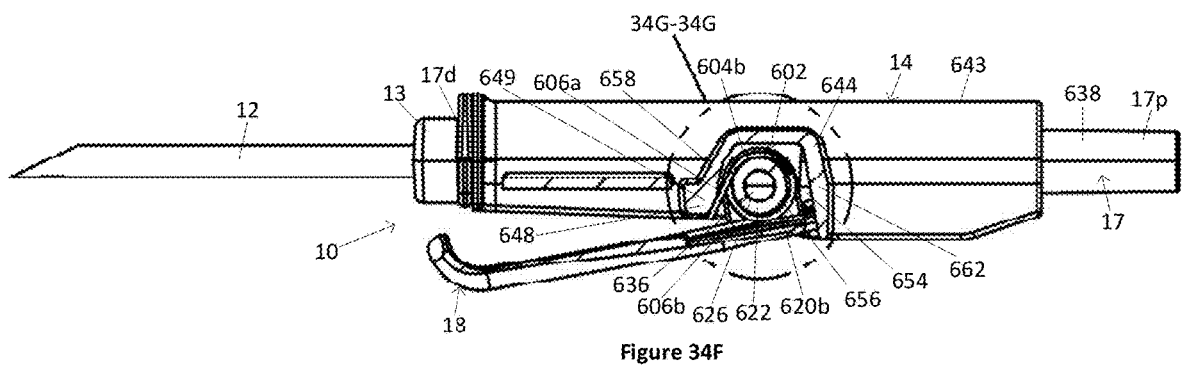

FIG. 34F illustrates a side and cross-sectional view of the device of FIG. 34C taken along line Y-Y when the sensor is in an open configuration.

Figure 34G:
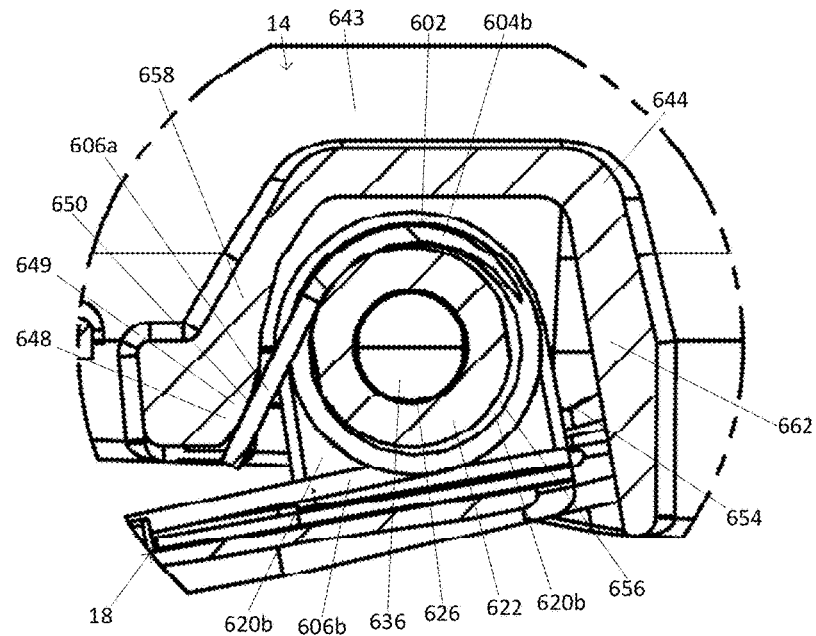

FIG. 34G illustrates a magnified view of FIG. 34F at section 34G-34G.

Figure 34H:
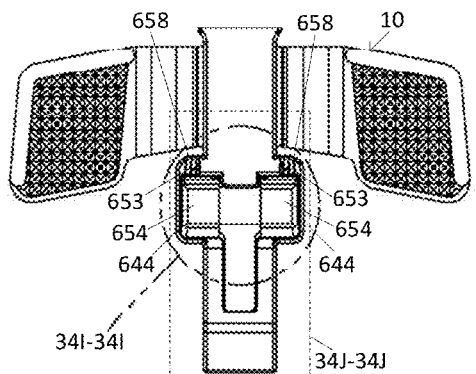

FIG. 34H illustrates the bottom view of FIG. 34B at section 34H-34H.

Figure 34I:
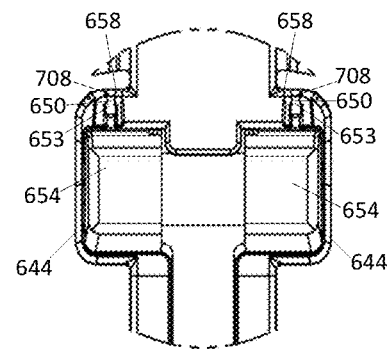

FIG. 34I illustrates a magnified view of FIG. 34H at section 34I-34I.

Figure 34J:
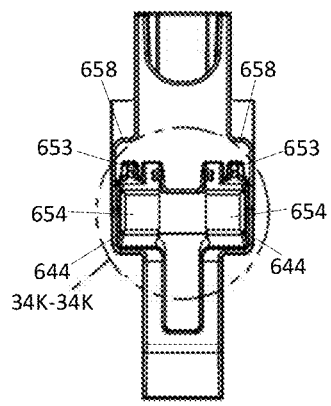

FIG. 34J illustrates a variation of the bottom view of FIG. 34H at section 34J-34J.

Figure 34K:
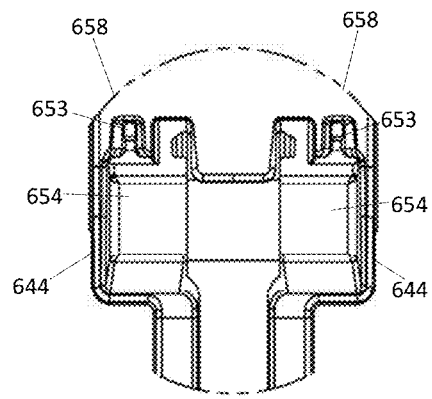

FIG. 34K illustrates a magnified view of FIG. 34J at section 34K-34K.

Figure 34L:
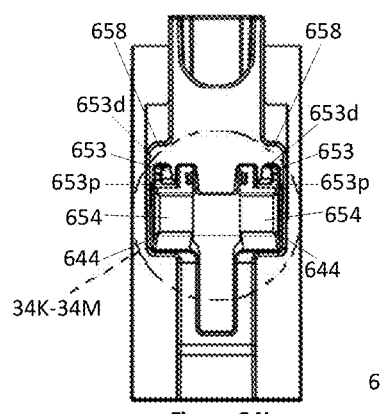

FIG. 34L illustrates a variation of the bottom view of FIG. 34J.

Figure 34M:
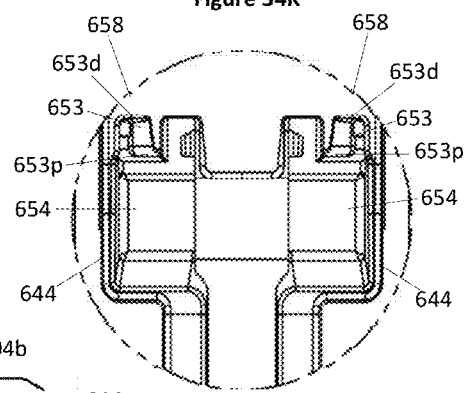

FIG. 34M illustrates a magnified view of FIG. 34L at section 34M-34M.

Figure 34N:
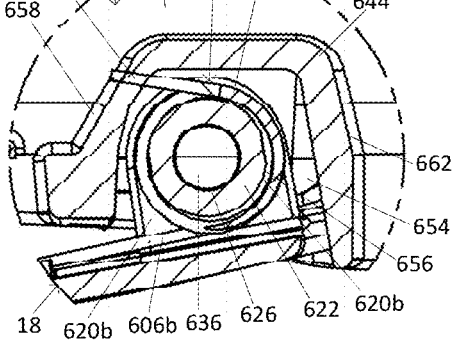

FIG. 34N illustrates a variation of the device of FIG. 34G.

Figure 35A:
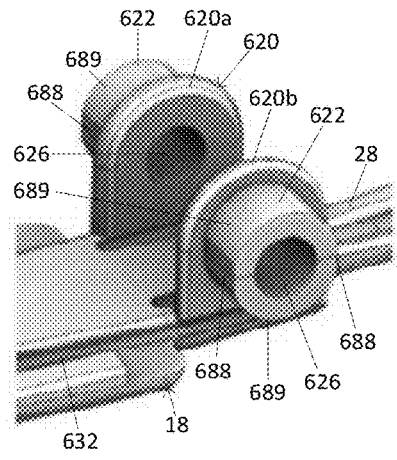

FIG. 35A illustrates a perspective view of a variation of a sensor.

Figure 35B:
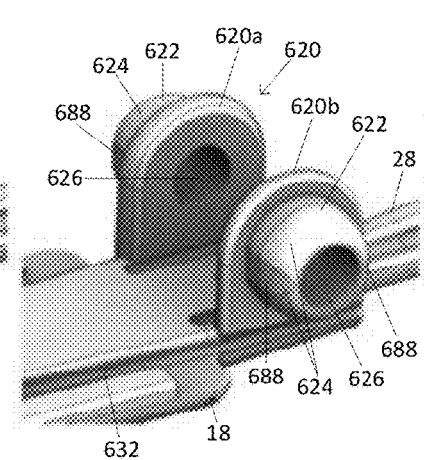

FIG. 35B illustrates a perspective view of a variation of a sensor.

Figure 35C:
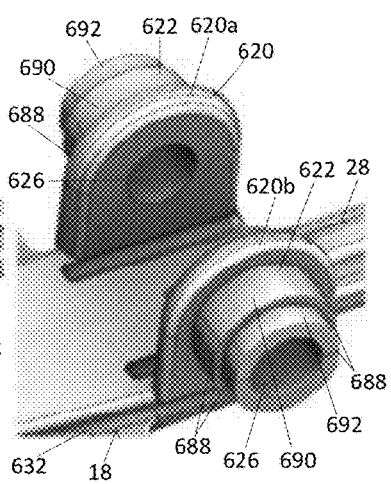

FIG. 35C illustrates a perspective view of a variation of a sensor.

Figure 36:
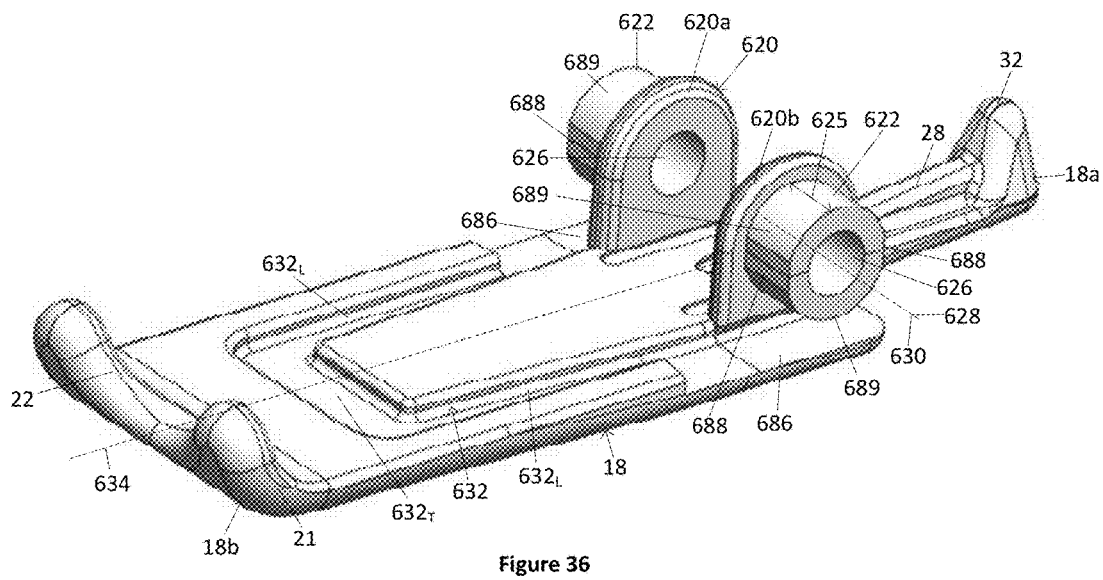

FIG. 36 illustrates a perspective view of a variation of a sensor.

Figure 37A:
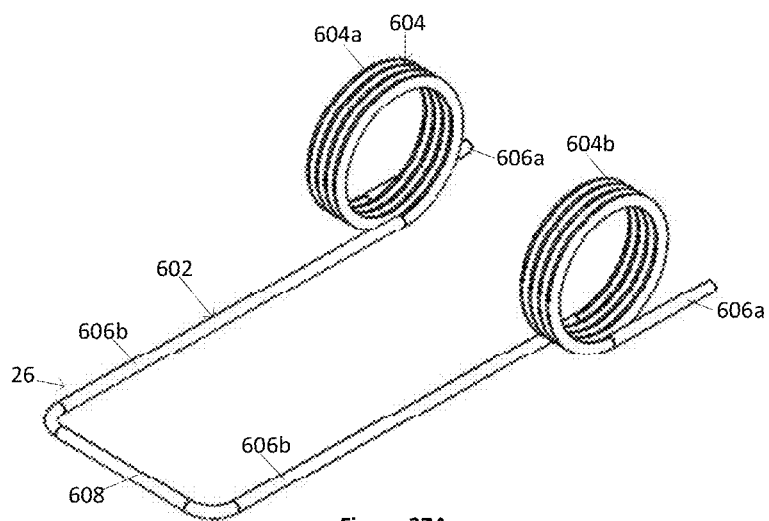

FIG. 37A illustrates a perspective view of a variation of a spring.

Figure 37B:
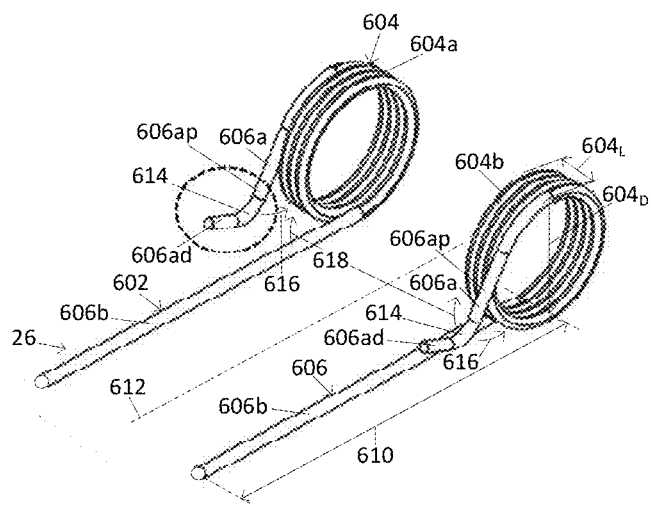

FIG. 37B illustrates a perspective view of a variation of the spring of FIG. 28A.

Figure 37C:
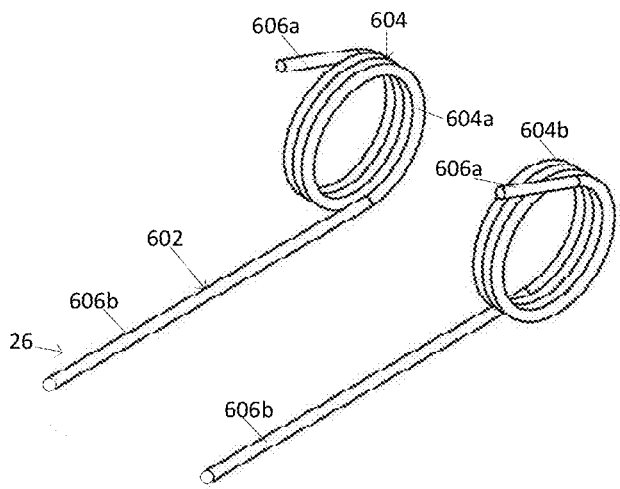

FIG. 37C illustrates a perspective view of a variation of the spring of FIG. 33C.

FIG. 38A illustrates a perspective view of the housing of FIG. 34A with the wings in a folded configuration.

FIG. 38B illustrates a perspective view of the housing of FIG. 30A with the wings in a folded configuration.

FIG. 39A illustrates a front perspective view of a device taped to a patient.

FIG. 39B illustrates a side view of a device taped to a patient.

Figure 40A:
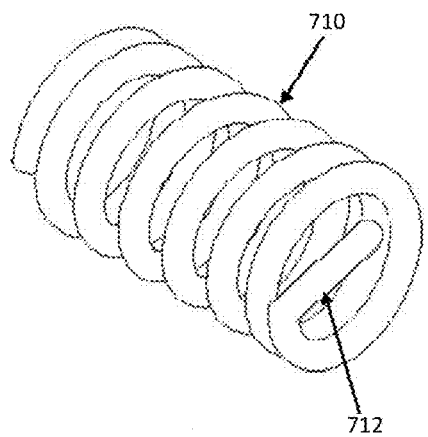

FIG. 40A illustrates a perspective view of a variation of a spring.

Figure 40B:
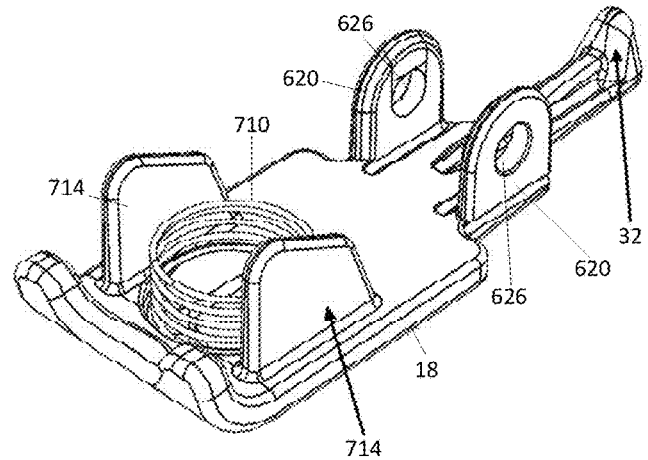

FIG. 40B illustrates a perspective view of a variation of the spring of FIG. 40A attached to a variation of a sensor.

Figure 40C:
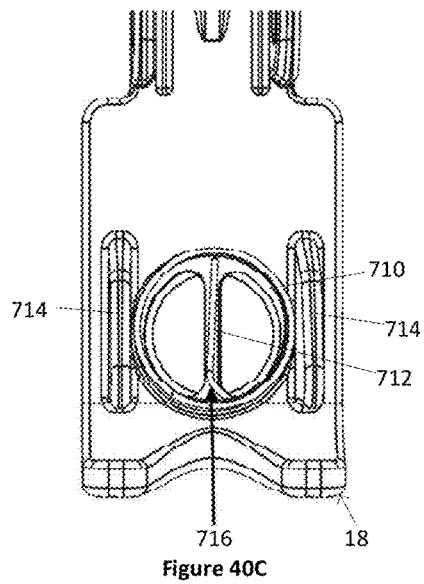

FIG. 40C illustrates a top view of FIG. 40B while loading the spring onto the sensor.

Figure 40D:
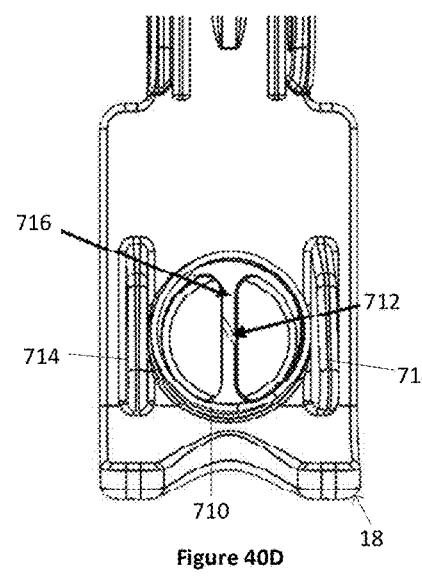

FIG. 40D illustrates a top view of FIG. 40B while loading the spring onto the sensor.

Figure 40E:
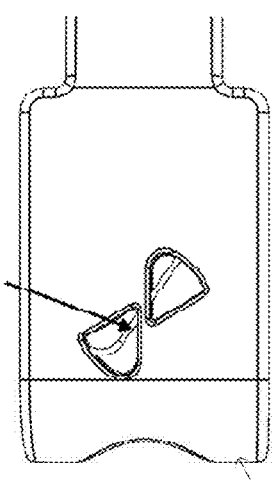

FIG. 40E illustrates a bottom view of FIG. 40D.

Figure 41A:
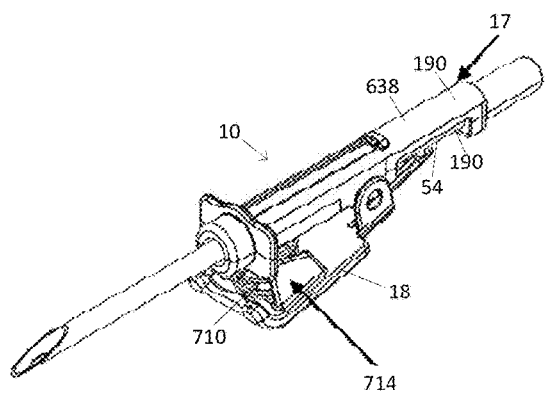

FIG. 41A illustrates a perspective view of a variation of the spring-sensor component of FIG. 40B attached to a variation of a tube.

Figure 41B:
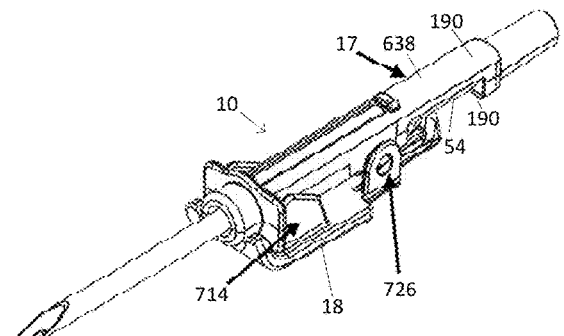

FIG. 41B illustrates a perspective view of a variation of the spring-sensor component of FIG. 40B attached to a variation of a tube.

Figure 41C:
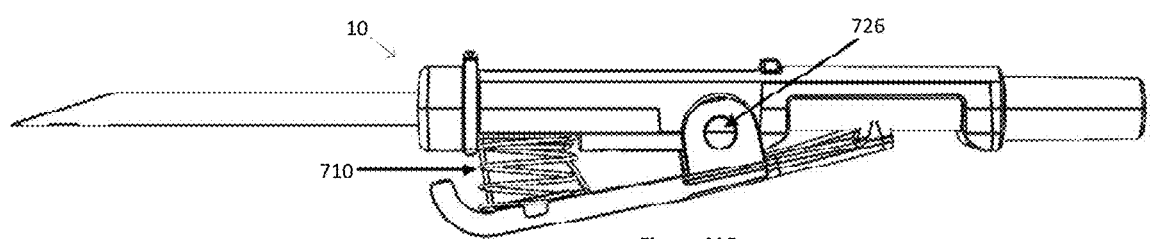

FIG. 41C illustrates a side view of FIG. 41A.

Figure 41D:
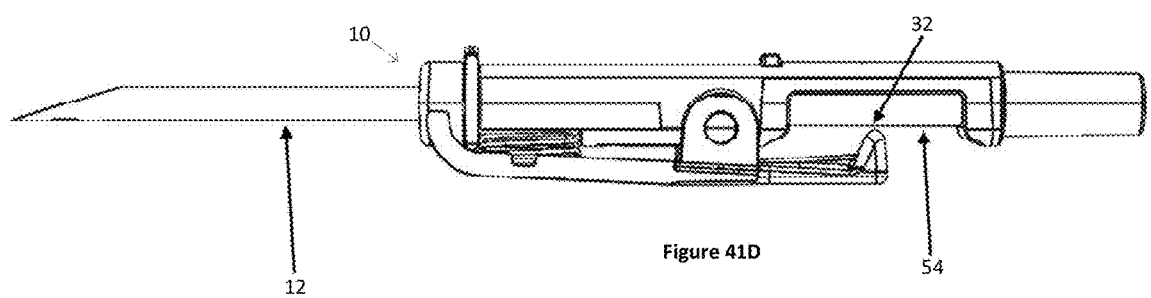

FIG. 41D illustrates a side view of FIG. 41B.

FIG. 42A illustrates a perspective view of a variation of a tissue access device with the sensor in an open configuration.

FIG. 42B illustrates the device of FIG. 30A with the sensor in a closed configuration.

FIG. 42C illustrates a side view of FIG. 42A.

FIG. 42D illustrates a side view of FIG. 42B.

DETAILED DESCRIPTION

The features in FIGS. 1-42D can be combined with each other in any combination.

Tissue access devices (also referred to as fluid access devices, vessel access devices, blood access devices, and needles) are disclosed. The tissue access devices disclosed can withdraw and/or deliver fluid directly into a patient. In hemodialysis that fluid is blood. In other cases, that fluid may be saline or medications. Vascular access is routinely performed in hospitals, clinics and other medical locations as well as the home (during home hemodialysis for example). For example, vascular connections are disclosed, and more particularly, systems and methods for detecting dislodged vascular connections, and systems and methods for interrupting flow when vascular connections are dislodged are disclosed.

Needle safety systems that have a contact sensing mechanism configured to be put on a patient's skin to determine when a needle/tubing set that has been inserted into a patient and/or has become dislodged from the patient are disclosed. Dislodgement can occur, for example, when tape holding a tissue access device or a vascular access needle in place fails or the line connected to the device is pulled out.

Needle safety systems and methods of using a force-sensing mechanism within the device to determine if and when a given needle/tubing set that has been inserted into a patient has experienced a dislodgement are disclosed. This can occur during medical therapy when the tubing leading to a vascular access needle is purposely or inadvertently 'pulled' or 'tugged'. It can also occur when the medical tape used to hold an inserted needle into position on the skin becomes loose either due to excessive patient hairiness or an increase in sweatiness/humidity that reduces the tape adhesion.

Needle safety systems that have a fluid stop valve configured to automatically deploy to stop the flow of fluid through a needle/tube when the needle delivering that fluid into the body is accidentally dislodged from the patient during fluid delivery are disclosed.

Needle safety systems that have a pinch valve configured to be activated by a mechanical linkage to a mechanical 'skin-sensing' element in a needle system that has been pre-manufactured to include a compressible segment of tubing are disclosed.

Needle safety systems that have the pinch valve configured to block flow acts on an internally formed flow path that is formed within a 'butterfly' housing of a traditional needle are disclosed.

Systems and methods for automatic flow termination for fluid delivery, including a housing configured for coupling a fluid delivery tube to a needle configured for subcutaneous (into vasculature) delivery of fluid within a tissue of a patient and a spring-loaded or fluid-sensitive activation mechanism having a first orientation corresponding to a condition where the housing is disposed substantially adjacent to the tissue and the needle lodged within the tissue and a second orientation corresponding to a condition where the housing is disposed away from the tissue or the needle being dislodged from the tissue and a third orientation corresponding to a condition where the housing is substantially adjacent to the tissue but in a position pulled back from the original insertion point, causing the needle to no longer be delivering fluid into the vasculature are disclosed. A flow termination mechanism coupled to the activation mechanism and having an open configuration allowing flow from the fluid delivery tube to the needle when the activation mechanism is in the first orientation and a closed configuration substantially terminating flow from the fluid delivery tube to the needle when the activation mechanism is in either the second or third orientations is disclosed.

Specialized needles for protecting patients from fluid delivery problems during medical therapies are disclosed. For example, a specialized needle is disclosed that can have a spring-loaded integrated footplate, that, when in a dislodged position (e.g., not taped to skin and needle body off of skin) results in a footplate occlusion member moving into a device flow channel and blocking fluid flow through the needle.

Systems and methods for automatic flow termination for fluid delivery, including a housing configured for coupling a fluid delivery tube to a needle configured for subcutaneous (into vasculature) delivery of fluid within a tissue of a patient and a force-sensitive activation mechanism (shown as a footplate here) having a first flattened orientation (e.g., straight or less straight orientation) corresponding to a condition where the fluid delivery through the needle body is permitted while using the U-opening to protect the needle access hole and a second orientation corresponding to a condition where the fluid tube is occluded via an fluid occlusion member of the footplate during needle dislodgement via the spring force provided by a curved element molded into the footplate are disclosed. When the footplate is created with a curved end, device cannulation is improved due to the low frictional forces associated with the curvature against the skin during insertion. Additionally, the curved end of the footplate encourages mechanical contact with the skin even if the insertion angle is very high (e.g., up to 50 degrees). This enhances dislodgement detection functionality. The use of a curved central portion on the footplate creates an effective internal hinge point for the occlusion arm and removes the need for any external hinge point attachments on the needle body itself. This greatly improves the function of the device by removing any possible mechanical parts of the system from potential interference from any of the overlying medical tape typically used to hold the needle in place during therapy.

Needle safety systems that can be efficiently and cost effectively manufactured by using a 'molded-in' spring design for the footplate sensing unit are disclosed. An effective spring can be manufactured by molding the footplate unit with a curved portion. When this footplate is put into a straightened position, mechanical stress on the curved portion results in the generation of an effective spring force, the direction and magnitude of the force being dependent on the mechanical shape and size of the related appendages. By creating a central 'mechanical arm' the spring force can be harnessed to serve as an occlusion technique by allowing the end of the arm to move directly into and block or occlude the fluid flow through the center of the needle body.

Needle safety systems having a spring-loaded footplate affixed to the bottom of a needle to sense errant flow from a dislodged needle are disclosed. Further, by curving the distal end of the footplate, an effective system can be made that provides for the essential safety and ease of the cannulation process while also simultaneously protecting the patient from needle over-insertion following initial insertion. The curved end also provides a mechanism by which the needle dislodgement detection function can be made effective even for needles inserted at a steep (e.g., up to 45 degrees) insertion angles. The opposite end of this footplate can include an occlusion member which can be pushed into the flow path within the needle body and used to block fluid flow. Further, by molding a curvature into the footplate base and forming an opposable member within the central portion of the footplate, a 'spring' can be formed to aid in the 'sensing' operation and engage the end of the central member to move into the flow path within the needle body and block fluid flow upon removal of the needle from the surface of the patient.

The use of a spring-loaded footplate as the 'detector' of presence of underlying skin to determine if and when a needle body inserted for fluid delivery has been dislodged from the patient is disclosed.

Systems and methods for automatic flow termination for fluid delivery, including a housing configured for coupling a fluid delivery tube to a needle configured for subcutaneous (into vasculature) delivery of fluid within a tissue of a patient and a force-sensitive activation mechanism having a first orientation corresponding to a condition where the fluid delivery tube is pinched internally within the needle body in the event of an axial pull and a second orientation corresponding to a condition where the fluid tube is pinched in an external arrangement for any other non-axial pulling direction are disclosed. A flow termination mechanism can be active in each pull case but otherwise have an open-flow configuration allowing flow from the fluid delivery tube to the needle when the tubing experiences no pulling force or a pulling force below a certain threshold.

Needle safety systems and methods of use are disclosed that use force-sensing mechanisms within the device to determine if and when a given needle/tubing set that has been inserted into a patient has experienced a 'pull force' approaching that which might be reasonably expected to dislodge the tubing from the patient. This can occur during medical therapy, for example, when the tubing leading to a vascular access needle is purposely or inadvertently 'pulled' or 'tugged'. It can also occur when the medical tape used to hold an inserted needle into position on the skin becomes loose either due to excessive patient hairiness or an increase in sweatiness/humidity that reduces the tape adhesion.

Needle safety systems and tubing 'cinch' or 'pinch' methods to stop the flow of fluid through a tube leading to patient in the event that forces on that tube approach those expected to dislodge the needle are disclosed.

Needle safety systems having a device with a mechanically optimized pinch valve on the external portion of the device configured in such a way that the tubing can be pinched by compression of the tubing through optimized pinch points in the event of the tubing being pulled in any other direction beyond axial out of its usual position are disclosed.

Needle safety systems having a device with a mechanically optimized pinch valve on the internal portion of the device configured in such a way that the tubing can be pinched by compression of the tubing via 'pincher arms' within the needle body in the event of the tubing being pulled with an above threshold force in an axial direction sometime after insertion and taping of that needle are disclosed.

Needle safety systems that can override the skin sensing elements described herein are disclosed. The override systems disclosed can insure that the skin sensing elements are not activated during the process of cannulation and/or during needle insertion into the patient. During cannulation, and before the needle are taped down, it is critical that fluid flow is enabled through the needle/tube so that clinical personnel have the ability to visualize blood 'flashback' from the patient through the needle into the fluid flow tube. Any needle with a fluid flow blockage mechanism can have the blockage mechanism temporarily disabled during this cannulation and/or needle insertion period. A needle safety device feature that accomplishes this will be termed a 'cannulation lock' in this document.

Needle safety systems are disclosed that have the ability to 'lock-out' the skin sensing mechanism after it has been activated due to a sliding or other type of off-the-skin dislodgement. In such cases when fluid flow is blocked, it can be important for other aspects of therapy delivery for clinical staff to assess the situation and replace the needle. A 'lock-out' feature insures that no additional and potentially dangerous fluid flow can start again following full activation of the flow stop mechanism.

Needle safety systems for sensing skin contact using a button-like sensor that comes out of (e.g., straight out of) the bottom of a needle body and halting flow using a blockage technique that involves rotating or sliding an opening from close to open within the needle valve are disclosed.

Needle safety systems that have a contact sensing mechanism on the patient's skin to determine when a given needle/tubing set that has been inserted into a patient has potentially become disengaged from the patient in those cases that involve the needle 'sliding' out of the vasculature but not necessarily fully 'dislodging' off-the-body, away from the skin are disclosed. Such incomplete or partial dislodgement can occur when the tape holding a vascular access needle in place provides enough downward pressure to keep the needle against the skin but fails to prevent relevant motion of the access needle away from the original insertion point. One version of this type of failure whereby the needle slides out of the vasculutare but not out of the skin is called 'infiltration' in the medical literature. When the needle slides completely out of the skin, this can be defined as 'slip dislodgement'. Dislodgement throughout the disclosure refers to both partial and complete dislodgement.

Needle safety systems for sensing relative motion of the taped down needle body in the direction opposite to the path the needle was originally inserted are disclosed. One way this can be achieved is by using adhesive on the bottom of the needle or a modified surface providing enhanced frictional contact between the needle body and skin and incorporating a method that detects when frictional forces on the needle body are high enough against the needle bottom in the direction opposite of insertion to suggest the needle itself has or is being moved in that undesired (for therapy) direction. In such an event, any of the blockage methods described herein for halting flow within the needle can be activated.

Needle safety systems that can sense relative motion of the needle body in a direction away from the insertion site with reference to the tape above the needle body that is holding it in place are disclosed. This can be achieved by a mechanism which relies on a combination of position, and/or velocity and/or or acceleration change on a member positioned above and in contact with the needle body as well as in contact with the tape. A threshold change in the position, velocity or acceleration of the needle body in a direction away from its intended insertion point as determined by the relative difference between the taped member and the needle body would result in triggering of one of the methods of flow blockage via a linkage between the detection system and one of the integrated flow blockage systems.

The devices disclosed can use no electrical power, and thus require no external power source, batteries, or cables, thereby improving the ability of the devices to be adopted in medical workspaces that are complex and require simplified solutions. The devices disclosed are completely sterilizable and can be completely disposable. The devices disclosed can be manufactured inexpensively using high-volume injection molding processes. The devices disclosed advantageously do not require extensive clinical training.

The needle safety systems disclosed can be added to existing needles/tubing.

Systems designed to deliver fluid directly into a patient are disclosed. In hemodialysis that fluid is blood. In other cases, that fluid may be saline or medications. Vascular access is routinely performed in hospitals, clinics and other medical locations as well as the home (during home hemodialysis for example).

An aspect of the present disclosure is a 2-shot molded component that has both a structurally solid and mechanically sound cylindrical tube as well as a region of mechanically compressible soft material through which an external assemblage can be pushed to block flow through the solid tube.

A feature of the present disclosure offers an important distinction to the needle system manufacturing process that can enable efficient and cost-effective development of said needle systems. Among these methods is the use of 2-shot molding to create an internal part piece that can enable rapid and effective disruption of the internal flow path during needle dislodgement. 2-shot molding is used to create a hard-walled mechanically sound flow tube with an integrated mechanically soft and compressible region. This compressible region provides a means by which an exterior assemblage can be introduced within the flow path in order to obstruct flow. This flow obstruction can be temporary. When the assemblage (e.g., a footplate on the bottom of the needle body) is allowed to return to its original position the flow path becomes unobstructed once again.

Another aspect of the present disclosure is a variation in the soft membrane portion of the 2-shot component that incorporates a free standing pocket that improves closing and occlusion efficiency during activation of the footplate portion of the safety needle.

Another feature of the present disclosure is assembly methods and techniques that enable integration of a 2-shot molded interior piece part with the other components desirable in manufacturing an otherwise traditional needle assembly that includes the needle dislodgement safety mechanisms. These components include butterfly wings, the needle, tubing and a skin-sensing element (in this instance, a spring-loaded footplate). The use of 2-shot molding allows for an efficient needle manufacturing technique in which the other needle system components can be appropriately assembled around the 2-shot component resulting in a final product which is both functional, cost-effective and efficient to build. The 2-shot component allows for the assembly of these other components in a logical progression that conserves time and reduces the danger of spreading adhesive material onto surfaces where it can become problematic to later manufacturing steps or even lead to product failure. In certain cases (e.g., FIGS. 10A and 10B) butterfly wings can be slid onto the 2-shot component either from the back or from the front as most appropriate.

An aspect of the present disclosure is modifications to the footplate design which enable efficient device assembly/manufacturing. Such modifications of the footplate include the use of a U-type fitting which enables a snap-to-fit assembly approach or the use of a ring/collar system which allows for a press-fit assembly approach in which the ring/collar is slid over the 2-shot core piece for system integration. Snapping or sliding techniques may or may not be enhanced with additional adhesive approaches including but not limited to glue or ultrasonic welding.

Another aspect of the present disclosure is modification of the butterfly wing component to enable efficient integration of the wings onto the 2-shot molded interior piece part. Such wings can be modified to include a U-type snap feature or a ring/collar system that allows for a slide-type assembly method. Sliding can be done from the front or the back of the assembly. Snapping or sliding techniques may or may not be enhanced with additional adhesive approaches including but not limited to glue or ultrasonic welding.

An aspect of the present disclosure is a needle safety system or add-on to existing needles/tubing that uses a force-sensing mechanism within the device to determine if and when a given needle/tubing set that has been inserted into a patient has experienced a dislodgement. This can occur practically during medical therapy when the tubing leading to a vascular access needle is purposely or inadvertently pulled or tugged. It can also occur when the medical tape used to hold an inserted needle into position on the skin becomes loose either due to excessive patient hairiness or an increase in sweatiness/humidity that reduces the tape adhesion.

One embodiment of the systems and devices disclosed is the use of a spring-loaded footplate as the detector of presence of underlying skin to determine if and when a needle body inserted for fluid delivery has been dislodged from the patient.

A feature of the present disclosure offers important design features that enable the use of an appropriate spring to enable the requisite sensing of the patient arm underneath the needle body. An effective spring can be manufactured using a pre-curved piece of metal and integrating it into the existing footplate design.

Another feature of the present disclosure is that by modifying the metal spring, an extension of the spring towards the proximal end of the device could also serve as the occlusion piece which enters into the fluid path to induce the flow restriction that leads to automatic machine shut off.

Another feature of the present disclosure is by incorporating a living hinge during product molding, the needle butterfly assembly and the footplate can be molded at the same time, improving manufacturing efficiency. In the final product, the footplate is folded into place underneath the needle body.

Another feature of the present disclosure is the use of a plastic cap, to serve as a cover of a proximal extension of the metal spring which acts as the occlusion piece. By modifying the shape, size or profile of this plastic cap, the fluid flow path dynamics can be adjusted/controlled for improved functionality.

Another feature of the present disclosure is a modification of the standard needle cap to enable the cap to both cover and protect the needle and to serve as a means by which to hold the footplate in a range of positions from fully closed to fully open during shipping and in storage before use on the patient.

Multiple variations of protective needle guards. Sliding systems all have a common design with a plastic part that is actively moved into position over the sharp needle during intentional withdrawal from the patient following therapy.

This disclosure concerns potential modifications of these existing or other designs that will enable efficient use and configuration of the needle guard on a needle system equipped with a footplate or other type of integrated skin sensor used as part of an overall safety system to protect patients from the risks of unintended needle dislodgement during medical therapy (typically hemodialysis but any other therapy involving flow of fluid to or from a patient is possible, in hemodialysis that fluid is blood. In other cases, that fluid may be saline or medications.)

An aspect of the present disclosure is modification of the needle guard safety system for patient and caregiver protection from inadvertent needle sticks following therapy.

One embodiment of this modification is the use of a beveled or chamfered edge that can more easily enable effective automatic closure of the spring-loaded footplate as the needle guard is actively slid into its protective position during use. A beveled or chamfered edge may reduce the likelihood of the needle guard becoming hung up or stuck on the proximal portion of the footplate as the guard is slid into place by a caregiver. Such a beveled or chamfered edge is shown in FIG. 23.

A second embodiment of this modification is the development of a more extensive beveled or chamfered feature into the bottom design of the slidable needle guard. This type of technique enables effective closure via mechanical redesign of the bottom aspect of the guard such that the device presents an angled opening to the distal portion of the footplate within the transitional zone where the footplate slides into the needle guard. A redesigned opening feature may be simply realized by angling the downward portion of the transitional zone at some appropriate angle to extend over some appropriate depth into the needle guard. More complex is to build an angled entryway of some depth into the needle guard that will result in increased available space to accommodate the footplate.

The disclosure relates to means of improving the ability of any given needle guard to be smoothly and effectively placed so that the needle can be effectively covered while the footplate is not impeded in any way.

An aspect of the present disclosure is a needle safety system or add-on to existing needles/tubing that uses a force-sensing mechanism within the device to determine if and when a given needle/tubing set that has been inserted into a patient has experienced a dislodgement. This can occur practically during medical therapy when the tubing leading to a vascular access needle is purposely or inadvertently pulled or tugged. It can also occur when the medical tape used to hold an inserted needle into position on the skin becomes loose either due to excessive patient hairiness or an increase in sweatiness/humidity that reduces the tape adhesion.

A feature of the present disclosure offers important protection to patient during dislodgement by maximizing the device's ability to generate a pressure change in the fluid line that is of sufficient magnitude to induce pressure-triggered alarm-based automatic machine shut down. The disclosure relates to the process of creating a mechanical interruption within the needle body fluid flow path that artificially increases the line pressure in a standard needle set during therapy. It is a strong possibility that dislodgement of a standard needle is not detected by the machines in instances where the patient input pressure (venous access pressure or VAP in cases of hemodialysis) is less than the difference between the baseline operating pressure and the machine lower limit setting for pressure detection. A feature of the present disclosure is a footplate/flow-tube configuration that uses mechanical interruption within the flow path to artificially raise the patient's baseline venous line pressure during therapy. When needle dislodgement occurs, the increased pressure difference between the mechanically occluded venous needle set during normal fluid delivery and the state of the needle set during dislodgement would create a pressure change of significant magnitude to unequivocally trigger the pressure alarm limit of most machines.

FIG. 1 illustrates a variation of a tissue access device 10. The device 10 can withdraw fluid (e.g., blood, lymph, interstitial fluid) from tissue or a vessel lumen. The device 10 can deliver fluid (e.g., blood, lymph, saline, medications) to tissue or a vessel lumen. For example, the device 10 can be used for hemodialysis therapy to withdraw blood from a vessel for filtration and return filtered blood to the vessel. Multiple devices 10 can also be used. For example, for hemodialysis therapy, a first device 10 can be used to withdraw unfiltered blood from a vessel and a second device 10 can be used to return filtered blood to the same or a different vessel. The number of devices 10 used will depend on the number of access points required and can range, for example, from 1 to 5 or more, including every 1 device increment within this range. The device 10 can control the delivery and/or withdrawal of fluid through a channel in the device 10 (also referred to as a device channel and device flow path). For example, the device 10 can automatically decrease (e.g., partially or entirely block) the flow of fluid through the channel when the device 10 becomes dislodged during a dislodgement event.

The device 10 can have multiple device configurations. For example, the device 10 can have a non-occluded configuration and/or one or more occluded configurations. The occluded configurations can correspond to partially occluded configurations, fully occluded configurations, or any combination thereof. When the device 10 is in a non-occluded configuration, fluid can flow through the device channel unrestricted by the device 10. When the device 10 is in an occluded configuration, fluid flow through the device channel can be decreased or entirely blocked by the device 10. The device 10 can restrict or terminate fluid flow through the device channel by decreasing a channel cross-sectional area from a first cross-sectional area to a second cross-sectional area less than the first cross-sectional area. The second cross-sectional area can be about 1% to about 100% less than the first cross-sectional area, including every 1% increment within this range, where 100% can correspond to complete blockage of the channel in one or multiple channel cross-sections. The channel can have a channel longitudinal axis and a channel transverse axis. The channel cross-sectional area can be a transverse cross-sectional area perpendicular to the channel longitudinal axis.

The device 10 can allow less fluid to flow through the device 10 in an occluded configuration than in a non-occluded configuration, for example, as measured over a time interval T (e.g., about 0.25 seconds to about 60.0 seconds). The device 10 can allow less fluid to flow through the device in a first occluded configuration than in a second occluded configuration, for example, as measured over the time interval T, where the second occluded configuration obstructs more of a device flow path than the first occluded configuration. The device 10 can allow more fluid to flow through the device in a first occluded configuration than in a second occluded configuration, for example, as measured over the time interval T, where the second occluded configuration obstructs less of a device flow path than the first occluded configuration.

The device 10 can have a non-occluded configuration or a partially occluded configuration when the device 10 is inserted into or attached to tissue. The device 10 can have an occluded configuration before the device 10 is inserted into tissue, while the device 10 is being inserted into tissue, when the device 10 becomes dislodged or detached from tissue, or any combination thereof.

When the device 10 is inserted into tissue, the device 10 can progressively become less occluded by transitioning from a more occluded configuration to a less occluded configuration. For example, when the device 10 is inserted into tissue, the device 10 can transition from an occluded configuration to a non-occluded configuration. As another example, when the device 10 is inserted into tissue, the device 10 can transition from a first occluded configuration to a second occluded configuration less occluded than the first occluded configuration. The device 10 can have an inserted configuration when insertion into tissue is complete. The device 10 can be removably secured to a non-device 10 surface such as skin, for example, with tape, glue, an elastic band, or any combination thereof. The device 10 can have an attached configuration (also referred to as a non-dislodged configuration) when the device 10 is removably secured to the non-device surface. The inserted and attached configurations can be the same or different from one another. For example, the inserted and attached configurations can both be non-occluded configurations or partially occluded configurations. As another example, the inserted configuration can be an occluded (partial or full) configuration and the attached configuration can be a non-occluded configuration or an occluded configuration less occluded than the occluded inserted configuration.

When the device 10 becomes dislodged from the non-device surface, the device 10 can progressively become more occluded by transitioning from a less occluded configuration to a more occluded configuration. For example, when the device 10 becomes dislodged from the non-device surface, the device 10 can transition from a non-occluded configuration to an occluded configuration. As another example, when the device 10 becomes dislodged from the non-device surface, the device 10 can transition from a first occluded configuration to a second occluded configuration more occluded than the first occluded configuration. The device 10 can have a dislodged configuration when one or more portions of the device 10 move away from the non-device surface by an occlusion threshold distance of about 5 mm to about 25 mm, including every 1 mm increment within this range.

The device 10 can automatically move from an attached configuration to a dislodged configuration when the device 10 is dislodged or detached from the non-device surface. The device 10 can transition from the attached configuration to the dislodged configuration in less than 0.10 seconds, 0.25 seconds, 1 second, 5 seconds, 10 seconds, or 60 seconds. For example, the device 10 can automatically move from the attached configuration to the dislodged configuration in 0.01 seconds to 1.00 seconds, including every 0.01 second within this range (e.g., 0.10 seconds).

FIG. 1 illustrates a variation of an occluded configuration of the device 10, for example, a partially occluded configuration or a fully occluded configuration. FIG. 1 further illustrates that the device 10 can have the same configuration before the device 10 is inserted into tissue and attached to a non-device surface and after the device 10 is dislodged from the non-device surface. When the device 10 is detached from the non-device surface, the device 10 may remain in the tissue or become dislodged from the tissue as well. For example, when the device 10 is dislodged from the non-device surface, a portion of the device 10 that is in a vessel (e.g., a needle) may remain in the vessel, may be dislodged from the vessel but remain in tissue adjacent the vessel, or may be dislodged from the vessel and tissue altogether.

FIG. 1 further illustrates that the device 10 can have a device longitudinal axis A1. The device longitudinal axis A1 can be a center longitudinal axis of the device 10. The device longitudinal axis A1 can be a center longitudinal axis of a flow channel in the device 10. The device longitudinal axis A1 can be straight or curved. The device longitudinal axis A1 can be perpendicular to a device first transverse axis A2. The device longitudinal axis A1 can be perpendicular to a device second transverse axis A3. The device first and second transverse axes A2, A3 can be perpendicular to one another. The device first and second transverse axes A2, A3 can be straight or curved.

The device 10 can have a device proximal end 10a and a device distal end 10b. The device 10 can have a device first side 10c and a device second side 10d. The device first side 10c can be a bottom surface of the device 10 and the device second side 10d can be a top surface of the device 10.

FIG. 1 further illustrates that the device 10 can have a needle 12 and a housing 14 (also referred to as a needle body). The needle 12 can be, for example, an arteriovenous (AV) fistula butterfly needle or an AV fistula cannula needle housed in a flexible sheath (not shown). The needle 12 can have a needle proximal end 12a and a needle distal end 12b. The housing 14 can be a butterfly housing. For example, the housing 14 can have a first wing 15a and a second wing 15b. The housing can have a housing proximal end 14a and a housing distal end 14b. A needle hub 13 can connect the needle and housing 12, 14 together. The device 10 can have a connector 16 configured to connect a tube 8 to the device 10. The connector 16 can be outside and/or inside the housing 14. Additionally or alternatively, the connector 16 can be integrated with the housing 14. The tube 8 can be in fluid communication with the needle 12 via a flow channel in the housing 14 when connected to the device 10 (e.g., via the connector 16). The connector 16 can be a rigid material, a semi-rigid material, or a flexible material. The housing can be made of a rigid material, for example, plastic, metal, composite material, or any combination thereof. The tip of the needle 12 can be a distal terminal end of the device along the device longitudinal axis A1.

FIG. 1 further illustrates that the device 10 can have a sensor 18. The sensor 18 can be a non-device surface sensor, for example, a skin sensor. The sensor 18 can be a mechanical sensor. The sensor 18 can be a valve, for example, a pinch valve. One or more portions of the sensor 18 can be resiliently moveable. For example, one or more portions of the sensor 18 can be biased to resiliently strain away from a sensor neutral position (e.g., via compression and/or tension) and de-strain back to the sensor neutral position. The sensor 18 can change shape when a force is applied to the sensor 18 from a non-device surface (e.g., when the device 10 is inserted and attached to skin). The sensor 18 can change shape when a force is removed from the sensor 18 (e.g., when the device 10 becomes dislodged from skin).

The sensor 18 can comprise, for example, one or more arms, plates, protrusions, extensions, occluders, openings, channels, springs, spring regions, or any combination thereof. The sensor 18 can be positioned on a device first side (e.g., a first transverse side, a bottom side), a device second side (e.g., a second transverse side, a top side), a device third side (e.g., first lateral side, a left side), a device fourth side (e.g., a second lateral side, a right side), a device fifth side (e.g., first longitudinal side, a front side), a device sixth side (e.g., second longitudinal side, a back side), or any combination thereof. For example, the sensor 18 can be a bottom plate (also referred to as a footplate), a top plate, a side plate, a front plate, a back plate, or any combination thereof, such that at least a portion of the sensor 18 can detect contact and loss of contact with a non-device surface and/or can detect a contact force and a reduction of the contact force from a non-device surface. For example, FIG. 1 illustrates that the sensor 18 can be a skin-sensing footplate (also referred to as a moveable footplate).

The sensor 18 can have a sensor proximal end 18a and a sensor distal end 18b. The sensor proximal and/or distal ends 18a, 18b can be configured to slide across a non-device surface when the needle 12 is inserted into tissue. The sensor distal end 18b can have a sensor distal terminal end 24. The sensor distal terminal end 24 can be an edge or a surface.

The sensor 18 can be attached to the device 10 (e.g., the housing 14) with or without a hinge. For example, FIG. 1 illustrates that the sensor proximal end 18a can be directly or indirectly attached to the housing 14 on the device first side 10c without a hinge. The portion of the sensor 18 attached to the housing 14 (e.g., the sensor proximal end 18a) can be attached using glue, welding (e.g., sonic welding), a snap fit, a friction fit, or any combination thereof.

The sensor distal end 18b can move relative to the sensor proximal end 18a. For example, the sensor distal end 18b can rotate about a sensor hinge (not shown). The sensor hinge can be attached to or integrated with the sensor 18. The sensor hinge can be a spring. The sensor 18 can have multiple sensor hinges/springs.

A sensor spring (not shown, also referred to as a spring region) can result in the distal end 18b being located a distance away from the needle 12 during dislodgement (and before attachment). The sensor spring can cause the sensor distal end 18b to be biased in a neutral position a distance away from the needle 12 during dislodgement (and before attachment).

The sensor distal end 18b can have one or more distal end sections, for example, 1 to 10 or more sections, including every 1 section increment in this range (e.g., 2 sections, 3 sections). One or more of the distal end sections can be straight. One or more of the distal end sections can be curved. The sensor distal end sections can be angled relative to one another, for example, by about 0 degrees to about 120 degrees, including every 1 degree increment within this range (e.g., 90 degrees).

For example, FIG. 1 illustrates that the sensor distal end 18b can have a distal end first section 20a, a distal end second section 20b, and a distal end third section 20c between the distal end first and second sections 20a, 20b. FIG. 1 illustrates that the first and second sections 20a, 20b can be straight and that the third section 20c can have a curve 21. The first and second sections 20a, 20b can be angled relative to one another by about 90 degrees. Different distal end sections can be integrated with or attached to one another. For example, the sensor distal end 18b can be a monolithic structure. The sensor 18 can be a monolithic structure.

A curved sensor distal end (e.g., distal end 18b with curve 21) can improve caregiver usability of the device 10 by making the needle insertion process and/or the cannulation process easier by reducing friction between the device 10 and a non-device contact surface during insertion. For example, the curve/curved surface 21 can result in a sensor leading edge (e.g., the sensor terminal end 24) facing or extending away from the non-device surface (e.g., away from a patient's skin surface) during insertion. Having the sensor leading edge 24 face or extend away from the insertion surface during needle insertion can ensure easier cannulation by reducing or removing the possibility of the sensor leading edge catching on the insertion surface when the needle 12 is inserted.

A curved distal end 18b can also protect patients by preventing needle over-insertion. For example, the distal end second section 20b can be configured to prevent over insertion of the needle 12 into a vessel by acting as a barrier that prevents the needle 12 from being inserted past the second section 20b. The curved end offers protection to the patient in this position by 'blocking' the needle body from any forward motion into the existing needle access hole (not shown). The sensor distal end 18b can have a section (e.g., section 20b) that extends toward the needle 12 with or without a curve 21 in the sensor distal end 18b such that the sensor distal end 18b can define a needle over insertion barrier (e.g., section 20b) in any variation of the sensor 18. Such barriers can inhibit or prevent over insertion of the needle 12 longitudinally and/or transversely into the skin, for example, relative to a longitudinal axis of the needle 12 and/or relative to the needle insertion hole in the skin.

A curved distal end 18b can also desirably enable needle dislodgement detection even for needles (e.g., needle 12) inserted at steep insertion angles, for example, up to 45 degrees, up to 50 degrees, up to 60 or more degrees. The curved end allows for maximal contact between the skin and a closed sensor 18 (not shown, this can be the configuration of the sensor 18 when the device 10 is in an attached configuration) under these steep insertion angle conditions, offering increased device functionality by ensuring the sensor 18 is held in check against the needle 12 regardless of the insertion angle.

The sensor distal end 18b can have a sensor opening 22 (also referred to as a sensor slot). The sensor opening 22 can accept a portion of the needle 12. For example, FIG. 1 illustrates that the sensor distal end second section 20b can have the sensor opening 22. The sensor opening 22 can be configured to receive at least a portion of the needle 12 when the sensor distal end 18b is pressed by a non-device surface toward the needle 12, for example, when the device 10 is in an inserted or attached configuration. The sensor opening 22 can advantageously allow for closure (e.g., full closure) of the sensor 18 against the needle 12 when the sensor distal end 18*b* is pressed toward the housing 14 (e.g., against the housing 14). The sensor opening 22 can be, for example, a U-shape, a V-shape, or an irregular shape. At least a portion of the distal terminal end 24 can define the sensor opening 22.

A sensor opening 22 integrated with the sensor distal end 18*b* can allow the over insertion barrier (e.g., barrier 20*b*) to close around at least a portion of the needle 12 when the device is in an attached configuration. The sensor opening 22 can allow the barrier 20*b* to better prevent over insertion be increasing the surface area of the barrier near the needle 12 that can resist further insertion of the needle 12. The barrier 20*b* can positioned between the needle tip and the needle hub 13. The sensor opening 22 can be positioned between the needle tip and the needle hub 13. Such placement can ensure that the needle 12 cannot be inadvertently pushed deeper into the patient through the existing needle access hole.

FIG. 2A illustrates that the sensor 18 can have one or more sensor springs 26 (also referred to as spring regions), for example, 1 to 10 or more springs 26, including every 1 spring increment within this range (e.g., 1 spring, 2 springs). For example, FIG. 2A illustrates that the sensor 18 can have a first spring 26*a* and a second spring 26*b*. When multiple springs 26 are used, the multiple springs 26 (e.g., first and second springs 26*a*, 26*b*) can function together as a single spring.

The spring 26 (e.g., first and second springs 26*a*, 26*b*) can function like a leaf spring, a compression spring, a tension spring, a torsion spring, or any combination thereof. Each spring 26 can be, for example, a leaf spring, a compression spring, a tension spring, or a torsion spring. The first and second springs 26*a*, 26*b* can be the same or a different type of spring. For example, the first spring 26*a* can be a leaf spring and the second spring can be a compression spring. As another example, the first and second springs 26*a*, 26*b* can both be, or function like, a leaf spring.

The spring 26 can be integrated with, attached to, or embedded in the sensor 18. For example, the spring 26 can be a molded spring made of the same or different material as the rest of the sensor 18. A molded spring 26 can be manufactured by molding the sensor 18 with one or more non-straight resilient portions (e.g., first and second spring regions 26*a*, 26*b*) that can function as a spring when the shape of the resilient portions are changed (e.g., straightened). The non-straight resilient portions can be, for example, curved, polyarc, and/or polyline structures, members, bars, rods, shafts, sheets, laminates, or any combination thereof. A molded spring design can advantageously reduce manufacturing costs associated with the sensor 18, for example, as compared to attaching or embedding a separate spring 26 to or in the sensor 18.

The spring 26 can have the form of a curved or angled polyline structure when the spring 26 is in a neutral configuration (e.g., undeflected configuration, non-strained configuration, non-stressed configuration). The spring 26 can have a neutral configuration when the device 10 is in a dislodged configuration (e.g., the dislodged configuration of FIG. 2A) and/or before the device 10 is attached to tissue. The spring 26 can be less curved or angled when the device 10 is in an attached configuration, for example, when the spring 26 is in a compressed and/or tensioned configuration (e.g., non-neutral configuration). For example, when the sensor 18 in FIG. 2A is put into a straightened or less curved configuration, mechanical stress on the curved portion (the spring regions 26*a* and 26*b*) can result in the generation of an effective spring force. This spring force can bias the sensor 18 to return to the initial configuration. The direction and magnitude of the spring force can be dependent on the mechanical shape and size of the related appendages of the sensor 18 (e.g., a flow restrictor, the features of the sensor distal end 18*b*).

The spring 26 can be a sensor hinge configured to allow the sensor distal end 18*b* to move (e.g., rotate) relative to the sensor proximal end 18*a*.

The spring 26 (e.g., springs 26*a* and 26*b*) can connect the sensor proximal end 18*a* to the sensor distal end 18*b*. The spring 26 can be in a middle region of the sensor 18, and/or on the sensor distal end 18*b* or on the sensor proximal end 18*a*. As another example, the spring 26 can extend across all or a portion of both the device proximal and distal ends 18*a*, 18*b*. For example, FIG. 2A illustrates that the spring 26 can be on a sensor proximal end 18*a*, where the sensor proximal and distal ends 18*a*, 18*b* is shown separated by a sensor center transverse axis A4. The sensor transverse axis A4 can be curved or straight.

FIG. 2A further illustrates that the sensor 18 can have a flow restrictor 28. The flow restrictor 28 can have an occluder arm 30 and an occluder 32. The occluder 32 can be a protrusion that extends away from the occluder arm 30, for example, toward the device longitudinal axis A1. The flow restrictor 28 can be integrated with or attached to the sensor 18. The occluder 32 can be configured to occlude the device flow path when the device 10 is in a dislodged configuration. The occluder 32 can be rigid. The occluder 32 can be non-deformable. The occluder 32 can be flexible. The occluder 32 can have a blunt tip. The occluder 32 can have a sharp tip. The occluder 32 can be straight and/or curved. The occluder 32 can have an irregular shape. A spring region 26 can be on one or both lateral sides of the flow restrictor 28. The spring 26 can resiliently bias the flow restrictor 28 into a default occluding position. For example, the spring force of the spring 26 can move the occluder 32 directly into and block or occlude fluid flow through the device flow path when the device 10 becomes dislodged. The curved regions 26*a* and 26*b* create an internal or integrated hinge point for the flow restrictor 28. The sensor 18 can have a sensor hole 36 that can receive the flow restrictor 28 when the sensor is straightened. Alternatively or additionally, all or part of the sensor hole 26 can be a recess in the sensor 18. The flow restrictor 28 can be in a center of the hole/recess 36 or offset in the hole/recess 36.

By using a curved portion of the sensor 18 as the mechanical spring, a typical hinge that might otherwise be required for tilting a member from a flat position to an angled position is not required. Further, by tightly affixing one portion of the footplate 18 to the needle body 14 using glue, sonic welding or any other technique (e.g., friction fit, snap fit), the footplate 18 can be made to serve in a spring-like way to sense underlying skin and serve as the mechanism for occluding blood flow. A hinge point A5 becomes integrated into the footplate's central occlusion member 28 at the base of the occluder arm 30 as that point where the central curvature 26 creates a natural bending motion. This design can desirably remove the need for a traditional hinged attachment on the needle body 14, allowing the mechanics of the device 10 to become much less susceptible to interference, for example, from the standard medical tape that is typically placed over the needles devices 10 to hold them in place.

The sensor 18 can have one more attachment zones 34. The attachment zones 34 can allow for hingeless attachment of the sensor 18 to the housing 14. The attachment zones 34 can be attached to the housing 14. For example, the attachment zones can be glued or welded (e.g., sonic welded) to the housing 14. As another example, the attachment zones 34 can fit into corresponding recesses in the housing 14 with a snap fit, a friction fit, an adhesive fit, or any combination thereof.

FIG. 2B illustrates that the sensor 18 can have a sensor first longitudinal axis A6 and a sensor second longitudinal axis A7. The sensor first longitudinal axis A6 can be an occluder arm longitudinal axis. The sensor first longitudinal axis A6 can be a center longitudinal axis of the occluder arm 30. The sensor first longitudinal axis A6 can be curved or straight. The sensor second longitudinal axis A7 can be a longitudinal axis of the portion of the sensor proximal end 18a that is proximal to the spring portions 26. The sensor second longitudinal axis A6 can be a center longitudinal axis of the sensor proximal end 18a. The sensor second longitudinal axis A7 can be curved or straight. There can be an angle 38 between the sensor first and second longitudinal axes A6, A7. When the device 10 is in a dislodged configuration, the sensor 18 can be in an occluded configuration (also referred to as a sensor closed configuration) such that the angle 38 is about 10 degrees to about 75 degrees, including every 1 degree increment within this range (e.g., 25 degrees, 30 degrees). When the device 10 is in an attached configuration, the sensor 18 can be in a less occluded configuration than when the device 10 is in a dislodged configuration (also referred to as a sensor open configuration) such that the angle 38 is about 0 degrees to about 30 degrees, including every 1 degree increment within this range (e.g., 0 degrees, 2 degrees, 5 degrees). The angle 38 between the sensor first and second longitudinal axes A6, A7 can be less when the sensor 18 is in the open configuration than when the sensor 18 is in the closed configuration, for example, about 10 degrees to about 75 degrees less, including every 1 degree increment within this range.

FIG. 2B further illustrates that the sensor 18 can have a sensor first transverse axis A8 and a sensor second transverse axis A9. The sensor first transverse axis A8 can be an axis of the sensor distal terminal end (e.g., of sensor distal end second section 20b). The sensor first transverse axis A8 can be a center axis of the sensor distal end second section 20b. The sensor first transverse axis A8 can be curved or straight. The sensor second transverse axis A9 can be an axis of the occluder 32. The sensor second transverse axis A9 can be a center axis of the occluder 32. The sensor second transverse axis A9 can be perpendicular to an axis of the occluder arm 30 (e.g., perpendicular to axis A7). The sensor second transverse axis A9 can be curved or straight. The sensor first and second transverse axes A8 and A9 can be parallel or non-parallel to each other. As another example, one or both of the sensor first and second transverse axes A8 and A9 can extend at least partially in a longitudinal direction, for example, along axes A6 and/or A7. As yet another example, one or both of the sensor first and second longitudinal axes A6 and A7 can extend at least partially in a transverse direction, for example, along axes A8 and/or A9.

FIG. 2B further illustrates that the sensor distal end 18b can have a transverse dimension 40 as measured along axis A8 of about 5 mm to about 20 mm, including every 1 mm increment within this range (e.g., 8 mm). A sensor opening transverse dimension 42 can be about 2 mm to about 20 mm, including every 1 mm increment within this range (e.g., 5 mm). As another example, the sensor opening transverse dimension 42 can be the same as the transverse dimension 40. The sensor opening transverse dimension 42 can be selected so that the needle 12 is configured to contact or sit above a bottom surface of the sensor opening 22 when the device 10 is in an attached configuration. Selecting the opening transverse dimension 42 so that the needle 12 does not contact the bottom surface of the sensor opening 22 when the device 10 is in an attached configuration can advantageously allow the needle 12 to float within the sensor opening 22 so that the sensor distal end 18b does not push the needle 12 upward out of the skin during insertion. Allowing the needle 12 to float in the sensor opening 22 can be useful where the user must "fish" for a vessel during insertion such that the user is changing the angle of the device 10 with respect to a patient's skin while a portion of the needle is inserted in tissue. It can also be useful where the angle of the device 10 relative to skin is atypically low (e.g., less than 30 degrees, less than 20 degrees, less than 10 degrees). The angle of the device 10 relative to the skin can be measured between the skin surface and the device longitudinal axis A1.

FIG. 2B further illustrates that the occluder 32 can have a transverse dimension 44 as measured along axis A9 of about 1 mm to about 15 mm, including every 1 mm increment within this range (e.g., 4 mm, 5 mm).

FIG. 2B further illustrates that the sensor 18 can have a sensor first contact surface 48 and a sensor second contact surface 50. The sensor first contact surface 48 can be configured to removably contact a non-device surface such as skin, and is therefore also referred to as a skin contact surface 48. The sensor second contact surface 50 can be configured to removably contact a device surface such as a surface of the housing 14, and is therefore also referred to as a housing contact surface 50.

FIG. 2C illustrates that the occluder opening 22 can extend through the sensor distal end second and third sections 20b, 20c. A sensor opening longitudinal dimension 46 can be about 0 mm to about 50 mm, including every 1 mm increment within this range (e.g., 5 mm). Having a sensor opening longitudinal dimension 46 greater than zero can allow the needle 12 to float in the sensor opening 22 during low angle insertions. A sensor opening longitudinal dimension 46 greater than zero can also desirably decrease the material needed to make the sensor 18, thereby reducing the manufacturing costs.

FIG. 2C further illustrates that the sensor 18 can have a dimension 47 measured between the sensor proximal terminal end and the sensor distal terminal end. The dimension can be, for example, from about 10 mm to about 50 mm or more, including every 1 mm increment within this range. The dimension 47 can be the longitudinal length of the sensor 18 as measured along a straight axis or along a curved axis that follows the contour of the sensor 18 when in the neutral position of FIG. 2A.

FIGS. 1-2C illustrate that the device 10 can have a spring 26, a flow restrictor 28, an over insertion protector (e.g., sensor distal end second section 20b), or any combination thereof. Any combination of the spring 26, the flow restrictor 28, and the over insertion protector can be integrated with one another. For example, the spring 26 and the flow restrictor 28 can be integrated with each other. The spring 26, the flow restrictor 28, and the over insertion protector (e.g., sensor distal end 18b) can be integrated with one another. As another example, the spring 26 can have an integrated flow restrictor (e.g., flow restrictor 28). The spring 26 can have an integrated over insertion protector (e.g., distal end of the sensor distal end 18b). The spring 26 can have an integrated flow restrictor (e.g., flow restrictor 28) and an over insertion protector (e.g., distal end of the sensor distal end 18b).

Additionally or alternatively, the device 10 can have an over insertion protector attached to or integrated with the housing 14 and/or needle hub 13 different from the over insertion protector that can be part of the sensor 18. In such variations, the over insertion protector can be an elongate element (e.g., a bar, a plate) that extends at least partially in a longitudinal direction away from the needle hub 13 and at least partially in a transverse direction toward the needle 12. For example, the over insertion protector can have the same shape as the sensor distal end 18b, with it just being flipped upside down and attached to or integrated with the housing 14 (where the "same shape" can be without the sensor proximal end 18a, without the spring 26, and without the flow restrictor 28). The over insertion protector can have an opening similar to or the same as opening 22. The over insertion protector can be on the device second side 10d and/or one of the device lateral sides. Where the device 10 has an over insertion protector not attached to or integrated with the sensor 18b, but instead has one attached to the housing 14 and/or to the needle hub 13, the sensor distal end second section 20b can be shortened relative to what is shown in FIGS. 1-2C so that it does not extend as far toward the needle 12 (e.g., 5 mm to 15 mm shorter), for example, so that the sensor distal end second section 20b does not interfere with the over insertion protector. As another example, the device 10 can have both a first insertion protector attached to or integrated with the sensor 18 and a second insertion protector attached to or integrated with the housing 14 and/or the needle hub 13.

Another variation of the flow restrictor 28 can be a flow restrictor having the occluder arm 30 but no occluder 32. In such variations, the occluding portion of the sensor 18 can be the end of the straight bar 30 (e.g. where the occluder is positioned on flow restrictor 28). The occluder arm 30 can be a tapered bar. As another example, the occluder arm 30 can be one or more curved, polyline, and/or polyarc bar sections (e.g., different from the occluder projection 32) such that the bar 30 can still function as an occluder without having the occluder 32 illustrated in FIGS. 2A-2C.

The sensor 18 can have one spring 26. For example, another variation of the sensor 18 can be half of the sensor 18 shown in FIGS. 2A-2C. Such a sensor can still function as described herein, albeit with one spring 26 (e.g., spring 26a or spring 26b) instead of two. Axis A10 in FIG. 2C illustrates a variation of where the sensor 18 can be sliced to create a smaller sensor 18. One or both halves of the sensor can be manufactured. As another example, the sensor proximal end 18a can remain unchanged in a one-spring sensor, but the sensor distal end 18b attached to the sensor proximal end 18a can be half of the structure as split by axis A10 in FIG. 2C (e.g., the left or right side of the sensor 18). Such one-spring sensors 18 may or may not have sensor openings 22. If there is no opening 22, the sensor distal end 18b can still function as a barrier to prevent over insertion.

FIGS. 3A and 3B illustrate the device 10 in a variation of an attached configuration. To maintain this attached configuration, the device 10 can be taped against a non-device surface such as skin. Neither the tape nor the skin is illustrated in FIGS. 3A and 3B for purposes of clarity.

FIGS. 3A and 3B further illustrate that the device 10 can have an attached configuration when an external force 80 is applied by a non-device surface (e.g., skin) to the device first side 10c. Although not illustrated in FIGS. 3A and 3B, the device 10 can be attached to the skin, for example, with tape or glue to secure the device 10 in the attached configuration.

FIG. 3A illustrates that the housing contact surface 50 can abut the housing 14 when the device 10 is in an attached configuration. All or a portion of the skin contact surface 48 can contact skin when the device 10 is in an attached configuration, including, for example, the sensor proximal end 18a, the sensor distal end 18b, the spring region 26, the occluder arm 30, or any combination thereof. For example, for the sensor distal end 18b, the skin contact surface 48 of the sensor distal end third section 20c, the sensor distal end second section 20b, the sensor distal end first section 20a, the sensor distal end portion between the sensor distal end first section 20a and the sensor proximal end 18a, or any combination thereof, can contact skin when the device 10 is in an attached configuration. The sensor distal end first section 20a can extend from the sensor distal end third section 20c to the distal proximal end 18a and/or a distal end of the springs 26. The portion of the skin contact surface 48 that contacts tissue when the device 10 is in an attached configuration will depend on factors such as the insertion angle, the depth of needle insertion, and the location of the tape across the top of the device 10.

FIG. 3A further illustrates that the sensor second longitudinal axis A7 can be parallel to the device longitudinal axis A1 when the device 10 is in an attached configuration. In such variations, FIG. 3A illustrates that a portion of the sensor distal end 18b (e.g., the sensor distal end first section 20a) can extend at least partially in a longitudinal direction (e.g., in solely a longitudinal direction) toward device distal end 10b when the device 10 is in an attached configuration. As another example, the axis A7 can be angled from about 0 degrees to about 15 degrees relative to the device longitudinal axis A1 when the device 10 is an attached configuration, including every 1 degree increment within this range (e.g., 3 degrees). Non-parallel configurations (e.g., angles above 0 degrees) can occur where the skin surface is rough. A non-parallel configuration of the sensor axis A7 can also be transitory, for example, temporarily moving above 0 degrees when the patient moves and the needle 12 and/or the housing 14 slightly lifts off the skin or slightly moves further away from the skin (e.g., where the needle and the housing are not in contact with the skin other than at the needle insertion hole when the device 10 is in an attached configuration). The spring 26 can be biased to keep the sensor 18 in contact with the skin during patient movement such that the sensor distal terminal end 24 moves toward or past (e.g., via rotating) the device longitudinal axis A1 in the device configuration of FIG. 3A. The sensor axis A7 can return to a parallel orientation with the axis A1 once the patient has stopped moving (e.g., if the tape remains in place). Allowing the sensor 18 to move during patient movement gives the device 10 flexibility and can make movement for the patient more comfortable.

FIG. 3A further illustrates that the sensor first transverse axis A8 can be perpendicular to both the device longitudinal axis A1 and the sensor second longitudinal axis A7 when the device 10 is in an attached configuration. In such variations, FIG. 3A illustrates that a portion of the sensor distal end 18b (e.g., the sensor distal end second section 20b) can extend at least partially in a transverse direction (e.g., in solely a transverse direction). The sensor distal end second section 20b can also extend at least partially in a longitudinal direction toward the device distal end 10 and/or toward the device proximal end 10a when the device 10 is in an attached configuration. For example, the axis A8 can be angled about 0 degrees to about 150 degrees relative to axes A1 and/or A7 when the device 10 is an attached configuration, including every 1 degree increment within this range (e.g., 60 degrees, 90 degrees, 120 degrees). Angles less than 90 degrees can correspond to where the sensor distal end 18b extends at least partially in a longitudinal direction away from the needle tip and toward the device proximal end 10a when the device is in an attached configuration. Angles greater than 90 degrees can correspond to where the sensor distal end 18b extends at least partially in a longitudinal direction toward the needle tip and away from the device proximal end 10a when the device 10 is in an attached configuration. The angle between axes A7 and A8 can be the angle between the sensor distal end first and second sections 20a, 20b, respectively. The angle between axes A7 and A8 can be fixed such that the angle between the sensor distal end first and second sections 20a, 20b remains constant when the device 10 changes configurations. The portion of the sensor distal end 18b that extends transversely toward the needle 12 can comprise the over insertion barrier of the device 10.

FIG. 3A further illustrates that the sensor distal end 18b can extend beyond the needle hub 13 when the device 10 is in an attached configuration. For example, the sensor distal end 18b can extend a longitudinal distance 58 beyond a distal end of the needle hub, as measured to a proximal edge or surface of the sensor distal end 18b. The distance 58 can be, for example, about 1 mm to about 15 mm, including every 1 mm increment within this range (e.g., 1 mm, 2 mm, 3 mm).

FIG. 3A further illustrates that the sensor distal terminal end 24 can extend beyond the device longitudinal axis A1 when the device 10 is in an attached configuration. For example, the sensor distal terminal end 24 can extend a transverse distance 60 beyond the axis A1. The distance 60 can be, for example, 1.0 mm to about 7.5 mm, including every 0.1 mm increment within this range (e.g., 1.0 mm, 2.0 mm, 3.0 mm, 4.0 mm). The sensor distal terminal end 24 can be the sensor transverse terminal end. The sensor 18 can have a sensor longitudinal terminal end as well, which can be, for example, the distal edge or surface of the sensor distal end second section 20b. The sensor distal end 18b can be transversely below, partially adjacent to, and/or transversely beyond the shaft of the needle 12 (e.g., relative to an attachment orientation). For example, FIG. 3A illustrates that the that the sensor distal terminal end 24 can be above the shaft of the needle 12 when the device 10 is in an attached configuration.

The distances 58 and 60 can be the same or different from one another. For example, FIG. 3A illustrates that the distance 58 can be less than the distance 60, for example, by about 1 mm or about 2 mm. As another example, the distance 58 can be greater than the distance 60 (e.g., by about 1 mm to about 15 mm).

FIG. 3B illustrates that the device 10 can have an insert 17 (also referred to as a membrane insert). The insert 17 can be positioned in a housing space 51. The housing space 51 can define a housing channel. Part of the insert 17 can be inside the housing 14 and part of the insert 17 can be outside the housing 14. For example, the portion of the insert 17 outside of the housing 14 can define the connector 16. As another example, the insert 17 can be entirely within the housing 14. In such variations, the connector 16 can be attached to the housing 14, integrated with the housing 14, attached to the insert 17, or any combination thereof. The insert 17 can have ribs 49 that can grip the needle 12 to hold it in place. Glue can be in the space between the ribs. The ribs 49 can be on a proximal and/or distal end of the insert 17.

The insert 17 can be rigid, semi-rigid, flexible, resilient, and/or deformable. The insert 17 can be made of the same or a different material as the housing 14. The insert 17 can be softer, more flexible, more resilient, or more deformable than the housing 14. The insert 17 can be made of multiple materials. An insert first material can be softer, more flexible, more resilient, more deformable, or any combination thereof, than an insert second material. The insert 17 can have one or multiple thicknesses. For example, the insert 17 can have an insert first thickness 17a and an insert second thickness 17b less than the insert first thickness 17a. The insert first and second thicknesses 17a, 17b can be transverse thicknesses. The insert first thickness 17a can range from about 0.5 mm to about 3.0 mm, including every 0.1 mm increment within this range (e.g., about 1.5 mm). The insert second thickness 17b can range from about 0.1 mm to about 2.0 mm, including every 0.1 mm increment within this range (e.g., about 0.2 mm).

FIG. 3B further illustrates that the device 10 can have a resilient membrane 54 (also referred to as a deformable membrane and a deflectable membrane). The membrane 54 can be positioned adjacent the flow restrictor 28. The membrane 54 can be made of the same or different material as the insert 17. The membrane 54 can be attached to or integrated with the insert 17. A portion of the insert 17 can be the membrane 54. For example, the membrane 54 can be the portion of the insert made of the insert first material, the membrane 54 can be the portion of the insert 17 having the insert second thickness 17b, the membrane 54 can be the portion of the insert 17 adjacent the flow restrictor 28, or any combination thereof. As another example, the membrane 54 can be separate from the insert 17.

The insert 17 can have an outer surface and an inner surface. The insert outer surface can be attached to or in contact with an inner surface of the housing 14. The insert inner surface and/or an inner surface of the membrane 54 can define an insert channel 56 (also referred to as an insert flow channel, a housing conduit, and a device flow channel). The housing conduit 56 can extend from the housing proximal end 14a to the housing distal end 14b. The housing conduit 56 can be straight or curved. A proximal portion of the needle 12 can be in the insert channel 56. The insert inner surface can have a circular, elliptical, or polygonal transverse cross section (e.g., in a plane defined by axes A2 and A3). The insert outer surface can have a circular, elliptical, or polygonal transverse cross-section (e.g., in a plane defined by axes A2 and A3). The membrane 54 can be in the housing 14. The membrane 54 can be outside of the housing 14. The membrane 54 can be integrated with or attached to the housing. For example, the non-fluid contact side of the membrane 54 can form an exterior and/or interior surface of the housing 14.

Prior to the device 10 being inserted into tissue, the resilient membrane 54 can have a deformed shape from the spring 26 forcing the occluder 32 to press up against the membrane and force it into the housing conduit 56. When the device 10 is inserted into tissue, the resilient membrane 54 can undeform from the membrane first shape (e.g., occluded shape) to a membrane second shape (e.g., a non-occluded or less occluded shape). When the device 10 becomes dislodged, the occluder 32 can again deform the membrane 54 into the housing flow path 56 by the action of the spring 26, thereby decreasing the cross-sectional area of the housing flow path 56 in the occlusion area to restrict or terminate flow.

FIG. 3B further illustrates that the device 10 can have a device flow channel 62. The device flow channel 62 can include a needle flow channel 64 and one or both of the insert flow channel 56 and the housing channel 51. The device flow channel 62 can be in fluid communication with a tube flow channel 66 when the tube 8 is connected to the device 10. The housing conduit 56 (e.g., insert flow channel 56) can be parallel with the device longitudinal axis A1. The housing conduit 56 can be concentric with or offset from the device longitudinal axis A1. The needle flow channel 64 can be parallel with the device longitudinal axis A1. The needle flow channel 64 can be concentric with or offset from the device longitudinal axis A1. The needle 12 can be at an angle of about 0 degrees to about 45 degrees relative to the housing conduit 56 such that the needle flow channel 64 can be at an angle of about 0 degrees to about 45 degrees relative to the flow path of the housing conduit 56.

The device flow channel 62 can have a channel occlusion region 68 (also referred to as a conduit occlusion region). The channel occlusion region 68 of the device flow channel 62 can be at least partly defined by the membrane 54. For example, the membrane 54 can define at least part of the perimeter (e.g., circumference) of the transverse cross-sections of the device flow channel 62 in the occlusion region 68. The membrane 54 can define, for example, about 10% to about 75% of the perimeter, including every 1% increment within this range (e.g., 25% or less, 50% or less, 75% or less). FIG. 3B illustrates that the membrane 54 can define about 25% to about 50% (e.g., 50%) of the perimeter where the 25% to 50% forms or is part of the bottom half of the occlusion region 68 from a proximal to a distal end of the occlusion region 68. As another example, the channel occlusion region 68 can be entirely or at least partly defined by the insert 17 such that the insert 17 can partly or entirely define the perimeter (e.g., circumference) of the transverse cross-sections of the device flow channel 62 in the occlusion region 68. As yet another example, the perimeter (e.g., circumference) of the channel occlusion region 68 can be partly defined by the membrane 54, at least partly defined by the insert 17, at least partly defined by the housing 14, or any combination thereof, for example, about 0% to about 100% of the perimeter, depending on the combination, where all percentage permutations of these various perimeter combinations are hereby disclosed.

The membrane 54 can be opposite a housing surface, opposite an insert surface, opposite a housing protrusion (not shown), opposite an insert protrusion (not shown), or any combination thereof. One or more housing and/or insert protrusions can extend at least partially toward a longitudinal center of the device flow channel 62 in the housing 14, for example, toward a longitudinal center of the flow path defined by the housing conduit 56. The occluder 32 can be configured to engage the one or more protrusions when the moveable sensor 18 is in a closed configuration.

FIG. 3B further illustrates that the device 10 can have a housing opening 70 (also referred to as a housing window). The housing opening 70 can be on a device first, second, third, fourth, fifth, or sixth side, or any combination thereof. The orientation of these various sides is discussed above with reference to the sensor 18. For example, FIG. 3B illustrates that the housing opening 70 can be on the device first side 10c. The device first side 10c can be a bottom side of the device, for example, relative to when the device is in the attached configuration, where the bottom of the device 10 is the skin contact side of the device 10.

The housing opening 70 can have, for example, a circular, a polygonal (triangular, rectangular), a stadium, or an irregular shape. The housing opening 70 can be a hole (also referred to as a passageway) in a wall of the housing 14.

The housing opening 70 can have a housing opening longitudinal dimension 72 (also referred to as a housing opening first dimension). The housing opening longitudinal dimension 72 can range from about 2 mm to about 40 mm, including every 1 mm increment within this range (e.g., 10 mm). The housing opening longitudinal dimension 72 can be the maximum longitudinal dimension of the housing opening 70, for example, along an axis parallel to or at an angle with the device longitudinal axis A1.

Although not shown in FIG. 3B, the housing opening 70 can also have a housing opening first transverse dimension (also referred to as a housing opening second dimension). The housing opening first transverse dimension can range from about 2 mm to about 40 mm, including every 1 mm increment within this range (e.g., 10 mm). The housing opening first transverse dimension can be the maximum transverse dimension of the housing opening 70, for example, along an axis parallel to or at an angle with the device second transverse axis A3.

Although not shown in FIG. 3B, the housing opening 70 can also have a housing opening second transverse dimension (also referred to as a housing opening third dimension). The housing opening second transverse dimension can range from about 0.5 mm to about 10 mm, including every 0.1 mm increment within this range (e.g., 1.0 mm, 2.0 mm). The housing opening second transverse dimension can be the maximum transverse dimension of the housing opening 70, for example, along an axis parallel to or at an angle with the device first transverse axis A2. The housing opening second transverse dimension can correspond to the depth of the hole 70.

The housing opening first, second, and third dimensions can correspond to length, width, and height dimensions of a housing hole (e.g., hole 70), respectively. As another example, the housing opening first and second dimensions can be a housing opening radius dimension, and the housing opening third dimension can be the depth of the hole 70 (e.g., where the hole 70 is cylindrical).

The housing opening 70 can have a housing opening surface area. The housing opening surface area can be the area of the void defined by the housing opening 70. For example, the area of the void can be defined by a plane parallel to the plane defined by axes A1 and A3, or any other combination of axes A1, A2, and A3. The housing opening surface area can be, for example, 4 mm$^2$ to about 1,600 mm$^2$ or more, including every 1 mm$^2$ increment within this range (e.g., less than 25 mm$^2$, less than 50 mm$^2$, less than 100 mm$^2$, less than 200 mm$^2$, less than 500 mm$^2$).

The housing opening surface area can be less than a surface area of a housing surface. For example, the housing opening surface area can be a percentage of a surface area of a housing surface. The percentage can range, for example, from about 1% to about 90%, including every 1% increment within this range (e.g., less than 50%, less than 25%, less than 10%, less than 5%, 20%, 15%, 10%, 5%). The housing surface having the area that the area of the housing opening 70 is compared against can be on the same or a different side of the device 10 as the housing opening 70. For example, the housing surface can be on the device first side 10c (e.g., a bottom surface of the housing), the device second side 10d (e.g., a top surface of the housing), or another device side. When the two areas being calculated are on the same surface (e.g., bottom housing surface), the surface area of the hole 70 can be ignored or observed when calculating the surface area of the housing surface. For example, for a square bottom surface having a surface area of 900 mm$^2$ and a hole 70 having an opening surface area of 100 mm$^2$, the surface area of the bottom surface can be considered to be 1,000 mm$^2$ (hole 70 ignored) or 900 mm$^2$ (hole 70 observed) such that the housing opening surface area is about 10.0% (hole 70 ignored) or about 11.1% (hole 70 observed) of the surface area of the bottom surface. Another way of quantifying this is by stating that the housing opening surface area can be smaller than a housing surface through which the housing opening 70 extends. For example, the housing opening 70 that extends through a housing surface of the device 10 can have a housing opening surface area that is about 100 or more times smaller than the surface area of the housing surface through which the housing opening 70 extends, or more narrowly, about 50 or more times smaller, or more narrowly, about 25 or more times smaller, or more narrowly, about 10 or more times smaller (e.g., 14 times smaller, 10 times smaller, 5 times smaller).

Having a housing opening 70 with a size smaller than that of the size of the housing surface through which the housing opening 70 extends (e.g., a bottom surface or a skin contact surface of the device 10) can desirably allow the housing 14 to have a larger surface area to contact tissue which can be more comfortable for patients when the device is taped to their skin since the larger device surface area can more equally distribute the force of the device 10 against the skin, thereby being less likely to "dig" into tissue or leave an sensitive skin impression or indent after removal. This can be especially beneficial for patients undergoing hemodialysis treatment since the device 10 can be attached to their skin for hours at a time, for example, about 3 hours to about 6 hours. A small housing opening 70 can also allow the housing 14 to maintain a more secure seal around the device flow path 62 in the housing 14, for example, around the housing conduit 56, than if the housing space 51 were exposed by a large hole.

However, in some variations, the hole 70 can be larger than the than that of the size of the housing surface through which the housing opening 70 extends (e.g., opposite from the "less than" and "smaller" ratios/relationships above). In such variations, for a housing surface configured to contact skin, for example, a housing bottom surface, the hole 70 can be so large that the housing bottom surface can be an annular flange extending around the perimeter of the housing 14. For larger openings 70, the opening 70 can be a housing recess such that only a portion of the opening extends through a housing wall and exposes the housing space 51. Having such "larger" opening hole 70 sizes can be useful to lift the housing conduit 56 further away from the skin when attached to the patient. Where the opening hole 70 forms a large recess, a skin warming or cooling pack can be inserted in the recess and be in contact with the patient's skin during treatment to increase patient comfort. Such warm and cold packs can also help control vasodilation and vasoconstriction should such control be needed or helpful for the particular patient at hand.

The housing opening 70 can advantageously give the flow restrictor 28 access to the housing conduit 56 while maintaining a fluid tight seal between the tube 8 and the tip of the needle 12. The flow restrictor 28 can move within or through the housing opening 70, for example, to deform the membrane 54 to occlude flow through the housing conduit 56.

For example, the housing opening 70 can expose the membrane 54 by creating a passageway through a housing wall (e.g., a housing wall having an outer surface configured to contact skin). The housing opening 70 can open toward (e.g., face toward) the non-device surface (also referred to as the non-sensor surface and skin) when the sensor 18 is in the open configuration and the device 10 is attached to the non-device surface. The membrane 54 can be closer to the device longitudinal axis A1 than the housing opening 70. The membrane 54 can be closer to the longitudinal axis of the device flow path 62 than the housing opening 70. Some or all the membrane 54 can be in the housing opening 70. At least a portion of the membrane 54 can be attached to or integrated with an edge or surface defining the housing opening 70.

Some or all of the flow restrictor 28 can be in the housing opening 70 when the device 10 is in an attached configuration (also referred to as when the sensor 18 is in an open configuration). For example, at least a portion of the flow restrictor 28 can be in an opening plane defined between edges or surfaces of the housing opening 70. The opening plane can be, for example, a plane parallel to the plane defined by axes A1 and A3, or any other combination of axes A1, A2, and A3. For example, FIG. 3B illustrates that the occluder 32 can be in the housing opening 70 when the device 10 is in the attached configuration. Although not shown, a portion of the occluder arm 30 can also extend into the housing opening 70 when the device 10 is in an attached configuration.

FIG. 3B further illustrates that a portion of the occluder 32 (e.g., the tip of the occluder 32) can be in the housing 14 (e.g., in housing space 51) when the device 10 is in an attached configuration, for example, by extending past the housing opening 70 (e.g., past an inner opening plane of the opening window 70, where the inner opening plane can be defined between edges or surfaces that comprise interior edges, surfaces, or boundaries of the housing 14). Although not shown, a portion of the occluder arm 30 can also extend into the housing 14 (e.g., in housing space 51) when the device 10 is in an attached configuration.

FIG. 3B further illustrates that the tip of the occluder 32 can be in contact with the membrane 54 when the device 10 is in an attached configuration. Contact from the occluder 32 (e.g., the occluder tip) may or may not deform the membrane 54 when the sensor 18 is in an open configuration. For example, the occluder 32 in FIG. 3B is shown contacting but not deforming the membrane 54 when the sensor 18 is in an open configuration. However, in other variations, the occluder tip can deform the membrane 54 or can be spaced apart from the membrane 54 with a gap when the when the sensor 18 is in an open configuration. Such a deformation or gap can have a deformation/gap dimension of about 0.5 mm to about 2.5 mm, including every 0.1 mm increment within this range. The deformation/gap dimension can be measured along an axis parallel to or at an angle with a device axis such as axis A1, A2, or A3. For example, FIG. 3B illustrates that the deformation/gap dimension can be measured along an axis parallel to the device first transverse axis A2.

In variations where the occluder tip deforms the membrane 54 when the sensor 18 is in an open configuration, the inner surface of the membrane 54 that defines the housing conduit 56 can be deformed by the deformation dimension (e.g., by about 0.5 mm to about 2.5 mm or more) toward a housing surface opposite the occluder 32, toward a surface of the housing conduit 56 opposite the occluder 32, toward the device longitudinal axis A1, toward a longitudinal axis of the fluid conduit 56, or any combination thereof.

In variations where there is a gap between the occluder tip and the membrane 54 when the sensor 18 is in an open configuration, the gap dimension (e.g., about 0.5 mm to about 2.5 mm or more) can be measured between an outer surface of the membrane 54 (e.g., facing away from the housing space 51) and the occluder tip.

The occluder 32 can be attached to or integrated with the membrane 54. The occluder 32 can float relative to the membrane 54 such that the occluder 32 is not permanently attached to the membrane 54.

The occluder arm 30 can be in or outside of the housing space 51 when the device 10 is in an attached configuration. The occluder arm 30 can be in or outside of the housing window 70 when the device 10 is in an attached configuration. For example, FIG. 3B illustrates that the occluder arm 30 can be outside of (e.g., below) the housing opening 70 (e.g., below an outer opening plane of the housing window 70, where the outer opening plane can be defined between edges or surfaces that comprise outer edges, surfaces, or boundaries of the housing 14, for example, those edges surfaces or boundaries that are farther from the device longitudinal axis A1 than the edges, surfaces or boundaries associated with the inner opening plane of the housing window 70).

FIG. 3B further illustrates that the occluder arm 30 can extend over some or all of the housing opening 70 when the device 10 is in an attached configuration. The occluder arm 30 can extend along, for example, about 10% to about 90% of the housing opening longitudinal dimension 72. For example, where the housing opening longitudinal dimension 72 is 10 mm and the occluder arm 30 extends over 75% of the housing opening longitudinal dimension, the occluder arm 30 can extend 7.5 mm over the housing opening 70 along the housing opening longitudinal dimension 72 when the device 10 is in an attached configuration.

FIG. 3B further illustrates that when the sensor 18 is in an open configuration, the occluder axis A9 can be at an occluder angle of about 30 degrees to about 150 degrees relative to the device longitudinal axis A1. For example, FIG. 3B illustrates that the occluder angle can be 90 degrees, or perpendicular to the device longitudinal axis A1. Occluder angles less than 90 degrees can correspond to where the occluder 32 extends at least partially in a longitudinal direction toward the device distal end 10b or the sensor distal end 18b when the sensor 18 is in an open configuration. Occluder angles greater than 90 degrees can correspond to where the occluder 32 extends at least partially in a longitudinal direction toward the device proximal end 10a or the sensor proximal end 18a when the sensor 18 is in an open configuration.

Although not illustrated in FIG. 3B, the flow path defined by the housing conduit 56 can have one or more tapers. For example, the flow path defined by the channel occlusion region 68 can be tapered from a first transverse cross-sectional area to a second transverse cross-sectional area less than the first cross-sectional area, for example, such that the tapered region of the channel occlusion region 68 forms a frusto-conical shaped flow path. The outer surface of the conduit defining the tapered flow path (e.g., housing conduit 56) may or may not have a corresponding taper as well. The first transverse cross-sectional area can be closer to the proximal end of the device flow channel 62 than the second transverse cross-sectional area. The flow path can be tapered so that it can be easier or take less force to occlude the flow path with spring action of the flow restrictor 28. For example, the occluder 32 can be configured to deform the membrane 54 at the location of the second transverse cross-sectional of the channel occlusion region. As another example, the occluder 32 can be configured to deform the membrane 54 about 1 mm to about 20 mm longitudinally away from the location of the second transverse cross-sectional in a direction toward the distal end of the device flow path 62, including every 1 mm increment within this range (e.g., 5 mm, 10 mm). The membrane 54 can define some or all of the taper. The first cross-sectional area can be within or outside of the channel occlusion region 68.

As another example, the foregoing taper can be a first taper, and the flow path defined by the housing conduit 56 can have a second taper. For example, the flow path defined by the channel occlusion region 68 can be tapered from the second transverse cross-sectional area to a third transverse cross-sectional area greater than the second cross-sectional area, for example, such that the tapered region of the channel occlusion region 68 forms a second frusto-conical shaped flow path. The first and third transverse cross-sectional areas can have the same or different cross-sectional areas as each other. The outer surface of the conduit defining the second tapered flow path (e.g., housing conduit 56) may or may not have a corresponding taper as well. The second transverse cross-sectional area can be closer to the proximal end of the device flow channel 62 than the third transverse cross-sectional area. The second frusto-conical shaped flow path can be a mirror image the frusto-conical shaped flow path between the first and second transverse cross-sectional areas (also referred to as the first frusto-conical shaped flow path), for example, as reflected across the second transverse cross-sectional area. The first cross-sectional area can be within or outside of the channel occlusion region 68. As yet another example, the second transverse cross-sectional area between the first and third transverse cross-sectional areas can be elongated such that a channel having a constant, a less tapered, or more tapered cross flow path can extend between the first and second tapered flow paths (e.g., between the first and second frusto-conical shaped flow paths). This elongated channel can desirably give the occluder 32 a smaller cross-sectional area to partially or fully occlude.

FIGS. 4A and 4B illustrate the device 10 in a variation of an occluded configuration as described above with reference to FIG. 1.

FIGS. 4A and 4B further illustrate that the device 10 can change from an attached configuration with the sensor 18 in an open position to an occluded configuration with the sensor 18 in a closed position when the external force 80 is reduced or entirely removed from the sensor first contact surface 48, for example, as shown by arrow 82. FIGS. 4A and 4B also illustrate the external force 80 to show a variation of an external force that can be applied to the sensor first contact surface 48 of the device 10 to change the shape of the device 10 from an occluded configuration with the sensor 18 in a closed position to an attached configuration with the sensor 18 in an open position. The external force 80 illustrated in FIGS. 4A and 4B is not being applied to the device 10. In other variations, the force 80 is being applied to the device 10 in FIGS. 4A and 4B but with a magnitude that is less than that of the magnitude shown in FIGS. 3A and 3B, for example as shown coupled with the reduction or elimination of force arrow 82.

FIGS. 4A and 4B further illustrate that the pre-attached and dislodged configurations of the device 10 can be the same. However, the pre-attached and dislodged configurations can also be different from each other.

FIGS. 4A and 4B further illustrate that the sensor distal end 18b can move (e.g., arrow 84) away from the device longitudinal axis A1 when the external force 80 is reduced (e.g., arrow 82) or eliminated (e.g., arrow 82). The sensor distal end 18b can rotate and/or translate relative to the device longitudinal axis A1. For example, the sensor distal end 18b can rotate (e.g., arrow 84) away from the device longitudinal axis A1 when the external force 80 is reduced (e.g., arrow 82) or eliminated (e.g., arrow 82).

FIG. 4B further illustrates that the flow restrictor 28 can move (e.g., arrow 86) toward a housing surface opposite the occluder 32, toward a surface of the housing conduit 56 opposite the occluder 32, toward the device longitudinal axis A1, toward a longitudinal axis of the fluid conduit 56, or any combination thereof. The flow restrictor 28 can rotate and/or translate relative to any of these features. For example, FIG. 4B illustrates that the occluder 32 can rotate (e.g., arrow 86) toward a housing surface opposite the occluder 32, toward a surface of the housing conduit 56 opposite the occluder 32, toward the device longitudinal axis A1, toward a longitudinal axis of the fluid conduit 56, or any combination thereof.

The occluder 32 can move (e.g., arrow 86) into the device flow path 62, for example, in the channel occlusion region 68. Some of the occluder 32 (e.g., the tip of the occluder 32) can rotate past the device longitudinal axis A1. FIG. 4B illustrates that the occluder 32 can pierce the membrane 54 and rotate directly into the flow path to partially or fully occlude flow through the device flow channel 62 when the device 10 is in a dislodged configuration. The membrane 54 can self-seal around the base of the occluder (e.g., the occluder portion in contact with the membrane) such that fluid does not flow through the opening in the membrane 54. The membrane 54 can reseal against itself if the occluder 32 is removed from the flow path 62 and membrane 54, for example, if the device 10 is reattached to the skin.

FIG. 4B further illustrates that the sensor second longitudinal axis A7 can be at an angle relative to the device longitudinal axis A1 of about 10 degrees to about 75 degrees when the device 10 is in a non-attached configuration, including every 1 degree increment within this range (e.g., 30 degrees, 40 degrees, 50 degrees). In such variations, FIG. 4B illustrates that a portion of the sensor distal end 18b (e.g., the sensor distal end first section 20a) can extend at least partially in a longitudinal direction toward device distal end 10b and at least partially in a transverse direction away from the device longitudinal axis A1 when the device 10 is in a non-attached configuration. The sensor axis A7 can return to a parallel or less angled orientation relative to axis A1 when an external force (e.g., arrow 80) is applied to the sensor 18.

FIG. 4B further illustrates that the sensor first transverse axis A8 can be at an angle relative to the device longitudinal axis A1 of about 10 degrees to about 75 degrees when the device 10 is in a non-attached configuration, including every 1 degree increment within this range (e.g., 30 degrees, 40 degrees, 50 degrees). In such variations, FIG. 4B illustrates that a portion of the sensor distal end 18b (e.g., the sensor distal end second section 20b) can extend at least partially in a longitudinal direction toward device distal end 10b and at least partially in a transverse direction toward the device longitudinal axis A1 when the device 10 is in a non-attached configuration. The sensor distal end second section 20b can also extend at least partially in a longitudinal direction toward the device distal end 10 and/or toward the device proximal end 10a when the device 10 is in a non-attached configuration. The sensor axis A8 can return to a perpendicular or less angled orientation relative to axis A1 when an external force (e.g., arrow 80) is applied to the sensor 18.

FIG. 4B further illustrates that when the sensor 18 is in a closed configuration, the occluder axis A9 can be at an occluder angle of about 30 degrees to about 150 degrees relative to the device longitudinal axis A1. For example, FIG. 4B illustrates that the occluder angle can be about 50 degrees, about 60 degrees, or about 70 degrees relative to the device longitudinal axis A1. In such variations, FIG. 4B illustrates that the occluder 32 can extend at least partially in a longitudinal direction toward device distal end 10b and at least partially in a transverse direction away from the device longitudinal axis A1 when the device 10 is in a non-attached configuration. The sensor axis A9 can return to a perpendicular or less angled orientation relative to axis A1 when an external force (e.g., arrow 80) is applied to the sensor 18.

FIG. 4B further illustrates that the sensor distal terminal end 24 can be a dimension 90 away from the device longitudinal axis A1 when the sensor 18 is in a closed position. The dimension 90 can be measured along an axis perpendicular to the device longitudinal axis A1 and can range from about 1 mm to about 30 mm, including every 1 mm increment within this range (e.g., 5 mm, 10 mm, 15 mm). The dimension 90 can be the maximum dimension that the distal terminal end 24 can be from the device longitudinal axis A1 when the sensor 18 is in a closed configuration.

Figure 4C:
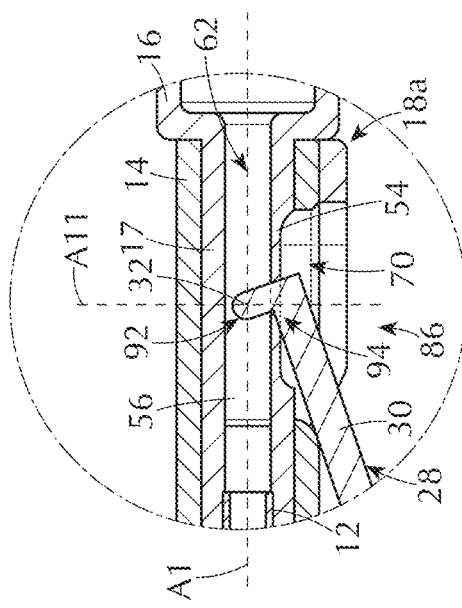
FIG. 4C is a magnified view of the tissue access device of FIG. 4B at section 4C-4C.

FIG. 4C illustrates that the device 10 can be partially occluded when the sensor 18 is in a closed position. For example, FIG. 4C illustrates that there can be a gap 92 between the occluder 32 a surface of the housing conduit 56 (e.g., a surface of the insert 17, a surface of the housing 14). The gap 92 can have a dimension of about 0.1 mm to about 2.0 mm or more, including every 0.1 mm increment within this range (e.g., 0.8 mm, 1.0 mm), for example, as measured along axis A11 between the occluder 32 and a surface defining the housing conduit 56. Axis A11 can be perpendicular to the device longitudinal axis A1.

FIG. 4C further illustrates that the device 10 can restrict fluid flow through the device channel 62 by decreasing a channel cross-sectional area from a first cross-sectional area (e.g., FIG. 3B) to a second cross-sectional area (e.g., FIG. 4B) less than the first cross-sectional area. The second cross-sectional area can be about 1% to about 100% less than the first cross-sectional area, including every 1% increment within this range, where 100% can correspond to complete blockage of the channel in one or multiple channel cross-sections. For example, FIG. 3B illustrates that the first cross-sectional area can be completely non-occluded, and FIG. 4C illustrates that the second cross-sectional area can be between about 80% to about 95% smaller relative to the first cross-sectional area, including every 1% increment within this range (e.g., 90%, 95%). The first cross-sectional area can correspond to the cross-section of the flow path when the device 10 is in an attached configuration and the second cross sectional area can correspond to when the device 10 is in a non-attached configuration (e.g., a dislodged configuration).

The flow restrictor configuration in FIG. 4C can be a default configuration of the flow restrictor 28. For example, the spring 26 can be biased to move the occluder 32 and the occluder arm 30 into the positions shown in FIG. 4C when no external force (e.g., force 80) is applied to the sensor 18 (e.g., to the sensor distal end 18b). In other variations, the flow restrictor configuration in FIG. 4C can correspond to when an external force (e.g., force 80) has been reduced (e.g., arrow 82) but not completely removed from the sensor first contact surface 48. The device 10 can still occlude about 80% to about 95% of the flow path 56 and effectively help the patient by reducing fluid loss or delivery in such partial dislodgement scenarios.

Figure 4E:
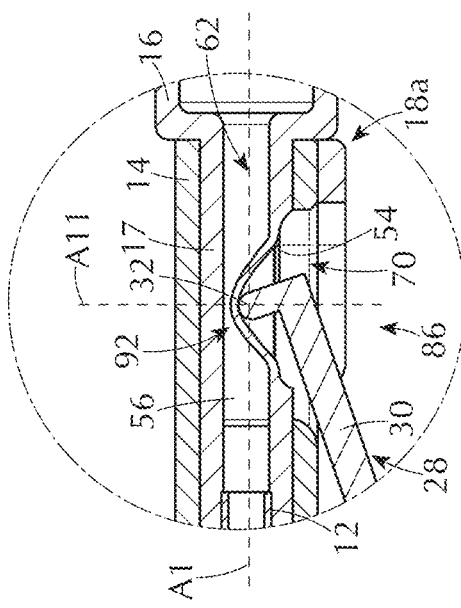
FIG. 4E illustrates another variation of the occluded configuration of the tissue access device of FIG. 3B at section 4C-4C.
Figure 4D:
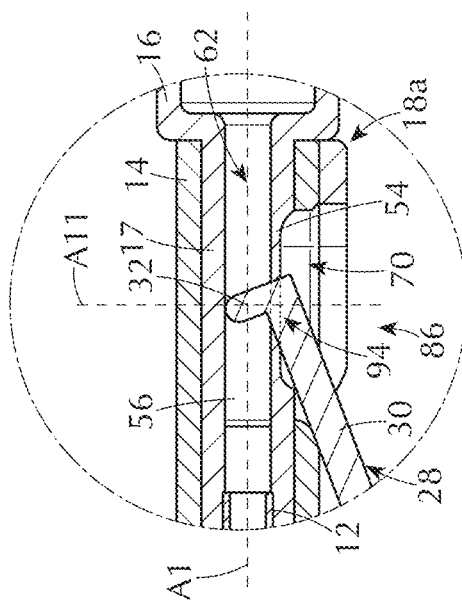
FIG. 4D illustrates another variation of the occluded configuration of the tissue access device of FIG. 4B at section 4C-4C.

FIG. 4D illustrates that the flow restrictor 28 can fully occlude the housing conduit 56, for example, by moving (via the spring 26) the occluder 32 further into the flow path 56 during occlusion of the device 10. In such variations, the second cross-sectional area can be about 100% relative to a first cross sectional area.

The flow restrictor configuration in FIG. 4D can be a default configuration of the flow restrictor 28. For example, the spring 26 can be biased to move the occluder 32 and the occluder arm 30 into the positions shown in FIG. 4D when no external force (e.g., force 80) is applied to the sensor 18 (e.g., to the sensor distal end 18b).

FIGS. 4C and 4D illustrate that the occluder 32 can pierce and reseal around the membrane 54 when the sensor is in the closed position. The pierce point is shown as element 94.

FIG. 4E illustrates that the flow restrictor 28 (e.g., the occluder 32 and/or the occluder arm 30) can deflect the membrane 54 into the housing conduit 56 to occlude flow through the device 10, for example, in a direction away from the window 70. The occluder 32 can deflect the membrane 54 into the housing conduit 56 during occlusion of the device 10. The gap 92 can have a dimension of about 0.1 mm to about 2.0 mm or more, including every 0.1 mm increment within this range (e.g., 0.8 mm, 1.0 mm), for example, as measured along axis A11 between the occluder 32 and a surface defining the housing conduit 56 (e.g., a surface of the insert 17 and/or a surface of the housing 14). Axis A11 can be perpendicular to the device longitudinal axis A1 With the gap 92, FIG. 4E illustrates that the second cross-sectional area can be between about 80% to about 95% smaller relative to the first cross-sectional area (e.g., FIG. 3B), including every 1% increment within this range (e.g., 90%, 95%).

The flow restrictor configuration in FIG. 4E can be a default configuration of the flow restrictor 28. For example, the spring 26 can be biased to move the occluder 32 and the occluder arm 30 into the positions shown in FIG. 4E and deform the membrane 54 into the housing conduit 56 when no external force (e.g., force 80) is applied to the sensor 18 (e.g., to the sensor distal end 18b). In other variations, the flow restrictor configuration in FIG. 4E can correspond to when an external force (e.g., force 80) has been reduced (e.g., arrow 82) but not completely removed from the sensor first contact surface 48. The device 10 can still occlude about 80% to about 95% of the flow path 56 and effectively help the patient by reducing fluid loss or delivery in partial dislodgement scenarios.

Figure 4F:
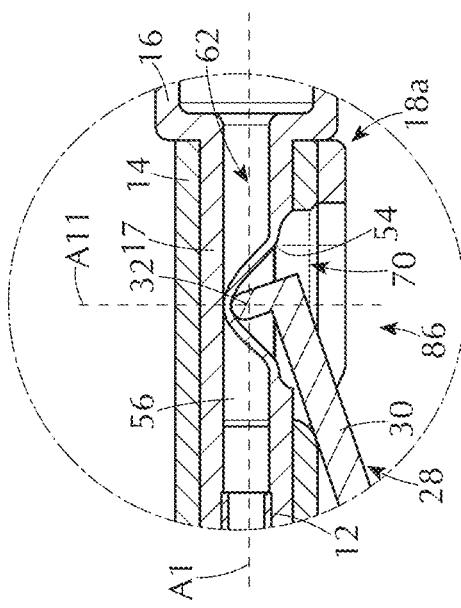
FIG. 4F illustrates another variation of the occluded configuration of the tissue access device of FIG. 3B at section 4C-4C.

FIG. 4F illustrates that the flow restrictor 28 (e.g., the occluder 32 and/or the occluder arm 30) can fully occlude the housing conduit 56, for example, by moving (via the spring 26) the occluder and membrane 32, 54 further into the flow path 56. The membrane 54 and the occluder 32 (e.g., on the proximal side of the sensor 18) is shown fully pressed into the flow path 56, for example, via the spring 26. For example, the force to push this member upward can come from the curved spring region portion of the central part of the sensor 18. A portion (e.g., an apex) of the membrane 54 in the deformed configuration can contact a surface that defines at least a portion of the housing conduit (e.g., a surface of the insert 17 and/or a surface of the housing 14) when the sensor 18 is in a closed position. When the occluder 32 pushes the membrane 54 into contact with another surface, the second cross-sectional area can be about 100% less than the first cross sectional area such that the housing conduit 56 is fully occluded.

The flow restrictor configuration in FIG. 4F can be a default configuration of the flow restrictor 28. For example, the spring 26 can be biased to move the occluder 32 and the occluder arm 30 into the positions shown in FIG. 4F when no external force (e.g., force 80) is applied to the sensor 18 (e.g., to the sensor distal end 18b).

The spring 26 can have a spring constant k such that the weight of the device 10 is configured to be insufficient to move the sensor 18 from a closed position to a partially open or a fully open position. This feature can prevent further fluid loss should the device 10 become dislodged and fall onto a surface (e.g., a floor or a patient's lap) and land such that the device is resting on the flow restrictor 28 (e.g., resting on the sensor distal end 18b).

FIGS. 3A and 4A illustrate that the spring 26 can be outside of the housing 14 when the sensor is in an open configuration and in a closed configuration, respectively. For example, when the device 10 is in an attached configuration, the spring 26 can be between the housing 14 and the skin, and when the device 10 is in a pre-attached or dislodged configuration, the spring 26 can be between the housing and the environment. In other variations, some or all of the spring can be inside the housing 14 when the device 10 is in the attached configuration and/or when the device 10 is in the pre-attached or dislodged configuration. FIGS. 3A and 3B further illustrate that that a first end of the spring 26 (e.g., the end of the spring closer to the device proximal end 10a) can be closer to the device longitudinal axis A1 when the device 10 is in an attached configuration (e.g., FIG. 3A) than when the device 10 is in a pre-attached or dislodged configuration (e.g., FIG. 4A).

FIGS. 3A-4B illustrate that the sensor distal end first section 20a can extend parallel to the device longitudinal axis A1 when the device is in an attached configuration (e.g., FIGS. 3A and 3B) and away from the device longitudinal axis A1 when the device 10 is in a pre-attached or dislodged configuration (e.g., FIGS. 4A and 4B). As another example, the sensor distal end first section 20a can extend more away from the device longitudinal axis A1 when the device 10 is in a pre-attached or dislodged configuration than when the device 10 is in an attached configuration (e.g., by about 5 degrees to about 60 degrees more, including every 1 degree increment within this range).

FIGS. 3A-4B illustrate that the sensor distal end second section 20b can extend parallel to the device first transverse axis A2 when the device is in an attached configuration (e.g., FIGS. 3A and 3B) and away from the device first transverse axis A2 when the device 10 is in a pre-attached or dislodged configuration (e.g., FIGS. 4A and 4B). As another example, the sensor distal end second section 20b can extend more away from the device first transverse axis A1 when the device 10 is in a pre-attached or dislodged configuration than when the device 10 is in an attached configuration (e.g., by about 5 degrees to about 60 degrees more, including every 1 degree increment within this range).

FIGS. 3A-4B illustrate that the sensor distal end 18b (e.g., the needle over insertion barrier 20b) can be closer to a longitudinal access of the needle 12 when the device 10 is in an attached configuration (e.g., FIGS. 3A and 3B) than when the device 10 is in a pre-attached or dislodged configuration (e.g., FIGS. 4A and 4B). FIGS. 3A-4B further illustrate that the sensor distal end 18b (e.g., the needle over insertion barrier 20b) can be closer to the tip of the needle 12 or to a device distal end 10b when the device 10 is in an attached configuration (e.g., FIG. 3A) than when the device 10 is in a pre-attached or dislodged configuration (e.g., FIG. 4A).

FIGS. 3A-4B illustrate that a needle over insertion barrier (e.g., section 20b) can be closer to a longitudinal access of the needle 12 when the device 10 is in an attached configuration (e.g., FIGS. 3A and 3B) than when the device 10 is in a pre-attached or dislodged configuration (e.g., FIGS. 4A and 4B). FIGS. 3A-4B further illustrate that a needle over insertion barrier (e.g., section 20b) can be closer to the tip of the needle 12 or to a device distal end 10b when the device 10 is in an attached configuration (e.g., FIG. 3A) than when the device 10 is in a pre-attached or dislodged configuration (e.g., FIG. 4A). Additionally or alternatively, the device 10 can have an over insertion barrier that remains in a fixed position when the sensor 18 moves between open and closed configurations. For example, the device 10 can have an over insertion barrier attached to or integrated with the housing 14 and/or the needle hub 13 as described above.

FIGS. 3A-4B illustrate that the sensor 18 (e.g., movable footplate) has a sensor first configuration when the sensor first contact surface 48 applies a first force to a non-sensor surface (e.g., skin) and a sensor second configuration when the sensor first contact surface 48 applies a second force less than the first force to the non-sensor surface. The spring 26 can be biased to move the moveable sensor 18 from the sensor first configuration to the sensor second configuration when the force applied by the sensor first contact surface 48 against the non-sensor surface changes from the first force to the second force. As another example, the spring 26 can be biased to move the sensor 18 from the sensor first configuration to the sensor second configuration when the first force decreases to the second force. The second force can be 0 Newtons.

At least a first portion of the occluder 32 can occlude the housing conduit 56 when the movable sensor 18 is in the sensor second configuration. At least a second portion of the occluder 32 can be in the housing opening 70 when the movable sensor 18 is in the sensor second configuration and outside the housing opening 70 when the movable sensor 18 is in the sensor first configuration.

The sensor distal end 18*b* can have a barrier configured to prevent over insertion of the needle 12 into tissue (e.g., into a vessel). At least a portion of the barrier can be closer to the needle 12 when the moveable sensor 18 is in the sensor first configuration than when the moveable sensor 18 is in the sensor second configuration. At least a portion of the barrier can abut or be next to a side of the needle 12 when the moveable sensor 18 is in the sensor first configuration. At least a portion of the barrier can be closer to the needle 12 when the moveable sensor 18 is in the sensor first configuration than when the moveable sensor 18 is in the sensor second configuration The sensor distal end 18*b* can have a curved surface (e.g., curved surface 21) configured to reduce friction against the non-sensor surface when the needle 12 is inserted into tissue (e.g., into a vessel). At least a portion of the curved surface can be closer to the needle 12 when the moveable sensor 18 is in the sensor first configuration than when the moveable sensor 18 is in the sensor second configuration.

The occluder 32 can be configured to at least partly occlude the housing conduit 56 when the moveable sensor 18 is in the sensor second configuration.

Flow through the housing conduit 56 can be about 1% to about 100% less when the moveable sensor 18 is in the sensor second configuration than when the moveable sensor 18 is in the sensor first configuration, including every 1% increment within this range (e.g., 80%, 90%, 95%, 97%, 100%).

A housing conduit cross-sectional area can be decreased by about 1% to about 100% when the moveable sensor moves from the sensor first configuration to the sensor second configuration, including every 1% increment within this range (e.g., 80%, 90%, 95%, 97%, 100%).

The occluder 32 can be closer to a surface of the housing conduit 56 opposite the deformable membrane 54 when the moveable sensor 18 is in the sensor second configuration than when the moveable sensor is in the sensor first configuration. The spring 26 can be biased to move the occluder 32 closer to the surface of the housing conduit 56 when the movable sensor 18 moves from the sensor first configuration to the sensor second configuration The deformable membrane 54 can be deformed by the occluder 32 when the moveable sensor 18 is in the sensor second configuration. A surface of the deformable membrane can be closer to a housing conduit surface when the moveable sensor 18 is in the sensor second configuration than when the moveable sensor 18 is in the sensor first configuration The deformable membrane 54 can be less deformed or deflected by the occluder 32 when the moveable sensor 18 is in the sensor first configuration than when the moveable sensor 18 is in the sensor second configuration.

The deformable membrane 54 may not deformed by the occluder 32 when the moveable sensor 18 is in the sensor first configuration.

The sensor distal end 18*b* can be closer to the needle 12 and the housing conduit 56 when the moveable sensor 18 is in the sensor first configuration than when the sensor 18 is in the sensor second configuration. The spring 26 can be biased to move the sensor distal end 18*b* away from the needle 12 and the housing conduit 56 when the movable sensor 18 moves from the sensor first configuration to the sensor second configuration.

The sensor distal end 18*b* (e.g., the sensor distal end second section 20*b*) can have a sensor opening 22. A portion of the needle 12 can be in the sensor opening 22 when the movable sensor 18 is in the sensor first configuration and outside the sensor opening 22 when the movable sensor 18 is in the sensor second configuration.

The sensor distal end 18*b* can have a barrier configured to prevent over insertion of the needle into a vessel.

At least a portion of the sensor proximal end 18*a* can extend along a direction parallel to the device longitudinal axis A1 when the moveable sensor is in the sensor first and second configurations. At least a portion of the sensor distal end 18*b* can extend along a direction parallel to the device longitudinal axis A1 when the moveable sensor 18 is in the sensor first configuration and a direction angled relative to the device longitudinal axis A1 when the moveable sensor 18 is in the sensor second configuration The housing 14 can have a housing first side and a housing second side opposite the housing first side. The housing first side can be closer to the sensor first contact surface than the housing second side. The housing window 70 can be on the housing first side such that the housing window 70 faces toward the non-sensor surface (e.g., skin) when the moveable sensor 18 is in the sensor first configuration.

The sensor 18 can have a sensor second contact surface 50. The sensor second contact surface 50 can be closer to the housing 14 when the moveable sensor 18 is in the sensor first configuration than when the moveable sensor 18 is in the sensor second configuration.

The device distal end 10*b* can be moveable relative to the device proximal end 10*a*. For example, the device distal end 10*b* can be longitudinally and/or transversely moveable along the device longitudinal axis A1 relative to the device proximal end 10.

The needle 12 can be longitudinally and/or transversely moveable along the device longitudinal axis A1.

The needle 12 can be retractable into the housing 14 or into a needle channel adjacent the housing 14 such that the needle 12 has a non-retracted position and a retracted position. The needle distal end (e.g., the tissue cutting tip) can be closer to the housing proximal end 14*a* when the needle 12 is in the retracted position than when the needle 12 is in the non-retracted position.

At least a portion of the needle 12 can be outside the housing 14 or the needle channel adjacent the housing 14 in the non-retracted position and inside the housing 14 or the needle channel adjacent the housing 14 in the retracted position.

The needle distal end (e.g., the tissue cutting tip) can be the distal terminal end of the device 10 when the needle 12 is in at least one of the non-retracted position and the retracted position.

The needle 12 can be retracted by a user after the device becomes dislodged from an attached configuration. A button on the housing 14 can be pr The needle 12 can automatically retract when the device becomes dislodged from an attached configuration. For example, the sensor can be connected to the needle 12 (e.g., the base of the needle 12). The spring 26 can be biased to retract the needle 12 when the sensor changes from an open position to a closed position following initial insertion of the needle 12. The spring 26 can be connected to the needle with a link (not shown).

Figure 5:
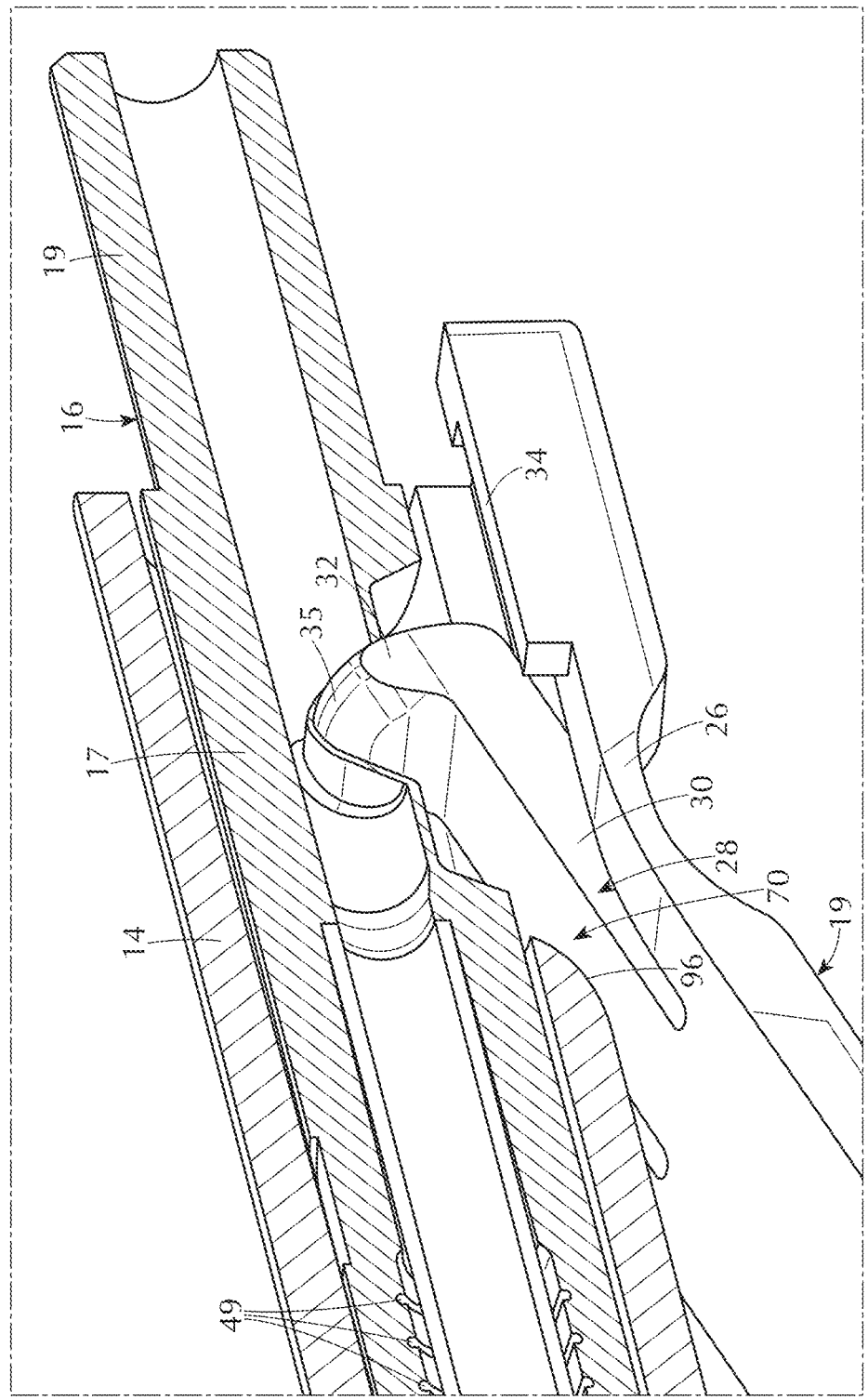
FIG. 5 is a magnified perspective view of the occluded configuration of the tissue access device of FIG. 4E.

FIG. 5 illustrates that a housing surface 96 defining the housing window 70 can be tapered to allow the occluding arm 30 to move the occluder 32 into to deflect the membrane 54 into the housing conduit 56 to occlude the device 10.

FIG. 5 further illustrates that the occluder 32 can have an occluder terminal end 35 having a curved surface configured not to puncture the membrane 54 when the sensor 18 is in a closed configuration.

FIG. 5 further illustrates that the connector 16 can comprise a nipple 19. The nipple 19 can be integrated with or attached to the insert 17. The tube 8 can be connected to the nipple 19.

Figure 6A:
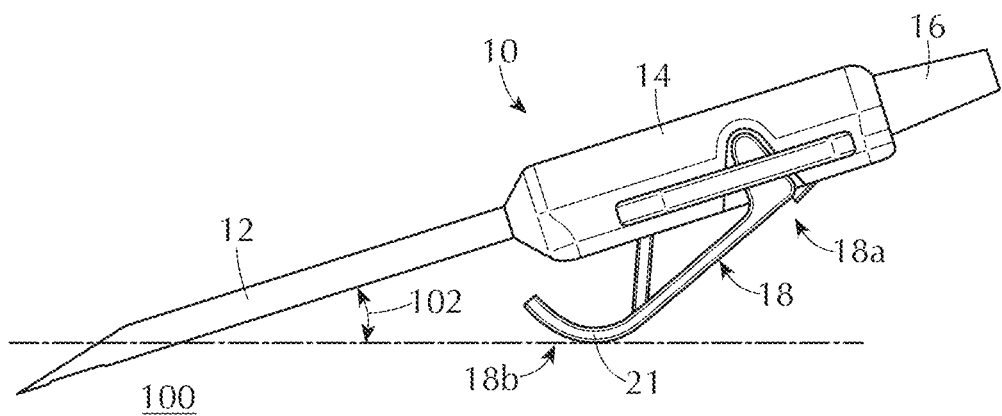
FIG. 6A illustrates a side view of a variation of a tissue access device being inserted into tissue and being dislodged tissue.
Figure 6B:
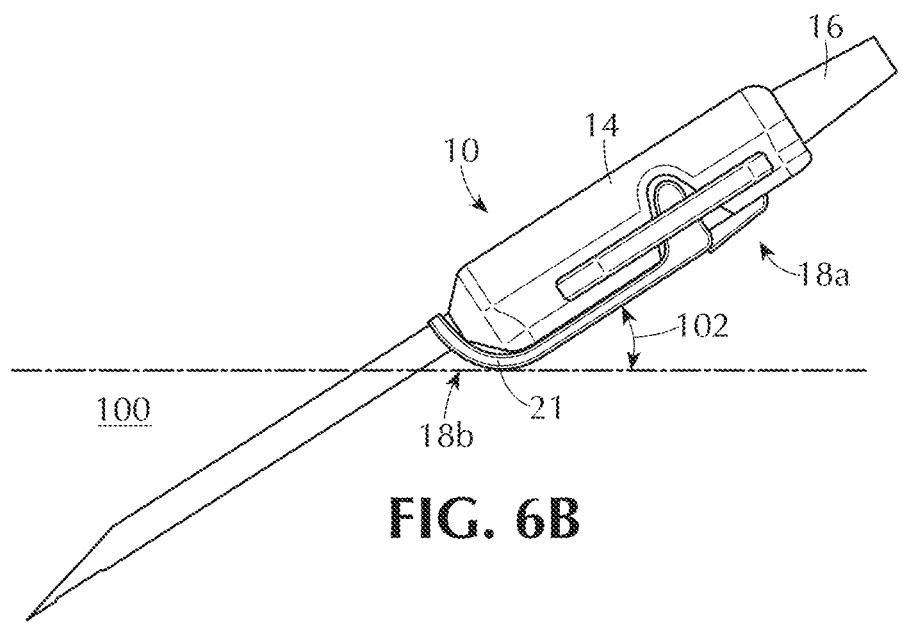
FIG. 6B illustrates the tissue access device of FIG. 6A inserted into tissue.

FIGS. 6A and 6B illustrate a variation of the device 10 being inserted into tissue 100 and being dislodged from the tissue 100. From FIG. 6A to FIG. 6B, the device 10 is shown being inserted into the tissue 100, with the sensor changing from a closed position (also referred to as an occluding position) to an open position (also referred to as a less occluding position). From FIG. 6B to FIG. 6A, the device 10 is shown becoming dislodged from the tissue 100, with the sensor 18 changing from an open position to a closed position.

FIG. 6A illustrates that the curved portion 21 (also referred to as a curved distal end) of the sensor 18 can reduce frictional forces against the skin 100 during insertion, thereby enabling the needle 12 to be inserted with less force and less possible injury to the patient. The curved end of the sensor 18 (e.g., sensor distal end 18b) can encourage a low friction insertion process. The device 10 is shown being inserted at an insertion angle 102 with respect to a patient skin surface 100. The insertion angle 102 can be, for example, from about 10 degrees to about 60 degrees, including every 1 degree increment within this range. For example, the insertion angle 102 can be a typical insertion angle of about 25 degrees, or between about 18 degrees and about 32 degrees.

FIG. 6A further illustrates that the curved distal end 18b (e.g., with curve 21) can also reduce frictional forces against the skin 100 during dislodgement.

FIG. 6B illustrates that the curved distal end 18b can enable the device 10 to maintain a mechanical interface with the skin 10 that can continue to hold the sensor 18 in check against the housing 14 and/or the needle 12 regardless of the insertion angle 102, thereby enhancing functionality of the dislodgement detection system. For example, FIG. 6B illustrates that the curved distal end 18b (e.g., with curve 21) can maintain the sensor 18 in an open position (also referred to as maintain the device in an attached configuration) after the needle 12 has been fully inserted and thus preserve dislodgement detection functionality of the sensor 18 even if the insertion angle 102 is as high as 50 degrees. FIG. 6B illustrates that the insertion angle can be 25 degrees for a "typical angle" insertion and can be up to about 50 degrees for a "high angle" insertion.

FIG. 6B further illustrates that the curved end of the sensor 18 can rest against the needle 12 and/or the needle hub 13 upon insertion, with the needle 12 protruding through the sensor opening 20 (e.g., a U-shaped opening) on the sensor distal end 18b.

Figure 7B:
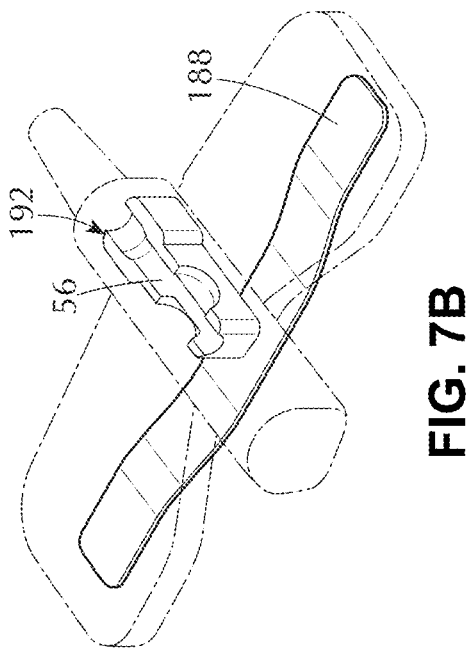
Figure 7A:
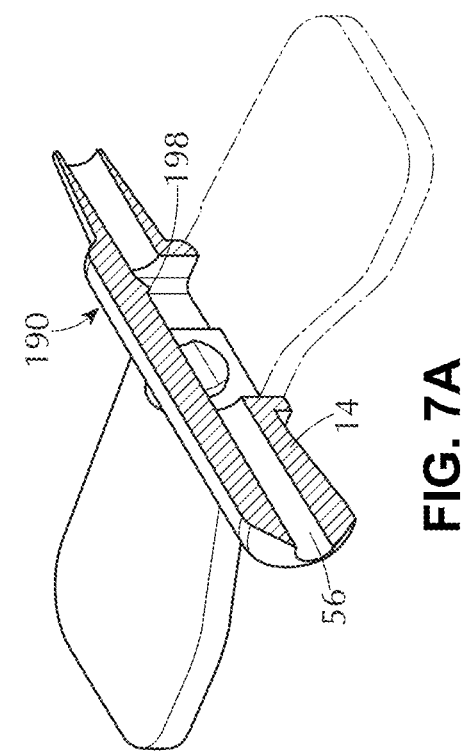

FIGS. 7A-7I illustrate that the device 10 can be manufactured using a two-shot mold process having a first-shot mold 190 and a second-shot mold 192. FIG. 7A illustrates a variation of the first-shot mold 190. The first-shot mold 190 can be molded with a single material or with a composite material. The first-shot mold 190 can include the needle wings 15a and 15b and part of the central body (e.g., part of the housing 14). FIG. 7B illustrates a variation of the second-shot mold 192. The second-shot mold 192 can be molded with a single material or with a composite material. The material of the second-shot mold 192 can be the same or different as the material of the first-shot mold 190. For example, the material of the second-shot mold 192 can be softer, more flexible, more resilient, more deformable, or any combination thereof, than the material of the first-shot mold 190. The second-shot mold 192 can be done within or outside of the needle wing/body unit (e.g., within the housing 14 defined by the first-shot mold 190). The second-shot mold 192 can be attached to the first-shot mold 190, for example, with glue, adhesive, and/or welds (e.g., sonic welds). The second-shot mold 192 can incorporate a compressible membrane (e.g., membrane 54). The compressible membrane can be a thin compressible membrane, for example, having a thickness of about 0.5 mm to about 2.0 mm, including every 0.1 mm increment within this range (e.g., 0.5 mm, 1.0 mm). The compressible membrane (e.g., membrane 54) can be a pinch point for the sensor 18 to act upon when the needle 12 is inadvertently withdrawn from the patient. The second-shot mold 192 can be the insert 17.

FIG. 7A illustrates that at least a portion of the housing 14 can define the housing conduit 56. FIG. 7A further illustrates that the first-shot mold 190 can include a protrusion 198. The protrusion 198 can extend at least partially toward a longitudinal center of the device flow channel in the housing 14, for example, toward a longitudinal center of the flow path defined by the housing conduit 56. The occluder 32 can be configured to engage the housing protrusion 198 when the moveable sensor 18 is in a closed configuration (e.g., when the device 10 becomes dislodged after cannulation).

FIG. 7B illustrates that at least a portion of the second-shot mold 192 can define the housing conduit 56. FIG. 7B further illustrates a variation of a strap 188 that can be integrated with the device 10. The strap 188 can provide a cannulation lock. For example, the strap 188 can be configured to force the sensor 18 into an open configuration during cannulation. When the needle wings 15a and 15b are bent, rotated, and/or flexed toward each other during cannulation (e.g., toward the device first transverse axis A2 in FIG. 1), the strap 188 can pull the sensor 18 into a position that enables fluid flow through the needle body. For example, the strap 188 can pull the sensor 18 into an open position. In this open position, blood flashback during insertion can be seen and naturally viewed by the person inserting the needle, for example, where the device 10 has a visual indicator 186. When this needle is taped into position, fluid can flow (e.g., freely flow) through the device 10 until the needle 12 is purposely or inadvertently removed from the body and the flow stop mechanism (e.g., sensor 18) is activated. The strap 188 can be integrated with or attached to the housing 14 and/or to the wings 15a and 15b. The strap 188 can be an elastic material. The strap 188 can be an in-elastic material. The strap 188 can be a strip of material having a flexible shape. The strap can bend with the wings 15a and 15b are rotated and de-rotated.

Figure 7C:
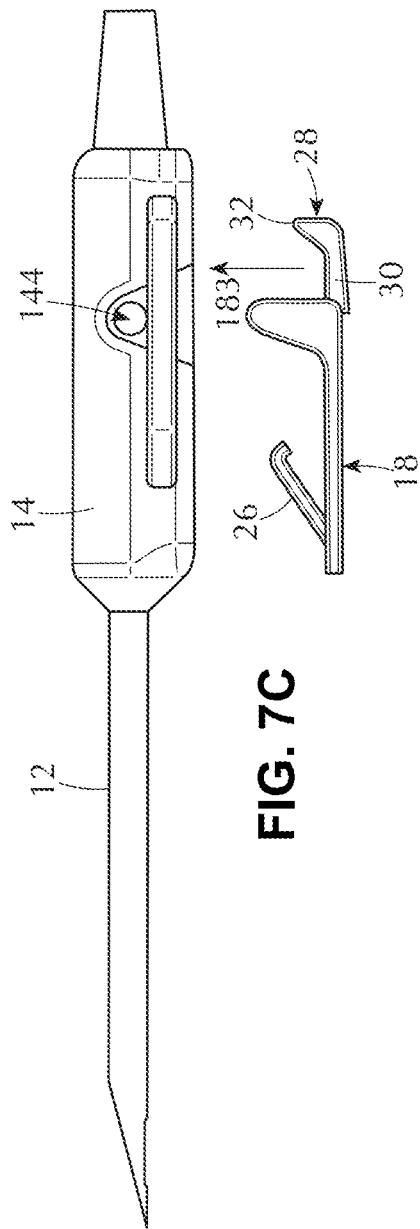

FIG. 7C illustrates a variation of a sensor 18 being attached (arrow 183) to the housing 14 after the second-shot mold 192 is complete.

Figure 7D:
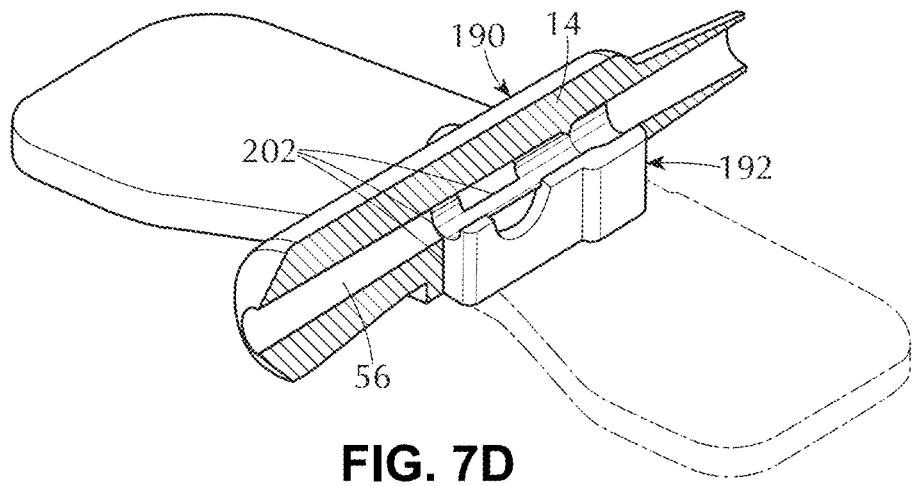

FIG. 7D illustrates that the first-shot and second-shot molds 190, 192 can be attached to maintain a fluid tight seal 202. The fluid tight seal 202 can withstand the high flow pressures associated with hemodialysis treatment. FIG. 7D illustrates that at least a portion of the first-shot mold 190 (e.g., the housing 14) and at least a portion of the second-shot mold 192 (e.g., the insert 17) can define the housing conduit 56. The first-shot and second-shot molds 190, 192 can together define the housing 14.

Figure 7E:
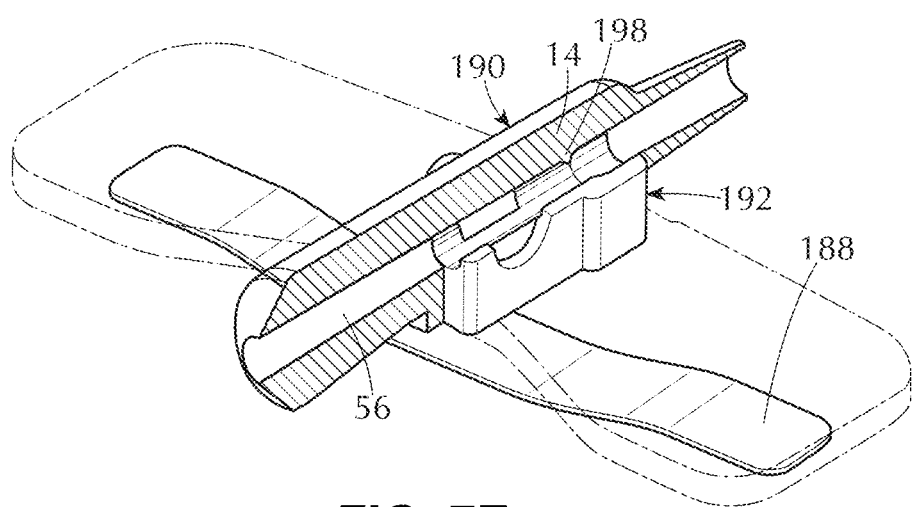

FIG. 7E illustrates the strap 188 relative to the first-shot and second-shot molds 190, 192.

FIGS. 7F and 7G illustrate the two-shot mold manufacturing process 204 for the first-shot mold 190 (FIG. 7F) and the second-shot mold 192 (FIG. 7G).

Figure 7H:
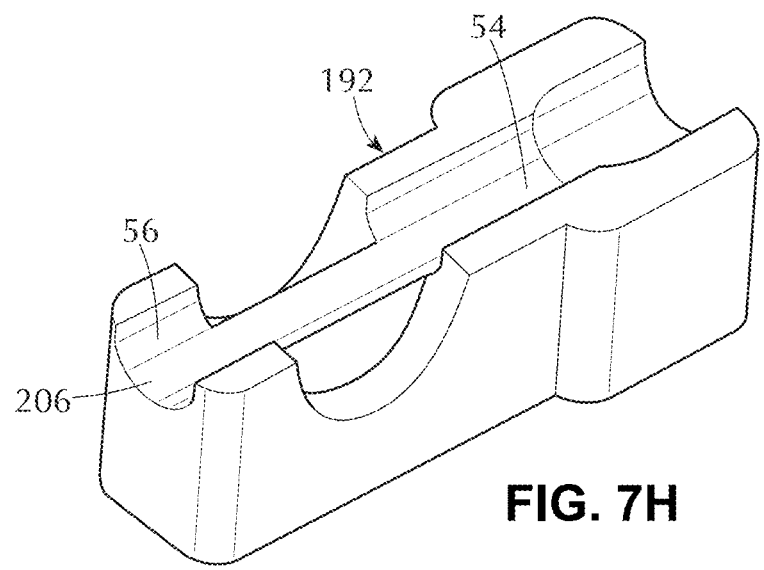
Figure 7I:
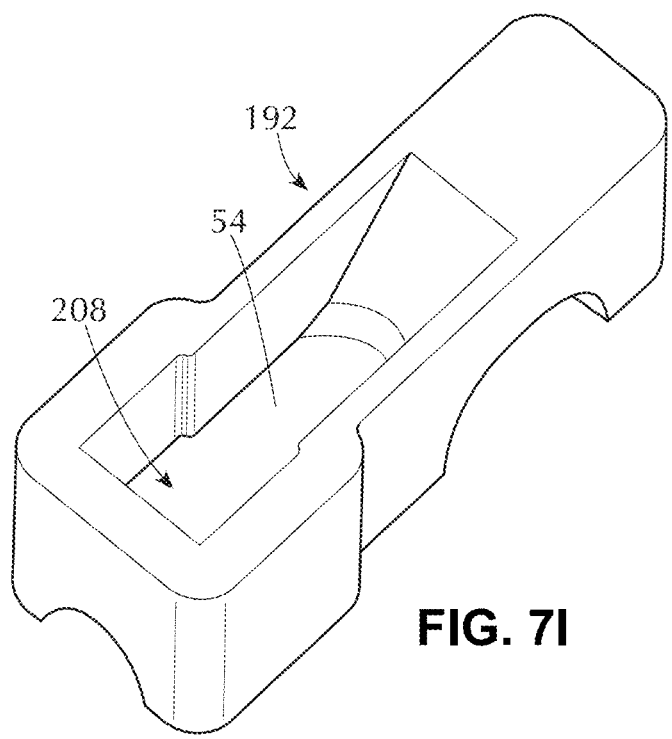

FIGS. 7H and 7I illustrate a variation of the second-shot mold 192. FIG. 7H illustrates that the second-shot mold 192 can have surface 206 that at least partly defines the housing conduit 56. FIG. 7H further illustrates a variation of the location of the membrane 54 on the insert 17 (also referred to as the second-shot mold 192). FIG. 7I illustrates that the second-shot mold 192 can have a recess 208 for the flow restrictor 28 to move in. The recess 208 can give the sensor 18 access to the housing conduit 56 by allowing the occluder 32 to deflect the membrane 54 toward the protrusion 198, for example, when the sensor moves from an open position to a closed position.

Figure 8A:
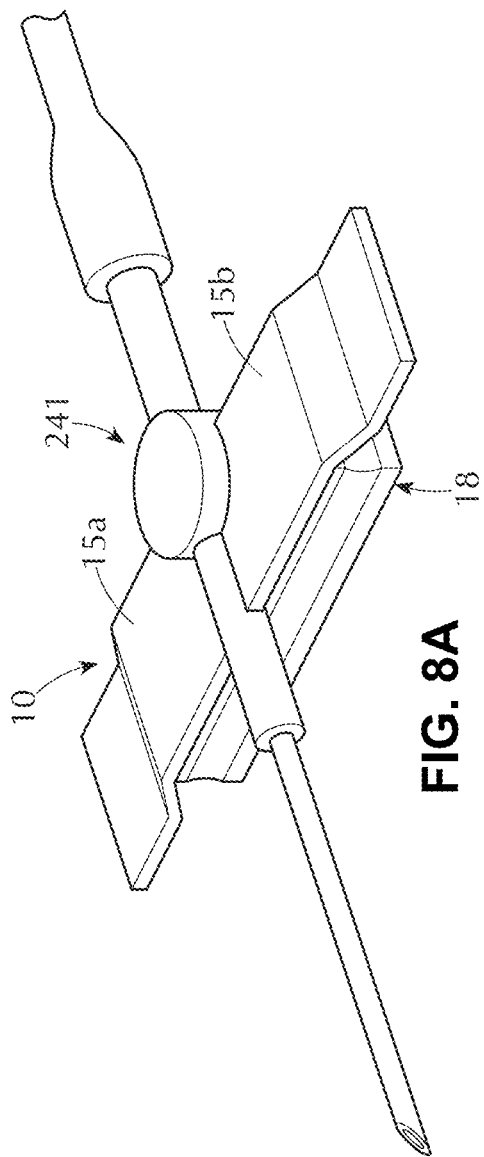
FIGS. 8A-8C illustrate a variation of an insert configured to support flow stoppage during dislodgement.
Figure 8C:
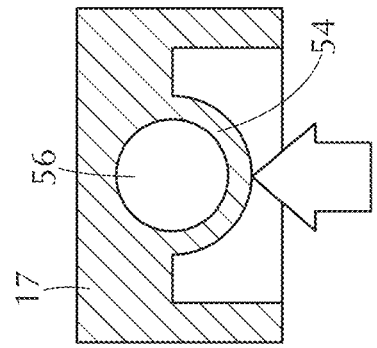
Figure 8B:
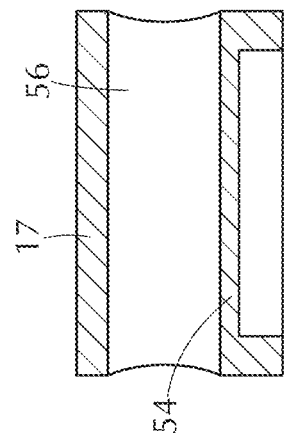

FIGS. 8A-8C illustrate a variation of an insert 17 configured to support flow stoppage during dislodgement. It uses a molded through-path 56 with a thinned wall 54 to act as a closing point for a structural assembly that is part of or linked to a blade skin-sensing arm 18. FIG. 8A illustrates a device 10 with a drop-in component 241 having a needle (e.g., needle 12) and a body connectable to a tube (e.g., tube 8). FIG. 8B illustrates a longitudinal cross-sectional view of the insert 17 in an open configuration. FIG. 8C illustrates a transverse cross-sectional view of the insert 17 in an open configuration. FIG. 8C further illustrates that the through-path 56 can be closed by applying a force 249 against the membrane 54. FIGS. 8A-8C illustrate a blade/diaphragm system that can stop fluid flow upon dislodgement using the dislodgement mechanisms described herein.

Figure 9B:
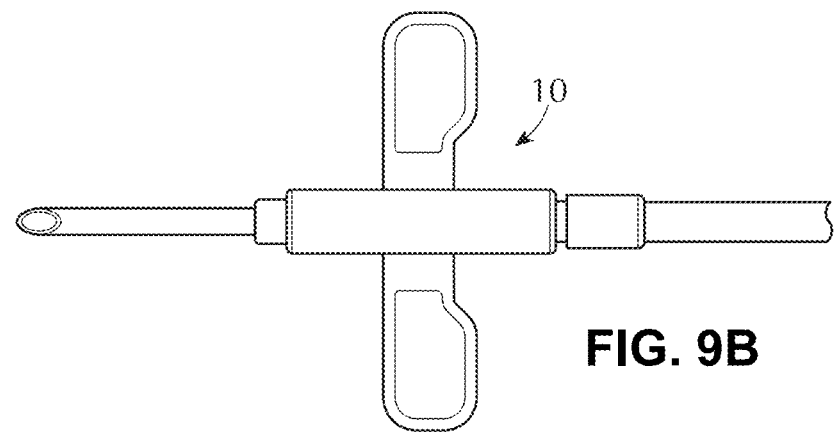
Figure 9C:
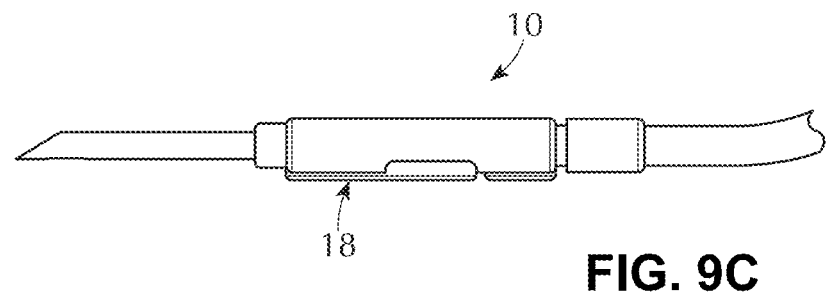
Figure 9D:
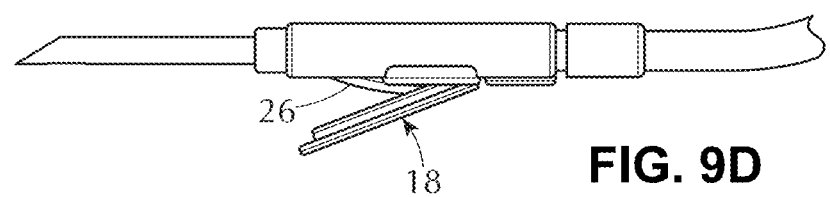
Figure 9E:
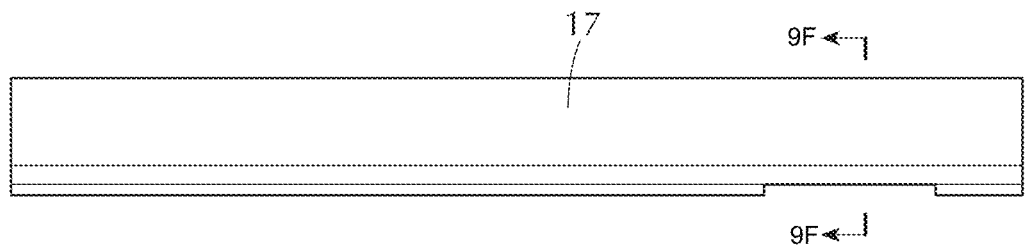
Figure 9F:
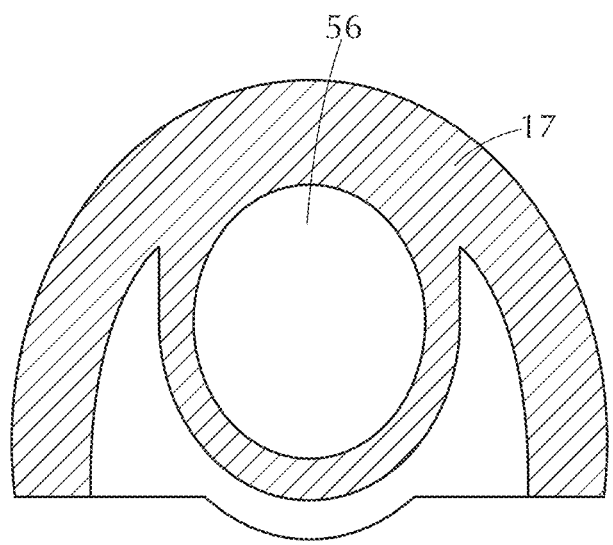

FIGS. 9A-9F illustrate a variation of a device 10 having an insert 17 defining a housing conduit 56. A finishing cap 251 can be placed over a proximal end of the spring 26. FIG. 9C illustrates the device 10 in an attached configuration. FIG. 9D illustrates the device 10 in an occluded configuration, with the spring 26 forcing the distal end of the sensor 18 away from the flow path 56 and the occluder 32 into the membrane 54 to close the flow path.

Figure 10A:
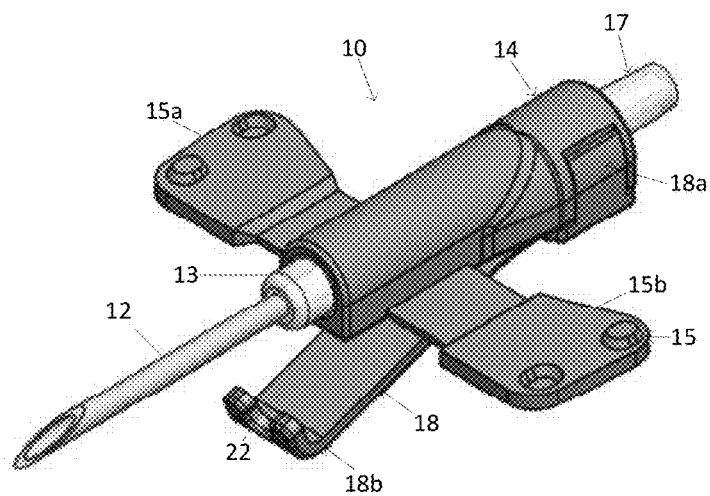
FIG. 10A illustrates a perspective view of a variation of a tissue access device.

FIG. 10A illustrates a variation of a device 10 having a needle 12, a housing 14, an insert 17, and a sensor 18 (e.g., a skin-sensing component). The housing 14 can have the wings 15. The device 10 can protect patients from the risks associated with needle dislodgement, for example, by inhibiting or stopping the flow of fluid through the device flow channel 56 via the sensor 18 when the needle 12 becomes dislodged from the patient. FIG. 10A further illustrates that the device 10 can have an integrated feature that allows for flow stop during inadvertent needle dislodgement (not entirely visible in FIG. 10A). The integrated feature can be the insert 17, the sensor 18, or both. For example, FIG. 10A illustrates that the insert 17 and the sensor 18 can be attached to the housing 14. The insert 17 can be removably or permanently attached to the housing 14. For example, the insert 17 can be attached to the housing 14 via a snap fit, a friction fit, a magnetic fit, a screw fit, a glue fit, or any combination thereof. To attach the insert 17 to the housing 14, the insert 17 can be inserted into the housing channel 51. When the insert 17 is attached to the housing 14 (e.g., when the insert 17 is fully inserted into the housing channel 14 as shown in FIG. 10A), the insert 17 can be the central core of the device 10. The insert 17 can define the device flow channel 56.

When the device 10 is taped to a person's skin, the footplate (also referred to as the sensor 18) closes against the needle body 12 and allows unobstructed fluid flow. If the needle 12 becomes dislodged, the sensor 18 (e.g., spring-loaded footplate) will extend outward away from the needle body (e.g., to the position shown in FIG. 10A), resulting in flow blockage through the device flow channel 56 that extends through the housing 14. The blockage can be induced by a mechanical feature (e.g., a flow restrictor 28 having an occluder 32) on the footplate 18 that is introduced into the flow path (e.g., the device flow channel 56) when the occluder 32 is pressed against the membrane 54. The blockage can be induced, for example, by permanently or temporarily obstructing the device flow channel 56 with the membrane 54 when the occluder 32 is forced against the membrane 54.

Figure 10B:
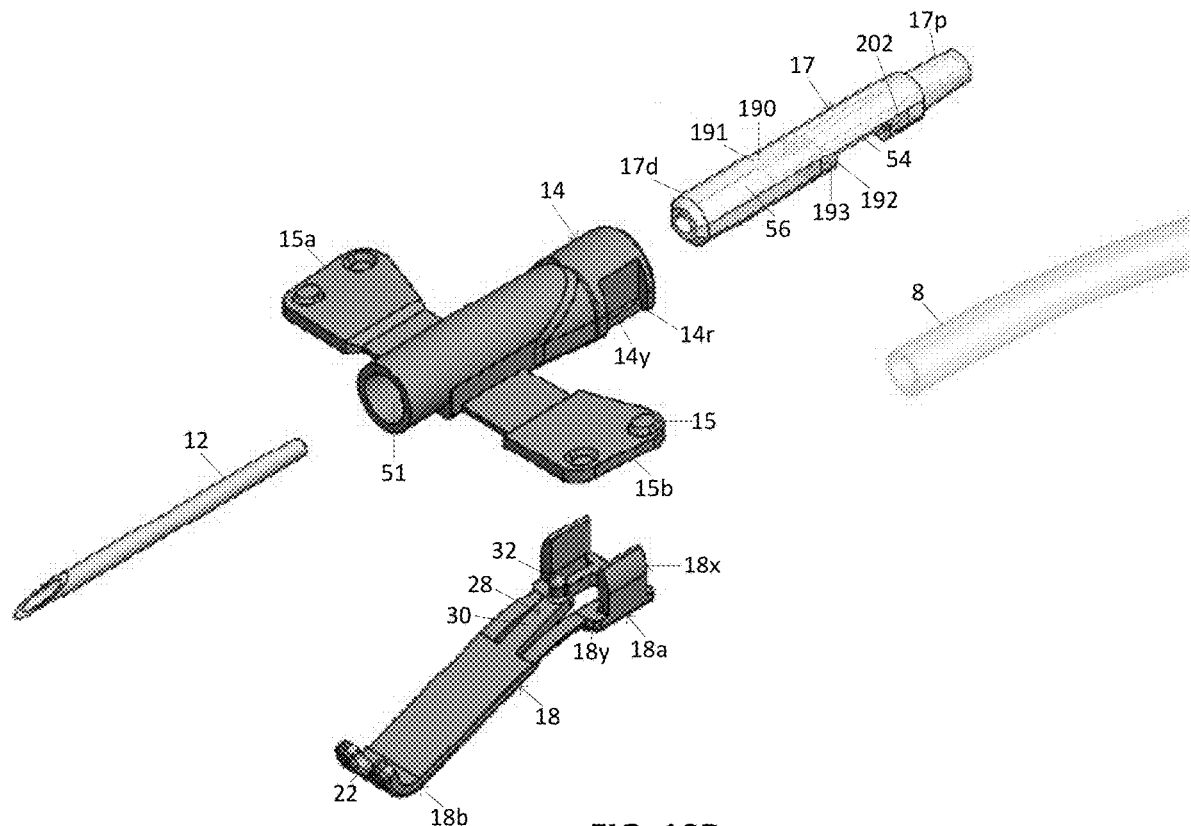
FIG. 10B illustrates an exploded view of the device FIG. 10A.

FIG. 10B illustrates a variation of the device 10 in a dissembled state showing the device 10 (also referred to as the safety needle system 10) of FIG. 10A. The device 10 is shown disassembled into the needle 12, the housing 14, the insert 17, and the sensor 18. FIG. 10B further illustrates that the insert 17 can have a first portion 191 (also referred to as the insert first portion 191) and a second portion 193 (also referred to as the insert second portion 193). The first portion 191 can be harder than the second portion 193. The second portion 193 can be softer than the first portion 191 such that the second portion 193 can be compressed by the occluder 32 when the occluder 32 is forced against the second portion 193. The first portion 191 can extend the length of the insert 17 and have a compressible region (e.g., the second portion 193) that can serve as the entry point for a flow blocking mechanism (e.g., the flow restrictor 28). The compressible region can have a contact surface for the flow restrictor 28. For example, the second portion 193 (e.g., the compressible region of the second portion 193) can be deformed into the flow path 56 when the occluder 32 is forced against the second portion 193. The first portion 191 can be a hard structural element. The second portion 193 can have one or multiple flexible membranes 54 (e.g., 1, 2, 3 or more flexible membranes 54). For example, FIG. 10B illustrates that the second portion 193 can have one flexible membrane 54. As another example, the second portion 193 can be the flexible membrane 54. The membrane 54 can be a soft compressible membrane 54. The device 10 can have a flow obstructed configuration and a flow unobstructed configuration. When the device 10 is in the flow obstructed configuration, the occluder 32 may or may not be in contact with the membrane 54. When the device 10 is in the flow unobstructed configuration, the membrane 54 can have a curved or flat shape. When the device 10 is in the flow unobstructed configuration, the membrane 54 can extend into the device flow channel 56, or may not extend into the device flow channel 56 (e.g., as shown in FIGS. 10A and 10B). When the device 10 is in the flow obstructed configuration, the occluder 32 can be in contact with the membrane 54. When the device 10 is in the flow obstructed configuration, the membrane 54 can be stretched or compressed into the device flow channel 56.

FIGS. 10A and 10B further illustrate that the insert 17 can be manufactured using a two-shot mold process having a first-shot mold 190 and a second-shot mold 192. The first-shot mold 190 can be the insert first portion 191 and the second-shot mold 192 can be the insert second portion 193, or vice versa. The first-shot mold 190 can be molded with a single material or with a composite material and the second-shot mold 192 can be molded with a single material or with a composite material, for example, as described above with reference to FIGS. 7A-7I. For example, FIG. 10B illustrates that the insert 17 can be a 2-shot molded tube (also referred to as a 2-shot core, a 2-shot molded part, and other terms having the term "2-shot" in it) that can provide the needle flow path through the device 10 (also referred to as the device flow channel 56). The needle 12 can define a first portion of the device flow channel 56 and the insert 17 can define a second portion of the device flow channel 56. FIG. 10B further illustrates that the 2-shot molded part (e.g., the insert 17) can have a soft compressible membrane 54, for example, on the underside of the needle body (also referred to as the housing 14) when the components of the device 10 are oriented as shown in FIG. 10B.

The insert 17 can be constructed of materials with varying mechanical properties and can be created at the time of or before full needle system assembly. The 2-shot tube can then attached via adhesive or other technique to the other system components (e.g., the needle 12, the housing 14, the sensor 18, or any combination thereof). The order of attachment can be varied to insure that, where used, adhesive material is not accidentally spread to unwanted regions due to the assembly process. The wing feature (e.g., the part of the device 10 having the wings 15) can be slid onto the 2-shot tube from the front or the back as most appropriate. The 2-shot part can be a combination of polycarbonate (PC) and thermoplastic elastomer (TPE). The butterfly and footplate (also referred to as a blade) could be manufactured using a variety of possible materials, including, for example, polyethylene (PE), polyvinyl chloride (PVC), polypropylene (PP), Acetal (Delrin), or any combination thereof. The footplate (e.g., sensor 18) can be designed, for example, to snap into place on the needle body 14, to have a friction fit with the housing 14, to magnetically couple to the housing (e.g., to another magnet or magnets in the housing 14), to be glued to the housing, or any combination thereof. As another example, the sensor 18 can be welded to the housing 14, to the insert 17, or both.

FIGS. 10A and 10B further illustrate that the insert 17 can define the device flow channel 56 (also referred to as the internal tube). FIGS. 10A and 10B further illustrate that the insert 17 can define the flow path through the housing 14, for example, through the housing channel 51. FIGS. 10A and 10B further illustrate that the first-shot and second-shot molds 190, 192 (e.g., first and second portions 191, 193) can be attached to maintain a fluid tight seal 202. The fluid tight seal 202 can withstand the high flow pressures associated with hemodialysis treatment. The second-shot mold 192 can have the compressible region of the insert 17. For example, the second-shot mold 192 can have the membrane 54.

FIGS. 10A and 10B further illustrate that the insert 17 can have an insert proximal end 17p and an insert distal end 17d. The tube 8 can be attached to the insert proximal end 17p. For example, the tube 8 can be attached (e.g., slid) over the insert proximal end 17p such that the distal end of the tube 8 abuts the housing 14, extends into a space in the housing 14 (e.g., into the housing channel 51), or stops short of the housing 14 such that there is a gap between the housing 14 and distal end of the tube 8.

FIGS. 10A and 10B further illustrate that the sensor 18 can be attached to the housing 14 with a snap fit. For example, the housing 14 can have a clip recess 14r and the sensor 18 can have a clip 18x. The clip 18x can be attached to the housing 14 by sliding the clip 18x into the clip recess 14r. The clip 18x can be locked (e.g., permanently or removably locked) into place when the clip lip 18y is pushed over the recess lip 14y.

Figure 11A:
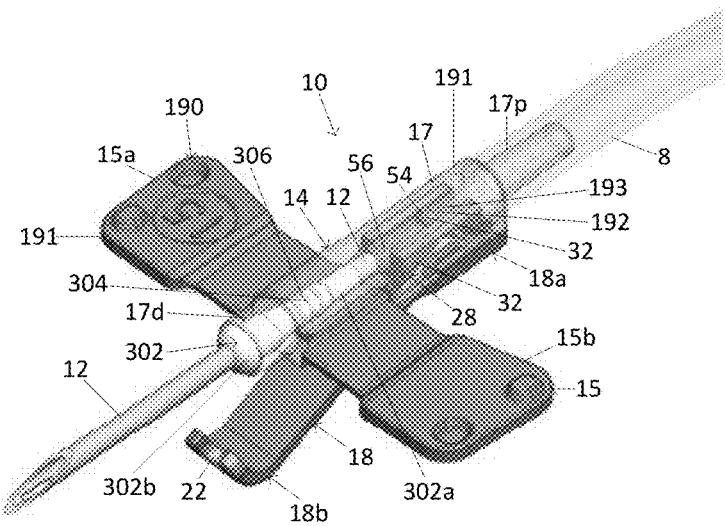
FIG. 11A illustrates a perspective view of a variation of a tissue access device.
Figure 11B:
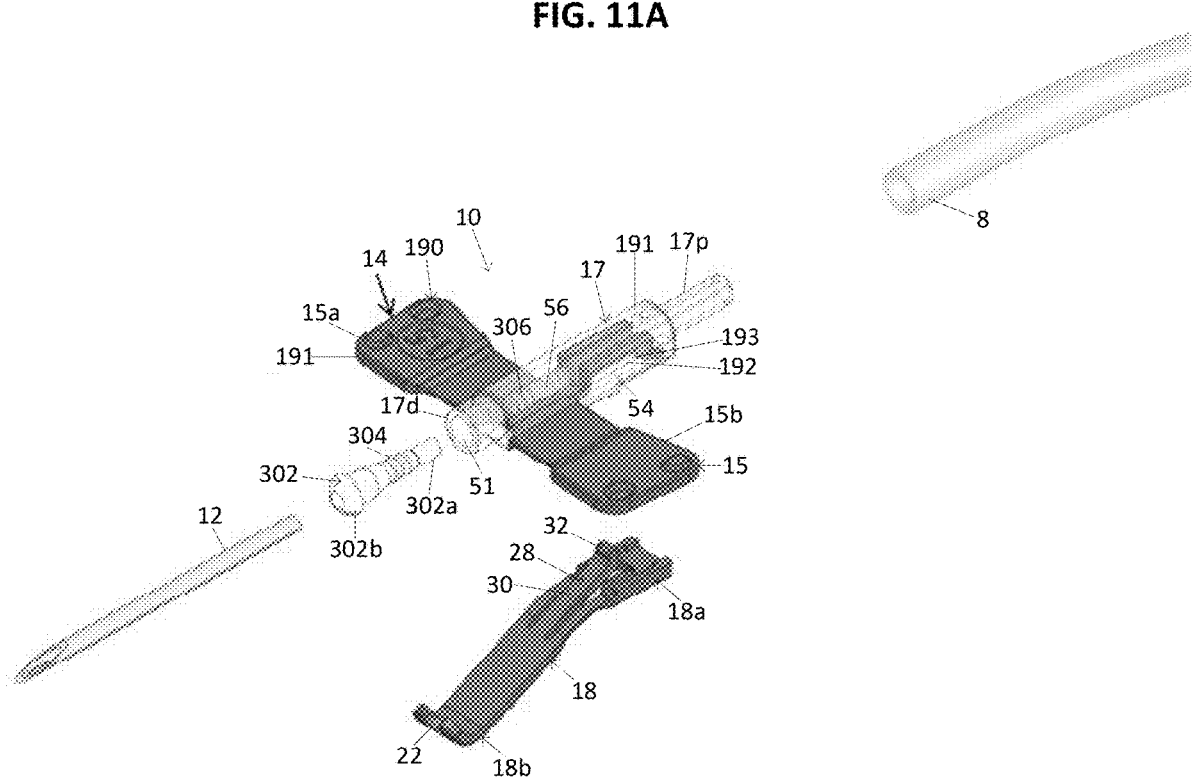
FIG. 11B illustrates an exploded view of the device of FIG. 11A.

FIGS. 11A and 11B illustrate that the housing 14 can include the wings 15, the insert 17, and the membrane 54 and that the housing 14 can be manufactured using a two-shot mold process having a first-shot mold 190 and a second-shot mold 192. For example, the first-shot mold 190 can include the wings 15 and the insert first portion 191, and the second-shot mold 192 can be the insert second portion 193, or vice versa. FIGS. 11A and 11B illustrate that the insert 17 can be integrated with the wings 15 (e.g., via a 2-shot molding process) instead of being manufactured separately from the wings 15 and then attached to the wings 15. FIGS. 11A and 11B illustrate that the two-shot mold process can advantageously decrease the amount of material needed to make the housing 14, for example, eliminating the need for the portion of the housing 14 in FIGS. 10A and 10B that define the housing channel 51 since the wings 15 and the insert first portion 191 can be formed as the first-shot mold 190 as a unitary piece.

As another example, FIGS. 11A and 11B further illustrate that the 2-shot molded component can be the housing 14 and the insert 17 together, for example, including the wings 15 (e.g., as shown in FIGS. 11A and 11B) or not including the wings 15. FIGS. 11A and 11B illustrate that the housing 14 and the insert 17 can be formed together via a 2-shot molding process rather than forming them separately and then attaching them together during assembly (e.g., such as for the device 10 shown in FIGS. 10A and 10B). The first-shot mold 190 can be molded with a single material or with a composite material and the second-shot mold 192 can be molded with a single material or with a composite material, for example, as described above with reference to FIGS. 7A-7I. The first-shot mold 190 can include the wings 15a and 15b and part of the central body (e.g., part of the housing 14). The second-shot mold 192 can be done within or outside of the needle wing/body unit (e.g., within the housing 14 defined by the first-shot mold 190). The second-shot mold 192 can be attached to the first-shot mold 190, for example, with glue, adhesive, and/or welds (e.g., sonic welds). The second-shot mold 192 can incorporate a compressible membrane (e.g., membrane 54). The compressible membrane (e.g., membrane 54) can be a pinch point for the sensor 18 to act upon when the needle 12 is inadvertently withdrawn from the patient.

For example, the housing 14 (e.g., the 2-shot component, also referred to as a 2-shot tube, the 2-shot molded part) can be constructed of materials with varying mechanical properties and can be created at the time of or before full needle system assembly. The 2-shot tube can then attached via adhesive or other technique to the other system components (e.g., the needle 12, the sensor 18, or any combination thereof). The order of attachment can be varied to insure that, where used, adhesive material is not accidentally spread to unwanted regions due to the assembly process. The 2-shot part can be a combination of polycarbonate (PC) and thermoplastic elastomer (TPE). The butterfly and footplate (also referred to as a blade) could be manufactured using a variety of possible materials, including, for example, polyethylene (PE), polyvinyl chloride (PVC), polypropylene (PP), Acetal (Delrin), or any combination thereof. The footplate (e.g., sensor 18) can be designed, for example, to 'snap' into place on the needle body, to have a friction fit with the housing 14 (e.g., to the first-shot mold 190 and/or to the second-shot mold 192), to magnetically couple to the housing (e.g., to another magnet or magnets in the housing 14), to be glued to the housing, or any combination thereof. As another example, the sensor 18 can be welded to the housing 14 (e.g., to the first-shot mold 190 and/or to the second-shot mold 192).

FIGS. 11A and 11B illustrate a variation of a device 10 having a needle 12 with a sensor 18 (e.g., a skin-sensing component) designed to protect patients from the risks associated with needle dislodgement. FIG. 11A further illustrates that the device 10 can have an integrated feature that allows for flow stop during inadvertent needle dislodgement (not entirely visible in FIG. 11A). FIG. 11B is a dissembled view of the safety needle system of FIG. 11A. Here, a 2-shot molded tube defining the device flow channel 56 includes a structural aspect (e.g., the first-shot mold 190) and a soft compressible region (e.g., the second-shot mold 192) which also comprises the wing structure in this instance. The insert 17 serves as the axial flow path through the body of the needle system. The 2-shot component is constructed of materials with varying mechanical properties and is created at the time of or before full needle system assembly. The 2-shot tube having the wings is then attached via adhesive or other technique to the other system components (e.g., to the needle 12, to the sensor 18, and to the tube 8). The order of attachment can be varied to insure that, where used, adhesive material is not accidentally spread to unwanted regions due to the assembly process. FIG. 11B illustrates the device 10 in a dissembled state showing the safety needle system of FIG. 11A. The device 10 is shown disassembled into the tube 8, the needle 12, the housing 14, the sensor 18, and the connector 302.

When the device 10 is taped to a person's skin, the footplate (also referred to as the sensor 18) closes against the needle body 12 and allows unobstructed fluid flow. If the needle 12 becomes dislodged, the sensor 18 (e.g., spring-loaded footplate) will extend outward away from the needle body (e.g., to the position shown in FIG. 11A), resulting in flow blockage through the device flow channel 56 that extends through the housing 14. The blockage can be induced by a mechanical feature (e.g., a flow restrictor 28 having an occluder 32) on the footplate 18 that is introduced into the flow path (e.g., the device flow channel 56) when the occluder 32 is pressed against the membrane 54. The blockage can be induced, for example, by permanently or temporarily obstructing the device flow channel 56 with the membrane 54 when the occluder 32 is forced against the membrane 54.

FIGS. 11A and 11B further illustrates that the device 10 can have a connector 302 having a connector first end 302a and a connector second end 302b. The connector 302 can have the needle hub 13. When the device 10 is assembled, the connector 302 can be attached to the housing 14, for example, via a snap fit or friction fit with the integrated insert 17 via, for example, ribs 304 on the connector 302 and grooves 306 on the integrated insert 17. For example, the ribs 304 can fit into the grooves 306. As another example, the connector 302 can be attached to the 2-shot molded housing 14 with a screw fit, magnetic fit, or any combination thereof. The needle 12 can be attached to the connector second end 302b and can extend through a channel in the connector 302 and into the housing channel 51.

FIGS. 11A and 11B show a portion of the insert first portion 191 transparent so that the internal features of the first-shot mold 190 can be visible.

FIG. 11A further illustrates the membrane 54 in a deflected configuration, for example, deflected into the device flow channel 56 by the occluder 32.

FIGS. 12A and 12B illustrate a variation of a single 2-shot component piece (also referred to as the insert 17) that can comprise the axial center of the device 10 (e.g., the single 2-shot component piece that is shown in FIGS. 10A and 10B). The insert 17 can be or can be part of the housing 14. The wings 15 can be attached to or integrated with the insert 17. In FIG. 12A the insert 17 is shown as it would be manufactured (with the compressible membrane 54 positioned on the top side in FIG. 12A). In FIG. 12B the result of each molding shot (e.g., the first-shot mold 190 and the second-shot mold 192) is broken out for illustration purposes only. The 2-shot component (e.g., the insert 17) can include butterfly wings 15 as shown in FIGS. 11A and 11B.

FIGS. 12A and 12B further illustrate that the internal 2-shot piece (also referred to as the insert 17) enables effective flow blockage via the compressible membrane 54 as part of a safety needle system (also referred to as the device 10) for protecting patients from the risk of needle dislodgement. FIG. 12A shows a version of a 2-shot piece as would be assembled for the device 10. The longer darker-shaded material can be polycarbonate or other hard material or other material having a hardness that is greater than the shorter clear piece. The shorter clear inset piece can be a mechanically soft thermoplastic elastomer. The overall piece (also referred to as the insert 17) can be about 0.25 inches to about 1.50 inches long, including every 0.05 inch increment in this range (e.g., 0.75 inches, 1.00 inches, 1.25 inches). FIG. 12B shows the 2 pieces (e.g., the first-shot and second shot molds 190, 192) as they would look if made separately. FIG. 12A shows the 2 pieces made via a 2-shot molding process. The 2 pieces in FIGS. 12A and 12B are placed with the soft region (e.g., the membrane 54) of the insert 16 facing upwards. In the final full configuration of the device 10, the soft region (e.g., the membrane 54) can face downward such that when the device 10 is attached to a person, the soft region faces toward the person's skin.

FIGS. 12A and 12B further illustrate that the membrane 54 can be curved. For example, the membrane 54 can define a portion of a surface of the device flow channel 56. The membrane 54 can define a portion of, for example, a cylindrical-shaped device flow channel 56, a frustoconical-shaped device flow channel 56, or both.

FIGS. 12A and 12B further illustrate that the device flow channel 56 can be defined by the first-shot and second-shot molds 190, 192.

FIGS. 12A and 12B further illustrate the membrane 54 in a non-deflected configuration (also referred to as a relaxed configuration).

FIG. 12B further illustrates that the second-shot mold 192 can be attached to (e.g., via the 2-shot molding process) the first-shot mold 190 to cover an opening 203 in the first-shot mold 190. The opening 203 can be at the insert proximal end 17p (e.g., as shown in FIG. 12A), at the insert distal end 17d, or at a location in between the insert proximal and distal ends 17p, 17d. Likewise, the second-shot mold 192 can be attached to the first-shot mold 190 at a proximal end of the first-shot mold 190 (e.g., as shown in FIG. 12A), at a distal end of the first-shot mold 190, or at a location between the proximal and distal ends of the first-shot mold 190.

FIGS. 13A and 13B illustrate a variation of a pre-formed pocket 208 (also referred to as the recess 208) within the soft compressible membrane region of the 2-shot component (e.g., of the insert 17). The pocket 208 can advantageously reduce the closing force required to move the sensor 18 (e.g., footplate) into an occlusion position. During pressurized fluid flow, the pocket 208 can extend into the flow path (e.g., as shown in FIG. 13A by the solid line 54). As another example, during pressurized fluid flow, the pocket 208 can be naturally inverted into an open position so that it does not limit flow (e.g., as shown in FIG. 13A by the dotted line 54). During closure of the footplate, the pocket 208 can be stretched by the sensor 18 to allow for internal occlusion of the fluid path (e.g., as shown in FIG. 13B).

FIG. 13A further illustrates that the sensor 18 may or may not extend into the pocket 208 during pressurized fluid flow. For example, FIG. 13A illustrates that when the pocket 208 (e.g., defined by solid line 54) extends into the flow path during fluid flow, a portion of the sensor 18 (e.g., the occluder 32) can extend into the pocket 208. As another example, FIG. 13A illustrates that when the pocket 208 (e.g., defined by dotted line 54) is in a relaxed inverted configuration, a portion of the sensor 18 (e.g., the occluder 32) can extend into the pocket 208. When the pocket 208 (e.g., defined by dotted line 54) is in a relaxed inverted configuration, some of the membrane 54 can extends outward away from the flow path.

FIG. 13A further illustrates that the sensor 18 may or may not contact the membrane 54 during pressurized fluid flow. For example, FIG. 13A illustrates that when the pocket 208 (e.g., defined by solid line 54) extends into the flow path during fluid flow, a portion of the sensor 18 (e.g., the occluder 32) may or may not contact the membrane 54. As another example, FIG. 13A illustrates that when the pocket 208 (e.g., defined by dotted line 54) is in a relaxed inverted configuration, a portion of the sensor 18 (e.g., the occluder 32) can contact the membrane 54.

FIGS. 13A and 13B further illustrate that the pocket 208 can be integrated with the compressible portion of the 2-shot component. The pre-formed pocket 208 can reduce the closing force required to occlude the internal flow using the external assemblage of the footplate. FIG. 13A illustrates the sensor 18 (e.g., footplate) as it would appear when the device is in a taped position on the patient's arm. The pocket 208 can remain in place (e.g., the curved solid line above the dotted line in FIG. 13A) or become inverted or partially inverted through the course of normal fluid flow (e.g., as shown by the dotted line in FIG. 13A). FIG. 13B illustrates the sensor 18 (e.g., footplate) in an activated position, for example, during needle dislodgement off the skin, or after the device 10 has become dislodged from the skin. The occluder 32 (e.g., of the footplate) can push through the soft compressible pocket 208 to occlude fluid flow when the device 10 becomes dislodged from the patient's skin.

FIGS. 10A-13B illustrate details of manufacturing methods and various variations of the device 10, including, for example, (1) the making and use of a 2-shot core with or without wings 15 as an efficient means to enable interruption of fluid flow during dislodgment, where part of this core is a soft membrane (e.g., membrane 54), (2) a pre-formed pocket 208 within the soft portion of the 2-shot core to increase efficiency and (3) assembly techniques, or any combination thereof.

FIGS. $14A_1$ and $14A_2$ illustrate a variation of attaching wings 15 to the insert 17 (also referred to as the 2-shot core). For example, the wings 15 can be attached (arrow 308) to the insert 17 with a snap fit, or vice versa. As another example, FIGS. $14A_1$ and $14A_2$ illustrate that the housing 14 (e.g., having wings 15) and the insert 17 can be attached (arrow 308) to each other with a snap fit. As yet another example, the insert 17 can be the housing 14 and the wings 15 can be attached to the housing 14 with a snap fit. For example, FIGS. $14A_1$ and $14A_2$ further illustrate that the wings 15 can have a connector 310 that is attachable to the 2-shot core (e.g., to the insert 17). The connector 310 can be attached (e.g., via a snap fit) to the 2-shot core. The wings 15 can include a wing core having the connector 310. FIGS. $14A_1$ and $14A_2$ illustrate that the connector 310 can be a clip. For example, FIGS. $14A_1$ and $14A_2$ illustrate that that the connector 310 can have, for example, clip arms (e.g., two clip arms) that are engageable with the 2-shot core. The connector 310 can be attached to the distal end of the 2-shot core (e.g., as shown in FIG. $14A_2$), to the proximal end of the 2-shot core, or to somewhere in between the proximal and distal end of the 2-shot core. As yet further examples, FIGS. $14A_1$ and $14A_2$ illustrate butterfly assembly techniques. For example, FIGS. $14A_1$ and $14A_2$ show a snap-to-fit U-type butterfly wing unit 15 that can be snapped onto the central core consisting of the 2-shot component. As another example, FIGS. $14A_1$ and $14A_2$ show a snap-to-fit U-type butterfly wing unit that can be snapped onto the housing 14 having the 2-shot component (e.g., having first and second shots 190 and 192). The snap fitting of the two components can be further enhanced with the use of adhesive or welding. The connector 310 can be removably attachable to the insert 17.

FIGS. $14B_1$ and $14B_2$ illustrate that the connector 310 can have a ring or collar having an opening that enables a press-to-fit approach via sliding (arrow 312) the wings 15 onto the central 2-shot component (e.g., onto the insert 17). FIGS. $14B_1$ and $14B_2$ illustrate that the connector 310 can have a ring or collar having an opening that enables the wings 15 to be attached (arrow 312) to the 2-shot core (e.g., to the insert 17) via a press fit. As another example, FIGS. $14B_1$ and $14B_2$ illustrate a central wing core opening 310 that enables a press-to-fit approach via sliding (arrow 312) the wings 15 onto the central 2-shot component (e.g., onto the insert 17). The press-to-fit attachment of these two components can be further enhanced with the use of adhesive or welding. The device needle, and the device footplate are not shown.

FIGS. $14C_1$ and $14C_2$ illustrate that the connector 310 can have a ring having an opening that enables a press-to-fit approach via sliding (arrow 314) the wings 15 onto the central 2-shot component (e.g., onto the insert 17). FIGS. $14C_1$ and $14C_2$ illustrate that the connector 310 can have a ring or collar having an opening that enables the wings 15 to be attached (arrow 314) to the 2-shot core (e.g., to the insert 17) with a press fit. As another example, FIGS. $14C_1$ and $14C_2$ illustrate a central wing core opening 310 that enables a press-to-fit approach via sliding (arrow 314) the wings 15 onto the central 2-shot component (e.g., onto the insert 17). The sliding can be done from the front (e.g., FIGS. $14B_1$ and $14B_2$) or the back (e.g., FIGS. $14C_1$ and $14C_2$). The press-to-fit attachment of the two components can be further enhanced with the use of adhesive or welding. The device needle, and the device footplate are not shown.

FIGS. 14A₁-14C₂ illustrate the 2-shot component and the butterfly wing of the device 10 to protect patients from venous needle dislodgement. The butterfly wing 15 can be manufactured in a way that enables a snap-on method for integration with the 2-shot component (e.g., as shown in FIGS. 14A₁ and 14A₂). The wings 15 can be constructed with an opening hole to allow sliding of the wing piece over/onto the 2-shot component (e.g., as shown in FIGS. 14B₁ and 14B₂ and FIGS. 14C₁ and 14C₂). FIGS. 14A₁ and 14A₂ show a snap fit connection. FIGS. 14B₁ and 14B₂ show a press fit connection, with the wings 15 slid from the distal side. FIGS. 14C₁ and 14C₂ show a press fit connection, with the wings 15 slid from the proximal side.

FIGS. 15A₁ and 15A₂ illustrate a dissembled (FIG. 15A₁) and assembled (FIG. 15A₂) view of the device 10 including the sensor 18 (e.g., spring-loaded footplate). The needle 12 is shown attached to 2-shot component (also referred to, for example, as the insert 17 and the 2-shot core) in FIGS. 15A₁ and 15A₂. FIGS. 15A₁ and 15A₂ illustrate that the sensor 18 (e.g., footplate) can have a connector 315 that enables an efficient press-to-fit assembly of the sensor 18 to the 2-shot component. The fitting of the sensor 18 to the 2-shot core can be further enhanced with the use of adhesive or welding. FIGS. 15A₁ and 15A₂ illustrate that the connector 315 can have a ring or collar having an opening that enables the sensor 18 to be attached (arrow 316) to the 2-shot core (e.g., to the insert 17) with a press fit. For example, the connector 15 can be slid (arrow 316) over the insert proximal end 17p. The sensor 18 can (e.g., footplate) can be welded or secured directly to the underside of the 2-shot core. The connector 315 (e.g., ring or collar) can be on an end (e.g., the sensor proximal end 18a) of the sensor 18. The ring or collar can be used to enable efficient device assembly/manufacturing. FIG. 15A₁ illustrates a variation of an exploded view that shows the sensor 18 before the sensor 18 is attached to the 2-shot core or after the sensor 18 is removed from the 2-shot core. FIG. 15A₂ illustrates the device 10 in an assembled configuration showing the ring or collar of the sensor 18 (e.g., footplate) slid into position over the 2-shot component (e.g., over the insert 17).

FIGS. 15B₁ and 15B₂ illustrate a dissembled (FIG. 15B₁) and assembled (FIG. 15B₂) view of the device 10 including the sensor 18 (e.g., spring-loaded footplate). FIGS. 15B₁ and 15B₂ illustrate that the connector 315 can enable an efficient snap-to-fit assembly. The connector 315 can be a clip (e.g., clip 18x). As another example, FIGS. 15B₁ and 15B₂ illustrate that the connector 315 can have a snap-to-fit U-shape modification that enables efficient snap-to-fit assembly. The fitting of these two components could be further enhanced with the use of adhesive or welding. For example, FIGS. 15B₁ and 15B₂ illustrate that the sensor 18 can be attached (arrow 318) to the insert 17 (also referred to as the 2-shot core) with a snap fit, or vice versa. The connector 315 can be attached (e.g., via a snap fit) to the 2-shot core (e.g., to the insert 17).

FIGS. 16A and 16B illustrate a dissembled (FIG. 16A) and assembled (FIG. 16B) view of the wings 15 and the insert 17. FIGS. 16A and 16B illustrate that the 2-shot molded tube (e.g., the insert 17) acts as the device core and the wing unit (e.g., the wings 15) is built with the connector 310 and a cover 320 (also referred to as the cover and the insert cover) that is used as a method for integrating the two components (e.g., for integrating the wings 15 with the insert 17). The cover 320 can be, for example, a hinged cover. As another example, FIGS. 16A and 16B illustrate a dissembled (FIG. 16A) and assembled (FIG. 16B) view of the housing 14 (e.g., having the wings 15) and the insert 17, where the 2-shot molded tube (e.g., the insert 17) acts as the device core and the wing unit (e.g., the housing 14) is built with the connector 310 and a hinged cover 320 that is used as a method for integrating the two components (e.g., for integrating the wings 15 with the insert 17). The hinged cover 320 can have a first hinge 322. The hinged cover 320 can extend from the first hinge 322. The first hinge 322 can be, for example, a living hinge. The first hinge 322 connect the hinged cover 320 to the needle hub 13 (e.g., as shown in FIG. 16A) or to the connector 310. Although not visible in FIG. 16A, the wings 15 can have a second hinge 323 (e.g., visible in FIG. 16C), for example, on the opposite side of the needle hub 13 that connects the needle hub 13 to the housing 14 when the cover 320 is in an open configuration as shown in FIG. 16A. The second hinge 323 can be, for example, a living hinge. The connector 310 can include the cover 320, the first hinge 322, and/or the second hinge such that when the connector 310 is in an open configuration (e.g., as shown in FIG. 16A), the needle hub 13 and/or the cover 320 can have the arrangement shown in FIG. 16A. When the cover 320 is closed (e.g., as shown in FIG. 16B), the hinged wing piece encompasses the core 2-shot component. FIG. 16C illustrates that a sensor 18 (e.g., footplate) can be integrated to this system via sliding (arrow 330) using a sensor 18 having the connector 315. FIG. 16C further illustrates that the tube 8 can be integrated to this system via sliding (arrow 330) by sliding the tube 8 onto the insert proximal end 17p. FIG. 16C further illustrates that the connector 315 can have a ring/collar type of modification. Adhesion or welding may be used to enhance the component interconnections (e.g., between the housing 14 and the insert 17, between the sensor 18 and the insert 17, between the sensor 18 and the housing 14, or any combination thereof). As yet another example, the connector 310 can have the first hinge 322 but not the second hinge 323 such that when the cover 320 is in an open configuration, the needle hub 13 can be in the configuration shown in FIG. 16B in FIG. 16A, and such that when the cover 320 is in the open configuration, the needle hub 13 can be a stop for the insert 17, preventing over insertion of the insert 17 into the channel 51.

FIGS. 16A-16C further illustrate that the 2-shot molded part 17 can have a soft compressible membrane 54 on the underside of the needle body and that the wings 15 can be flexible butterfly wings. One method of integration of these 2 components is a hinge type approach that allows the wings 15 to be wrapped around the core (e.g., around the insert 17) via a molded in cover 320. The sensor 18 (e.g., footplate) can be integrated onto this type of structure via a collar/ring type of modification that allows sliding assembly (e.g., as shown in FIG. 16C).

FIGS. 16A-16C further illustrate that the insert 17 can have one or multiple aligners 324 (e.g., 1 to 4 or more aligners 324, including every 1 aligner increment within this range, e.g., 2 aligner as shown in FIGS. 16A-16C). The connector 310 can have aligner grooves 325 that the aligners can be slid into when the insert 17 is inserted (arrow 326) into the connector 310. As another example, the connector 310 can be slid over (e.g., arrow 314) the insert 17 into the chamber 51 when the aligners and aligner grooves 324, 325 are aligned. The aligners and aligner grooves 324, 325 can advantageously ensure that the membrane 54 is in the proper location when the device 10 is in an assembled state, and can lock the insert 17 in place so that the insert does not translate or rotate when the occluder 32 is forced against the membrane 54. FIGS. 16A-16C further illustrate that the connector 310 can be a clip and can have, for example, clip arms (e.g., two clip arms) that are engageable with the cover 320 such that the cover 320 can be snapped into the connector 310 (e.g., as shown in FIG. 16B). As another example, FIGS. 16A-16C illustrate that the connector 310 can have the cover 320.

FIGS. 14A₁-16C illustrate details of manufacturing methods and various variations of the device 10, including, for example, (1) variations in the butterfly shape to enable efficient assembly, (2) addition of a collar to the sensor 18 (e.g., footplate) or incorporation of a snap-to-fit feature to enable efficient assembly and (3) introduction of a living hinge to serve as a cover 320 that enables efficient incorporation of wings 15 into the device 10.

FIGS. 17A and 17B illustrate a variation of the device 10. The device 10 can be an AV fistula butterfly needle with tubing 8 that can be utilized for hemodialysis therapy. FIGS. 17A and 17B illustrate the device 10 in a state of dislodgement, with the needle body (also referred to as the housing 14) lifted off of and away from the skin of the patient. The device 10 can also be in the state shown in FIGS. 17A and 17B before the device 10 is attached to the patient. The device 10 can be equipped with the sensor 18 (e.g., skin-sensing footplate mechanism).

FIGS. 17C-17E illustrate that the footplate body can be attached to a spring 332 (e.g., to a pre-formed metal spring). The spring 332 can have a spring first extension 334a, a spring second extension 334b, and a spring third extension 334c. The spring second extension 334b can serve as an occlusion member (e.g., as the occluder 32) in the internal flow path 56 during needle dislodgement. A living hinge 336 can simplify manufacturing, allowing both the needle butterfly assembly and the footplate to be molded at the same time (the hinge 336 can allow the footplate to be bent into position following molding). The living hinge 336 can be integrally formed with the housing and can connect the sensor 18 to the housing. The housing 14, the sensor 18, and the living hinge 336 can be made, for example, of the same material, of multiple materials, can be formed with a single mold, or any combination thereof. The curved end of the footplate and the U-opening that allows for full closure against the shaft of the needle are visible. FIGS. 17A-17E illustrate that the spring 332 can be, for example, a stamped and bent flat metal spring instead of a molded plastic spring that is shown in FIGS. 1-6B. As another example, FIGS. 17A-19 illustrates that the spring 332 can be, for example, a flat metal spring instead of a standard coil metal spring.

FIGS. 17A-17E illustrate various cross-sectional and angle views of the specialized needle (also referred to as the device 10) for protecting patients from fluid delivery problems during medical therapies. The device 10 can have a sensor 18 (e.g., a spring-loaded two component footplate having a sensor first portion and a sensor second portion), that, in the dislodged position shown (not taped, and needle body off of skin) results in an occlusion member (also referred to as the occluder 320 of the back end of the footplate moving into and blocking the fluid flow path 56 through the device 10. The sensor first portion can be the portion of the sensor 18 connected to the housing 14 via the living hinge 336 and the sensor second portion can be the spring 332. The flow path 56 through the device 10 is shown as the dotted line in FIG. 17B. FIGS. 17A-17E further illustrate that the device 10 can have a spring 332 (e.g., an all-metal pre-shaped spring) integrated with the housing 14 and the sensor 18, and that the sensor 18 can be integrally formed with the housing 14 such that the sensor 18 (e.g., the sensor first portion) is an extension of the housing 14. The spring 332 can be integrated into the plastic footplate and needle body. For example, FIGS. 17A-17E illustrate that the spring 332 (e.g., the spring first extension 334a) can be embedded in the sensor 18. The spring second extension 334b of the spring 332 (e.g., of the same piece of metal) can be used to form the occluder 32 that serves as the member which impedes internal flow through the device 10 during dislodgement. To simplify manufacturing, the needle butterfly assembly can be molded at the same time as the footplate along with a living hinge that allows for easy placement of the footplate under the needle body.

FIGS. 17A-17E further illustrate that the spring first extension 334a can be embedded in the housing 14. FIGS. 17A-17E further illustrate that the flow restrictor 28 can be the spring second extension 334b. FIGS. 17A-17E further illustrate that the spring second extension 334b can comprise two bends. One of the two bends can be the occluder 32, as can be seen in FIGS. 17C-17E. FIGS. 17A-17E further illustrate that the spring third extension 334c can be positioned between the housing 14 and the insert 17 (e.g., as shown in FIG. 17C), or that the third extension 334c can be embedded in the housing 14. FIGS. 17A-17E further illustrate that the sensor 18 can be an extension of the housing 14 and that the spring 332 can be attached to the housing 14.

FIGS. 18A and 18B illustrate a top angle and cross sectional views of a variation of the spring 332. The spring 332 can be, for example, a pre-formed metal spring that supplies the spring force for skin-service detection and the force for occlusion of the flow path via the activation of the occlusion piece (e.g., of the occluder 32) up into the flow path. FIGS. 18A and 18B further illustrate that the occlusion piece (e.g., the occluder 32) can be fitted with an occluder cap 338 (also referred to as an occluder cover). The occluder cap 338 can be, for example, a custom formed plastic cap which through modification of shape, size, form, profile or material, allows for optimization of the closure to maximize device performance. For example, FIGS. 18A and 18B illustrate that the occluder cap 338 can have a wedge shape.

FIG. 18A further illustrates, for example, a top angle view of the spring 332 with the occluder cap 338 on the occluder 32 (e.g., on the occlusion portion of the sensor 18). The spring 332 can be metal, plastic, or both. For example, FIG. 18A illustrates that the spring 332 can be metal. The cap 338 can be metal, plastic, or both. For example, FIG. 18A illustrates that the cap 338 can be plastic. The shape, size, form, profile or material of the plastic cover can be modified in any way necessary to improve occlusion function of the occlusion. FIG. 18B further illustrates a cross-section view showing the plastic cover 338 on the occlusion piece (also referred to as the occluder 32) in place during a dislodgement (off of skin).

FIG. 19 illustrates that the device 10 can have a needle cap 340, a sensor support 342, or both. FIG. 19 further illustrates that the needle cap 340 can be transparent so that the needle 12 can be seen inside the needle cap 340. FIG. 19 further illustrates that the needle cap 340 can be removably attached to the device 10. FIG. 19 further illustrates that when the needle cap 340 is attached to the device 10, the needle 12 can be inside the needle cap 340, for example, in a needle cap chamber as shown in FIG. 19. When the needle cap 340 is removed from the device 10, the needle 12 can be outside of the needle cap 340.

FIG. 19 further shows that the needle cap 340 (also referred to, for example, as a needle cover, protective cover, and cap) can include the sensor support 342. As another example, the sensor support 342 can be separate from the needle cap 340 such that the device 10 can have the needle cap 340, the sensor support 342, or both the needle cap 340 and the sensor support 342. The sensor support 342 can hold the sensor 18 (e.g., a spring-loaded footplate or a sensor 18 having the spring 332) in any position between fully closed (e.g., the sensor 18 against the needle body) or fully open (e.g., the sensor 18 distended or extended away from the needle body as shown in FIG. 19) during shipping and storage before use on a patient. To maximize device functionality it may be advantageous to keep the sensor 18 (e.g., footplate) fully closed, fully open or at any physical position in between closed and open before patient use, as different positions can put differing amounts of mechanical stress on the device components over time. For example, keeping the sensor 18 (e.g., footplate) in a fully closed position, a fully open position, or at any physical position in between fully closed and fully open before patient use such as on the sensor 18 can reduce the stress on the membrane 54, the spring of the sensor 18 (e.g., an integrated spring and/or the spring 332), or any combination thereof before the device is attached to the patient and thereby advantageously prolong the shelf life of the device 10 prior to use. The needle cap 340 can have a recess 344 having a recess height $344_H$. The recess 344 permits holding of the sensor 18 (e.g., footplate) at any proposed position based on the formed height (e.g., the recess height $344_H$ of the recess 344, where a smaller height holds the sensor 18 closer to the needle 12, and where a larger height holds the sensor 18 further away from the needle 12. FIG. 19 further illustrates that when the sensor 18 is in the recess 344, the sensor 18 can rest against the sensor support 342. The sensor support 342 can be integrally formed with the needle cap 340 such that the sensor support 342 and the needle cap 342 are a monolithic piece. As another example, the sensor support 342 can be removably attached to the needle cap 340. The needle cap 340 can be tethered or untethered to the device 10.

FIG. 19 further illustrates, for example, a side view of the device showing a protective cover 340. The cap 340 can include an extended step 342 (also referred to as the sensor support), a recess 344, or both, which allows for both standard protection of the needle 12 when affixed to the needle body (e.g., to the housing 14) but also permits stabilization of the sensor 18 (e.g., footplate) in any chosen position based on the height of the recess 344. Controlling the position of the footplate can lead to increased device longevity over storage by relieving stress on the spring (e.g., the spring integrated with the sensor 18 or the spring 332) and on the inner membrane (e.g., membrane 54) that allows for access to the internal flow channel 56 via the occlusion piece (e.g., via the occluder 32). FIG. 19 further illustrates that the footplate can be molded separately, with no living hinge.

FIGS. 17A-19 illustrate details of manufacturing methods and various variations of the device 10, including, for example, (1) the use of a living hinge to enable efficiency in part count and assembly, (2) an all-metal pre-shaped spring assembly, (3) a small plastic cover (e.g., the occluder cap 338) that can be modified to influence the flow in favorable ways during device activation, (4) a needle cap 340 which can hold the footplate in a partially extended state before use to help relieve stress on the internal core to help extend product shelf life.

FIGS. 20A-22C outline several known designs for protective needle guards 360. Major needle manufacturers each use a technique of their own design. Medi-Systems, Nipro and JMS are popularly available AVF needles for dialysis in the US. Each has a unique slideable system, with three different systems shown in FIGS. 20A-20C, 21A-21C, and 22A-22C, respectively, for a protective needle cover designed to be activated at the end of dialysis therapy. FIGS. 20A-22C show commercially available needle guards. For example, FIGS. 20A-20C from FIG. 20A to FIG. 20C show a needle being withdrawn from a patient into the protective covering of the Medi-Systems MasterGuard needle guard 360. As another example, FIG. 21A-21C from FIG. 21A to FIG. 21C show the progression of the Nipro Tulip needle guard 360 as it is slid from the off position into the protective position. As yet another example, FIGS. 22A-22C from FIG. 22A to FIG. 22C show the progression of the JMS Wingeater system 360 as it is slid from the off position into the protective position. However, the designs in FIGS. 21A-23C would need improvements for use to fully accommodate the device 10 or any needle system with an integrated footplate or other skin sensing unit designed to help protect patients from the dangers of needle dislodgement. To enable effective use of these types of designs (e.g., those in FIGS. 21A-23C), certain modifications will be necessary. The present disclosure relates to the type of modifications that would enable efficient use of these types of sliding needle guards.

FIG. 23 illustrates that a needle guard 360 can be used to guard the needle 12 of the device 10. The needle guard 360 can have a first piece 362 that can have a beveled or chamfered edge 364. The first piece 362 can be a bottom piece configured to slide against the patient's skin and which is configured to slide under the sensor 18. The first piece 362 can be integrated into the edge design of the bottom piece of the slideable needle guards 360, for example, shown in FIGS. 20A-20C so that the needle guards shown in FIGS. 20A-22C can go over the sensor 18 (e.g., over the footplate). The beveled or chamfered edge 364 can enable a smoother and easier transition from the unprotected to the protected state for devices having the sensor 18. FIG. 23 illustrates an example of a modification to the bottom edge of existing needle guards 360 (e.g., those shown in FIGS. 20A-22C) to enable more effective sliding of the needle guard 360 over a needle equipped with a footplate for skin sensing as part (e.g., sensor 18) of a system to protect patients from inadvertent needle dislodgement. FIG. 23 illustrates that the bottom edge 364 of the needle guard can be beveled or chamfered at the transitional zone where the bottom edge meets the sensor 18 (e.g., footplate) during sliding. This angle enables effective and smooth sliding of the guard over the needle body and footplate. Arrow 366 shows the slide direction to protect (e.g., cover) the needle 12.

FIGS. 24A and 24B details a modified version of the MasterGuard Needle protection design 360 illustrated in FIGS. 20A-20C. FIGS. 24A and 24B illustrate that a portion 372 of the flat bottom 374 of the needle guard 360 of FIGS. 20A-20C can be positioned at an angle 370 to the traditional bottom. The portion 372 is also referred to as the needle guard angled slide, the needle guard slide, the transitional zone, the angled portion and other similar terms. The angle 370 enables a smoother movement of the needle guard over the footplate during operation. FIGS. 24A and 24B illustrate another example of a modification to the bottom edge of the needle guards 360 of FIGS. 20A-20C to enable more effective sliding of the guard 360 over a needle equipped with a footplate for skin sensing as part of a system to protect patients from inadvertent needle dislodgement. FIGS. 24A and 24B illustrate that the MasterGuard bottom edge 374 can be modified to have a transitional zone 372 where the bottom edge meets the sensor 18 (e.g., footplate) during sliding is offset at the angle 370 for a distance 375 to enable effective and smooth sliding of the guard over the needle body and footplate. The distance 375 can be, for example, about 8 mm to about 20 mm, including every 1 mm increment within this range (e.g., 15 mm). The modification results in a small section of the transitional zone being placed at an angle 370 of about 10 degrees to about 40 degrees downward from the existing needle guard bottom, including every 1 degree increment within this range (e.g., 25 degrees). When the needle guard 360 is fully advanced in direction 366, the needle 12 can be covered by the needle guard 360 and the sensor 18 can be in a partially closed position or in a fully closed position, where FIG. 24A illustrates the sensor in a fully open position.

FIG. 25 illustrates a variation of a protective needle guard design 360. FIG. 25 illustrates that the bottom of the guard has a larger angled shape which acts as a funnel 376 (also referred to as an entryway, a footplate funnel, a footplate guide, a footplate channel) for the footplate to be efficiently funneled into the needle guard 360 during sliding. FIG. 25 illustrates another example of a modification to the bottom edge of the needle guards 360 of FIGS. 20A-20C to enable more effective sliding of the guard over a needle equipped with a footplate for skin sensing as part of a system to protect patients from inadvertent needle dislodgement. FIG. 25 illustrates that the MasterGuard bottom edge 374 can be modified to have a transitional zone 372 where the bottom edge meets the sensor 18 (e.g., footplate) during sliding is offset at the angle 370 for a distance 375 to enable effective and smooth sliding of the guard over the needle body and footplate. The modification results in a small section of the transitional zone being placed at an angle 370 of about 10 degrees to about 40 degrees downward from the existing needle guard bottom, including every 1 degree increment within this range (e.g., 25 degrees). When the needle guard 360 is fully advanced in direction 366, the needle 12 can be covered by the needle guard 360 and the sensor 18 can be in a partially closed position or in a fully closed position, where FIG. 24A illustrates the sensor in a fully open position.

The needle guard modifications shown in FIGS. 23-25 can be applied to any existing needle guard 360, and can be combined with each other in any combination. For example, FIG. 25 illustrates that the transitional zone 372 having the funnel 376 can have a beveled or chamfered edge 364, or can have a non-beveled or non-chamfered edge.

The techniques for modifying the bottom piece of the needle guards 360 illustrated and described herein are also applicable to guards 360 without an obvious bottom piece, such as the Nipro Tulip in which case, modifications are done to any or all pieces as appropriate for effective function.

Other needle guard modification techniques include modifying the material of the sensor 18 (e.g., footplate) or guard 360 or combination thereof to enable a lower frictional interface against each other that enables more efficient sliding of the guard 360 over the footplate. As another example, the surfaces of the sensor 18 (e.g., footplate), the guard 360, or both could be modified to induce low frictional sliding.

FIGS. 19-25 illustrate details various modifications of the device 10, of existing needle guards 360, or both, for example, showing various modifications of existing needle guards 360 so that they can be compatible with the device 10 given that the device 10 has the sensor 18 (e.g., footplate) that needs to be accounted for. All needles are federally required to have guards 360 put into place upon removal from the patient. FIGS. 19-25A illustrate various examples of this can be achieved. For example, FIGS. 19-25 illustrate various needle guards 360 that can cover up the sharp end of the needle 12 after patient usage to reduce danger of subsequent needle sticks of staff or patients. For example, the needle guard can be moveable over the needle 12 to cover up the sharp end of the needle 12 when the needle 12 becomes dislodged from a patient or when the needle 12 is removed from the patient. The needle guards 360 can have a needle guard body having a needle chamber that can receive the needle 12. The needle guards 360 can have a needle guard body having a needle chamber that can protect the needle 12. The needle guards 360 can be slide over the device 10, for example, to cover the needle 12. The needle guards 360 can have a needle guard first position relative to the needle 12 and a needle guard second position relative to the needle 12. When the needle guard 360 is in the needle guard first position, the needle 12 can be uncovered (also referred to as exposed). When the needle guard 360 is in the needle guard second position, the needle 12 can be covered such that the device 10 can comply with the federal mandate that requires needle guards (e.g., needle guards 360. The device 10 can have or be outfitted with a needle cap 340, a needle guard 360, or both.

FIGS. 1-25 further illustrate, for example, that the device 10 can have the 12 needle, the first-shot mold 190, and the second-shot mold 192. The device 10 can have the needle cap 340, the needle guard 360, or both the needle cap 340 and the needle guard 360. The first-shot mold 190 and the second-shot mold 192 can define the device flow channel 56. As another example, a tube in a channel defined by the first-shot and second-shot molds 190, 192 can define the device flow channel 56. The device 10 can have the occluder 32. The occluder 32 can be moveable into and out of the device flow channel 56. As another example, the occluder 32 can be moveable from an occluder first position to an occluder second position, where when the occluder 32 is the occluder first position, the occluder 32 can be out of the device flow channel 56, and when the occluder 32 is in the occluder second position, the occluder 32 can be in the device flow channel 56. As yet another example, less of the occluder 32 can be in the device flow channel 56 when the occluder 32 is in the occluder first position than when the occluder 32 is in the occluder second position. The occluder 32 can be moveable back and forth between the occluder first and second positions. As another example, when the occluder 32 moves from the occluder first position to the occluder second position, the occluder 32 can be locked in the occluder second position. The device 10 can have a device closed configuration and a device open configuration. When the device 10 is in the device closed configuration, the occluder 32 can be in the device flow channel 56. When the device 10 is in the device open configuration, less of the occluder 32 can be in the device flow channel than when the device is in the device closed configuration. For example, when the device 10 is in the device open configuration, the occluder 32 can be in the occluder first position and when the device 10 is in the device closed configuration, the occluder 32 can be in the occluder second position. When the device 10 is in the device closed configuration, the occluder 32 can restrict or stop fluid flow through the device flow channel 56, for example, by causing a portion of the device flow channel 56 to have a smaller cross-sectional area when the device 10 is in the device closed configuration than when the device 10 is in the device open configuration. For example, when the device 10 changes from the device open configuration to the device closed configuration, the occluder 32 can be forced against a conduit defining the device flow channel 56 to create a kink in the device flow channel 56 to partially or fully restrict flow through the device flow channel 56. The conduit can be a channel defined by the first-shot mold 190 and the second-shot mold 192, for example, the wall or walls that define the device flow channel 56. When the device 10 changes from the device open configuration to the device closed configuration, the occluder 32 can be forced against the membrane 54 such that the membrane 54—which can define a portion of the device flow channel 56—is pushed into the device flow channel 56 such that the occluder 32 causes the membrane 54 to move into the device flow channel 56 to partially or fully occlude the device flow channel 56. When the device 10 is in the device open configuration, the device flow channel 56 can have a first transverse cross-sectional area. When the device 10 is in the device closed configuration, the device flow channel 56 can have a second transverse cross-sectional area such that the second cross-sectional area is less than the first-cross-sectional area.

FIGS. 1-25 further illustrate, for example, that the device 10 can have the 12 needle and the housing 14 (also referred to as the device housing). The device 10 can have the needle cap 340, the needle guard 360, or both the needle cap 340 and the needle guard 360. The housing 14 can define the device flow channel 56. As another example, a tube in the housing 14 can define the device flow channel 56. The device 10 can have the occluder 32. The occluder 32 can be moveable into and out of the device flow channel 56. As another example, the occluder 32 can be moveable from an occluder first position to an occluder second position, where when the occluder 32 is the occluder first position, the occluder 32 can be out of the device flow channel 56, and when the occluder 32 is in the occluder second position, the occluder 32 can be in the device flow channel 56. As yet another example, less of the occluder 32 can be in the device flow channel 56 when the occluder 32 is in the occluder first position than when the occluder 32 is in the occluder second position. The occluder 32 can be moveable back and forth between the occluder first and second positions. As another example, when the occluder 32 moves from the occluder first position to the occluder second position, the occluder 32 can be locked in the occluder second position. The device 10 can have a device closed configuration and a device open configuration. When the device 10 is in the device closed configuration, the occluder 32 can be in the device flow channel 56. When the device 10 is in the device open configuration, less of the occluder 32 can be in the device flow channel than when the device is in the device closed configuration. For example, when the device 10 is in the device open configuration, the occluder 32 can be in the occluder first position and when the device 10 is in the device closed configuration, the occluder 32 can be in the occluder second position. When the device 10 is in the device closed configuration, the occluder 32 can restrict or stop fluid flow through the device flow channel 56, for example, by causing a portion of the device flow channel 56 to have a smaller cross-sectional area when the device 10 is in the device closed configuration than when the device 10 is in the device open configuration. For example, when the device 10 changes from the device open configuration to the device closed configuration, the occluder 32 can be forced against a conduit defining the device flow channel 56 to create a kink in the device flow channel 56 to partially or fully restrict flow through the device flow channel 56. The conduit can be a channel defined by the housing 14, by a tube that extends through the housing channel 51, or both, for example, the wall or walls that define the device flow channel 56. When the device 10 changes from the device open configuration to the device closed configuration, the occluder 32 can be forced against the membrane 54 such that the membrane 54—which can define a portion of the device flow channel 56—is pushed into the device flow channel 56 such that the occluder 32 causes the membrane 54 to move into the device flow channel 56 to partially or fully occlude the device flow channel 56. When the device 10 is in the device open configuration, the device flow channel 56 can have a first transverse cross-sectional area. When the device 10 is in the device closed configuration, the device flow channel 56 can have a second transverse cross-sectional area such that the second cross-sectional area is less than the first-cross-sectional area.

FIGS. 1-25 further illustrate, for example, that the device 10 can have a spring (e.g., any of the springs disclosed, contemplated, and/or illustrated herein), where the spring can be biased to move the occluder into the device flow channel 56 when the device 10 changes from the device open configuration to the device closed configuration. The spring can be, for example, coil spring, a flat spring, or a spring-loaded sensor (e.g., a spring-loaded footplate). The spring can be, for example, at least one of a coil spring, a flat spring, or a spring-loaded sensor (e.g., a spring-loaded footplate). The spring can be metal, plastic, a composite material, or any combination thereof. For example, the spring can be plastic. As another example, the spring can be plastic. The device 10 can have the sensor 18. The sensor 18 can be spring-loaded or not spring-loaded. For example, the sensor 18 can be a spring-loaded sensor (e.g., can be a spring-loaded footplate). As another example, the sensor 18 (e.g., the footplate) can be not spring-loaded but instead have a spring attached to the sensor 18 (e.g., footplate). The spring can be attached to the sensor 18 (e.g., footplate). The spring can be integrally formed with the sensor 18 such that the sensor 18 is a spring. The sensor 18 (e.g., footplate) can have the occluder 32. The first-shot mold 190 can have butterfly wings 15. The first-shot mold 190 can have the sensor 18 (e.g., the footplate). The device 10 can have the membrane 54. The membrane 54 can be deformable. For example, the membrane 54 can be stretchable, compressible, unfoldable, foldable, or any combination thereof. The second-shot mold 192 can have the membrane 54 (e.g., the deformable membrane). The spring can have the occluder 32. The occluder 32 can be moveable via movement of the spring. The sensor 18 (e.g., footplate) can have the occluder 32. The occluder 32 can be moveable via movement of the sensor 18 (e.g., footplate). The membrane 54 can be deformed by the occluder when the device is in the device closed configuration. The membrane 54 can be less deformed by the occluder 32 when the device 10 is in the device open configuration than when the device 10 is in the device closed configuration. When the device 10 is in the device open configuration, the device flow channel 56 can have a first transverse cross-sectional area. When the device 10 is in the device closed configuration, the device flow channel 56 can have a second transverse cross-sectional area, where the second cross-sectional area can be less than the first-cross-sectional area. When the device 10 is in the device open configuration, the device flow channel 56 can have a first transverse cross-sectional area. When the device 10 is in the device closed configuration, the device flow channel 56 can have a second transverse cross-sectional area, where the second cross-sectional area can be smaller than the first-cross-sectional area. The membrane 54 can be invertible. The membrane 54 can define the pocket 208 for the occluder 32. The membrane 54 can be invertible and can define the pocket 208 for the occluder 32. The occluder 32 can have the occluder cover 338 configured to deform the membrane 54. The sensor 18 (e.g., footplate) can be moveable via movement of the spring. The device 10 can have the insert 17. The insert 17 can have the first-shot mold 190 and the second-shot mold 192. The first-shot mold 190 and the second-shot mold 192 can be the insert 17. The housing 14 can have the connector 310. The connector 210 can be configured to connect to the first-shot mold 190. The housing 14 can have the connector 310. The connector 210 can be configured to connect to the insert 17. The housing 14 can have the cover 320 configured to cover the first-shot-mold 190. The housing 14 can have the cover 320 configured to cover the insert 17. The cover 320 can be a hinged cover. The cover 320 can be connected to the housing 14 with a hinge, for example, via hinge 322, via hinge 323, or via both hinge 322 and hinge 323. The hinge can be a living hinge. The device 10 can have the needle hub 13. The needle hub 13, for example, can be part of the insert 17, part of the first-shot mold 190, part of the housing 14, or any combination thereof. As another example, the needle hub 13 can be attached to the insert 17, to the first-shot mold 190, to the housing 14, or any combination thereof. The cover 320 can be connected to the housing 14 with the first hinge 322, and the cover 320 can be connected to the housing 14 with the second hinge 323. The hinge (e.g., hinge 322, hinge 323) can be a living hinge. The first hinge 322 can be a living hinge. The second hinge 32 can be a living hinge. The device 10 can have the needle cap 340. The device 10 can have the sensor support 342. The sensor support 342 can be configured to reduce the strain on the spring before the device is attached to a patient. The sensor support 342 can be configured to prolong a shelf life of the device. The needle cap 340 can have a needle cap chamber and the sensor support 342. The device 10 can have the needle guard 360. The needle guard 360 can be moveable over the needle 12 to cover up the needle 12 when the needle 12 becomes dislodged from a patient or when the needle 12 is removed from the patient. The needle guard 360 can have a needle guard body having a needle chamber configured to receive the needle 12. The needle guard 360 can be slideable over the device 10 to cover the needle 12. The needle guard 360 can have a needle guard first position relative to the needle 12 and a needle guard second position relative to the needle 12. When the needle guard 360 is in the needle guard first position, the needle 12 can be exposed. When the needle guard 360 is in the needle guard second position, the needle 12 can be covered by the needle guard 360. When the needle guard 360 is in the needle guard second position, the needle 12 can be covered such that the device 12 is in compliance with the federal mandate that requires needle guards. When the needle guard 360 is in the needle guard second position, the needle 12 can be covered such that the device 12 is in compliance with legally imposed safety requirements. The needle guard body can have a bottom edge slideable under the sensor 18 (e.g., footplate) when the device 10 is attached to a patient. The needle guard body can have a bottom edge slideable under the sensor 18 (e.g., footplate) after the device 10 becomes dislodged from the patient or after the device 10 is removed from the patient. The needle guard body can have a bottom edge slideable under the sensor 18 (e.g., footplate) after the needle 12 becomes dislodged from the patient or after the needle 12 is removed from the patient. When the needle guard 360 moves from the needle guard first position to the needle guard second position, the sensor 18 (e.g., footplate) is moveable toward at least one of the housing 14, the insert 17, the first-shot mold 190, and the needle 12 via the needle guard 360. The bottom edge of the needle guard 360 can be a chamfered or beveled edge. The needle guard body can have a flat bottom portion and an angled portion configured to enable more effective sliding of the needle guard 360 over the needle 12 when the device 10 has the sensor 18 (e.g., footplate). The needle guard body can have a footplate channel (also referred to as a sensor channel) configured to enable more effective sliding of the needle guard 360 over the needle 12 when the device 10 has the sensor 18 (e.g., footplate) by guiding the footplate into the needle guard 360. As another example, the needle 12 can be retractable into the device 10, for example, into the device flow channel 56, into the channel 51, into the housing 14, into the insert 17, into the first-shot mold 190, or any combination thereof. The device 10 can have a needle retraction mechanism, such as a needle retractor (e.g., a retractor spring) that can be activated, for example, when the device 10 when the needle 12 becomes dislodged from a patient or when the needle 12 is removed from the patient. For example, when the sensor 18 senses a dislodgement event, whether unintentional or intentional, the needle 12 can automatically retract into the device 10. A method of assembling the device 10 can include, for example, attaching wings 15 to a 2-shot core (e.g., the insert 17) having a first-shot mold 190 and a second-shot mold 192. The first-shot mold 190 can have connector (e.g., the insert proximal end 17p) for a tube (e.g., the tube 8). The second-shot mold 192 can have the membrane 54. The membrane 54 and the first-shot mold 190 can define the device flow channel 56. The method of assembling the device 10 can include attaching the sensor 18 (e.g., a moveable footplate) having the occluder 32 to the first-shot mold 190. The sensor 18 can be moveable. For example, the method can include attaching the moveable sensor 18 (e.g., the moveable footplate) to the first-shot mold 190. As another example, a method of assembling the device 10 can include attaching butterfly wings 15 to a device central core (e.g., to the insert 17) defining the device flow channel 56. The insert 17 can be a 2-shot mold having, for example, the first-shot mold 190 and the second-shot mold 192. As another example, the insert 17 may not be a 2-shot mold, where, for example, the insert 17 have the first portion 191, and where the second portion 193 can be attached to the first portion 191. The sensor 18 can be attached to the first portion 191 and/or to the second portion 193. The method can include attaching the sensor 18 (e.g., moveable footplate) having the occluder 32 to the device central core (e.g., to the insert 17). As yet another example, a method of assembling the device can include attaching a moveable sensor 18 (e.g., moveable footplate) having the occluder 32 to the housing 14. The methods can include attaching butterfly wings 15 to the housing 14. The housing 14 (or a portion thereof) can define the device flow channel 56. The methods can include attaching the tube 8 to a tube connector. The tube connector can be, for example, the insert proximal end 17p. Attaching wings 15 to the 2-shot core can include clipping the wings 15 onto the 2-shot core or sliding the wings 15 onto the 2-shot core. The device 10 can be configured to have the device open configuration when the device 10 is attached to a person. The device 10 can be configured to change from the device open configuration to the device closed configuration when the device 10 becomes dislodged from the person or when the device 10 is removed from the person. The device 10 can be configured to change from the device open configuration to the device closed configuration when the needle 12 becomes dislodged from the person or when the needle 12 is removed from the person. As still yet another example, the device 10 can have the needle 12. The device 10 can have the first-shot mold 190 and the second-shot mold 192. The first-shot mold 190 and the second-shot mold 192 can define the device flow channel 56. The device 10 can have the occluder 32. The occluder 32 can be moveable into and out of the device flow channel 56. The device 10 can have a device closed configuration and a device open configuration. When the device 10 is in the device closed configuration, the occluder 32 can be in the device flow channel 56. When the device 10 is in the device open configuration, less of the occluder 32 can be in the device flow channel than when the device 10 is in the device closed configuration. As still yet another example, the device 10 can have the needle 12. The device 10 can have the housing 14 having the device flow channel 56. The device 10 can have the occluder 32. The occluder 32 can be moveable into and out of the device flow channel 56. The device 10 can have a device closed configuration and a device open configuration. When the device 10 is in the device closed configuration, the occluder 32 can be in the device flow channel 56. When the device 10 is in the device open configuration, less of the occluder 32 can be in the device flow channel than when the device 10 is in the device closed configuration.

FIG. 26A shows a generalized time vs. pressure plot 378 that outlines the essence of the pressure detection problem. Venous line pressure over time is plotted for a hypothetical normal patient undergoing dislodgement. The graph 378 shows an estimate of how the venous line pressure can change during the dislodgement event. For patients with low venous access pressure, the drop in pressure due to dislodgement is often not large enough to trigger a pre-set machine lower pressure alarm limit, where "Up Lim" is the upper pressure alarm limit of the pump, where "Low Lim" is the lower pressure alarm limit of a pump, and where "VND OCCURS" indicates where the venous dislodgement event occurs. FIG. 26A illustrates Venous Line Pressure (VLP) vs. Time for a hypothetical venous needle dislodgement during hemodialysis. In the dislodgement event shown in FIG. 26A, the pressure variation due to dislodgement is not large enough to trigger the machine pump high or low pressure alarm limit window settings. For such cases, the machines would continue to pump blood, possibly endangering the life of the patient. FIG. 26A shows, for example, the pressure dropping from a first venous line pressure $VLP_1$ to a second venous line pressure $VLP_2$.

FIGS. 26B-27B illustrate a variation of shutting off fluid flow during a venous dislodgement event. FIGS. 27A and 28B illustrate that the device 10 can have a sensor 18 (e.g., footplate) and an occluder 32 (e.g., membrane pincher) that moves out of the flow path (e.g., out of the device flow channel 56) during a dislodgement event instead of into it. The device 10 may or may not have a spring. When the device 10 does not have a spring, the occluder 32 can fall away from the membrane 54 and the device flow channel 56 during a dislodgement event. When the device 10 does have a spring, for example, attached to or integrated with the sensor 18, the spring can be biased to pull the occluder 32 away from the membrane 54 and the device flow channel 56 during a dislodgement event. For example, with or without a spring, FIGS. 27A and 27B illustrate that activation of the device 10 can cause the occluder 32 (e.g., pincher) to move out of the device flow channel 56 causing a drop in line pressure. This drop in pressure can be detected by the hemodialysis machine and leads to machine shut off as shown in FIG. 26B. FIGS. 27A and 27B illustrate that the device 10 can be, for example, a spring-less system.

FIG. 26B details estimates of venous pressure over time plot 380 of a hypothetical patient undergoing needle dislodgement using the device 10 of FIGS. 27A and 27B. If this patient is equipped with the device 10 of FIGS. 27A and 27B, the mechanical interruption of the fluid flow path during normal therapy allows the system to respond much more vigorously in the event of dislodgement (that is, the pressure drop is of a much higher magnitude). This vigorous response is much more likely to trigger the lower pressure alarm limit setting and result in automatic machine shut down during dislodgement as shown in FIG. 26B, where "Up Lim" is the upper pressure alarm limit of the pump, where "Low Lim" is the lower pressure alarm limit of a pump, and where "VND OCCURS" indicates where the venous dislodgement event occurs. FIG. 26B illustrates Venous Line Pressure (VLP) vs. Time for a hypothetical venous needle dislodgement during hemodialysis for a patient using this disclosure. In the dislodgement event shown in FIG. 26B, a mechanical intrusion in the flow path has created a higher than usual venous line pressure during standard therapy. In the case of needle dislodgement using any of the devices 10, the lower limit alarm is easily breached as the dislodgement also removes the mechanical flow barrier within the needle body. Exceeding the lower alarm limit can generate automated machine shut down and protects patients from blood loss.

FIG. 27A illustrates that the needle body/footplate feature (e.g., housing 14/sensor 18 feature, insert 17/sensor 18 feature, or any combination thereof) as it would appear during therapy. While the device 10 is taped onto the skin, the sensor 18 (e.g., footplate member) has a subsection (e.g., the occluder 32) which, via the thin elastic membrane 54, is able to protrude into the fluid flow path 56 through the center of the needle body. By varying the size and shape of the protrusion (e.g., of the occluder 32), the line pressure can be increased for any given constant flow setting. For example, a large protrusion that nearly blocks the flow path would induce a significantly large line pressure increase as opposed to the relatively smaller protrusion shown in FIG. 27A. FIG. 27A illustrates that the sensor 18 can increase the pressure in the device flow channel 56 while the needle 12 is fully taped to the body and fluid is flowing through the device 10. FIG. 27A further illustrates the line occlusion feature (e.g., the sensor 18) shown in cross section. The occluder 32 (e.g., occlusion member) pushes against a flexible membrane in the normal therapy delivery state (taped to the arm). Based on the size and shape of the occlusion, the magnitude of the line pressure increase can be controlled.

FIG. 27B illustrates the occlusion feature in the dislodged mode. When the needle becomes un-taped or otherwise is inadvertently removed from the vascular access during normal therapy, the pressure rising protrusion (e.g., the occluder 32) is pulled away from the flow path 56, for example, via the spring-loaded footplate (e.g., the sensor 18). Removal of the protrusion from the flow path allows for a significant pressure drop as the mechanical barrier (e.g., the occluder 32) no longer impedes flow. Simple physics dictates the magnitude of the pressure decrease this feature generates during dislodgement. The device 10 in FIGS. 27A and 27B can thereby generate a pressure drop which acts as a very reliable and unequivocal signal for the machine to automatically shut down due to violation of low pressure limits. FIG. 27B further illustrates the footplate/line occlusion feature shown in cross-section during a venous needle dislodgement (device no longer taped flat against patient skin). Removal of the occlusion member (e.g., the occluder 32) from the flow path 56 causes a proportional drop in line pressure. That drop is used to unequivocally trigger the lower alarm limit settings of the fluid pump and induce pump shut off, protecting patient. FIGS. 27A and 27B illustrate that when the device 10 is in the device open configuration, the device flow channel 56 can have a first transverse cross-sectional area, and that when the device 10 is in the device closed configuration, the device flow channel 56 can have a second transverse cross-sectional area, and that the second cross-sectional area can be greater than the first-cross-sectional area.

The device 10 in FIGS. 27A-27B can have any of the features, and any combination of the features shown, for example, in FIGS. 1-25.

For example, FIGS. 27A and 27B further illustrate, for example, that the device 10 can have the needle 12 and the housing 14. The housing 14 can have the device flow channel 56. The device 10 can have the occluder 32. The occluder 32 can be moveable into and out of the device flow channel 56. The device 10 can have a device first open configuration and a device second open configuration. When the device 10 is in the device first open configuration, the occluder 32 can be in the device flow channel 56. When the device 10 is in the device second open configuration, less of the occluder 32 can be in the device flow channel 56 than when the device 10 is in the device first open configuration. The housing 14 can define the device flow channel 56. As another example, a tube in the housing 14 can define the device flow channel 56. The device 10 can have the occluder 32. The occluder 32 can be moveable into and out of the device flow channel 56. As another example, the occluder 32 can be moveable from an occluder first position to an occluder second position, where when the occluder 32 is the occluder first position, the occluder 32 can obstruct the device flow channel 56 (e.g., partially obstruct the device flow channel 56 as shown in FIG. 27A), and when the occluder 32 is in the occluder second position, the occluder 32 can be out of the device flow channel 56. As another example, the occluder 32 can be moveable from an occluder first position to an occluder second position, where when the occluder 32 is the occluder first position, the occluder 32 can obstruct the device flow channel 56 (e.g., partially obstruct the device flow channel 56 as shown in FIG. 27A), and when the occluder 32 is in the occluder second position, the occluder 32 can obstruct the device flow channel 56 less than when the occluder 32 is in the occluder first position. As yet another example, more of the occluder 32 can be in the device flow channel 56 when the occluder 32 is in the occluder first position than when the occluder 32 is in the occluder second position. The occluder 32 can be moveable back and forth between the occluder first and second positions. The device 10 can have the device first open configuration and the device second open configuration. When the device 10 is in the device first open configuration, the occluder 32 can be in the device flow channel 56. When the device 10 is in the device second open configuration, less of the occluder 32 can be in the device flow channel 56 than when the device 10 is in the device first open configuration. When the device is in the device second open configuration, some or none of the occluder 32 can occlude the device flow channel 56. For example, when the device 10 is in the device first open configuration, the occluder 32 can be in the occluder first position and when the device 10 is in the device second open configuration, the occluder 32 can be in the occluder second position. When the device 10 is in the device first open configuration, the occluder 32 can restrict fluid flow through the device flow channel 56, for example, by causing a portion of the device flow channel 56 to have a smaller cross-sectional area when the device 10 is in the device first open configuration than when the device 10 is in the device second open configuration. For example, when the device 10 changes from the device first open configuration to the device second open configuration, the occluder 32 can move out of the flow channel thereby eliminating or reducing the kink in the device flow channel 56 caused by the occluder 32 when the device is in the device first open configuration. When the device 10 changes from the device first open configuration to the device second open configuration, the occluder 32 can deform the membrane 54 less, including, for example, not at all. When the device 10 is in the device first open configuration, the device flow channel 56 can have a first transverse cross-sectional area. When the device 10 is in the device second open configuration, the device flow channel 56 can have a second transverse cross-sectional area such that the second cross-sectional area is greater than the first-cross-sectional area. The device 10 can have a spring (e.g., any of the springs disclosed, contemplated, and/or illustrated herein), where the spring can be biased to move the occluder 32 out of the device flow channel 56 when the device 10 changes from the device first open configuration to the device second open configuration. The device 10 can be configured to have the device first open configuration when the device is attached to a person. The device 10 can be configured to change from the device first open configuration to the device second open configuration when the device 10 becomes dislodged from the person or when the device 10 is removed from the person. The device 10 can be configured to change from the device first open configuration to the device second open configuration when the needle 12 becomes dislodged from the person or when the needle 12 is removed from the person. When the device 10 changes from the device first open configuration to the device second open configuration, a pressure drop in the device flow channel can be detectable, for example, by a pressure sensor. A pump can have the pressure sensor. The pressure sensor can be part of a pump. The housing 14 can have the first-shot mold 190 and the second-shot mold 192. The first-shot mold 190 and the second-shot mold 192 can define the device flow channel 56. The first-shot mold can have butterfly wings 15. The second-shot mold 192 can have the membrane 54. The membrane 54 can be deformable. The membrane 54 (e.g., deformable membrane) can be less deformed by the occluder 32 when the device 10 is in the device second open configuration than when the device 10 is in the device first open configuration.

Any of the devices (e.g., devices 10) disclosed herein can have any combination of the features described, contemplated, and/or illustrated herein. For example, any of the devices (e.g., devices 10) disclosed herein can have any combination of the features or properties illustrated in any combination of FIGS. 1-27B, including any subset of figures in FIGS. 1-27B (e.g., FIGS. 10A-25, FIGS. 10A-27B, FIGS. 26A-27B, FIGS. 10A-26A). Every permutation of the features disclosed, contemplated, and/or illustrated herein is hereby disclosed, and illustrated, for example, by virtue of the figures presented herein and their corresponding description. For example, the housing 14, the insert 17, the first-shot mold 190, and the second-shot mold 192 can be interchangeable with one another in any combination. For example, for the devices 10 illustrated having the housing 14 without the insert 17, the device 10 can be modified to have the insert 17 with or without the housing 14 (e.g., with or without the first-shot mold 190, and/or with or without the second-shot mold 192). As another example, the device 10 can have the housing 14. The housing 14 can be configured for coupling a fluid delivery tube to the needle 12. The needle 12 can be configured for subcutaneous delivery of fluid within a tissue of a patient. The device 10 can have the sensor 18 coupled to the housing. The sensor 18 can be, for example, a spring-loaded activation mechanism such as a footplate. The sensor 18 can have a first orientation corresponding to a condition where the housing 14 is disposed adjacent to the tissue and the needle 12 is lodged within the tissue. The sensor 18 can have a second orientation corresponding to a condition where the housing 14 is disposed away from the tissue or the needle 12 is dislodged from the tissue. The device 10 can have the occluder 32. The occluder 32 can be a flow termination mechanism. The occluder 32 can be directly or indirectly coupled to the sensor 18. The occluder 32 can have an open configuration allowing flow from the fluid delivery tube to the needle 12 when the sensor 18 is in the first orientation. The occluder 32 can have a closed configuration reducing, terminating, or substantially terminating flow from the fluid delivery tube to the needle 12 when the sensor 18 is in the second orientation. The sensor 18 can be disposed adjacent the patient's skin when the sensor 18 is in the first orientation. The sensor 18 can articulate with respect to the housing 14 to the second orientation. The occluder 32 can be a pinch valve that reduces, terminates, or substantially terminates flow from the fluid delivery tube to the needle 12 when the sensor 18 is in the second orientation. The occluder 32 can articulate in response to articulation of the sensor 18 in from the first orientation to the second orientation to pinch-off flow from the fluid delivery tube to the needle 12 when the sensor 18 is in the second orientation. The sensor 18 can be a pinch valve. The footplate can be a pinch valve. The device 10 can have the needle cap 340, the needle guard 360, or both the needle cap 340 and the needle guard 360. The occluder 32 can pinch the device flow path 56, for example, by being forced against the membrane 54. As another example, the housing 14 can have a compliant tube coupling the fluid delivery tube 8 to the needle 12. The occluder 32 can articulate against the compliant tube in the second orientation to reduce, terminate, or substantially terminate flow from the fluid delivery tube 8 to the needle 12. As still yet another example, the device 10 can have a device longitudinal axis. The device 10 can have the needle 12 having a needle proximal end and a needle distal end. The device 10 can have the housing 14 having a housing opening and a housing conduit. The housing conduit can extend from a housing proximal end to a housing distal end. The device can have a deformable membrane. The deformable membrane can define a portion of the housing conduit. The device can have a movable footplate having a footplate proximal end, a footplate distal end, a footplate first surface, a spring, and an occluder. The footplate proximal end can be attached to the housing. The movable footplate can have a footplate first configuration when the footplate first surface applies a first force to a non-footplate surface and a footplate second configuration when the footplate first surface applies a second force less than the first force to the non-footplate surface. The spring can be biased to move the movable footplate from the footplate first configuration to the footplate second configuration when the first force decreases to the second force. At least a first portion of the occluder can occlude the housing conduit when the movable footplate is in the footplate second configuration. At least a second portion of the occluder can be in the housing opening when the movable footplate is in the footplate second configuration and outside the housing opening when the movable footplate is in the footplate first configuration. As still yet another example, the device 10 can have a device longitudinal axis. The device 10 can have the needle 12 having a needle proximal end and a needle distal end. The device 10 can have the housing 14 having a housing opening and a housing conduit. The housing conduit can extend from a housing proximal end to a housing distal end. The device can have a deformable membrane. The deformable membrane can define a portion of the housing conduit. The device can have a movable footplate having a footplate proximal end, a footplate distal end, a footplate first surface, a spring, and an occluder. The footplate proximal end can be attached to the housing. The spring can be biased to move the moveable footplate from a footplate first configuration to a footplate second configuration when a force applied by the footplate first surface against a non-footplate surface changes from a first force to a second force less than the first force. At least a first portion of the occluder can occlude the housing conduit when the movable footplate is in the footplate second configuration. The footplate distal end can have a barrier configured to prevent over insertion of the needle into a vessel. At least a portion of the barrier can be closer to the needle when the moveable footplate is in the footplate first configuration than when the moveable footplate is in the footplate second configuration. The device 10 can have the needle cap 340, the needle guard 360, or both the needle cap 340 and the needle guard 360. As still yet another example, the device 10 can have a device longitudinal axis. The device 10 can have a needle 12 having a needle proximal end and a needle distal end. The device 10 can have the housing 14 having a housing opening and a housing conduit. The housing conduit can extend from a housing proximal end to a housing distal end. The device can have a deformable membrane. The deformable membrane can define a portion of the housing conduit. The device can have a movable footplate having a footplate proximal end, a footplate distal end, a footplate first surface, a spring, and an occluder. The footplate proximal end can be attached to the housing. The spring can be biased to move the moveable footplate from a footplate first configuration to a footplate second configuration when a force applied by the footplate first surface against a non-footplate surface changes from a first force to a second force less than the first force. At least a first portion of the occluder can occlude the housing conduit when the movable footplate is in the footplate second configuration. The footplate distal end can have a curved surface configured to reduce friction against the non-footplate surface when the needle is inserted into a vessel. At least a portion of the curved surface can be closer to the needle when the moveable footplate is in the footplate first configuration than when the moveable footplate is in the footplate second configuration. The device 10 can have the needle cap 340, the needle guard 360, or both the needle cap 340 and the needle guard 360.

Presented here are manufacturing methods that can enable needle safety systems for automatic flow termination of fluid delivery, including a housing configured for coupling a fluid delivery tube to a needle configured for subcutaneous (into vasculature) delivery of fluid within a tissue of a patient and a force-sensitive activation mechanism (shown as a footplate here) having a first 'flattened' orientation corresponding to a condition where the fluid delivery through the needle body is permitted when taped to the patient and a second 'dislodged' condition in which the spring-loaded footplate is configured to push into a soft region and result in an internal flow blockage. The methods include the use of 2-shot molding component that enables efficient occlusion of an internal flow path, a variation in that component in which a pre-formed 'pocket' is used to help reduce overall force required to generate a flow occlusion and efficient assembly techniques regarding multi-piece construction of the full needle system.

Presented here are device modifications/assembly methods that can enable the efficient manufacturing of needle safety systems for automatic flow termination of fluid delivery during dislodgment. The presented aspects of the current disclosure include the use of U-shape snap-fit or press-to-fit modifications that enable integration of individual system components including the butterfly wings to the 2-shot core or the footplate to the 2-shot core. Systems can be assembled in various scenarios (front to back, back to front) most conducive to effective assembly.

Systems and methods for automatic flow termination for fluid delivery, including a housing configured for coupling a fluid delivery tube to a needle configured for subcutaneous (into vasculature) delivery of fluid within a tissue of a patient and a force-sensitive activation mechanism (shown as a plastic footplate here) having a first 'flattened' orientation corresponding to a condition where the fluid delivery through the needle body is permitted while using the U-opening to protect the needle access hole and a second orientation corresponding to a condition where the fluid tube is occluded via an fluid occlusion member of the footplate during needle dislodgement via a spring force provided by pre-formed metal spring integrated into the plastic footplate. This spring can be designed to also include a proximal portion that can act directly as the occlusion piece, alternatively, the metal occlusion piece can be covered with a small plastic cap, mechanically molded with a custom shape and design as needed to enhance device functionality. The plastic footplate can be attached to the needle butterfly assembly via the use of a living hinge, providing a means for efficient manufacturing and assembly. Lastly, a specialized protective needle cover can be designed to include an extension with recess that fits the distal end of the footplate. By controlling the height of this recess, the footplate can be made to rest in any physical position from fully closed to fully open during shipping and storage before patient use, thereby optimizing maximum performance by changing the mechanical stresses delivered before use.

Systems and methods for automatic flow termination for fluid delivery, including a housing configured for coupling a fluid delivery tube to a needle configured for subcutaneous (into vasculature) delivery of fluid within a tissue of a patient and a force-sensitive activation mechanism (shown as a footplate here) having a first 'flattened' orientation corresponding to a condition where unimpeded fluid delivery through the needle body is permitted and a second orientation corresponding to a condition where the fluid tube becomes occluded via spring-loaded activation of the footplate during inadvertent needle dislodgement. When the footplate is allowed to 'spring' out into the second orientation, the fluid flow path is blocked but this also results in a challenge for subsequent placement of legally required needle safety guards. By controlling the shape, size, material, orientation or surface property of the lower portion of the needle guard (or footplate if needed), we present here, embodiments that will enable easier, smoother and more successful placement of the needle safety guard into place while accommodating the excess bulk of a footplate or other skin-sensing mechanism that is part of an overall safety system to help protect patients from venous needle dislodgement.

Systems and methods for automatic flow termination for fluid delivery, including a housing configured for coupling a fluid delivery tube to a needle configured for subcutaneous (into vasculature) delivery of fluid within a tissue of a patient and a force-sensitive activation mechanism (shown as a footplate here) having a first 'flattened' orientation corresponding to a condition where the fluid delivery through the needle body is permitted while using a mechanical protrusion into the flow path that significantly occludes flow and results in a pressure line increase during normal fluid delivery into a patient and a second orientation corresponding to a condition where the fluid tube becomes un-occluded via spring-loaded activation of the footplate during needle dislodgement. When the footplate is allowed to 'spring' out into the second orientation, the protrusion is removed from within the flow path and the line pressure is reduced proportionally. By controlling the shape and size of this occlusion member, the pressure magnitude can be maximized to insure that the low pressure setting limits of the fluid pumping machine are violated, leading to automated machine pump shut off. Machine shut off serves to efficiently protect patients from the dangers associated with needle dislodgement in a package that is self-contained, relatively inexpensive and very easy to implement. Another advantage of this dislodgement protection technique over other techniques is that a relatively weak footplate spring element could be used, thus creating a device that is likely to be comfortable on a patient arm during a several hour fluid delivery therapy session (such as dialysis).

FIG. 28A illustrates that the spring 26 can be a torsion spring 602. The torsion spring 602 can be biased to move the sensor 18 from a closed configuration to an open configuration. The torsion spring 602 can function as an energy source for opening the sensor 18 when the device 10 is dislodged from the body. For example, when the device 10 is dislodged, the torsion spring 602 can be the sole energy source that opens the sensor 18 from a closed configuration to an open configuration, moving the sensor opening 22 away from the flow path and moving the occluder 32 into the flow path. The torsion spring 602 can be the energy source for any of the devices 10 disclosed herein. For example, the torsion spring 602 can be the energy source for the full device 10 shown in FIGS. 30A-30D.

FIG. 28A illustrates that the torsion spring 602 can have one or multiple coils 604, for example, a first coil 604a and a second coil 604b. FIG. 28A illustrates that the first coil 604a can be on a first side of the torsion spring 602 and the second coil 604b can be on a second side of the torsion spring 602. For example, the first coil 604a can be on a lateral first side of the torsion spring 602 and the second coil 604b can be on a lateral second side of the torsion spring 602. The first and second lateral sides of the torsion spring 602 can be symmetrical about a torsion spring center longitudinal axis 612. The first coil 604a can be opposite the second coil 604b. The coils 604 can be the proximal terminal end of the torsion spring 602.

FIG. 28A illustrates that the torsion spring 602 can have arms 606 that extend from the coils 604. For example, FIG. 28A illustrates that a first arm 606a and a second arm 606b can extend from each of the coils 604. The first arms 606a can be shorter than the second arms 606b, or vice versa. The first arms 606a can be engageable with a first arm engager (e.g., shown in FIGS. 31A-31C) and the second arms 606b can be engageable with a second arm engager (e.g., shown in FIG. 28C). The first arm engager can be a surface of the body 14, a surface of the insert 17, or both. The second arm engager can be a surface of the sensor 18. The coils 604 can function as hinges for the first and second arms 606a, 606b.

FIG. 28A illustrates that the torsion spring 602 can have a bridge 608. The bridge 608 can connect the two second arms 606b to each other. The bridge 608 can be a distal terminal end of the torsion spring 602. The bridge 608 can be a first longitudinal end of the torsion spring 602 and the coils 604 can be a second longitudinal end of the torsion spring. The bridge 608 can be a distance 610 from the coils 604. The distance 610 can be measured, for example, from the center of the bridge 608 to the center of the coils 604 as shown in FIG. 28A. The longer the distance 610 between the bridge 608 and the coils 604, the greater the leverage that can be generated by the torsion spring 602, allowing for reduced closing forces and reduced impact on the patient's arm during use when the sensor 18 is in a closed configuration against the skin.

FIG. 28A illustrates that the first arms 606a can have a bend 614. The bend 614 can enable efficient assembly and device function. The bend 614 can be located anywhere on the first arms 606a, for example, in the position shown in FIG. 28A. For example, the first arms 606a can have a first arm proximal portion 606ap before the apex of the bend 614 and a first arm distal portion 606ad after the apex of the bend 614. The first arm proximal and distal portions 606ap, 606ad can be straight and/or curved. Any portion of the first arms 606 (e.g., straight first arms 606a or first arms 606a with the bend 614, for example, the first arm proximal portion 606ap, the bend 614, and/or the first arm distal portion 606ad) can be engageable with the first arm engager. As another example, the first arms 606a can be straight without a bend 614. First arms 606a without a bend 614 can also enable efficient assembly and device function and can additionally decrease the cost of the manufacturing the torsion spring 602, for example, relative to the cost of manufacturing the torsion spring 602 with the bends 614.

FIG. 28A illustrates the torsion spring 602 in a neutral, non-loaded configuration. When the torsion spring 602 is in the non-loaded configuration, the coils 604 can have a coil diameter 604D and a coil length 604L. The torsion spring 602 can be loaded with energy by winding up the coils 604, for example, by rotating the first arms 606a in a first direction 616 (e.g., in a counterclockwise direction) and/or by rotating the second arms 606b in a second direction 618 (e.g., in a clockwise direction) about the center of the coils 604. As FIG. 28A shows, the first and second directions 616, 618 can be opposite each other. As the coils 604 are wound up, the coils 604 can tighten, which can cause the coil length 604L to increase and the coil diameter 604D to decrease. When the torsion spring 602 is in a non-neutral, loaded configuration, the coil length 604L can be greater than the coil length 604L shown in FIG. 28A (e.g., greater by about 1.0 mm to about 5.0 mm, including every 0.1 mm increment within this range) and the coil diameter 604D can be less than the coil diameter 604D shown in FIG. 28A (e.g., lesser by about 1.0 mm to about 5.0 mm, including every 0.1 mm increment within this range). When the coils 604 are in a loaded configuration, the first and/or second arms 606a, 606b can be displaced away from the neutral arm positions shown in FIG. 28A.

As the torsion spring 602 is loaded with energy, the first and second directions 616, 618 can both be toward the coils 604 such that the distal terminal end of the first arms 606a are closer to the coils 604 when the first arms 606a are in a loaded configuration than when the first arms 606a are in an unloaded configuration and/or such that the distal terminal end of the second arms 606b (e.g., where the second arms 606b attach to the bridge 608) are closer to the coils 604 when the second arms 606b are in a loaded configuration than when the second arms 606b are in an unloaded configuration. As another example, the first and second arms 606a, 606b can be closer to each other after the torsion spring 602 is loaded with energy by moving the first arms 606a in the first direction 616 and/or by moving the second arms 606b in the second direction 618.

The coils 604 can store loaded energy until the first arms 606a and/or the second arms 606b are allowed to return to their respective neutral positions shown in FIG. 28A. The coils 604 can release energy when the coils 604 unwind via the first arms 606a and/or the second arms 606b unwinding back toward the neutral configuration shown in FIG. 28A. When the first arms 606a unwind from a loaded position, the first arms 606a can move in the second direction 618. When the second arms 606b unwind from a loaded position, the second arms 606b can move in the first direction 616.

The amount that the torsion spring 602 can be loaded can be controlled, for example, by configuring the relative change in location of the first arms 606a (e.g., straight first arms 606a or first arms 606a with the bend 614, for example, the first arm proximal portion 606ap, the bend 614, and/or the first arm distal portion 606ad) before and after assembly of the torsion spring 602 with the device 10 at a mating point (e.g., the first arm engager). The amount that the torsion spring 602 can be loaded can be controlled, for example, by configuring the relative change in location of the second arms 606b before and after assembly of the torsion spring 602 with the device 10 at a mating point (e.g., the second arm engager).

The overall closing force needed to move the sensor 18 from a sensor open configuration (occluded configuration) to a closed configuration (non-occluded configuration) can be controlled via the number of coil revolutions that the coils 604 have. The greater the number of turns or revolutions, the greater the closing force can be. The coils 604 can have multiple turns, for example, 2 to 10 or more turns, or more narrowly, 2 to 6 or more turns, including every 0.1 turn increment within these ranges. For example, FIG. 28A illustrates that the first and second coils 604a, 604b can each have 3.0 to 4.0 turns (e.g., 3.7 turns). FIG. 28A further illustrates that the turns can be helical turns.

FIG. 28A illustrates that the torsion spring 602 can be a single wire, where the proximal terminal end of the wire can be the distal terminal end of one of the first arms 606a and the distal terminal end of the wire can be the distal terminal end of the other of the first arms 606a.

As another example, the torsion spring 602 can be viewed as having two first arms 606a and one U-shaped second arm 606b, where the one U-shaped second arm 606b can be connected to two coils 604.

FIG. 28B illustrates a variation of a sensor 18 designed to accommodate the torsion spring 602. As shown, the sensor 18 can be a footplate. FIG. 28B illustrates that the sensor 18 can have one or multiple connectors 620. The torsion spring 602 can have, for example, a connector 620 for each of the coils 604 that the torsion spring 602 has. For example, the sensor 18 can have a first connector 620a for the first coil 604a and can have a second connector 620b for the second coil 604b.

FIG. 28B illustrates that the connectors 620 can have a connector extension 622. The coils 604 can be attached to the connector extensions 622. For example, the first coil 604a can be attached to the connector extension 622 of the first connector 620a and the second coil 604b can attached to the connector extension 622 of the second connector 620b. The connector extensions 622 can be hinges that can allow or accommodate the twisting and untwisting of the coils 604 while the coils 604 are connected to the connector extensions 622. The connector extension 622 can have any shape that allows the coils 604 to be attached to the connector extensions 622. For example, FIG. 28B illustrates that the connector extensions 622 can have a cylindrical shape. The connector extensions 622 can be, for example, mandrels, hubs, or shafts that have a cylindrical shape. FIG. 28B illustrates that the distal ends of the connector extensions 622 can have a tapered surface 624. The tapered surface 624 can terminate at the distal terminal face of the connector extensions 622. The tapered surface 624 can advantageously give the first arms 606a space to deflect when the coils 604 are twisted, for example, when the torsion spring 602 is loaded with energy during attachment to the device 10 (e.g., to the insert 17 and/or to the housing 14), during attachment to the patient, or during both attachments. As another example, the connector extensions 620 may not have the tapered surface 624. FIG. 28B illustrates that the connector extensions 622 can have an extension longitudinal length 625. The extension longitudinal length 625 can be measured as shown in FIG. 28B, for example, between the proximal terminal end of the connector extensions 622 and the start of the tapered surface 624. For variations in which the connector extension 622 does not have a tapered surface 624, the extension longitudinal length 625 can be measured between the proximal terminal end of the connector extensions 622 and the distal terminal end of the connector extensions 622.

FIG. 28B illustrates that the connectors 620 can have a connector channel 626. The connectors 620, via the connector channels 626, can be attached to an extension on the housing 14, to an extension on the insert 17, or to an extension on both. The connector channels 626 can extend fully or partially through any portion of the connectors 620. For example, the connector channels 626 can extend fully or partially through the connector extensions 622. For example, FIG. 28B illustrates that the connector channels 626 can be through-holes that extend fully through the first and second connectors 620a, 620b. As another example, the connector channels 626 can be recesses in the connector extensions 622 that do not extend all the way through the first and second connectors 620a, 620b. The connector channels 626 can have a cylindrical shape.

The connector channels 626 can be centered in the connector extensions 622 or can be offset from the center of the connector extensions 622. FIG. 28B illustrates, for example, that the connector extensions 622 can have a connector extension center longitudinal axis 628 and that the connector channels 626 can have a connector channel center longitudinal axis 630. Axes 628 and 630 can be parallel to each other. Axes 628 and 630 can be coincident with each other or can be vertically and/or horizontally offset from each other. For example, FIG. 28B illustrates that the connector channel center longitudinal axis 630 can be vertically offset (e.g., closer to a top surface of the connector extensions 622) from the connector extension center longitudinal axis 628. This offset between axes 628 and 630 can advantageously allow the torsion spring 602 to open the sensor 18 more efficiently when the device 10 becomes dislodged from the patient than configurations where axes 628 and 630 are both centered in the connector extensions 622.

FIG. 28B illustrates that the sensor 18 can have a groove 632 for the second arms 606b and/or for the bridge 608. The groove 632 can be a recess in a surface of the sensor 18. The second arms 606b and the bridge 608 can fit in the groove 632. The second arms 606b and the bridge 608 can be in the groove when the torsion spring 602 is attached to the sensor 18. The groove 632 can inhibit or prevent the second arms 606b and the bridge 608 from slipping out of place as the sensor 18 is opened and closed. The groove 632 can have the same or similar shape as the second arms 606b and the bridge 608. For example, FIG. 28B illustrates that the groove 632 can have longitudinal sections 632L for the second arms 606b and a transverse section 632T for the bridge 608.

FIG. 28B illustrates that the first connector 620a can be on a lateral first side of the sensor 18 and the second connector 620b can be on a lateral second side of the sensor 18. The first and second lateral sides of the sensor 18 can be symmetrical about a sensor center longitudinal axis 634.

FIG. 28B illustrates that that the occluder 32 can be a proximal terminal end of the sensor 18 and that the opening 22 can be a distal terminal end of the sensor 18.

FIG. 28C illustrates the torsion spring 602 assembled onto the sensor 18 and ready for assembly into the device 10 (e.g., onto the insert 17 and/or onto the housing 14). The assembled spring-sensor component shown in FIG. 28C can be pushed (e.g., pushed vertically upward) into the housing 14, allowing for appropriate mating of the hinges (e.g., the connector extensions 622) and the first arms 606a (e.g., straight first arms 606a or first arms 606a with the bend 614, for example, the first arm proximal portion 606ap, the bend 614, and/or the first arm distal portion 606ad).

FIG. 28C illustrates the torsion spring 602 attached to the sensor 18. FIG. 28C illustrates that when the torsion spring 602 is attached to the sensor 18, the coils 604 can be attached to the connector extensions 622. When the torsion spring 602 is attached to the sensor 18, the second arms 606b and/or the bridge 608 can be in the groove 632. For example, FIG. 28C illustrates that the second arms 606b and the bridge 608 can be in the groove 632. When the torsion spring 602 is attached to the sensor 18, the second arms 606b and/or the bridge 608 can contact the surface defining the base of the groove 632. For example, FIG. 28C illustrates that the second arms 606b and the bridge 608 can contact the base of the groove 632. The base of the groove 632 can be the second arm engager. For example, the base of the longitudinal sections 632L can be the second arm engager. The base of the groove 632 can be a bridge engager. For example, the base of the transverse section 632T can be the bridge engager. FIG. 28C illustrates that the groove 632 can inhibit or prevent lateral movement of the second arms 606b and the bridge 608 as the sensor 18 is opened and closed and/or as the torsion spring 602 is loaded (e.g., wound) and unloaded (e.g., unwound). For example, the longitudinal walls of the groove 632 can inhibit or prevent such lateral movement. The transverse walls of the groove 632 (e.g., the distal terminal wall of the groove 632) can inhibit or prevent longitudinal movement of the second arms 606b and the bridge 608.

FIG. 28C illustrates that when the torsion spring 602 is attached to the sensor 18 and before the spring-sensor component is attached to the rest of the device 10, the torsion spring 602 can have the neutral configuration shown in FIG. 28A.

FIG. 28C illustrates that when the torsion spring 602 is attached to the sensor 18 and the torsion spring 602 is in a neutral configuration, the coils 604 can fully fit onto the connector extensions 622 such that the coils 604 terminate before the distal terminal end of the connector extensions 622. For example, FIG. 28C illustrates that when the torsion spring 602 is attached to the sensor 18 and the torsion spring 602 is in a neutral configuration, the coil length 604L can be equal to or less than the extension longitudinal length 625 such that the coils 604 terminate before the tapered surface 624. When the torsion spring 602 is in a loaded configuration, the coil length 604L can increase such that the first arms 606a can extend over and/or contact the tapered surface 624. As another example, when the torsion spring 602 is attached to the sensor 18 and the torsion spring 602 is in a neutral configuration, the coil length 604L can be greater than the extension longitudinal length 625 such that the coils 604 extend over the tapered surface 624.

FIG. 28C illustrates that when the torsion spring 602 is attached to the sensor 18, the center longitudinal axis of the coils 604 can be coincident with the connector extension center longitudinal axis 628 such that the connector extension center longitudinal axis 628 can also be the coil center longitudinal axis.

To reiterate, FIG. 28A is an example of a torsion spring 602 designed to function as the footplate opening energy source for the full system shown in FIGS. 30A-30D. The torsion spring 602 can have two separate coil regions (e.g., first and second coils 604a, 604b) designed to reside on either side of the footplate hinge points (e.g., the connector extensions 622). The torsion spring 602 assembly can have a connecting bridge (e.g., the bridge 614) that can be placed at some distance (e.g., distance 610) away from the hinge coils (e.g., the first and second coils 604a, 604b). The longer the distance between the connecting bridge and the side coils, the greater the leverage that can be generated, allowing for reduced closing forces and reduced impact on patient arm during use in the footplate closed state. The first arms 606a of the torsion spring 602 can be designed with or without an end bend (e.g., the bend 614) to enable efficient assembly and device function. The first arms 606a (e.g., straight first arms 606a, first arms 606a with the bend 614) can fit into a corresponding slot on the needle body (e.g., the housing 14). The amount of pre-stress built into the torsion spring 602 can be controlled by configuring the relative change in physical location of the first arms 606a (e.g., straight first arms 606a, first arms 606a with the bend 614) before and after assembly into the needle body at a mating point (e.g., at first arm engagers). The overall closing force can be controlled via the number of coil revolutions that the side coils (e.g., the first and second coils 604a, 604b) have. FIG. 28B is a top/angled view of a footplate 18 (also referred to as sensor 18) designed to accommodate the torsion spring 602 in FIG. 28A. The footplate 18 can include side hinge points (e.g., the connector extensions 622) large enough to accommodate the side coils as well as precisely placed grooves (e.g., the groove 632) designed to accommodate the connecting bridge (e.g., the bridge 608) and bridge to coil connector regions (e.g., the second arms 606b). FIG. 28C is a top/angled view of a torsion spring 602 assembled into a footplate 18 and ready for assembly into a full device. The entire component shown in FIG. 28C can be pushed (e.g., pushed vertically upward or downward) into the needle body (e.g., the housing 14 shown in FIGS. 30A-30D)/fluid flow core (e.g., the tube 638 shown in FIGS. 29A-29D) allowing for appropriate mating of the hinge points (e.g., the connector extensions 622) and the first arms 606a (e.g., straight first arms 606a, first arms 606a with the bend 614).

FIG. 29A illustrates that the device 10 can have a tube 638. The tube 638 can be, for example, the insert 17. The tube 638 can have tube extensions 636 (also referred to as insert extensions 636). The connectors 620 and/or the coils 604 can be attached to the tube extensions 636. The insert extensions 636 can be hinges that can allow the sensor 18 to rotate while attached to the insert 17, for example, so that the sensor 18 can be opened and closed. For example, the connector extensions 622 can rotate on the insert extensions 636 as the sensor 18 is opened and closed. The insert extensions 636 can have any shape that allows the sensor 18 to pivot about the connector extensions 622. The sensor 18 can pivot about the connector channel center longitudinal axis 630. For example, FIG. 29A illustrates that the insert extensions 636 can have a cylindrical shape. The insert extensions 636 can be, for example, mandrels, hubs, or shafts that have a cylindrical shape.

FIG. 29A illustrates that when the spring-sensor component of FIG. 28C is attached to the insert extensions 636, the connector extensions 622 and the coils 604 can be attached to the insert extensions 636. FIG. 29A illustrates that when the spring-sensor component of FIG. 28C is attached to the insert extensions 636, the insert extensions 636 can extend through the connector channels 626 and through the coils 604. The insert extensions 636 can extend fully or partially through any portion of the connector channels 626. For example, FIG. 29A illustrates that the insert extensions 636 can extend through the connector channels 626 such that the distal terminal end of the insert extensions 636 can be flush with the distal terminal end of the connector extensions 622. As another example, the insert extensions 636 can extend beyond the distal terminal end of the connector extensions 622, for example, such that a proximal end of the insert extensions 636 can extend through the mating channels of the extensions 622 (e.g., through the connector channels 626) and such that a distal end of the insert extensions 636 can extend through a mating channel on the housing 14.

The insert 17 can have an insert extension 636 for each of the coils 604 that the torsion spring 602 has and/or for each of the connectors 620 that the sensor 18 has. For example, FIG. 29A illustrates that the insert 17 can have two insert extensions 636, one that the first connector 620a can be attached to and one that the second connector 620b can be attached to. FIG. 29A illustrates the spring-sensor component of FIG. 28C attached to two insert extensions 636, where one of the insert extension 636 in FIG. 29A is obstructed from view for illustrative purposes only. The insert extension 636 obstructed from view in FIG. 29A can be the same as the insert extension 636 shown in FIG. 29A but on the opposite side of the tube 638. For example, FIG. 29A illustrates that the tube 638 can be symmetrical about a center longitudinal axis of the tube 638. FIG. 29A illustrates the first coil 604a attached to the insert extension 636 that is obstructed from view in FIG. 29A.

FIG. 29A illustrates that the insert 17 can have a recess 640 that the housing 14 can contact or engage with.

FIG. 29A illustrates the sensor 18 in a closed configuration and the torsion spring 602 in a neutral configuration.

FIG. 29B illustrates the sensor 18 in an open configuration and the torsion spring 602 in a neutral configuration.

FIG. 29C illustrates a side view of the device 10 of FIG. 29A.

FIG. 29D illustrates a side view of the device 10 of FIG. 29B. The tip of the occluder 32 and the engagement of the occluder 32 with the membrane 54 is shown transparent in FIG. 29D for illustrative purposes only, as box 694 in FIG. 29D depicts that the occluder 32 and the membrane 54 can be engaged as shown in FIG. 4E or as shown in FIG. 4F.

FIGS. 29A-29D illustrate multiple views of a device 10 that is designed to protect patients from the risks of needle dislodgement. In FIGS. 29A-29D, the housing 14 (e.g., the outer shell having the butterfly wings) is shown transparent so that the arrangement of the sensor 18, the torsion spring 602, and the tube 638 (e.g., the insert 17) can be illustrated. The tube 638 can have a hard section and a soft section. The soft section can be deflectable by the occluder 32. For example, FIGS. 29A-29D illustrate that the flow channel through the device 10 can extend through the tube 638, and that the tube 638 can comprise a hard portion (e.g., the first portion 191, the first-shot mold 190) and a soft section (e.g., the membrane 54, the second portion 193, the second-shot mold 192) that can enable protrusion of the occluder 32 at the sensor proximal end to obstruct fluid flow when the sensor 18 is in an open configuration (e.g., the open configuration shown in FIGS. 29B and 29D) to create increased back pressure during needle dislodgement. The increase in backpressure can be high enough trigger a fluid pump's automatic shut-off mechanism. In the variation of the device 10 shown in FIGS. 29A-29D, the tube 638 (e.g., the insert 17) can be the fluid flow component, whereby fluid can flow through the hard portion of the tube 638 and past the soft portion of the tube 638. The tube 638 (e.g., the insert 17) can be created for example, using a 2-shot molding process. Where a 2-shot molding process is used, the hard portion can be, for example, the first-shot mold 190 and the soft portion can be, for example, the second-shot mold 192.

FIG. 29A illustrates the device 10 with the sensor 18 in a footplate closed position before dislodgement, for example, after cannulation and when the device 10 is firmly affixed in place against the skin (e.g., FIGS. 39A and 39B). In the configuration shown in FIG. 29A, pressure of the applied tape (e.g., FIGS. 39A and 39B) from above against the skin surface below (e.g., FIGS. 39A and 39B) can compress the torsion spring 602 and prohibit the coils 604 of the torsion spring 602 from uncoiling or unwinding, and can keep the sensor 18 in the footplate closed position to enable fluid flow through the flow path that extends through the tube 638 (e.g., the insert 17).

FIG. 29B illustrates the device 10 with the sensor 18 in a footplate open position after dislodgement, for example, in which the tape (e.g., FIGS. 39A and 39B) has failed, the needle has become dislodged from the skin (e.g., FIGS. 39A and 39B), and the sensor 18, via energy provided by the uncoiling or unwinding of the coils 604 of the torsion spring 602, has opened, moving the sensor distal end 18*d* (e.g., the opening 22) a distance away from the needle 12 and moving the sensor proximal end 18*p* (e.g., the occluder 32) into the flow path against the soft portion (e.g., the membrane 54, the second portion 193, the second-shot mold 192) of the tube 638, thus blocking fluid flow through the flow path through the tube 638 (e.g., the insert 17).

In FIGS. 29A-29D, the torsion spring 602 is shown in the neutral configuration for illustrative purposes only. In FIGS. 29A-29D, the mating surfaces for the first arms 606*a* (e.g., surfaces of the first arm engagers) that enable pre-stress of the torsion spring 602 by pressing against the first arms 606*a* (e.g., straight first arms 606*a* or first arms 60*a* with the bend 614) when the spring-sensor component in FIGS. 28C-29D are attached to the housing 14 shown in FIGS. 30A-30D and the footplate 18 is in an open configuration are not shown. The mating surfaces for the first arms 606*a* can bias the sensor 18 to have the footplate open position shown in FIGS. 29B and 29D. Because the mating surfaces for the first arms 606*a* that can dictate the pre-stress level of the torsion spring 602 are not shown in FIGS. 29A-29D, FIGS. 29A-29D illustrate that the first arms 606*a* (e.g., straight first arms 606*a* or first arms 60*a* with the bend 614) rotate into a new position as the sensor 18 rotates from the footplate closed position (e.g., FIGS. 29A and 29C) to the footplate open position (e.g., FIGS. 29B and 29D). However, when the device 10 is fully assembled, for example, when the spring-sensor-tube component shown in FIGS. 29A-29D is attached to the housing 14 (e.g., FIGS. 30A-30D), the first arms 606*a* can be engaged with one or multiple mating surfaces (e.g., surfaces of the first arm engagers) in both the footplate open and closed positions such that the first arms 606*a* can have the position shown, for example, in FIGS. 29B and 29D, when the sensor 18 is in the footplate closed position and when the sensor 18 is in the footplate open position. In this way, the coils 604 can activate when the device 10 becomes dislodged and instill the pre-stress into the torsion spring 602 to move the sensor 18 from the footplate closed position (e.g., FIGS. 29A and 29C) to the footplate open position (e.g., FIGS. 29B and 29D).

FIGS. 29E and 29F illustrate the tube 638 illustrated in FIGS. 29A-29D, where FIG. 29E illustrates the tube extension 636 illustrated in FIGS. 29A-29D and FIG. 29F illustrates the tube extension 636 shown obstructed in FIGS. 29A-29D. As shown, the two tube extensions 636 can be mirror images of each other, for example, reflected across a tube center longitudinal axis 642.

FIGS. 30A-30D illustrate the housing 14 that is shown transparent in FIGS. 29A-29D attached to the spring-sensor-tube component that is illustrated in FIGS. 29A-29D.

FIGS. 30A and 30B illustrate that the housing 14 can have a housing core 643. The housing core 643 can be a center of the housing 14. The housing core 643 can have a recess or a channel that the tube 638 can fit into. For example, FIGS. 30A and 30B illustrate that the tube 638 can be in the recess or channel of the housing core 643. FIGS. 30A and 30B illustrate that when the tube 638 is in the recess or channel of the housing core 643, the housing core 643 can extend over or enclose the tube 638 (e.g., the insert 17).

FIGS. 30A and 30B illustrate that the housing 14 can have one or multiple build-outs 644, for example, a first build-out 644*a* and a second build-out 644*b*. The housing 14 can have a build-out 644 for each of the hinges (e.g., the connector extensions 622 and/or the insert extensions 636) that the device 10 has. The build-outs 644 can extend from the housing 14. For example, the build-outs 644 can extend from the core 643. The build-outs 644 can be extensions of the housing 14. For example, the build-outs 644 can be extensions of the core 643. The build-outs 644 can have a recess that the insert extensions 636, the connector extensions 622, and the coils 604 can fit into. The build-outs 644 can enclose the insert extensions 636, the connector extensions 622, and the coils 604. For example, FIGS. 30A and 30B illustrate that the first coil 604*a*, the insert extension 636 that the first coil 604*a* extends over, and the connector extension 622 that the first coil 604*a* extends over can each be in the recess of the first build-out 644*a*. As another example, FIGS. 30A and 30B illustrate that the second coil 604*b*, the insert extension 636 that the second coil 604*b* extends over, and the connector extension 622 that the second coil 604*b* extends over can each be in the recess of the second build-out 644*b*. The build-outs 644 can protect the insert extensions 636, the connector extensions 622, and the coils 604, for example, from foreign substances (e.g., clothing, tape, fingers, skin, hair, sweat, blood, fluid) from interfering with the rotation of the sensor 18 and with the winding and unwinding of the coils 604 as the sensor 18 is opened and closed. The build-outs 644 can thereby protect the hinges of the device 10 (e.g., the insert extensions 636 and the connector extensions 622) from foreign substances.

FIGS. 30A and 30B illustrate that the housing 14 can have wings 15, for example, a first wing 15*a* and a second wing 15*b*. The wings 15 can extend from the housing 14. The wings 15 can be extensions of the housing 14. The wings 15 can have hinges 646 that the wings 15 can rotate about. The hinges 646 can be, for example, an area of decreased thickness of the wings 15 such that the wings 15 can bend about the hinges 646. The hinges 646 can be, for example, a living hinge. The hinges 646 can be a flexible portion of the wings 15. The hinges 646 can be at the base of the wings 15. FIGS. 30A and 30B illustrate, for example, that the wings 15 can have a first rigid portion 647a, a flexible portion 647b, and a second rigid portion 647c. The flexible portion 647b can be the hinge 646. The flexible portion 647b can be a living hinge. The flexible section can have multiple thin segments each connected via a living hinge. During insertion of the needle 12 into the body, the wings can be rotated (e.g., to the positions shown in FIGS. 38A and 38B) to make it easier for the user to hold the device 10 and cannulate a blood vessel. Once the blood vessel has been cannulated the user can rotate the wings 15 to the positions shown in FIGS. 30A and 30B and tape the device 10 to the body (e.g., as shown in FIGS. 39A and 39B). As another example, the wings 15 may not have hinges 646 such that the wings 15 may not be moveable from the positions shown in FIGS. 30A and 30B.

FIGS. 30A and 30B illustrate that the wings 15 can extend from the housing core 643 and from the build-outs 644. For example, a distal end of the wings can extend from the housing core 643 and a proximal end of the wings 15 can extend from the build-outs 643.

FIGS. 30A and 30B illustrate that the housing 14 can be a unitary structure. FIGS. 30A and 30B illustrate that the housing core 643, the build-outs 644, and the wings 15 can be integrated with each other.

FIGS. 30A and 30B illustrate that the top edge of the build-outs 644 can be rounded to allow the wings 15 to reduce or eliminate interference from the build-outs 644 when the wings are folded or are in a folded configuration (e.g., see FIG. 38B).

FIG. 30A illustrates the device 10 with the sensor 18 in a footplate closed configuration.

FIG. 30B illustrates the device 10 with the sensor 18 in a footplate open configuration.

FIG. 30C illustrates a side view of the device 10 of FIG. 30A.

FIG. 30D illustrates a side view of the device 10 of FIG. 30B.

FIGS. 30A-30D illustrate that the torsion spring 602 can have a spring first loaded configuration and a spring second loaded configuration. A spring first loaded configuration is shown in FIGS. 30B and 30D and a spring second loaded configuration is shown in FIGS. 30A and 30C. The torsion spring 602 can have the spring first loaded configuration when the sensor 18 is in the footplate open position (e.g., as shown in FIGS. 30B and 30D). The torsion spring 602 can have the spring second loaded configuration when the sensor 18 is in the footplate closed position (e.g., as shown in FIGS. 30A and 30C).

When the torsion spring 602 is in the spring first loaded configuration (e.g., FIGS. 30B and 30D), the first arms 606a can be in a first arm loaded position (e.g., the positions shown in FIGS. 31A-31C), and the second arms 606b can be in a second arm neutral position (e.g., the positions shown in FIGS. 28A, 28C, 30B, and 30D). The first arms 606a can be moved into the first arm loaded positions, for example, by rotating the first arms 606a in direction 616 as shown in FIGS. 28A and 28C. The first arms 606 can be kept in the first arm loaded positions via engagement with first arm engagers (e.g., as shown in FIGS. 31A-31C). The first arm loaded positions can bias the sensor 18 to have a footplate open position (e.g., the open configuration shown in FIGS. 30B and 30D). Moving the first arms 606a away from their neutral positions to the first loaded positions can wind the coils 604 into a first wound configuration. The first wound configuration can bias the sensor 18 to have the open configuration shown in FIGS. 30B and 30D. The first arms 606a can be moved into the first arm loaded positions when the device 10 is assembled, for example, when the spring-sensor-tube component shown in FIGS. 29A-29D is attached to the housing 14. For example, as the spring-sensor-tube component is inserted into the recesses of the build-outs 644, a first arm engager of the build-outs 644 an press against the first arms 606, thereby forcing the first arms 606a in the first direction 616 which winds the coils 604 into the first wound configuration. The spring first loaded configuration can thus be a pre-loaded or pre-stressed configuration that the torsion spring 602 before the device 10 is attached to the patient.

When the torsion spring 602 is in the spring second loaded configuration (e.g., FIGS. 30A and 30C), the first arms 606a can be in the first arm loaded position (e.g., the positions shown in FIGS. 31A-31C), and the second arms 606b can be in a second arm loaded position (e.g., the positions shown in FIGS. 30A and 30C). The second arms 606b can be moved into the second arm loaded positions, for example, by rotating the second arms 606b in direction 618 as shown in FIGS. 28A and 28C. The second arms 606b can be moved in direction 618 by moving the sensor 18 from an open configuration into a closed configuration, for example, during insertion of the needle 12 into the patient. For example, as the sensor 16 is closed from an open state, the sensor 18 can push the second arms in direction 618 toward the tube 638. This can further wind the coils 604 from the first wound configuration to a second wound configuration. The second wound configuration can be the maximum load that the coils 604 can be loaded with. For example, as the sensor 18 is closed, the base of the groove 632 can rotate the second arms 606b in direction 618 to further wind the coils 604. The second arms 606b can be kept in the second arm loaded positions via engagement of the sensor 18 with the skin before dislodgement and via engagement of the second arms 606b with the base of the groove 632. When the needle 12 is dislodged, the torsion spring 602 can move the sensor 18 from the closed configuration to an open configuration via the coils 604 unwinding, returning the second arms 606b to a neutral position or to a less-loaded position.

The first arms 606a can be in the first arm loaded position when the torsion spring 602 is in the spring first and second loaded configurations. The second arms 606b can be in a neutral (e.g., non-wound) position when the torsion spring 602 is in the spring first loaded configuration and can be in the second arm loaded position when the torsion spring 602 is in the spring second loaded configuration. As another example, the second arms 606a can be in a second arm first loaded position when the torsion spring 602 is in the spring first loaded configuration and can be in a second arm second loaded position when the torsion spring 602 is in the spring second loaded configuration. In such variations, the second arms 606b can be displaced further from their neutral positions when the torsion spring 602 is in the spring second loaded configuration than when the torsion spring 602 is in the spring first loaded configuration.

The torsion spring 602 can thus have the spring first loaded configuration when the sensor 18 is in an open state and can have the spring second loaded configuration when the sensor 18 is in a closed state. The spring first loaded configuration can be a pre-loaded configuration of the torsion spring 602 that can bias the torsion spring 602 to keep the sensor 18 in an open configuration when not engaged with a patent (e.g., during dislodgement). When the sensor 18 is in an open state, closing the sensor 18 can further wind the torsion spring 602 (thereby storing yet more energy in the coils 604). As the coils 604 are further wound, the first arms 606a can remain fixed in position and the second arms 606b can move relative to the first arms 606a (e.g., toward the first arms 606a). During a dislodgement event, the sensor 18 can move from the closed state to the open state via the coils 604 unwinding. As the coils 604 unwind, the first arms 606a can remain fixed in position and the second arms 606b can move relative to the first arms 606a (e.g., away from the first arms 606a).

To reiterate, FIGS. 30A-30D illustrate multiple views of a device 10 that is designed to protect patients from the risks of needle dislodgement. FIG. 30A illustrates the device 10 with the sensor 18 in a footplate closed position before dislodgement, for example, after cannulation and when the device 10 is firmly affixed in place against the skin (e.g., FIGS. 39A and 39B). In the configuration shown in FIG. 30A, pressure of the applied tape (e.g., FIGS. 39A and 39B) from above against the skin surface below (e.g., FIGS. 39A and 39B) can compress the torsion spring 602 and prohibit the coils 604 of the torsion spring 602 from uncoiling or unwinding, and can keep the sensor 18 in the footplate closed position to enable fluid flow through the flow path that extends through the tube 638 (e.g., the insert 17). FIG. 30A illustrates that the torsion spring coils can be positioned around the hinge points (e.g., the connector extensions 22, the insert extensions 636) and can be protected by the build-outs 644. FIG. 30B illustrates the device 10 with the sensor 18 in a footplate open position after dislodgement, for example, in which the tape (e.g., FIGS. 39A and 39B) has failed, the needle has become dislodged from the skin (e.g., FIGS. 39A and 39B), and the sensor 18, via energy provided by the uncoiling or unwinding of the coils 604 of the torsion spring 602, has opened, moving the sensor distal end 18d (e.g., the opening 22) a distance away from the needle 12 and moving the sensor proximal end 18p (e.g., the occluder 32) into the flow path against the soft portion (e.g., the membrane 54, the second portion 193, the second-shot mold 192) of the tube 638, thus blocking fluid flow through the flow path through the tube 638 (e.g., the insert 17).

FIGS. 31A-31C illustrate that the device 10 can have first arm engagers 648. FIGS. 31A-31C illustrate that when the first arms 606a and the first arm engagers 648 are engaged with one another (e.g., pressed against each other), the first arms 606a can contact the first arm engagers 648 and the first arms 606a can be in the first arm loaded positions. The first arm engagers 648 can, for example, push the first arms 606a into the first arm loaded positions when the torsion spring 602 is loaded into the housing 14 and can, for example, keep the first arms 606a in the first arm loaded positions as the sensor 18 moves back and forth between the footplate open and closed positions. FIGS. 31A-31C illustrate variations of the spring second loaded configuration for three different first arm loaded positions. FIGS. 31A-31C illustrate that the first arms 606a can be positioned such that the torsion spring 602 is biased to open the sensor 18.

The first arm engagers 648 can be one or more surfaces of the housing 14. For example, FIGS. 31A-31C illustrate that the first arm engagers 648 can be one or more surfaces of the build-outs 644. The first arm engagers 648 have one or multiple mating points and/or one or multiple mating surfaces that can contact the first arms 606a. For example, FIGS. 31A-31C illustrate that the first arm engagers 648 can be one or multiple inner surfaces of a distal wall of the build-outs 644. FIGS. 31A-31C illustrate that any portion of the first arms 606a (e.g., straight first arms 606a or first arms 606a with the bend 614, for example, the first arm proximal portion 606ap, the bend 614, and/or the first arm distal portion 606ad) can be engageable with the first arm engagers 648.

For variations in which the first arms 606a have the bend 614, FIG. 31A illustrates that the first arm engagers 648 can be two surfaces of the build-outs 644, for example, a first surface 650 and a second surface 652. The first and second surfaces 650, 652 can be mating surfaces or can be mating points of the build-outs 644. The first surface 650 can be angled relative to the second surface 652. As shown in FIG. 31A, when the first arms 606a are in the first arm loaded position, the first arm proximal portion 606ap can contact the first surface 650, the first arm distal portion 606ad can contact the second surface 652, and the bend 614 can contact both the first surface 650 and the second surface 652. FIG. 31A further illustrates that the first and second surfaces 650, 652 can be surfaces of a slot 653 in the wall of the build-outs 644. For variations in which the first arms 606a are straight (e.g., without the bend 614), the first arm engagers 648 can be, for example, a single surface such as the first surface 650. Exemplary straight first arms 606a without the bend 614 can be shorter versions of the first arms 606a shown in FIGS. 28A, 28C, and 31A-31C such that the straight first arms 606a do not have the bend 614 and the first arm distal portion 606ad. In such variations, the first arms 606a may only have the first arm proximal portion 606ap, which relative to first arms 606a illustrated in FIGS. 28A, 28C, and 31A-31C, can terminate before the bend 614, for example, exactly where the bend 614 begins.

FIG. 31B illustrates that the first arm engager 648 can be the first surface 650 or the second surface 652, for example, only the second surface 652. When the first arms 606a and the first arm engagers 648 are engaged with one another, the first arms 606a can be in the first arm loaded position, which can have the arrangement shown in FIG. 31B. For example, as shown in FIG. 31B, when the first arms 606a are in the first arm loaded position, the first arm proximal portion 606ap and the bend 614 may not contact the build-outs 644 and the first arm distal portion 606ad can contact the second surface 652.

FIG. 31C illustrates that the first arm engager 648 can be the first surface 650 or the second surface 652, for example, only the first surface 650. FIG. 31C further illustrates that the first surface 650 can be a surface of a protuberance 649. The protuberance 649 can be, for example, an extension of the build-outs 644 or can be a thicker portion of a wall of the build-outs 644. For example, the distal wall of the build-outs 644 can be made thicker to create the protuberance 649. The protuberance 649 may or may not have a slot. For example, FIG. 31C illustrates the protuberance 649 without a slot (e.g., without the slot 653). When the first arms 606a and the first arm engagers 648 are engaged with one another, the first arms 606a can be in the first arm loaded position, which can have the arrangement shown in FIG. 31C. For example, as shown in FIG. 31C, when the first arms 606a are in the first arm loaded position, the first arm proximal portion 606ap can contact the first surface 650 and the bend 614 and the first arm distal portion 606ad may not contact the build-outs 644.

FIGS. 31A-31C thereby illustrate that the first arm engagers 648 can be a surface (e.g., surfaces 650 and/or 652) of the build-outs 644, a protuberance 649 of the build-outs 644, a slot 653 in the build-outs 644, or any combination thereof. As another example, the first arm engagers 648 can be another surface of the device 10, for example, a surface of the insert 17 that extends into the build-out 644.

FIGS. 31A-31C illustrate that the amount of pre-stress and thus pre-load built into the torsion spring 602 when the device 10 is in an assembled state can be controlled by configuring the relative change in location of the first arms 606a before assembly (e.g., FIGS. 28A and 28C) and after assembly (e.g., FIGS. 30A-31C) of the torsion spring 602 with the first arm engagers 648. The pre-load on the torsion spring 602 can be adjusted by changing the mounted position of the first arms 606a (e.g., the first arm loaded positions) relative to the first arm engagers 648. The more the first arm engagers 648 move the first arms 606a away from their neutral positions (e.g., shown in FIGS. 28A and 28C), the greater the pre-load can be. For example, of FIGS. 31A-31C, the first arms 606a are shown the least rotated away from their neutral position in the first arm loaded position in FIG. 31A and are shown the most rotated away from their neutral position in the first arm loaded position in FIG. 31C. By manipulating the size and shape of the first arm engagers 648 and changing the resulting pre-tension in the coils 604, critical adjustments can be provided that enable an optimal spring force for opening and closing the sensor 18, thereby improving overall device performance. The first arm loaded positions can be adjusted, for example, by adjusting the position of the surfaces 650 and/or 652, the size and shape of the protuberance 649, and/or the size and/or shape of the slot 653. Exemplary adjustments are shown in FIGS. 31A-31C. For example, FIG. 31A illustrates a first arm engager 648 configuration that can result in a low pre-load on the torsion spring, and FIGS. 31B and 31C show two other configurations that can result in successive increases in the amount of pre-load in the torsion spring 602 (e.g., relative to the first pre-load illustrated in FIG. 31A) by varying the amount of material that protrudes from the housing 14 (e.g., from the build-outs 644), and thus varying the amount by which the first arms 606a are moved in direction 616 by the first arm engagers 648. FIGS. 31A-31C thus illustrate the first arms 606a in three different first arm loaded positions that result in three progressively increasing pre-loads on the torsion spring 602, with FIG. 31A illustrating the lowest pre-load of the pre-loads illustrated in FIGS. 31A-31C and with FIG. 31C illustrating the highest pre-load of the pre-loads illustrated in FIGS. 31A-31C.

To reiterate, and by way of another example, FIGS. 31A-31C illustrate close-up views along the line 4-4 in FIG. 30A of the coils 604 of a torsion spring 602 inserted in the housing 14. The torsion spring 602 can have multiple coils encasing a central hub (e.g., the connector extensions 622). These hubs can reside on either side of the inner core body of the needle system. The torsion spring 602 can have two coils 604. The resulting force of the torsion spring applied to the footplate 18 can be dependent on the pre-load applied to the coils 604 on each side. The first arms 606a can be configured to fit into a corresponding slot (e.g., the slot 653) or onto a corresponding protuberance (e.g., the protuberance 649) within the butterfly portion of the needle system (e.g., within the build-outs 644). The amount of pre-stress and thus pre-load built into the coils 604 can be controlled by configuring the relative change in location of the first arms 606a before and after assembly into the butterfly portion at a mating point (e.g., the first surface 650 and/or the second surface 652). Pre-load on the coils 604 can be applied by changing the mounting position of the first arms 606a (e.g., the first arm loaded positions). By manipulating the first arm loaded positions and changing the resulting pre-tension, critical adjustments can be provided that enable optimal spring force for opening and closing, thereby improving overall needle system performance FIG. 31A illustrates a protuberance configuration that results in a low pre-load on the torsion spring, where the protuberance can be the wall of the build-outs 644 themselves. FIGS. 31B and 31C show two other configurations that can enable successive increases in the amount of pre-load of the coils 604 by varying the amount of material that protrudes from the butterfly body, for example, toward the coils 604.

FIGS. 31A-31C illustrate that the build-outs 644 can define a recess 654. FIGS. 31A-31C each illustrate that when the coils 604 are fully wound (e.g., in the second wound configuration), the recess 654 can define a space between the coils 604 and the build-outs 644. This space can advantageously allow the coils 604 to radially expand as the coils 604 unwind back to the first wound configuration as the sensor 18 opens, for example, when the sensor 18 is forced into the footplate open position during dislodgement.

FIGS. 31A-31C illustrate that when the coils 604 are fully wound (e.g., in the second wound configuration), a space 656 can be between the coils 604 and the connector extensions 622 to reduce friction between the coils 644 and the connector extensions 622. The space 656 can advantageously reduce friction with the connector extensions 622 during winding and unwinding of the coils 604, for example, when the sensor 18 is moved from the footplate open position to the footplate closed position (e.g., winding) and when the sensor 18 is moved from the footplate closed position to the footplate open position (e.g., unwinding).

The device 10 can have a first arm engager 648 for each first arm 606a that the torsion spring 602 has. FIGS. 31A-31C illustrate the first arm engagers 648 on the side of the device having the second coil 604b.

FIGS. 31A-31C illustrate that the connector extensions 622 can have a cylindrical shape and may not have the tapered surface 624.

FIG. 31D illustrates an underside of a housing 14 with the torsion spring 602 and the proximal portion of the sensor 18 shown transparent so that the build-outs 644 and the recesses 654 can be illustrated. FIG. 31D illustrates that the protuberance 649 can have the slot 653.

FIG. 31E illustrates that the distal wall 658 of the build-outs 644 can have the protuberance 649 and that the slot 653 can extend through the protuberance 649. The slot 653 can control the position and angle of the first arms 606a, for example, to optimize the pre-load of the coils 604 and device functionality (e.g., the opening and closing of the sensor 18). For example, the slot 653 can inhibit or prevent the first arms 606a from slipping out of the first arm loaded positions when the sensor 18 is opened and closed by inhibiting or preventing lateral movement of the first arms 606a.

FIG. 31E illustrates that het protuberance 649 can have multiple portions, for example, the three portions shown in FIG. 31E. FIG. 31E illustrates that the protuberance 649 and the slot 653 can create a nest 655 for the first arms 606a to be in when the first arms 606a are in the first arm loaded position. The nest 655 can control the position and angle of the first arms 606a, for example, to optimize the pre-load of the coils 604 and device functionality (e.g., the opening and closing of the sensor 18). For example, the nest 655 can inhibit or prevent the first arms 606a from slipping out of the first arm loaded positions when the sensor 18 is opened and closed. The middle portion of the protuberance 649 can define the first and second surfaces 650, 652 that the first arms 606a can rest against, and the two lateral portions of the protuberance 649 can inhibit or prevent lateral movement or overextension of the first arms 606a. The first and second surfaces 650, 652 can be the base of the slot 653. The lateral portions of the protuberance 649 can be the side walls of the slot 653.

FIGS. 31D and 31E illustrate that the slot 653 can be straight such that the proximal and distal terminal end of the slot are the same distance away from the housing center longitudinal axis shown 660 in FIG. 31D. As another example, the slot 653 can be angled such that the proximal terminal end of the slot is closer to the housing center longitudinal axis 660 than the distal terminal end of the slot, or vice versa.

FIG. 31E illustrates that the slots 653 can be tapered to guide the first arms 606a into their pre-loaded positions (e.g., their first arm loaded positions). FIG. 31E illustrates that the slots 653 can have a funnel shape. The slots 653 can funnel the first arms 606a into their loaded positions.

FIGS. 32A-32C illustrate that the wings 15 can be positioned more distally on the device 10 compared to the position of the wings 15 shown in FIGS. 30A and 30B. For example, FIGS. 32A-32C illustrate that the wings 15 can be closer to the needle 12 and closer to the insert distal end 17d than the position of the wings 15 shown in FIGS. 30A and 30B. The more distal position of the wings 15 in FIGS. 32A-32C can, for example, advantageously allow greater balance and control of the device 10 during cannulation than the more proximal position of the wings 15 shown in FIGS. 30A and 30B. Relative to FIGS. 30A and 30B, FIGS. 32A-32C illustrate that the wings 15 can likewise extend from the housing core 643 and from the build-outs 644. FIGS. 32A-32C also show that a distal end of the wings 15 can extend from the housing core 643 and a proximal end of the wings 15 can extend from the build-outs 643. However, relative to the position of the wings 15 in FIGS. 30A and 30B, both the proximal and distal end of the wings can be closer to the needle 12. As another example, relative to the position of the wings 15 in FIGS. 30A and 30B, the proximal end of wings 15 can be closer to the distal wall 658 of the build-outs 644 and the distal end of the wings 15 can be farther from the distal wall 658 of the build-outs 644.

FIGS. 32A-32C illustrate the device 10 with the sensor 18 in a footplate closed configuration.

FIG. 32A illustrates that the proximal wall 662 of the build-outs 644 can more angled (e.g., more vertical) than the distal wall 658 of the build-outs 644. The distal wall 658 of the build-outs 644 can be sized and shaped, for example, to achieve the desired pre-load of the torsion spring 602 when the torsion spring 602 is attached to the housing 14.

FIG. 32A illustrates that the lateral walls 665 of the build-outs 644 can extend between the distal and proximal walls 658, 662 of the build-outs 644.

FIG. 32B illustrates that a gap 664 can be between the sensor 18 and the lateral walls 665 of the build-outs 644 such that the coils 604 can be visible when the device 10 is viewed from the bottom.

FIG. 32B illustrates that the sensor 18 can have a distal section having a first width, a middle section having a second width, and a proximal section having a third width. As shown in FIG. 32B, the first width can be smaller than the second width, and the second width can be smaller than the third width. The step down from the third width to the second width can create the gap 664. The middle section can have a smaller width than the distal section to create the gap 664. When the device is attached to the patient and the sensor 18 is in the footplate closed positon, the distal section of the sensor 18 can be the portion of the sensor 18 between the skin and the second arms 606a. When the device is attached to the patient and the sensor 18 is in the footplate closed positon, the middle section of the sensor 18 can be the portion of the sensor 18 between the skin and the coils 604. When the device is attached to the patient and the sensor 18 is in the footplate closed positon, the proximal section of the sensor 18 can be the portion of the sensor 18 between the skin and the membrane 54. As additional examples, the groove 332 can be in the distal section of the sensor 18, the connectors 620 can be extend from the middle section of the sensor 18, the occluder 32 can extend from the proximal section of the sensor 18.

FIG. 32C illustrates the arrangement of features shown, for example, that the build-outs 644 can be between the lateral terminal ends of the wings 15 (e.g., the ends farthest from the device longitudinal axis) and the housing core 643.

FIGS. 32D and 32E illustrate the arrangement of features shown, for example, when the sensor 18 is in the footplate closed position. For example, FIGS. 32D and 32E illustrate that the distal wall 658 of the build-outs 644 can be the first arm engagers 648 and/or that the distal wall 658 of the build-outs 644 can define the protuberance 649.

FIGS. 32F and 32G illustrate the arrangement of features shown, for example, when the sensor 18 is in the footplate open position.

FIGS. 32D and 32F illustrate that as the sensor 18 is opened and closed, the second arms 606b can move relative to the first arms 606a and the first arms 606a can remain in the same position. For example, FIGS. 32D-32G illustrate that the first arms 606a can be in the same position when the sensor 18 is in the footplate closed position and when the sensor 18 is in the footplate open position. FIGS. 32D-32G illustrate that the second arms 606b can be farther from the first arms 606a when the sensor 18 is in the footplate open position and when the sensor 18 is in the footplate closed position. FIGS. 32D-32G illustrate that as the coils 604 unwind when the device 10 is dislodged, the torsion spring 602 can move the sensor 18 from the footplate closed position to the footplate open position as the coils 604 unwind from the second wound configuration (e.g., FIGS. 32A-32E) to the first wound configuration (e.g., FIGS. 32F and 32G). The first wound configuration shown in FIGS. 32F and 32G can be the pre-loaded configuration of the torsion spring 602.

FIGS. 32D-32G illustrate that the diameter of the coils 604 can be larger when the sensor 18 is in the footplate open position than when the sensor 18 is in the footplate closed position. FIGS. 32D-32G illustrate, for example, that the space 656 can be larger between the coils 604 and the connector extensions 622 when the sensor 18 is in the footplate open position than when the sensor 18 is in the footplate closed position. FIGS. 32D-32G illustrate, for example, that the coils 604 can be closer to the proximal wall 662 of the build-outs 644 when the sensor 18 is in the footplate open position than when the sensor 18 is in the footplate closed position. FIGS. 32D-32G illustrate, for example, that the gap between the coils 644 and the proximal wall 662 of the build-outs 644 can be smaller when the sensor 18 is in the footplate open position than when the sensor 18 is in the footplate closed position. FIGS. 32D-32G illustrate that the first arms 606a can contact the connector extension 622 when the sensor 18 is in the footplate open position than when the sensor 18 is in the footplate closed position. FIGS. 32D-32G illustrate that the first arms 606a can contact the first arm engagers 648 when the sensor 18 is in the footplate open position than when the sensor 18 is in the footplate closed position. FIGS. 32E and 32F illustrate that more of the first arms 606a can contact the first arm engagers 648 when the sensor 18 is in the footplate open position than when the sensor 18 is in the footplate closed position. For example, FIG. 32E illustrate that the first arm distal portions 606*ad* can contact the first arm engagers 648 when the sensor 18 is in the footplate closed position and FIG. 32G illustrates that the first arm distal portions 606*ad* and the bends 614 can contact the first arm engagers 648 when the sensor 18 is in the footplate open position.

FIGS. 32D-32G illustrate that the protuberance 649 can be the distal wall 658 of the build-outs 644 and that the distal wall 658 may not have a slot 653. As another example, the distal wall 658 of the build-outs 644 can have the slot 653.

FIGS. 32D-32G illustrate the arrangement of features shown, for example, that the distal wall 658 of the build-outs 644 can be the first arm engagers 648 and/or that the distal wall 658 of the build-outs 644 can define the protuberance 649.

FIGS. 33A-33F illustrate three variations of the torsion spring 602 with straight first arms 606*a*. FIGS. 33A-33F illustrate that the first arms 606*a* may not have a bend (e.g., the bend 614). FIGS. 33A-33F illustrate the torsion spring 602 in a neutral, non-loaded configuration. FIGS. 33A-33F illustrate that when the torsion spring 602 is in the neutral configuration, an angle 668 can be between the first and second arms 606*a*, 606*b*. The angle 668 can be, for example, about 8 degrees to about 40 degrees, including every 1 degree increment within this range. For example, FIGS. 33A and 33B illustrate that the angle 668 can be about 15 degrees, FIGS. 33C and 33D illustrate that the angle 668 can be about 20 degrees, and FIGS. 33E and 33F illustrate that the angle 668 can be about 25 degrees. The 15 degree torsion spring 602 (e.g., FIGS. 33A and 33B) can provide about 359 mN of downward force. The 20 degree torsion spring 602 (e.g., FIGS. 33C and 33D) can provide about 379 mN of downward force. The 25 degree torsion spring 602 (e.g., FIGS. 33E and 33F) can provide about 416 mN of downward force.

FIGS. 33A, 33C, and 33E illustrate that the coils 604 can have from about 2.00 turns to about 6.00 turns, or more narrowly, from about 3.00 turns to about 4.00 turns, including every 0.01 turn increment within these ranges. For example, FIG. 33A illustrates that the coils 604 can have about 3.45 turns, FIG. 33C illustrates that the coils 604 can have about 3.44 turns, and FIG. 33E illustrates that the coils 604 can have about 3.43 turns.

FIGS. 33A-33F illustrate that the first and second arms 606*a*, 606*b* can extend in the same longitudinal direction when the torsion spring 602 is in the neutral configuration.

FIG. 33G illustrates a close-up of the side view of FIG. 33D to illustrate the dimensions and arrangement of features shown in FIG. 33G.

FIG. 33G illustrates that the distance 610 can be measured as shown, and that the distance 610 can be about 8.00 mm to about 16.00 mm, or more narrowly from about 10.00 mm to about 14.00 mm, including every 0.01 mm increment within these ranges. For example, FIG. 33G illustrates that the distance 610 can be about 12.86 mm.

FIG. 33G illustrates that the length 670 of the torsion spring 602 can be measured as shown, and that length 670 can be about 10.00 mm to about 20.00 mm, or more narrowly from about 12.00 mm to about 18.00 mm, including every 0.01 mm increment within these ranges. For example, FIG. 33G illustrates that the length 670 can be about 15.00 mm.

FIG. 33G illustrates that the first arms 606*a* can have a length 672 measured as shown, and that het length 672 can be about 2.00 mm to about 6.00 mm, or more narrowly from about 2.50 mm to about 3.50 mm, including every 0.01 mm increment within these ranges. For example, FIG. 33G illustrates that het length 672 can be about 2.95 mm.

FIG. 33G illustrates that the coils 604 can have an inner diameter 674 and an outer diameter 676. The inner diameter 674 can be about 2.50 mm to about 4.50 mm and the outer diameter 676 can be about 3.50 mm to about 5.50 mm, including every 0.01 mm increment within these ranges. For example, FIG. 33G illustrates that the inner diameter 674 can be about 3.65 mm and that the outer diameter 676 can be about 4.29 mm.

FIG. 33H illustrates a top view of the torsion spring 602 illustrated in FIGS. 33C, 33D, and 33G. FIG. 33H illustrates the dimensions and the arrangement of features shown.

FIG. 33H illustrates that the bridge 608 can have a length 678 measured as shown, and that the width can be about 4.50 mm to about 7.00 mm, including every 0.01 mm increment within this range. For example, FIG. 33H illustrates that the length 678 can be about 5.57 mm.

FIG. 33H illustrates that the radius of curvature 680 of the bends at the two ends of the bridge 608 can be about 0.75 mm to about 1.25 mm, including every 0.01 mm increment within this range. For example, FIG. 33H illustrates that the radius of curvature 680 can be about 1.07 mm.

FIG. 33H illustrates that when the torsion spring 602 is in the neutral configuration, an angle 682 can be between the second arms 606*b* and the bridge 608. The angle 682 can be about 85 degrees to about 95 degrees, including every 1 degree increment within this range. For example, FIG. 33H illustrates that the angle 682 can be about 90 degrees. The angle 682 can be the same when the sensor 18 is in the footplate open position and when the sensor 18 is in the footplate closed position. As another example, when the angle 682 can increase or decrease by about 1 degree to about 3 degrees when the coils 604 are wound and unwound between the first and second wound configurations.

FIG. 33H illustrates that the torsion spring 602 can be a wire having a diameter 684 from about 0.150 mm to about 0.500 mm, or more narrowly, from about 0.220 mm to about 0.420 mm, including every 0.001 mm increment within these ranges (e.g., 0.150 mm, 0.220 mm, 0.420 mm, 0.500 mm). For example, FIG. 33H illustrates that the diameter 684 can be about 0.320 mm.

FIG. 33H illustrates that the first arms 606*a* can be farther from the torsion spring center longitudinal axis 612 than the second arms 606*b*. As another example, first arms 606*a* can extend from the inner side of the coils 604 and the second arms 606*b* can extend from the outer side of the coils 604 (e.g., opposite to what is shown in FIG. 33H).

FIG. 33I illustrates the arrangement of features shown, for example, the relative arrangement of the features shown.

FIGS. 34A-34G illustrate that the device 10 can have a torsion spring 602 with first arms 606*a* that are straight (e.g., that may not have the bend 614). For example, aside from the differences in the features shown in FIGS. 34A-34G and the differences explained below relative to FIGS. 32A-32G, FIGS. 34A-34G can illustrate, for example, the device 10 of FIGS. 32A-32G with straight first arms 606*a* instead of curved first arms 606*a*.

FIGS. 34A-34C illustrate that the wings 15 can be positioned more distally on the device 10 compared to the position of the wings 15 shown in FIGS. 32A-32C. For example, FIGS. 34A-34C illustrate that the wings 15 can be closer to the needle 12 and closer to the insert distal end 17*d* than the position of the wings 15 shown in FIGS. 32A-32C. The more distal position of the wings 15 in FIGS. 34A-34C can, for example, advantageously allow greater balance and control of the device 10 during cannulation than the more proximal position of the wings 15 shown in FIGS. 32A-32C. FIGS. 34A-34C illustrate that the wings 15 can extend from the portion of the housing core 643 that is distal the build-outs 644. For example, FIGS. 34A-34C illustrate that both the distal and proximal ends of the wings 15 can extend from the housing core 643 proximal the build-outs 644. The proximal and distal ends of the wings 15 in FIGS. 34A-34C can be closer to the needle 12 than the proximal and distal ends of the wings 15 shown in FIGS. 32A-32C.

FIGS. 34A-34C illustrate the device 10 with the sensor 18 in a footplate closed configuration.

FIG. 34A illustrates a variation of a needle cap 340 attached to the device 10. For example, FIG. 34A illustrates that the needle cap 340 can have a snap fit or a friction fit with the needle hub 13.

FIG. 34A illustrates that the proximal wall 662 of the build-outs 644 can more angled (e.g., more vertical) than the distal wall 658 of the build-outs 644. The distal wall 658 of the build-outs 644 can be sized and shaped, for example, to achieve the desired pre-load of the torsion spring 602 when the torsion spring 602 is attached to the housing 14.

FIG. 34A illustrates that the lateral walls 665 of the build-outs 644 can extend between the distal and proximal walls 658, 662 of the build-outs 644.

FIG. 34B illustrates that the device 10 may not have the gap 664 between the sensor 18 and the lateral walls 665 of the build-outs 644 such that the coils 604 may not be visible when the device 10 is viewed from the bottom. For example, relative to FIG. 32B, FIG. 34B illustrates that both the distal and middle sections of the sensor 18 can have the first width, and that the proximal section of the sensor 18 can have the third width. That is, compared to FIG. 32B, FIG. 34B illustrates that the first width can step down directly to the third width without a step (e.g., the second width) between them. The middle section can thereby have a ledge 686 that covers the recess 654 and extends over both the connectors 620 and the coils 64, thereby covering both the connectors and coils 620, 604.

FIG. 34C illustrates the arrangement of features shown, for example, that the base of the wings 15 can be fully distal the build-outs 644. For example, the proximal and distal ends of the base of the wings 15 can both be distal the distal wall 658 of the build-outs 644. This can advantageously prevent the build-outs 644 from interfering with the folding of the wings 15 when the wings 15 are rotated (e.g., rotated upward) about the hinge 646.

FIGS. 34D and 34E illustrate the arrangement of features shown, for example, when the sensor 18 is in the footplate closed position. For example, FIGS. 34D and 34E illustrate that the distal wall 658 of the build-outs 644 can be the first arm engagers 648 and/or that the distal wall 658 of the build-outs 644 can define the protuberance 649. FIGS. 34D and 34E illustrate that when the sensor 18 is in the footplate closed position, the coils 604 can have the second wound configuration. FIGS. 34D and 34E illustrate that when the sensor 18 is in the footplate closed position, the first arms 606a can extend toward the second arms 606b.

FIGS. 34F and 34G illustrate the arrangement of features shown, for example, when the sensor 18 is in the footplate open position.

FIGS. 34D and 34F illustrate that as the sensor 18 is opened and closed, the second arms 606b can move relative to the first arms 606a and the first arms 606a can remain in the same position. For example, FIGS. 34D-34G illustrate that the first arms 606a can be in the same position when the sensor 18 is in the footplate closed position and when the sensor 18 is in the footplate open position. FIGS. 34D-34G illustrate that the second arms 606b can be farther from the first arms 606a when the sensor 18 is in the footplate open position and when the sensor 18 is in the footplate closed position. FIGS. 34D-34G illustrate that as the coils 604 unwind when the device 10 is dislodged, the torsion spring 602 can move the sensor 18 from the footplate closed position to the footplate open position as the coils 604 unwind from the second wound configuration (e.g., FIGS. 34A-34E) to the first wound configuration (e.g., FIGS. 34F and 34G). The first wound configuration shown in FIGS. 34F and 34G can be the pre-loaded configuration of the torsion spring 602.

As shown in FIGS. 34D-34G, the build-outs 644 can have a different shape than the build-outs 644 in FIGS. 32D-32G to accommodate the straight first arms 606a. For example, FIGS. 34D-34G illustrate that the first arm engagers 648 can have the first surface 650. As another example, FIGS. 34D-34G illustrate that the first arm engagers 648 may not have the second surface 652.

FIGS. 34D-34G illustrate that the diameter of the coils 604 can be larger when the sensor 18 is in the footplate open position than when the sensor 18 is in the footplate closed position. FIGS. 34D-34G illustrate, for example, that the space 656 can be larger between the coils 604 and the connector extensions 622 when the sensor 18 is in the footplate open position than when the sensor 18 is in the footplate closed position. FIGS. 34D-34G illustrate, for example, that the coils 604 can be closer to the proximal wall 662 of the build-outs 644 when the sensor 18 is in the footplate open position than when the sensor 18 is in the footplate closed position. FIGS. 34D-34G illustrate, for example, that the gap between the coils 644 and the proximal wall 662 of the build-outs 644 can be smaller when the sensor 18 is in the footplate open position than when the sensor 18 is in the footplate closed position. FIGS. 34D-34G illustrate that the first arms 606a can contact the connector extension 622 when the sensor 18 is in the footplate open position than when the sensor 18 is in the footplate closed position. FIGS. 34D-34G illustrate that the first arms 606a can contact the first arm engagers 648 when the sensor 18 is in the footplate open position than when the sensor 18 is in the footplate closed position. FIGS. 34E and 34F illustrate that more of the first arms 606a can contact the first arm engagers 648 when the sensor 18 is in the footplate open position than when the sensor 18 is in the footplate closed position. For example, FIG. 34E illustrate that the first arm distal portions 606ad can contact the first arm engagers 648 when the sensor 18 is in the footplate closed position and FIG. 34G illustrates that the first arm distal portions 606ad and the bends 614 can contact the first arm engagers 648 when the sensor 18 is in the footplate open position.

FIGS. 34D-34G illustrate that the protuberance 649 can be the distal wall 658 of the build-outs 644 and that the distal wall 658 may not have a slot 653. As another example, the distal wall 658 of the build-outs 644 can have the slot 653.

FIGS. 34D-34G illustrate the arrangement of features shown, for example, that the distal wall 658 of the build-outs 644 can be the first arm engagers 648 and/or that the distal wall 658 of the build-outs 644 can define the protuberance 649.

FIGS. 35A-35C illustrate three different shapes that the connector extensions 622 can have. The connector extensions 622 can have any combination of the features and shapes shown, for example, in FIGS. 28B and 35A-35C. For example, FIGS. 35A-35C illustrate that the outer surface of the connector extensions 622 can have flat sections 688 and curved sections 689. For example, FIGS. 35A-35C illustrate that the connector extensions 622 can have two flat sections 688 and two curved sections 689. As another example, the connector extensions can have one flat section 688 and one curved section. As yet another example, FIG. 28B illustrates that the connector extensions 622 can have a single curved section 689 such that the connector extensions have a cylindrical shape. The flat sections 688 can advantageously reduce friction between the coils 604 and the connector extensions 622 by increasing the size of the space 656 between the coils 604 and the connector extensions 622.

FIG. 34H illustrates the bottom view of FIG. 34B at section 34H-34H with the sensor 18 and the tube 638 shown transparent so that the slots 653 and the recesses 654 can be illustrated. The slot 653 can be a pre-load channel for the first arms 606a. The pre-load channels can be an arc that form a tangent point on the first arms 606a. for example, the cross-section line Y-Y in FIG. 34C can cut right through the center of the slot 653 such that the first surface 650 that the first arms 606a are in contact with in FIGS. 34D-34G can be the base of the slot 653. FIG. 34H illustrates that the slots 653 can be tapered to guide the first arms 606a into their pre-loaded positions (e.g., their first arm loaded positions). FIG. 34H illustrates that the slots 653 can have a funnel shape. The slots 653 can funnel the first arms 606a into their loaded positions. The slots 653 can thereby function as assembly channels. Exemplary first arm loaded positions are shown in FIGS. 34D-34G.

FIG. 34I illustrates that the slots 653 can have a funnel 708 at their distal ends. The funnel 708 can be taper or a proximal to distal widening of the slots 653 to assist with assembling the first arms 606a into their pre-loaded positions in the slots 653. The funnel 708 can guide the first arms 606a into the first arm loaded positions. The first surface 650 can be curved.

FIGS. 34H and 34I illustrate that the slots 653 can be in the distal wall 658 of the build-outs 644. FIGS. 34H and 34I illustrate that the first surface 650 can be an inner surface of the distal wall 658 of the build-outs 644.

FIG. 34J illustrates that the slots 653 in FIG. 34H in a more proximal position to increase the pre-load on the first arms 606a. For example, FIG. 34J illustrates that the slots 653 are farther from the distal wall 658 of the build-outs 644 in FIG. 34J than in FIG. 34H. This adjustment can increase the pre-load on the first arms 606a when the torsion spring 602 is inserted into the housing 14.

FIGS. 34H-34K illustrate that the slots 653 can be straight such that the slots 653 are parallel to the device longitudinal axis.

FIGS. 34L and 34M illustrate that the slots 653 can be straight such that the slots 653 can be angled relative to the device longitudinal axis. For example, FIGS. 34L and 34M illustrate that the slot proximal ends 653p are closer to a center of the device 10 than the slot distal ends 653d. FIGS. 34L and 34M also illustrate that the slots 653 can be further away from the center of the device than the position of the slots 653 illustrated in FIGS. 34J and 34K. This can splay the first arms 606a outward such that the coils 604 do not contact with the connector extensions 622 when the torsion spring 602 is in the first loaded configuration (e.g., when the torsion spring 602 is in the pre-loaded configuration shown in FIGS. 34F and 34G. This can advantageously remove a key source of frictional forces that can apply between the connector extensions 622 as the sensor 18 is opened and closed. The slots 653 can thereby inhibit or prevent the coils 604 from contacting the connector extensions 622 as the sensor 18 is moved back and forth between the open position in FIGS. 34F and 34G and the closed position in FIGS. 34D and 34E. The coils 604 can rotate a fraction of the rotational degree of freedom of the sensor 18.

FIG. 34N illustrates the first arms 606 of the device 10 displaced out of the slots 653, for example, displaced out of the pre-loaded configuration shown in FIG. 34G. FIG. 34N illustrates, for example, the arrangement of FIG. 34G in a displaced configuration.

FIGS. 35B and 35C illustrates that the connector extensions 622 can be tapered. The tapers illustrated in FIGS. 35B and 35C can advantageously give the first arms 606a space to deflect when the coils 604 are wound, for example, when the torsion spring 602 is loaded with energy during attachment to the device 10 (e.g., to the insert 17 and/or to the housing 14), during attachment to the patient (e.g., when the coils 604 are wound from the first wound configuration to the second wound configuration), or during both attachments. As the coils 604 are wound (e.g., from the first wound configuration to the second wound configuration), the diameter of the coils 604 can become smaller. The tapers in FIGS. 35B and 35C can reduce the friction between the coils 604 and the connector extensions 604 as the coils 604 are wound by increasing the size of the space 656 between the coils 604 and the connector extensions 622, thereby giving the coils 604 more room to contract.

FIG. 35B illustrates that the connector extension 622 can be tapered from their proximal ends to their distal ends. For example, FIG. 35B illustrates that the tapered surface 624 illustrated in FIG. 28B can be longitudinally longer as shown in FIG. 35B. For example, FIG. 35B illustrates that the tapered surface 624 can extend a full length of the connector extensions 622, for example, from a proximal terminal end to a distal terminal end. As another example, the tapered surface 624 can extend along a partial length of the connector extensions 622, where the taper can start, for example, about 1.5 mm to about 7.0 mm from the proximal terminal end of the connector extensions 622. For example, FIG. 28B illustrates that the tapered surface 624 can start about 1 mm to 2 mm before the distal terminal end of the connector extensions 622. The flat sections 688 and/or the curved sections 689 can have the tapered surface 624. For example, FIG. 35B illustrates that both the flat sections 688 and the curved sections 689 can be tapered, for example, can have the tapered surface 624.

FIG. 35B illustrates that that the connector extensions 622 can have a tapered round shape with two flat sections 688, where FIG. 35B illustrates that the taper can be a sloped or non-stepped taper. The taper can be gradual. The taper can be variable. For example, FIG. 35B illustrates that the tapered surface 624 can be less angled near the proximal end of the connector extensions 622 and more angled near the distal end of the connector extensions 622. The taper can be constant. For example, FIG. 28B illustrates that the tapered surface 624 can have a constant angle (e.g., a constant slope).

FIG. 35C illustrates that the connector extensions 622 can have a stepped taper. For example, FIG. 35C illustrates that the connector extensions 622 can have a first step 690 and a second step 692. The first step 690 can have a larger diameter or width than the second step 692. The steps can have the flat sections 688 and/or the curved sections 689. For example, FIG. 35C illustrates that the first and second steps 690, 692 can each have the flat sections 688 and the curved sections 689.

FIG. 35C illustrates that that the connector extensions 622 can have a tapered round shape with two flat sections 688, where FIG. 35C illustrates that the taper can be a stepped taper.

The connector extensions 622 shown in FIGS. 35A-35C can result in more efficient energy transfer to and from the torsion spring 602, for example, by reducing friction between the coils 604 and the connector extensions 622 when the coils 604 are wound as the sensor 18 is closed and by reducing friction between the coils 604 and the connector extensions 622 when the coils 604 unwind as the sensor 18 opens (e.g., passively opens due to the coils 604 unwinding).

The position of the spring first arms 606a when the sensor 18 is in the footplate open configuration can be controlled by changing the shape and size of the connector extensions 622, for example, as shown in FIGS. 35A-35C.

FIG. 36 illustrates a perspective view of the sensor 18 in FIGS. 34A-34G. FIG. 36 illustrates, for example, that the base of the sensor 18 can be extended underneath the connector extensions 622 to reduce potential for spring-skin contact and/or to reduce potential for spring-hair contact. FIG. 36 illustrates, for example, that the base of the sensor 18 can be extended underneath the connector extensions 622 to inhibit or prevent skin and/or hair from contacting or interfering with the coils 604 and/or with the movement of the sensor 18. The portion extended underneath the connector extensions can be the ledge 686. FIG. 36 illustrates that the sensor 18 can have the connector extensions 622 illustrated in FIG. 35A. FIG. 36 illustrates that axes 628 and 630 can be coincident with each other.

FIG. 37A illustrates that the first and second arms 606a, 606b can extend from the coils 604 in opposite directions. FIG. 37A illustrates the torsion spring 602 is a neutral configuration.

FIGS. 37B and 37C illustrate that the torsion spring 602 may not have the bridge 608. For example, FIG. 37B illustrates that the torsion spring 602 in FIG. 28A may not have the bridge 608, and FIG. 37C illustrates that the torsion spring in FIG. 33C may not have the bridge 608.

FIG. 38A illustrates that the wings 15 can be positioned distal the build-outs 644. This can advantageously prevent the build-outs 644 from interfering with the with the folding of the wings. For example, FIG. 38A illustrates the housing 14 of FIGS. 34A-34G with the wings 15 in a folded configuration. FIGS. 34A-34G illustrate the wings of FIG. 38A in a non-folded or unfolded configuration.

FIG. 38B illustrates that the top edge of the build-outs 644 can be rounded to reduce or eliminate interference from the build-outs 644 when the wings 15 are folded or are in a folded configuration. For example, FIG. 38B illustrates the housing 14 of FIGS. 30A-30D with the wings 15 in a folded configuration. FIGS. 30A-30D illustrate the wings of FIG. 38B in a non-folded or unfolded configuration. The user of the device 10 can pinch the wings 15 into a folded configuration during cannulation, after which the user can release the wings 15 and tape them against the patient in a non-folded or unfolded configuration.

FIGS. 39A and 39B illustrate the device 10 in a cannulated position with the sensor 18 in the footplate closed position before dislodgement. FIG. 39A illustrates a piece of tape 698 holding the device 10 in place on the skin 700. FIG. 39A illustrates two pieces of tape 698 holding the device 10 in place on the skin 700. FIG. 39A illustrates that the piece of tape 698 can extend across the housing 14, for example, across both of the wings 15. FIG. 39B illustrates that one piece of tape 698 can extend across the housing 14 over the top of the device 10 and that one piece of tape 698 can extend around the rear of the device 10 under the tubing 8. FIGS. 39A and 39B illustrate that a piece of gauze 702 can be between the device 10 and the skin 700.

FIG. 40A is an example of a coil spring 710 designed to function as the footplate opening energy source for the full coil spring device shown in FIGS. 42A-42D. The spring 710 can be a standard linear compression spring with a spring force equivalent to the amount of compression applied. Manipulation of coil numbers, pitch, material type and wire dimensions can also be used to influence the final spring force. To enable ease of assembly during manufacturing, the coil end of this type of coil spring can terminate in a crossing member 712, a section of wire that can be used as an attachment point for the spring 710 to a purposely designed mating point on the footplate 18.

FIG. 40B is a top/angled view of the coil spring 710 assembled into a footplate 18 and ready for assembly into a full device. This entire component can be pushed (e.g., pushed vertically upward) into the needle body/fluid flow core (e.g., housing 14) allowing for appropriate mating of the hinge points (e.g., connectors 620). FIG. 40B illustrates that the connectors 620 may not have the connector extensions 622 but can have the connector channels 626. The coil spring 710 can be affixed into the footplate 18 via the mechanism shown in FIG. 40C. FIG. 40B illustrates that the footplate 18 can have two side walls 714 that can protect the coil spring 710.

FIG. 40C illustrates that the footplate 18 can have a mating groove 716 that the crossing member 712 can fit into. To fix the coil spring 710 onto the footplate 18 in the first step of assembly, the coil spring bottom can be rotated until the crossing member 712 is aligned with a corresponding mating groove 716 in the footplate 18 as shown in FIG. 40C. FIG. 40C illustrates the crossing member 712 in the mating groove 716.

FIG. 40D is a top view and FIG. 40E is a bottom view of the footplate 18 after the coil spring 710 has been aligned with the footplate mating groove 716, the coil spring has been pushed downward and rotated to set the crossing member 712 at an angle and fully into the slot provided by the mating groove 716. Once set, the coil spring 710 can be engaged against the footplate 18 and in this configuration can be manipulated as a single component to efficiently aid later assembly steps.

FIGS. 41A-41D show multiple views of a coil-spring version of the full needle system designed to protect patients from the risks of needle dislodgement. For example, FIGS. 41A-41D can be a coil-spring version of FIGS. 29A-29D. FIGS. 41A-41D do not include the needle body butterfly wings but do include the central fluid flow path consisting of hard tube 638 with a single soft section 54 that enables protrusion of a solid occlusion member 32 at the footplate proximal end to obstruct fluid flow, creating increased back pressure during dislodgement. That increase in backpressure is designed to be high enough trigger a fluid pump's automatic shut-off mechanism. The fluid flow component can be created using a 2-shot molding process.

FIG. 41A is a top/angled view showing a coil spring device 10 in the footplate open position in which the tape (not shown) has failed and the needle has become dislodged from the skin (not shown) and the footplate via, energy provided by the coil spring, has opened, moving a set distance away from the needle body, enabling protrusion of a solid occlusion member at the footplate proximal through the compressible region of, for example, a 2-shot core, thus blocking fluid flow through the central flow path within the needle body.

FIG. 41B shows a top/angled view showing a coil spring device 10 in the footplate closed position as it can appear after cannulation and firmly affixed in place against the skin (not shown). In this position, pressure of the applied tape (not shown) from above against the skin surface below (not shown), compresses the coil spring and prohibits the spring from uncoiling, and keeps the footplate in the closed position enabling fluid flow through the central flow path within the needle body.

FIG. 41C is a side view showing a coil spring device 10 in the footplate open position in which the tape (not shown) has failed and the needle has become dislodged from the skin (not shown) and the footplate via, energy provided by the coil spring, has opened, moving a set distance away from the needle body, thus blocking fluid flow through the central flow path within the needle body via a solid occlusion member at the footplate proximal end.

FIG. 41D is a side view showing a coil spring device 10 in the footplate closed position as it can appear after cannulation and firmly affixed in place against the skin (not shown). In this position, pressure of the applied tape (not shown) from above against the skin surface below (not shown), compresses the coil spring and prohibits the spring from uncoiling, and keeps the footplate in the closed position enabling fluid flow through the central flow path within the needle body.

FIG. 42A is a top/angled view showing a coil spring device 10 in the footplate open position in which the tape (not shown) has failed and the needle has become dislodged from the skin (not shown) and the footplate via, energy provided by the torsion spring, has opened, moving a set distance away from the needle body, thus blocking fluid flow through the central flow path within the needle body via a solid occlusion member on the footplate proximal end. FIG. 42A illustrates that the housing 14 can have build-outs 718 with recesses for the side walls 714.

FIG. 42B shows a top/angled view showing a coil spring device in the footplate closed position as it can appear after cannulation and firmly affixed in place against the skin (not shown). In this position, pressure of the applied tape (not shown) from above against the skin surface below (not shown), compresses the coil spring and prohibits the spring from uncoiling, and keeps the footplate in the closed position enabling fluid flow through the central flow path within the needle body. The needle body can include the build outs 644 to provide protection to the footplate hinge points. Hinge protection builds-out for the coil spring model (e.g., FIGS. 40A-42D) can be smaller than builds-outs 644 to accommodate the side coils of the torsion spring model (e.g., FIGS. 28A-37C).

FIG. 42C is a side view showing a coil spring device in the footplate open position in which the tape (not shown) has failed and the needle has become dislodged from the skin (not shown) and the footplate via, energy provided by the coil spring, has opened, moving a set distance away from the needle body, thus blocking fluid flow through the central flow path within the needle body via a solid occlusion member on the footplate proximal end.

FIG. 42D is a side view showing a coil spring device in the footplate closed position as it can appear after cannulation and firmly affixed in place against the skin (not shown). In this position, pressure of the applied tape (not shown) from above against the skin surface below (not shown), compresses the coil spring and prohibits the spring from uncoiling, and keeps the footplate in the closed position enabling fluid flow through the central flow path within the needle body.

Positioning the coil assemblies on the side of the device 10 (e.g., using the torsion spring 602) can enable the overall height of the device 10 to become smaller in comparison to a standard single coil compression spring placed underneath the device 10 (e.g., as shown in FIGS. 42A-42D).

FIGS. 1-42D support the exemplary variations described below that span from "Tissue access devices are disclosed . . . The first coil can have a first coil first arm (e.g., 606*a*) and a first coil second arm (e.g., 606*b*)" to "The first loaded configuration can be a non-zero load". As another example, FIGS. 28A-42D support the exemplary variations described below that span from "Tissue access devices are disclosed . . . The first coil can have a first coil first arm (e.g., 606*a*) and a first coil second arm (e.g., 606*b*)" to "The first loaded configuration can be a non-zero load". As yet another example, FIGS. 28A-39B support the exemplary variations described below that span from "Tissue access devices are disclosed . . . The first coil can have a first coil first arm (e.g., 606*a*) and first coil second arm (e.g., 606*b*)" to "The first loaded configuration can be a non-zero load".

Tissue access devices are disclosed. For example, a tissue access device is disclosed that can have a needle and a housing having wings. The device can have a tube having a flow channel, a tube first extension, a tube second extension. The device can have a torsion spring having a first coil and a second coil. The first coil can have a first coil first arm (e.g., 606*a*) and a first coil second arm (e.g., 606*b*). The first coil first arm can be shorter than the first coil second arm. The second coil can have a second coil first arm and a second coil second arm. The second coil first arm can be shorter than the second coil second arm. The device can have a sensor having a first connector, a second connector, and an occluder. The occluder can be connected to the first connector and the second connector. The first connector can have a first connector extension (e.g., 622). The second connector can have a second connector extension (e.g., 622). The sensor can have a sensor open configuration and a sensor closed configuration. When the device is in a fully assembled configuration, the tube first extension can be in the first connector extension and in the first coil. When the device is in the fully assembled configuration, the tube second extension can be in the second connector extension and in the second coil. When the device is in the fully assembled configuration and the sensor is in the sensor open configuration, the torsion spring can have a first loaded configuration. When the device is in the fully assembled configuration and the sensor is in the sensor closed configuration, the torsion spring can have a second loaded configuration. More energy can be stored in the torsion spring when the torsion spring is in the second loaded configuration than when the torsion spring is in the first loaded configuration.

Tissue access devices are disclosed. For example, a tissue access device is disclosed that can have a needle and a housing having wings. The device can have a tube having a flow channel, a tube first extension, and a tube second extension. The device can have a torsion spring having a first coil, a second coil, a first arm, a second arm, and a third arm. The third arm can be longer than the first arm. The third arm can be longer than the second arm. The device can have a sensor having a first hinge, a second hinge, and an occluder. When the device is in a fully assembled configuration, the tube first extension can be in the first hinge. When the device is in the fully assembled configuration, the tube second extension can be in the second hinge. When the device is in the fully assembled configuration and the sensor is in a sensor open configuration, the torsion spring can have a first loaded configuration. When the device is in the fully assembled configuration and the sensor is in a sensor closed configuration, the torsion spring can have a second loaded configuration. More energy can be stored in the torsion spring when the torsion spring is in the second loaded configuration than when the torsion spring is in the first loaded configuration.

Tissue access devices are disclosed. For example, a tissue access device is disclosed that can have a needle and a housing having wings. The device can have a tube having a flow channel, a tube first extension, and a tube second extension. The device can have a spring on a first lateral side of the housing and on a second lateral side of the housing. The device can have a sensor having a first hinge, a second hinge, and an occluder. Shen the device is in a fully assembled configuration, the tube first extension and the spring can be connected to the first hinge. When the device is in a fully assembled configuration, the tube second extension and the spring can be connected to the second hinge. When the device is in the fully assembled configuration and the sensor is in a sensor open configuration, the torsion spring can have a first loaded configuration. When the device is in the fully assembled configuration and the sensor is in a sensor closed configuration, the torsion spring can have a second loaded configuration. Less energy can be stored in the spring when the spring is in the first loaded configuration than when the spring is in the second loaded configuration.

Tissue access devices are disclosed. For example, a tissue access device is disclosed that can have a needle, a housing, a tube having a flow channel, a torsion spring, and a sensor. Tissue access devices are disclosed. For example, a tissue access device is disclosed that can have a needle, a housing, a tube having a flow channel, a torsion spring, and a pre-loaded sensor. Tissue access devices are disclosed. For example, a tissue access device is disclosed that can have a needle, a housing, a tube having a flow channel, a pre-loaded torsion spring, and a sensor.

The first loaded configuration can be a pre-loaded configuration that biases the sensor to be in the sensor open configuration. The sensor can be a footplate.

The housing can have a first engager (e.g., 648). The first coil first arm can be engaged with the first engager when the sensor is in the sensor open configuration and when the sensor is in the sensor closed configuration. The first engager can be a housing surface, a protuberance, and/or a slot. The housing can have a first build-out (e.g., 644) having a first build-out recess. The first engager can be in a first build-out recess. When the device is in the fully assembled configuration, the tube first extension, the first connector extension, and the first coil can be in the first build-out recess.

The housing can have a second engager (e.g., 648). The second coil first arm can be engaged with the second engager when the sensor is in the sensor open configuration and when the sensor is in the sensor closed configuration. The second engager can be a housing surface, a protuberance, and/or a slot. The housing can have a second build-out (e.g., 644) having a second build-out recess. The second engager can be in in a second build-out recess. When the device is in the fully assembled configuration, the tube second extension, the second connector extension, and the second coil can be in the second build-out recess. The housing has a third engager. The first coil second arm and the second coil second arm can be engaged with the third engager when the sensor is in the sensor open configuration and when the sensor is in the sensor closed configuration. The third engager can be the sensor. The third engager can be a groove in the sensor. The first build-out can be on lateral first side of the device and the second build-out can be on a lateral second side of the device. The first build-out can be opposite the second build-out.

The device can have a bridge. The bridge can connect the first coil second arm to the second coil second arm. The torsion spring can have a bridge. The first coil second arm and the second coil second arm can be connected to the bridge. The housing can have a third engager. The first coil second arm, the second coil second arm, and the bridge can be engaged with the third engager when the sensor is in the sensor open configuration and when the sensor is in the sensor closed configuration.

The third engager can have a U-shape.

The wings can have a base. The base can be distal the first and second build-outs. The wings can be foldable.

When the torsion spring is in the first loaded configuration, the first coil can have a first coil first loaded configuration and the second coil can have a second coil second loaded configuration. The first coil can have a smaller diameter when the first coil is in the first coil second loaded configuration than when the first coil is in the first coil first loaded configuration. The second coil can have a smaller diameter when the second coil is in the second coil second loaded configuration than when the second coil is in the first coil first loaded configuration.

When the torsion spring is in the second loaded configuration, the first coil second arm can be closer to the first coil first arm than when the torsion spring is in the first loaded configuration.

When the torsion spring is in the second loaded configuration, the first coil second arm can be closer to the needle than when the torsion spring is in the first loaded configuration.

When the torsion spring is in the second loaded configuration, the second coil second arm can be closer to the second coil first arm than when the torsion spring is in the first loaded configuration.

When the torsion spring is in the second loaded configuration, the second coil second arm can be closer to the needle than when the torsion spring is in the first loaded configuration.

When the device is in the fully assembled configuration, the first coil second arm can be moveable toward and away from the first coil first arm.

When the device is in the fully assembled configuration, the second coil second arm can be moveable toward and away from the second coil first arm.

When the device is attached to skin, the sensor can inhibit or prevent skin or hair from contacting the torsion spring.

The first connector extension can have a cylindrical shape.

The second connector extension can have a cylindrical shape.

The first connector extension can be tapered.

The first connector extension can have a non-stepped taper.

The first connector extension can have a stepped taper.

The first connector extension can have a flat outer surface and a curved outer surface.

The first connector extension can have two flat outer surfaces and two curved outer surfaces.

The second connector extension can be tapered.

The second connector extension can have a non-stepped taper.

The second connector extension can have a stepped taper.

The second connector extension can have a flat outer surface and a curved outer surface.

The second connector extension can have two flat outer surfaces and two curved outer surfaces.

The first engager, the second engager, and/or the third engager can be rigid.

The first engager, the second engager, and/or the third engager may not be deformable by the torsion spring.

The occluder can be moveable into and out of the flow channel.

When the sensor is in the sensor open configuration, the occluder can occlude the flow channel. When the sensor is in the sensor closed configuration, less of the flow channel can be occluded by the occluder than when the sensor is in the sensor open configuration.

When the device is attached to a patient, the sensor can be in the sensor closed configuration. When the device is dislodged from the patient, the sensor can be moveable from the sensor closed configuration to the sensor open configuration via the torsion spring unwinding from the second loaded configuration to the first loaded configuration.

The third arm can be connected to the first arm and the second arm.

The third arm can be connected to the first coil and the second coil.

The third arm can connect the first coil to the second coil.

The third arm can have a U-shape.

The housing can have a first engager. The first arm can be engaged with the first engager when the sensor is in the sensor open configuration and when the sensor is in the sensor closed configuration.

The housing can have a second engager. The second arm can be engaged with the second engager when the sensor is in the sensor open configuration and when the sensor is in the sensor closed configuration.

The housing can have a third engager. The third arm can be engaged with the third engager when the sensor is in the sensor open configuration and when the sensor is in the sensor closed configuration.

The first arm can extend from the first coil

The second arm can extend from the second coil.

The third arm can extend from the first coil and from the second coil. The first coil and second coils can be simultaneously windable via the sensor.

The first coil and second coils can be simultaneously unwindable via the sensor.

The first hinge can have a first connector having a first connector channel connected to the tube first extension. The second hinge can have a second connector having a second connector channel connected to the tube second extension.

The spring can be a torsion spring having a first coil and a second coil. The first coil can have a first coil first arm and a first coil second arm. The first coil first arm can be shorter than the first coil second arm. The second coil can have a second coil first arm and a second coil second arm. The second coil first arm can be shorter than the second coil second arm.

The spring can be a torsion spring having a first coil, a second coil, a first arm, a second arm, and a third arm. The third arm can be longer than the first arm. The third arm can be longer than the second arm.

The first loaded configuration can be a non-zero load.

Additional variations, features, elements and methods of use of needle safety systems (e.g., for automatic restriction or termination of flow due to needle dislodgement) are described in PCT Patent Application No. PCT/US2014/072573 filed Dec. 29, 2014, PCT Patent Application No. PCT/US2017/068021 filed Dec. 21, 2017, PCT Patent Application No. PCT/US2019/030703 filed May 3, 2019, U.S. patent application Ser. No. 15/286,274 filed Oct. 5, 2016, U.S. patent application Ser. No. 16/244,445 filed Jan. 10, 2019, and U.S. Provisional Application No. 61/978,671 filed Apr. 11, 2014, each of which is incorporated herein by reference in its entirety for all purposes, and can be combined with the present disclosure in any combination.

The variations disclosed herein are offered by way of example only. Many modifications will be apparent to those skilled in the art without departing from the scope of the present disclosure.

Like reference numerals in the drawings indicate identical or functionally similar features/elements.

All dimensions disclosed herein are exemplary. The dimensions disclosed herein can at least be expanded to ranges from about 50% to about 150% of the exemplary dimension shown herein, more narrowly from about 75% to about 125% of the exemplary dimension shown herein. Language such as "at least," "greater than," "less than," "between," and the like includes the number recited. Any of the dimensions can be modified as desired or as needed to combine any of the features in any of the drawings together or to omit any of the features from any of the drawings.

Any range disclosed can include any subrange of the range disclosed, for example, a range of 1-10 units can include 2-10 units, 8-10 units, or any other subrange.

The words "may" and "can" are interchangeable (e.g., "may" can be replaced with "can" and "can" can be replaced with "may").

Any elements described herein as singular can be pluralized (e.g., anything described as "one" can be more than one, anything referred to with an indefinite article, e.g., "a" or "an," can be more than one, anything referred to with the definite article "the" can be more than one, etc.).

Any species element of a genus element can have the characteristics or elements of any other species element of that genus.

The above-described and illustrated features, elements, configurations, assemblies, sub-assemblies, complete assemblies, and/or methods and their elements for carrying out the disclosure can be combined and/or modified with each other in any combination.

Any of the below claims and/or variations can be combined and/or modified with each other in any combination, as well as combined and/or modified with any other portion of the disclosure in any combination. The below claims are exemplary and not limiting.

Some elements may be absent from individual figures for reasons of illustrative clarity.

Any phrase involving an "A and/or B" construction can mean (1) A alone, (2) B alone, (3) A and B together.

The claims are not limited to the exemplary variations shown in the drawings, but instead may claim any feature disclosed or contemplated in the disclosure as a whole. Any elements described herein as singular can be pluralized (i.e., anything described as "one" can be more than one).

The above-described configurations, elements or complete assemblies and methods and their elements for carrying out the disclosure, and variations of aspects of the disclosure can be combined and modified with each other in any combination.

All devices, apparatuses, systems, and methods described herein can be used for medical (e.g., diagnostic, therapeutic or rehabilitative) or non-medical purposes.

We claim:

1. A tissue access device, comprising:
   a needle;
   a housing having wings;
   a tube having a flow channel, a tube first extension, and
      a tube second extension;

a torsion spring having a first coil and a second coil, wherein the first coil has a first coil first arm and a first coil second arm, wherein the first coil first arm is shorter than the first coil second arm, wherein the second coil has a second coil first arm and a second coil second arm, and wherein the second coil first arm is shorter than the second coil second arm; and a sensor having a first connector, a second connector, and an occluder, wherein the occluder is connected to the first connector and the second connector, wherein the first connector has a first connector extension, wherein the second connector has a second connector extension, and wherein the sensor has a sensor open configuration and a sensor closed configuration, wherein when the tissue access device is in a fully assembled configuration, the tube first extension is in the first connector extension and in the first coil, wherein when the tissue access device is in the fully assembled configuration, the tube second extension is in the second connector extension and in the second coil, and wherein when the tissue access device is in the fully assembled configuration and the sensor is in the sensor open configuration, the torsion spring has a first loaded configuration, wherein when the tissue access device is in the fully assembled configuration and the sensor is in the sensor closed configuration, the torsion spring has a second loaded configuration, and wherein more energy is stored in the torsion spring when the torsion spring is in the second loaded configuration than when the torsion spring is in the first loaded configuration.

2. The tissue access device of claim 1, wherein the housing has a first engager, and wherein the first coil first arm is engaged with the first engager when the sensor is in the sensor open configuration and when the sensor is in the sensor closed configuration.

3. The tissue access device of claim 2, wherein the housing has a second engager, and wherein the second coil first arm is engaged with the second engager when the sensor is in the sensor open configuration and when the sensor is in the sensor closed configuration.

4. The tissue access device of claim 1, further comprising a bridge, wherein the bridge connects the first coil second arm to the second coil second arm.

5. The tissue access device of claim 1, wherein the wings are foldable.

6. The tissue access device of claim 1, wherein when the torsion spring is in the second loaded configuration, the first coil second arm is closer to the first coil first arm than when the torsion spring is in the first loaded configuration, and wherein when the torsion spring is in the second loaded configuration, the second coil second arm is closer to the second coil first arm than when the torsion spring is in the first loaded configuration.

7. The tissue access device of claim 1, wherein when the torsion spring is in the second loaded configuration, the first coil second arm is closer to the needle than when the torsion spring is in the first loaded configuration, and wherein when the torsion spring is in the second loaded configuration, the second coil second arm is closer to the needle than when the torsion spring is in the first loaded configuration.

8. The tissue access device of claim 1, wherein the occluder is moveable into and out of the flow channel.

9. The tissue access device of claim 1, wherein when the sensor is in the sensor open configuration, the occluder occludes the flow channel, and wherein when the sensor is in the sensor closed configuration, less of the flow channel is occluded by the occluder than when the sensor is in the sensor open configuration.

10. The tissue access device of claim 1, wherein the first coil and the second coil are simultaneously windable via the sensor.

11. A tissue access device, comprising:
a needle;
a housing having wings;
a tube having a flow channel, a tube first extension, and a tube second extension;
a torsion spring having a first coil, a second coil, a first arm, a second arm, and a third arm, wherein the third arm is longer than the first arm, and wherein the third arm is longer than the second arm; and
a sensor having a first hinge, a second hinge, and an occluder,
wherein when the tissue access device is in a fully assembled configuration, the tube first extension is in the first hinge,
wherein when the tissue access device is in the fully assembled configuration, the tube second extension is in the second hinge, and
wherein when the tissue access device is in the fully assembled configuration and the sensor is in a sensor open configuration, the torsion spring has a first loaded configuration,
wherein when the tissue access device is in the fully assembled configuration and the sensor is in a sensor closed configuration, the torsion spring has a second loaded configuration, and wherein more energy is stored in the torsion spring when the torsion spring is in the second loaded configuration than when the torsion spring is in the first loaded configuration.

12. The tissue access device of claim 11, wherein the occluder is moveable into and out of the flow channel.

13. The tissue access device of claim 11, wherein the first arm extends from the first coil, and wherein the second arm extends from the second coil.

14. The tissue access device of claim 13, wherein the third arm extends from the first coil and from the second coil.

15. The tissue access device of claim 11, wherein the first coil and the second coil are simultaneously windable via the sensor.

16. A tissue access device, comprising:
a needle;
a housing having wings;
a tube having a flow channel, a tube first extension, and a tube second extension;
a spring on a first lateral side of the housing and on a second lateral side of the housing; and
a sensor having a first hinge, a second hinge, and an occluder,
wherein when the tissue access device is in a fully assembled configuration, the tube first extension and the spring are connected to the first hinge,
wherein when the tissue access device is in the fully assembled configuration, the tube second extension and the spring are connected to the second hinge, and
wherein when the tissue access device is in the fully assembled configuration and the sensor is in a sensor open configuration, the spring has a first loaded configuration, wherein when the tissue access device is in the fully assembled configuration and the sensor is in a sensor closed configuration, the spring has a second loaded configuration, and wherein less energy is stored in the spring when the spring is in the first loaded configuration than when the spring is in the second loaded configuration.

17. The tissue access device of claim 16, wherein the occluder is moveable into and out of the flow channel.

18. The tissue access device of claim 16, wherein the spring comprises a torsion spring having a first coil and a second coil, wherein the first coil has a first coil first arm and a first coil second arm, wherein the first coil first arm is shorter than the first coil second arm, wherein the second coil has a second coil first arm and a second coil second arm, and wherein the second coil first arm is shorter than the second coil second arm.

19. The tissue access device of claim 16, wherein the spring comprises a torsion spring having a first coil, a second coil, a first arm, a second arm, and a third arm, wherein the third arm is longer than the first arm, and wherein the third arm is longer than the second arm.

20. The tissue access device of claim 19, wherein the first coil and the second coil are simultaneously windable via the sensor.

\* \* \* \* \*